United States Patent [19]

Ohno et al.

[11] Patent Number: 5,496,849
[45] Date of Patent: Mar. 5, 1996

[54] SULFONIC ACID DERIVATIVE AND ITS PHARMACEUTICAL APPLICATION

[75] Inventors: Kiyotaka Ohno, Fujisawa; Atsushi Ohtake, Kamakura; Shintaro Nishio, Ebina; Kazuhiro Hoshi; Shunji Tsukamoto, both of Kamakura, all of Japan

[73] Assignee: Toray Industries, Inc., Japan

[21] Appl. No.: 244,141

[22] PCT Filed: Sep. 17, 1993

[86] PCT No.: PCT/JP93/01339

§ 371 Date: May 17, 1994

§ 102(e) Date: May 17, 1994

[87] PCT Pub. No.: WO94/06785

PCT Pub. Date: Mar. 3, 1994

[30] Foreign Application Priority Data

Sep. 18, 1992 [JP] Japan ................................ 4-249288
Jan. 27, 1993 [JP] Japan ................................ 5-011938

[51] Int. Cl.⁶ ........................ A61K 31/34; C07D 307/80; C07D 307/78
[52] U.S. Cl. ........................ 514/468; 549/458; 549/460; 549/461
[58] Field of Search ............................ 514/468; 549/458, 549/460, 461

[56] References Cited

U.S. PATENT DOCUMENTS 5,126,370  6/1992  Misra ........................ 514/469
5,158,967  1/1992  Hall ........................ 514/374

*Primary Examiner*—Yogendra N. Gupta
*Attorney, Agent, or Firm*—Austin R. Miller

[57] ABSTRACT

The present invention discloses sulfonamide derivative represented by the following general formula:

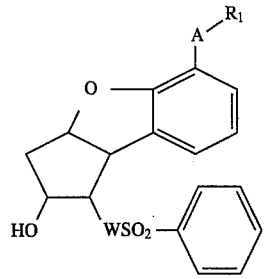

[wherein,
$R_1$ is
(i) —$COOR_2$ (where, $R_2$ is (1) hydrogen, (2) a pharmacologically acceptable cation, or (3) an alkyl having 1 to 14 carbon atoms) or,
(ii) —C(=O)—$R_3$ (wherein, $R_3$ represents an alkyl having 1 to 4 carbon atoms); A is
(i) —$(CH_2)_n$— (wherein, n represents an integer of 0 to 3),
(ii) —CH=CH—, or the group:
(iii) —O—C($R_4$) ($R_5$)— (wherein, $R_4$ and $R_5$ represent (1) hydrogen or (2) an alkyl having 1 to 4 carbon atoms, and $R_4$ and $R_5$ may be identical or different); and,
w is NH or —O—], as well as a thromboxane A2 receptor antagonistic drug having said derivative for its active ingredient.

Since the compound of the present invention has excellent thromboxane A2 receptor antagonistic action, it can be used as a thromboxane A2 receptor antagonist of high activity and long duration.

7 Claims, No Drawings

SULFONIC ACID DERIVATIVE AND ITS PHARMACEUTICAL APPLICATION

This application is a 371 of PCT/JP93/01339 filed on Sep. 17, 1993.

1. Technical Field

The present invention relates to a sulfonic acid derivative having a cyclopenta[b]benzofuran ring which is used as a therapeutic drug for disorders caused by thromboxane A2.

2. Background Art

Thromboxane A2 (TXA2), discovered by Samuelsson et al. in 1975, has strong platelet coagulating action and smooth muscle contracting action (see *Proc. Natl. Acad. Sci. U.S.A.*, vol. 72, p. 2994 (1975)). Thromboxane A2 is considered to be one of the causes which produces disorders such as ischemic heart disorders including angina pectoris and myocardial infarction, as well as cerebrovascular disease and bronchial asthma as a result of these actions. Thus, suppression of the action of thromboxane A2 is effective for treatment of disorders such as ischemic heart disorders including angina pectoris and myocardial infarction, cerebrovascular disease and bronchial asthma. Thromboxane A2 receptor antagonists have been reported to be drugs which suppress the action of thromboxane A2 (see *Circulation*, vol. 81, suppl. I, I-69 (1990)).

Thromboxane A2 receptor antagonists have attracted attention as therapeutic drugs for disorders caused by thromboxane A2, and a thromboxane A2 receptor antagonist is sought which has both high activity and long duration.

DISCLOSURE OF THE INVENTION

The present inventors, as a result of searching for a thromboxane A2 receptor antagonist having a novel structure, found a sulfonamide derivative that has a cyclopenta [b]benzofuran ring as a compound which has powerful thromboxane A2 receptor antagonistic action. Namely, the present invention relates to sulfonic acid derivatives represented with general formula [I]:

[I]

[wherein, $R_1$ is (i) —$COOR_2$ (wherein, $R_2$ is (1) hydrogen, (2) a pharmacologically acceptable cation, or (3) an alkyl having 1 to 4 carbon atoms) or the group:

$$-\overset{O}{\underset{\|}{C}}-R_3$$  (ii)

(wherein, —$R_3$ represents an alkyl having 1 to 4 carbon atoms);

A is (i) —$(CH_2)n$— (wherein, n represents an integer of 0 to 3), (ii) —CH=CH—, or the group:

$$-O-\underset{R_4}{\overset{C}{\diagup}}\underset{R_5}{\diagdown}-$$ (iii)

(wherein,

—$R_4$ and $R_5$ represent (1) hydrogen or (2) an alkyl having 1 to 4 carbon atoms, and $R_4$ and $R_5$ may be identical or different); and, B is represented with either formula [II] or formula [III]:

$$-CH_2-\underset{\underset{Y-W-SO_2R_8}{|}}{\overset{\overset{R_6}{|}}{CH}}-CH-$$ (II)

$$-CH_2-\underset{\underset{Y-W-SO_2R_8}{|}}{\overset{\overset{R_6}{|}}{CH}}-CH-$$ (III)

{wherein, $R_6$ represents (i) hydrogen, (ii) —$OR_9$ (wherein, $R_9$ represents (1) hydrogen, (2) an alkyl having 1 to 4 carbon atoms, (3) an acyl group having 2 to 5 carbon atoms, or (4) an aroyl group having 7 to 11 carbon atoms), (iii) a halogen, (iv) a cyano, or (v) formula (wherein, 1 represents an integer of 5 to 7 and $R_{10}$ represents hydrogen or a phenyl group), Y is —$(CH_2)m$— (wherein, m represents 0 or 1), W is $$-\underset{\underset{R_7}{|}}{N}-\text{ or}$$

—O—, $R_7$ is (i) hydrogen, or (ii) an alkyl having 1 to 4 carbon atoms, $R_8$ is (i) an alkyl having 1 to 14 carbon atoms, or (ii) —Z—$R_{11}$ (wherein, Z is a valence bond or a straight or branched alkylene represented by $C_tH_{2t}$ (wherein, t is an integer of 1 to 5), and $R_{11}$ represents an aryl group or aryl group having 6 to 16 carbon atoms substituted by 1 to 4 groups selected from the group consisting of alkyl, methoxy, chlorine, bromine, fluorine, iodine, trifluoromethyl, nitro, cyano, phenyl and phenoxy)}], as well as a thromboxane A2 receptor antagonistic drugs having said novel sulfonic acid derivative for its effective ingredient.

Among those compounds represented by the formula (I), those compounds wherein B is represented by the formula (II) or formula (III')

$$-CH_2-\underset{\underset{Y-W-SO_2R_8}{|}}{\overset{\overset{R_6}{|}}{CH}}-CH-$$ (II)

-continued

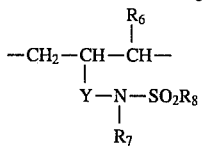

(wherein, $R_6$, $R_7$, $R_8$, Y and W are the same as previously defined) are used preferably.

In particular, the sulfonamide derivatives represented by the formula (I') below as well as the sulfonate ester derivatives represented by the formula (I") below are preferable.

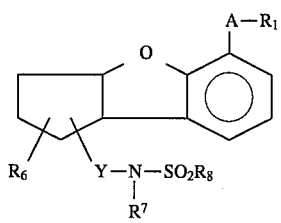

(wherein, $R_1$, $R_6$, $R_7$, $R_8$, A and Y are the same as previously defined)

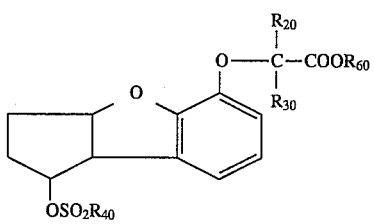

(wherein, $R_{60}$ is
 (i) hydrogen,
 (ii) a pharmacologically acceptable cation, or
 (iii) an alkyl having 1 to 14 carbon atoms, $R_{20}$ and $R_{30}$ are independently each other a hydrogen or alkyl having 1 to 4 carbon atoms, and $R_{40}$ is —($CH_2$)n—$R_{50}$ (wherein, n is an integer of 0–5, and $R_{50}$ is an aryl group non-substituted or substituted with 1 to 4 groups of alkyl, methoxy, chlorine, bromine, fluorine, iodine, trifluoromethyl, nitro, cyano, phenyl and phenoxy)].

In addition, among the sulfonamide derivatives indicated in the above-mentioned general formula (I'), preferable sulfonamides are those wherein $R_6$ is
 (i) hydrogen, or
 (ii) —$OR_2$ (wherein, $R_2$ is (1) hydrogen, (2) an alkyl having 1–4 carbon atoms, or (3) an acyl group), and $R_8$ is
 (i) an alkyl having 1–14 carbon atoms,
 (ii) —Z—$R_{11}$ (wherein, Z is a valence bond or a straight chain or branched alkylene represented by $C_tH_{2t}$ (where, t is an integer of 1–4), and $R_{11}$ represents a phenyl group or a phenyl group substituted by 1 to 4 groups selected from the group consisting of alkyl, methoxy, chlorine, bromine, fluorine, iodine, trifluoromethyl, nitro, cyano, phenyl and phenoxy), or
 (iii) —Z—$R_{12}$ (wherein, Z is the same as previously defined, and $R_{12}$ represents a 1-naphthyl group, 2-naphthyl group, or a 1-naphthyl or 2-naphthyl group substituted with 1 to 4 groups selected from the group consisting of alkyl, methoxy, chlorine, bromine, fluorine, iodine, trifluoromethyl, nitro, cyano, phenyl and phenoxy), and $R_1$, $R_7$, A and Y are same as previously defined.

In the case $R_2$ is a pharmacologically allowable cation, examples of $R_2$ include metal cation, ammonium, amine cation or quaternary ammonium cation. Particularly preferable examples of metal cations include those derived from alkaline metals such as lithium, sodium and potassium, and those derived from alkaline earth metals such as magnesium and calcium. Naturally, the cationic forms of other metals such as aluminum, zinc and iron are also included in the present invention.

Pharmacologically allowable amine cations are those derived from primary, secondary or tertiary amines. More preferable examples of amines include methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine as well as similar aliphatic, alicyclic and heterocyclic amines containing no more than 18 carbon atoms, examples of which include 1-methylpiperidine, 4-ethylmorpholine, 1-isopropylpyrrolidine, 2-methylpyrrolidine, 4-dimethylpiperazine and 2-methylpiperidine. Moreover, examples of water-soluble amines or amines containing hydrophilic groups include mono-, di-and triethanolamine, ethyldiethylamine, N-butylethanolamine, 2-amino-1-butanol, 2-amino-2-ethyl-1,3-propanediol, tris (hydroxymethyl) aminomethane, N-phenylethanolamine, N-(p-tertaminophenyl) diethanolamine, galactamine, N-methylglutamine, N-methylglucosamine, ephedrine, phenylephrine, epinephrine and procaine, while specific examples of acidic amino acids include lysine and arginine.

Examples of alkyl groups having 1–14 carbon atoms indicated for $R_2$ or $R_8$ include straight chain or branched alkyl groups such as methyl, ethyl, propyl, butyl, pentyl, hexyl, heptyl, octyl, nonyl, decanyl, undecanyl, dedecyl, isopropyl, sec-butyl, t-butyl, iso-butyl, 1-methylpentyl, 4-methylpentyl, 1-methylhexyl, 5-methylhexyl, 1-methylheptyl, 6-methylheptyl, 1-methyloctyl, 7-methyloctyl, 8-methylnonyl, 9-methyldecanyl, 1,1-dimethylbutyl, 2,2-dimethylbutyl, 1,1-dimethylpentyl, 4,4-dimethylpentyl, 1,1-dimethylhexyl, 5,5-dimethylhexyl, 1,1-dimethylheptyl, 6,6-dimethylheptyl, 1,1-dimethyloctyl, 1,1-dimethylnonyl, 1,1-dimethyldecanyl, 1,1,2,2-tetramethylpentyl, 1,1,3,3-tetramethylpentyl, 1,1,2,2-tetramethylhexyl, 1,1,3,3-tetramethylhexyl and 2,2,3,3-tetramethylhexyl. Furthermore, in the case $R_2$ represents an alkyl group, alkyl groups having 1–4 carbon atoms are used preferably.

Examples of alkyl groups having 1–4 carbon atoms indicated for $R_3$, $R_4$, $R_5$, $R_7$ and $R_9$ include methyl, ethyl, propyl, butyl, isopropyl, sec-butyl, t-butyl and isobutyl groups.

Specific examples in which A is —($CH_2$)n— include a valence bond, methylene, ethylene and trialkylene. In addition, in the case A represents

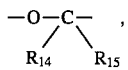

hydrogen or a methyl group is independently preferably used for $R_{14}$ and $R_{15}$.

Specific examples in which $R_{10}$ is an aryl group or aryl group substituted with 1–4 groups selected from the group consisting of alkyl, methoxy, chlorine, bromine, fluorine, iodine, trifluoromethyl, nitro, cyano, phenyl and phenoxy include phenyl, 1-naphthyl, 2-naphthyl, p-tolyl, m-tolyl, o-tolyl, p-ethylphenyl, p-propylphenyl, p-butylphenyl, p-anisyl, m-anisyl, o-anisyl, p-chlorophenyl, m-chlorophenyl, o-chlorophenyl, p-bromophenyl, m-bromophenyl, o-bromophenyl, p-fluorophenyl, m-fluorophenyl, o-fluorophenyl, p-iodophenyl, m-iodophenyl, o-iodophenyl, p-trifluoromethylphenyl, m-trifluoromethylphenyl, o-trifluoromethylphenyl, p-nitrophenyl, p-cyanophenyl, 4-biphenyl, p-phenoxyphenyl, 3,4-dimethylphenyl, 2,4-dimethylphenyl, 3,4-dimethoxyphenyl, 2,4-dichlorophenyl, 2,5-dichlorophenyl, 2,6-dichlorophenyl, 3,4-dichlorophenyl, 3,5-dichlorophenyl, 2-chloro-4-fluorophenyl, 3-chloro-4-methylphenyl, 3-fluoro-4-methylphenyl and 3-chloro-4-phenoxyphenyl.

Specific examples in which $R_{11}$ is a 1-naphthyl group, 2-naphthyl group or a 1-naphthyl or 2-naphthyl group substituted by 1–4 groups selected from the group consisting of alkyl, methoxy, chlorine, bromine, fluorine, iodine, trifluoromethyl, nitro, cyano, phenyl and phenoxy include 1-naphthyl, 2-naphthyl, 4-methyl-1-naphthyl, 4-methyl-2-naphthyl, 6-methyl-1-naphthyl, 6-methyl-2-naphthyl, 4-chloro-1-naphthyl, 4-chloro-2-naphthyl, 4-fluoro-1-naphthyl, 4-fluoro-2-naphthyl, 4-bromo-1-naphthyl, 4-bromo-2-naphthyl, 4-iodo-1-naphthyl, 4-iodo-2-naphthyl, 4-trifluoromethyl-1-naphthyl, 4-trifluoromethyl-2-naphthyl, 4-nitro-1-naphthyl, 4-nitro-2-naphthyl, 4-cyano-1-naphthyl, 4-cyano-2-naphthyl, 4-phenyl-1-naphthyl, 4-phenyl-2-naphthyl, 4-phenoxy-1-naphthyl and 4-phenoxy-2-naphthyl.

Specific examples of $C_rH_{2r}$ indicated for Z include methylene, methylmethylene, dimethylmethylene, ethylmethylene, ethylene, 1-methylethylene, 1,2-dimethylethylene, 1,1-dimethylethylene, trimethylene, 1-methyltrimethylene, 2-methyltrimethylene and tetramethylene.

Although asymmetric carbon atoms are present in the compound represented by the above-mentioned general formula [I], all possible stereoisomers are included in the compound represented with general formula [I] of the present invention.

The compound represented with the above-mentioned general formula [I] is named based on having a cyclopenta[b]benzofuran ring for its skeleton.

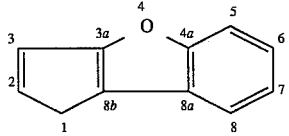

1H-cyclopenta[b]benzofuran

The names of the compounds included in the present invention are illustrated together with their structural formulas.

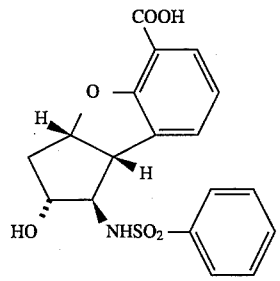

(1R, 2R, 3aS, 8bR)-1-benzenesulfonamide-2-hydroxy-2,3,3a,8b-tetrahydro- 1H-cyclopenta[b]benzofuran-5-carboxylic acid

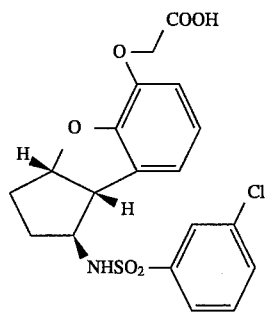

(1S, 3aS, 8bR)-1-(m-chlorobenzenesulfonamide)-2,3,3a,8b-tetrahydro-1H-cyclopenta[b]benzofuran-5-yloxyacetic acid The following lists specific examples of the compound of the present invention following this nomenclature. Although an indication of RS is not given, all possible stereoisomers are included in each compound.

1-Methanesulfonamido-2,3,3a,8b-tetrahydro- 1H-cyclopenta[b]benzofuran-5-yloxyacetic acid, 1-ethanesulfonamido-2,3,3a,8b-tetrahydro-1H -cyclopenta[b]benzofuran- 5-yloxyacetic acid, 1-propanesulfonamido- 2,3,3a,8b-tetrahydro-1H-cyclopenta[b]benzofuran- 5-yloxyacetic acid, 1-butanesulfonamido- 2,3,3a,8b-tetrahydro-1H -cyclopenta[b]benzofuran- 5-yloxyacetic acid, 1-pentanesulfonamido- 2,3,3a,8b-tetrahydro-1H -cyclopenta[b]benzofuran- 5-yloxyacetic acid, 1-hexanesulfonamido- 2,3,3a,8b-tetrahydro-1H-cyclopenta[b]benzofuran- 5-yloxyacetic acid, 1-heptanesulfonamido- 2,3,3a,8b-tetrahydro-1H-cyclopenta[b]benzofuran- 5-yloxyacetic acid, 1-octanesulfonamido- 2,3,3a,8b-tetrahydro-1H-cyclopenta[b]benzofuran- 5-yloxyacetic acid, 1-decanesulfonamido- 2,3,3a,8b-tetrahydro-1H-cyclopenta[b]benzofuran- 5-yloxyacetic acid, 1-benzenesulfonamido- 2,3,3a,8b-tetrahydro-1H-cyclopenta[b]benzofuran- 5-yloxyacetic acid, 1-(p-toluenesulfonamido)- 2,3,3a,8b-tetrahydro-1H-cyclopenta[b]benzofuran- 5-yloxyacetic acid, 1-(m-toluenesulfonamido- 2,3,3a,8b-tetrahydro-1H-cyclopenta[b]benzofuran- 5-yloxyacetic acid, 1-(o-toluenesulfonamido)- 2,3,3a,8b-tetrahydro-1H-cyclopenta[b]benzofuran- 5-yloxyacetic acid, 1-(p-methoxybenzenesulfonamido)- 2,3,3a,8b-tetrahydro-1H-cyclopenta[b]benzofuran- 5-yloxyacetic acid, 1-(m-methoxybenzenesulfonamido)- 2,3,3a,8b-tetrahydro-1H-cyclopenta[b]benzofuran- 5-yloxyacetic acid, 1-(o-methoxybenzenesulfonamido)- 2,3,3a,8b-tetrahydro-1H-cyclopenta[b]benzofuran- 5-yloxyacetic acid, 1-(p-chlorobenzenesulfonamido)- 2,3,3a,8b-tetrahydro-1H-cyclopenta[b]benzofuran- 5-yloxyacetic acid, 1-(m-chlorobenzenesulfonamido)- 2,3,3a,8b-tetrahydro-1H-cyclopenta[b]benzofuran- 5-yloxyacetic acid, 1-(o-chlorobenzenesulfonamido)- 2,3,3a,8b-tetrahydro-1H-cyclopenta[b]benzofuran- 5-yloxyacetic acid, 1-(p-bromobenzenesulfonamido)-2,3,3a,8b-tetrahydro-1H -cyclopenta[b]benzofuran-5-yloxyacetic acid, 1-(m-bromobenzenesulfonamido)-2,3,3a,8b-tetrahydro- 1H -cyclopenta[b]benzofuran-5-yloxyacetic acid, 1-(o-bromobenzenesulfonamido)-2,3,3a,8b-tetrahydro- 1H-cyclopenta[b]benzofuran-5-yloxyacetic acid, 1-(p-fluorobenzenesulfonamido)-2,3,3a,8b-tetrahydro-1H -cyclopenta[b]benzofuran-5-yloxyacetic acid, 1-(m-fluorobenzenesulfonamido)-2,3,3a,8b-tetrahydro- 1H-cyclopenta[b]benzofuran-5-yloxyacetic acid, 1-(o-fluorobenzenesulfonamido)-2,3,3a,8b-tetrahydro-1H -cyclopenta[b]benzofuran-5-yloxyacetic acid, 1-(p-iodobenzenesulfonamido)-2,3,3a,8b-tetrahydro-1H-cyclopenta[b]benzofuran-5-yloxyacetic acid, 1-(m-iodobenzenesulfonamido)-2,3,3a,8b-tetrahydro-1H-cyclopenta[b]benzofuran-5-yloxyacetic acid, 1-(o-iodobenzenesulfonamido)-2,3,3a,8b-tetrahydro-1H-cyclopenta[b]benzofuran-5-yloxyacetic acid, 1-(p-trifluoromethylbenzenesulfonamido)-2,3,3a,8b-tetrahydro-1H-cyclopenta[b]benzofuran-5yloxyacetic acid, 1-(m-trifluoromethylbenzenesulfonamido)- 2,3,3a,8b-tetrahydro- 1H-cyclopenta[b]benzofuran-5-yloxyacetic acid, 1-(o-trifluoromethylbenzenesulfonamido)-2,3,3a,8b-tetrahydro-1H-cyclopenta[b]benzofuran-5yloxyacetic acid, 1-(p-nitrobenzenesulfonamido)-2,3,3a,8b-tetrahydro-1H-cyclopenta[b]benzofuran-5-yloxyacetic acid, 1-(p-cyanobenzenesulfonamido)-2,3,3a,8b-tetrahydro-1H-cyclopenta[b]benzofuran-5-yloxyacetic acid, 1-(4-biphenylsulfonamido)-2,3,3a,8b-tetrahydro-1H-cyclopenta[b]benzofuran-5-yloxyacetic acid, 1-(p-phenoxybenzenesulfonamido)- 2,3,3a,8b-tetrahydro-1H-cyclopenta[b]benzofuran-5-yloxyacetic acid, 1-(p-phenoxybenzenesulfonamido)-2,3,3a,8b-tetrahydro-1H-cyclopenta[b]benzofuran-5-yloxyacetic acid, 1-(3,4-dimethylbenzenesulfonamido)-2,3,3a,8b-tetrahydro-1H-cyclopenta[b]benzofuran-5-yloxyacetic acid, 1-(2,4-dimethylbenzenesulfonamido)-2,3,3a,8b-tetrahydro- 1H-cyclopenta[b]benzofuran-5-yloxyacetic acid, 1-(3,4-dimethoxybenzenesulfonamido)-2,3,3a,8b-tetrahydro- 1H-cyclopenta[b]benzofuran-5-yloxyacetic acid, 1-(3,4-dichlorobenzenesulfonamido)-2,3,3a,8b-tetrahydro- 1H-cyclopenta[b]benzofuran-5-yloxyacetic acid, 1-(2,4-dichlorobenzenesulfonamido)-2,3,3a,8b-tetrahydro- 1H-cyclopenta[b]benzofuran-5-yloxyacetic acid, 1-(3,5-dichlorobenzenesulfonamido)-2,3,3a,8b-tetrahydro- 1H -cyclopenta[b]benzofuran-5-yloxyacetic acid, 1-(2,6-dichlorobenzenesulfonamido)-2,3,3a,8b-tetrahydro- 1H-cyclopenta[b]benzofuran-5-yloxyacetic acid, 1-(2-chloro-4-fluorobenzenesulfonamido)-2,3,3a,8b-tetrahydro-1H-cyclopenta[b]benzofuran-5-yloxyacetic acid, 1-(3-chloro-4-methylbenzenesulfonamido)- 2,3,3a,8b-tetrahydro-1H-cyclopenta[b]benzofuran- 5-yloxyacetic acid, 1-(3-fluoro- 4-methylbenzenesulfonamido)-2,3,3a,8b-tetrahydro- 1H-cyclopenta[b]benzofuran-5-yloxyacetic acid, 1-(3-chloro-4-phenoxybenzenesulfonamido)- 2,3,3a,8b-tetrahydro-1H-cyclopenta[b]benzofuran-5-yloxyacetic acid, 1-phenylmethanesulfonamido-2,3,3a,8b-tetrahydro-1H-cyclopenta[b]benzofuran-5-yloxyacetic acid, 1-(2-phenylethanesulfonamido)-2,3,3a,8b-tetrahydro-1H-cyclopenta[b]benzofuran-5-yloxyacetic acid, 1-(1-naphthalenesulfonamido)-2,3,3a,8b-tetrahydro-1H -cyclopenta[b]benzofuran-5-yloxyacetic acid, 1-(2-naphthalenesulfonamido)-2,3,3a,8b-tetrahydro-1H -cyclopenta[b]benzofuran-5-yloxyacetic acid, 2-hydroxy-1-methanesulfonamido-2,3,3a,8b-tetrahydro-1H-cyclopenta[b]benzofuran-5-yloxyacetic acid, 1-ethanesulfonamido-2-hydroxy-2,3,3a,8b-tetrahydro-1H-cyclopenta[b]benzofuran-5-yloxyacetic acid, 2-hydroxy-1-propanesulfonamido-2,3,3a,8b-tetrahydro-1H-cyclopenta[b]benzofuran-5-yloxyacetic acid, 1-butanesulfonamido-2-hydroxy-2,3,3a,8b-tetrahydro-1H-cyclopenta[b]benzofuran-5-yloxyacetic acid, 2-hydroxy-1-pentanesulfonamido-2,3,3a,8b-tetrahydro-1H-cyclopenta[b]benzofuran-5-yloxyacetic acid, 1-hexanesulfonamido-2-hydroxy-2,3,3a,8b-tetrahydro-1H-cyclopenta[b]benzofuran-5-yloxyacetic acid, 1-heptanesulfonamido-2-hydroxy-2,3,3a,8b-tetrahydro- 1H-cyclopenta[b]benzofuran-5-yloxyacetic acid, 2-hydroxy-1-octanesulfonamido-2,3,3a,8b-tetrahydro-1H-cyclopenta[b]benzofuran-5-yloxyacetic acid, 1-decanesulfonamido-2-hydroxy-2,3,3a,8b-tetrahydro-1H-cyclopenta[b]benzofuran-5-yloxyacetic acid, 1-benzenesulfonamido-2-hydroxy-2,3,3a,8b-tetrahydro- 1H-cyclopenta[b]benzofuran-5-yloxyacetic acid, 2-hydroxy-1-(p-toluenesulfonamido)-2,3,3a,8b-tetrahydro- 1H-cyclopenta[b]benzofuran-5-yloxyacetic acid, 2-hydroxy-1-(m-toluenesulfonamido)-2,3,3a,8b-tetrahydro- 1H-cyclopenta[b]benzofuran-5-yloxyacetic acid, 2-hydroxy-1-(o-toluenesulfonamido)-2,3,3a,8b-tetrahydro- 1H-cyclopenta[b]benzofuran-5-yloxyacetic acid, 2-hydroxy-1-(p-methoxybenzenesulfonamido)-2,3,3a,8b-tetrahydro-1H-cyclopenta[b]benzofuran-5-yloxyacetic acid, 2-hydroxy-1-(m-methoxybenzenesulfonamido)- 2,3,3a,8b-tetrahydro-1H-cyclopenta[b]benzofuran- 5-yloxyacetic acid, 2-hydroxy-1-(o-methoxybenzenesulfonamido)-2,3,3a,8b-tetrahydro-1H-cyclopenta[b]benzofuran-5-yloxyacetic acid, 1-(p-chlorobenzenesulfonamido)- 2-hydroxy-2,3,3a,8b-tetrahydro- 1H-cyclopenta[b]benzofuran-5-yloxyacetic acid, 1-(m-chlorobenzenesulfonamido)-2-hydroxy-2,3,3a,8b-tetrahydro-1H-cyclopenta[b]benzofuran-5-yloxyacetic acid, 1-(o-chlorobenzenesulfonamido)-2-hydroxy- 2,3,3a,8b-tetrahydro-1H-cyclopenta[b]benzofuran- 5-yloxyacetic acid, 1-(p-bromobenzenesulfonamido)- 2,3,3a,8b-tetrahydro-1H-cyclopenta[b]benzofuran- 5-yloxyacetic acid, 1-(m-bromobenzenesulfonamido)-2-hydroxy-2,3,3a,8b-tetrahydro-1H-cyclopenta[b]benzofuran-5-yloxyacetic acid, 1-(o-bromobenzenesulfonamido)-2-hydroxy- 2,3,3a,8b-tetrahydro-1H-cyclopenta[b]benzofuran-5-yloxyacetic acid, 1-(p-fluorobenzenesulfonamido)-2-hydroxy-2,3,3a,8b-tetrahydro- 1H-cyclopenta[b]benzofuran-5-yloxyacetic acid, 1-(m-fluorobenzenesulfonamido)-2-hydroxy-2,3,3a,8b-tetrahydro-1H-cyclopenta[b]benzofuran-5-yloxyacetic acid, 1-(o-fluorobenzenesulfonamido)-2-hydroxy- 2,3,3a,8b-tetrahydro-1H-cyclopenta[b]benzofuran- 5-yloxyacetic acid, 2-hydroxy-1-(p-iodobenzenesulfonamido)-2,3,3a,8b-tetrahydro-1H-cyclopenta[b]benzofuran-5-yloxyacetic acid, 2-hydroxy-1-(m-iodobenzenesulfonamido)-2,3,3a,8b-tetrahydro-1H-cyclopenta[b]benzofuran- 5-yloxyacetic acid, 2-hydroxy-1-(o-iodobenzenesulfonamido)-2,3,3a,8b-tetrahydro-1H-cyclopenta[b]benzofuran- 5-yloxyacetic acid, 2-hydroxy-1-(p-trifluoromethylbenzenesulfonamido)- 2,3,3a,8b-tetrahydro- 1H-cyclopenta[b]benzofuran-5-yloxyacetic acid, 2-hydroxy-1-(m-trifluoromethylbenzenesulfonamido)- 2,3,3a,8b-tetrahydro-1H-cyclopenta[b]benzofuran-5-yloxyacetic acid, 2-hydroxy-1-(o-trifluoromethylbenzenesulfonamido)- 2,3,3a,8b-tetrahydro- 1H-cyclopenta[b]benzofuran-5-yloxyacetic acid, 2-hydroxy-1-(p-nitrobenzenesulfonamido)- 2,3,3a,8b-tetrahydro-1H-cyclopenta[b]benzofuran-5-yloxyacetic acid, 1-(p-cyanobenzenesulfonamido)-2-hydroxy- 2,3,3a,8b-tetrahydro-1H-cyclopenta[b]benzofuran- 5-yloxyacetic acid, 1-(4-biphenylsulfonamido)- 2-hydroxy-2,3,3a,
8b-tetrahydro-1H-cyclopenta[b]benzofuran-5-yloxy-
acetic acid, 2-hydroxy- 1-(p-phenoxybenzenesulfona-
mido)-2,3,3a,8b-tetrahydro- 1H-cyclopenta[b]
benzofuran-5-yloxyacetic acid, 2-hydroxy-1-(3,4-
dimethylbenzenesulfonamido)-2,3,3a,8b-tetrahydro-
1H-cyclopenta[b]benzofuran-5-yloxyacetic acid, 2-hydroxy-1-(2,4-dimethylbenzenesulfonamido)-2,3,3a,
8b-tetrahydro-1H-cyclopenta[b]benzofuran-5-yloxy-
acetic acid, 2-hydroxy-1-(3,4-dimethoxybenzene-
sulfonamido)- 2,3,3a,8b-tetrahydro-1H-cyclopenta[b]
benzofuran- 5-yloxyacetic acid, 2-hydroxy-1-(3,4-
dichlorobenzenesulfonamido)-2,3,3a,8b-tetrahydro-
1H-cyclopenta[b]benzofuran-5-yloxyacetic acid, 1-(2,
4-dichlorobenzenesulfonamido)-2-hydroxy-2,3,3a,8b-
tetrahydro-1H-cyclopenta[b]benzofuran-5-yloxyacetic
acid, 1-(3,5-dichlorobenzenesulfonamido)- 2-hydroxy-
2,3,3a,8b-tetrahydro-1H-cyclopenta[b]benzofuran-
5-yloxyacetic acid, 1-(2,6dichlorobenzenesulfona-
mido)- 2-hydroxy-2,3,3a,8b-tetrahydro- 1H-cyclopenta
[b]benzofuran-5-yloxyacetic acid, 1-(2-chloro-4-fluo-
robenzenesulfonamido)-2-hydroxy-    2,3,3a,8b-
tetrahydro-1H-cyclopenta[b]benzofuran- 5-yloxyacetic
acid, 1-(3-chloro- 4-methylbenzenesulfonamido)-2-hy-
droxy- 2,3,3a,8b-tetrahydro-1H-cyclopenta[b]benzofu-
ran-5-yloxyacetic acid, 1-(3-fluoro-4-methylbenzene-
sulfonamido)-2-hydroxy-2,3,3a,8b-tetrahydro-
1H-cyclopenta[b]benzofuran-5-yloxyacetic acid, 1-(3-
chloro-4-phenoxybenzenesulfonamido)-2-hydroxy-
2,3,3a,8b-tetrahydro-1H-cyclopenta[b]benzofuran-
5-yloxyacetic acid, 2-hydroxy-1-phenylmethane-
sulfonamido-2,3,3a,8b-tetrahydro-1H-cyclopenta[b]
benzofuran- 5-yloxyacetic acid, 2-hydroxy-1-(2-phe-
nylethanesulfonamido)-2,3,3a,8b-tetrahydro-1H-
cyclopenta[b]benzofuran- 5-yloxyacetic acid,
2-hydroxy-1-(1-naphthalenesulfonamido)-2,3,3a,8b-
tetrahydro-1H-cyclopenta[b]benzofuran- 5-yloxyacetic
acid, 2-hydroxy-1-(2-naphthalenesulfonamido)-2,3,3a,
8b-tetrahydro-1H-cyclopenta[b]benzofuran- 5-yloxy-
acetic acid, 1-benzenesulfonamido- 2-methoxy-2,3,3a,
8b-tetrahydro-1H-cyclopenta[b]benzofuran-
5-yloxyacetic acid, 2-methoxy-1-(p-toluenesulfona-
mido)- 2,3,3a,8b-tetrahydro-1H-cyclopenta[b]benzofu-
ran- 5-yloxyacetic acid, 2-methoxy-1-(p-methoxybenzenesulfonamido)-2,3,3a,
8b-tetrahydro-1H-cyclopenta[b]benzofuran-5-yloxy-
acetic acid, 1-(p-chlorobenzenesulfonamido)-2-meth-
oxy-      2,3,3a,8b-tetrahydro-1H-cyclopenta[b]
benzofuran-    5-yloxyacetic    acid,    1-(p-
bromobenzenesulfonamido)-2-methoxy-2,3,3a,8b-
tetrahydro- 1H-cyclopenta[b]benzofuran-5-yloxyacetic
acid, 1-(p-fluorobenzenesulfonamido)-2-methoxy-2,3,
3a,8b-tetrahydro-1H-cyclopenta[b]benzofuran-5-
yloxyacetic acid, 1-(p-iodobenzenesulfonamido)-2-
methoxy-    2,3,3a,8b-tetrahydro-1H-cyclopenta[b]
benzofuran-  5-yloxyacetic acid, 2-methoxy-1-(p-
trifluoromethylbenzenesulfonamido)-2,3,3a,8b-
tetrahydro- 1H-cyclopenta[b]benzofuran-5-yloxyacetic
acid, 2-methoxy-1-(p-nitrobenzenesulfonamido)-2,3,
3a,8b-tetrahydro-1H-cyclopenta[b]benzofuran-5-
yloxyacetic acid, 1-(p-cyanobenzenesulfonamido)-2-
methoxy-    2,3,3a,8b-tetrahydro-1H-cyclopenta[b]
benzofuran-    5-yloxyacetic    acid,    1-(4-
biphenylsulfonamido)-    2-methoxy-2,3,3a,8b-
tetrahydro-1H-cyclopenta[b]benzofuran-5-yloxyacetic
acid, 2-methoxy- 1-(p-phenoxybenzenesulfonamido)-
2,3,3a,8b-tetrahydro- 1H-cyclopenta[b]benzofuran-5-
yloxyacetic acid, 2-methoxy-1-phenylmethanesulfona-
mido-2,3,3a,8b-tetrahydro-    1H-cyclopenta[b]
benzofuran-5-yloxyacetic acid, 2-methoxy-1-(2-
phenylethanesulfonamido)-2,3,3a,8b-tetrahydro-1H-
cyclopenta[b]benzofuran-5-yloxyacetic       acid,
2-methoxy-1-(1-naphthalenesulfonamido)- 2,3,3a,8b-
tetrahydro-1H-cyclopenta[b]benzofuran-5-yloxyacetic
acid, 2-methoxy-1-(2-naphthalenesulfonamido)-2,3,3a,
8b-tetrahydro-1H-cyclopenta[b]benzofuran- 5-yloxy-
acetic acid, 1-(N-methylbenzenesulfonamido)- 2-hy-
droxy-2,3,3a,8b-tetrahydro-       1H-cyclopenta[b]
benzofuran-5-yloxyacetic acid, 2-hydroxy-1-(N-
(methyl)phenylmethanesulfonamido)-     2,3,3a,8b-
tetrahydro- 1H-cyclopenta[b]benzofuran-5-yloxyacetic
acid, 2-hydroxy-1-(N-methyl-2-phenylethanesulfonamido)-2,
3,3a,8b-tetrahydro-1H-cyclopenta[b]benzofuran-5-
yloxyacetic acid, 1-((N-methylbenzenesulfonamido)m-
ethyl)- 2-hydroxy-2,3,3a,8b-tetrahydro- 1H-cyclopenta
[b]benzofuran-5-yloxyacetic acid, 2-hydroxy-1-((N-
(methyl)phenylmethanesulfonamido)methyl)- 2,3,3a,
8b-tetrahydro-       1H-cyclopenta[b]benzofuran-5-
yloxyacetic    acid,    2-hydroxy-1-((N-methyl-2-
phenylethanesulfonamido)methyl)-       2,3,3a,8b-
tetrahydro-1H-cyclopenta[b]benzofuran-5-yloxyacetic
acid, 1-((benzenesulfonamido)methyl)-2-hydroxy-2,3,
3a,    8b-tetrahydro-1H-cyclopenta[b]benzofuran-5-
yloxyacetic    acid,    2-hydroxy-1-((phenylmethane-
sulfonamido)methyl)-2,3,3a,8b-tetrahydro-1H-
cyclopenta[b]benzofuran-5-yloxyacetic       acid,
2-hydroxy-1-((2-phenylethanesulfonamido)methyl)-
2,3,3a,8b-tetrahydro-1H-cyclopenta[b]benzofuran-5-
yloxyacetic acid, 1-benzenesulfonamido-2-hydroxy-2,3,3a,8b-tetrahydro-
1H-cyclopenta[b]benzofuran-5-carboxylic acid, 2-hy-
droxy-1-phenylmethanesulfonamido-2,3,3a,8b-tet-
rahydro-   1H-cyclopenta[b]benzofuran-5-carboxylic
acid, 2-hydroxy-1-(2-phenylethanesulfonamido)-2,3,
3a,8b-tetrahydro-1H-cyclopenta[b]benzofuran-5-car-
boxylic acid, 1-((benzenesulfonamido)methyl)-2-hy-
droxy-      2,3,3a,8b-tetrahydro-1H-cyclopenta[b]
benzofuran-   5-carboxylic   acid,   2-hydroxy-
1-((phenylmethanesulfonamido)methyl)- 2,3,3a,8b-tet-
rahydro-1H-cyclopenta[b]benzofuran-5-carboxylic
acid,  2-hydroxy-1-((2-phenylethanesulfonamido)m-
ethyl)-2,3,3a,8b-tetrahydro- 1H-cyclopenta[b]benzofu-
ran-5-carboxylic acid, 1-benzenesulfonamido-2-hy-
droxy-2,3,3a,8b-tetrahydro-1H-cyclopenta[b]
benzofuran-5-acetic    acid,    2-hydroxy-1-
phenylmethanesulfonamido-2,3,3a,8b-tetrahydro-1H-
cyclopenta[b]benzofuran-5-acetic acid, 2-hydroxy-1-(2-phenylethanesulfonamido)-2,3,3a,8b-tet-
rahydro-1H-cyclopenta[b]benzofuran-5-acetic   acid,
1-((benzenesulfonamido)methyl)-2-hydroxy-2,3,3a,
8b-tetrahydro-1H cyclopenta[b]benzofuran-5-acetic
acid,   2-hydroxy-1((phenylmethanesulfonamido)m-
ethyl)- 2,3,3a,8b-tetrahydro- 1H-cyclopenta[b]benzo-
furan-5-acetic acid, 2-hydroxy-1-((2-phenylethane-
sulfonamido)methyl)-2,3,3a,8b-tetrahydro-1H-
cyclopenta[b]benzofuran-5-acetic       acid,
1-benzenesulfonamido-2,3,3a,8b-tetrahydro- 1H-cy-
clopenta[b]benzofuran-5-propionic acid, 1-(p-toluene-
sulfonamido)-2,3,3a,8b-tetrahydro- 1H-cyclopenta[b]
benzofuran-5-propionic     acid,      1-(p-
methoxybenzenesulfonamido)-    2,3,3a,8b-tetrahydro-
1H-cyclopenta[b]benzofuran- 5-propionic acid, 1-(p-
chlorobenzenesulfonamido)- 2,3,3a,8b-tetrahydro-1H- cyclopenta[b]benzofuran- 5-propionic acid, 1-(p-bromobenzenesulfonamido)- 2,3,3a,8b-tetrahydro-1H-cyclopenta[b]benzofuran- 5-propionic acid, 1-(p-fluorobenzenesulfonamido)- 2,3,3a,8b-tetrahydro-1H-cyclopenta[b]benzofuran- 5-propionic acid, 1-(p-iodobenzenesulfonamido)- 2,3,3a,8b-tetrahydro-1H-cyclopenta[b]benzofuran- 5-propionic acid, 1-(p-trifluoromethylbenzenesulfonamido)- 2,3,3a,8b-tetrahydro-1H-cyclopenta[b]benzofuran- 5-propionic acid, 1-(p-nitrobenzenesulfonamido)- 2,3,3a,8b-tetrahydro-1H-cyclopenta[b]benzofuran-5-propionic acid, 1-(p-cyanobenzenesulfonamido)-2,3,3a,8b-tetrahydro-1H-cyclopenta[b]benzofuran- 5-propionic acid, 1-(4-biphenylsulfonamido)-2,3,3a,8b-tetrahydro-1H-cyclopenta[b]benzofuran-5-propionic acid, 1-(p-phenoxybenzenesulfonamido)- 2,3,3a,8b-tetrahydro-1H-cyclopenta[b]benzofuran- 5-propionic acid, 1-phenylmethanesulfonamido- 2,3,3a,8b-tetrahydro-1H-cyclopenta[b]benzofuran- 5-propionic acid, 1-(2-phenylethanesulfonamido)- 2,3,3a,8b-tetrahydro-1H-cyclopenta-[b]benzofuran- 5-propionic acid, 1-(1-naphthalenesulfonamido)-2,3,3a,8b-tetrahydro-1H-cyclopenta[b]benzofuran-5-propionic acid, 1-(2-naphthalenesulfonamido)-2,3,3a,8b-tetrahydro- 1H-cyclopenta[B]benzofuran-5-propionic acid, 1-benzenesulfonamido-2-hydroxy-2,3,3a,8b-tetrahydro-1H-cyclopenta[b]benzofuran-5-propionic acid, 1-(p-toluenesulfonamido)-2-hydroxy-2,3,3a,8b-tetrahydro-1H-cyclopenta[b]benzofuran-5-propionic acid, 1-(p-methoxybenzenesulfonamido)-2-hydroxy-2,3,3a,8b-tetrahydro-1H-cyclopenta[b]benzofuran-5-propionic acid, 1-(p-chlorobenzenesulfonamido)-2-hydroxy- 2,3,3a,8b-tetrahydro-1H-cyclopenta[b]benzofuran- 5-propionic acid, 1-(p-bromobenzenesulfonamido)- 2-hydroxy-2,3,3a,8b-tetrahydro- 1H-cyclopenta[b]benzofuran-5-propionic acid, 1-(p-fluorobenzenesulfonamido)-2-hydroxy-2,3,3a,8b-tetrahydro-1H-cyclopenta[b]benzofuran-5-propionic acid, 1-(p-iodobenzenesulfonamido)-2-hydroxy- 2,3,3a,8b-tetrahydro-1H-cyclopenta[b]benzofuran- 5-propionic acid, 1-(p-trifluoromethylbenzenesulfonamido)-2-hydroxy- 2,3,3a,8b-tetrahydro-1H-cyclopenta[b]benzofuran-5-propionic acid, 1-(p-nitrobenzenesulfonamido)-2-hydroxy- 2,3,3a,8b-tetrahydro-1H-cyclopenta[b]benzofuran- 5-propionic acid, 1-(p-cyanobenzenesulfonamido)- 2-hydroxy-2,3,3a,8b-tetrahydro- 1H-cyclopenta[b]benzofuran-5-propionic acid, 1-(4-biphenylsulfonamido)-2-hydroxy-2,3,3a,8b-tetrahydro- 1H-cyclopenta[b]benzofuran-5-propionic acid, 1-(p-phenoxybenzenesulfonamido)-2-hydroxy-2,3,3a,8b-tetrahydro-1H-cyclopenta[b]benzofuran-5-propionic acid, 2-hydroxy-1-phenylmethanesulfonamido-2,3,3a,8b-tetrahydro-1H-cyclopenta[b]benzofuran-5-propionic acid, 2-hydroxy-1-(2-phenylethanesulfonamido)-2,3,3a,8b-tetrahydro-1H-cyclopenta[b]benzofuran- 5-propionic acid, 1-(1-naphthalenesulfonamido)- 2-hydroxy-2,3,3a,8b-tetrahydro- 1H-cyclopenta[b]benzofuran-5-propionic acid, 1-(2-naphthalenesulfonamido)-2-hydroxy-2,3,3a,8b-tetrahydro-1H-cyclopenta[b]benzofuran-5-propionic acid, 1-((benzenesulfonamido)methyl)-2-hydroxy- 2,3,3a,8b-tetrahydro-1H-cyclopenta[b]benzofuran- 5-propionic acid, 2-hydroxy-1-((phenylmethanesulfonamido)methyl)- 2,3,3a,8b-tetrahydro- 1H-cyclopenta[b]benzofuran-5-propionic acid, 2-hydroxy-1-((2-phenylethanesulfonamido)methyl)- 2,3,3a,8b-tetrahydro-1H-cyclopenta[b]benzofuran-5-propionic acid, 1-benzenesulfonamido-2,3,3a, 8b-tetrahydro- 1H-cyclopenta[b]benzofuran-5-acrylic acid, 1-(p-toluenesulfonamido)-2,3,3a,8b-tetrahydro-1H-cyclopenta[b]benzofuran- 5-acrylic acid, 1-(p-methoxybenzenesulfonamido)- 2,3,3a,8b-tetrahydro-1H-cyclopenta[b]benzofuran- 5-acrylic acid, 1-(p-chlorobenzenesulfonamido)- 2,3,3a,8b-tetrahydro-1H-cyclopenta[b]benzofuran- 5-acrylic acid, 1-(p-bromobenzenesulfonamido)- 2,3,3a,8b-tetrahydro-1H-cyclopenta[b]benzofuran- 5-acrylic acid, 1-(p-fluorobenzenesulfonamido)- 2,3,3a,8b-tetrahydro-1H-cyclopenta[b]benzofuran- 5-acrylic acid, 1-(p-iodobenzenesulfonamido)- 2,3,3a,8b-tetrahydro-1H-cyclopenta[b]benzofuran- 5-acrylic acid, 1-(p-trifluoromethylbenzenesulfonamido)- 2,3,3a,8b-tetrahydro- 1H-cyclopenta[b]benzofuran-5-acrylic acid, 1-(p-nitrobenzenesulfonamido)-2,3,3a,8b-tetrahydro-1H-cyclopenta[b]benzofuran- 5-acrylic acid, 1-(p-cyanobenzenesulfonamido)- 2,3,3a,8b-tetrahydro-1H-cyclopenta[b]benzofuran- 5-acrylic acid, 1-(4-biphenylsulfonamido)- 2,3,3a,8b-tetrahydro-1H-cyclopenta[b]benzofuran- 5-acrylic acid, 1-(p-phenoxybenzenesulfonamido)- 2,3,3a,8b-tetrahydro-1H-cyclopenta[b]benzofuran- 5-acrylic acid, 1-phenylmethanesulfonamido- 2,3,3a,8b-tetrahydro-1H-cyclopenta[b]benzofuran- 5-acrylic acid, 1-(2-phenylethanesulfonamido)-2,3,3a,8b-tetrahydro-1H-cyclopenta[b]benzofuran- 5-acrylic acid, 1-(1-naphthalenesulfonamido)-2,3,3a,8b-tetrahydro-1H-cyclopenta[b]benzofuran- 5-acrylic acid, 1-(2-naphthalenesulfonamido)- 2,3,3a,8b-tetrahydro-1H-cyclopenta[b]benzofuran- 5-acrylic acid, 1-benzenesulfonamido- 2-hydroxy-2,3,3a,8b-tetrahydro-1H-cyclopenta[b]benzofuran- 5-acrylic acid, 1-(p-toluenesulfonamido)- 2-hydroxy-2,3,3a,8b-tetrahydro-1H-cyclopenta[b]benzofuran- 5-acrylic acid, 1-(p-methoxybenzenesulfonamido)- 2-hydroxy-2,3,3a,8b-tetrahydro- 1H-cyclopenta[b]benzofuran-5-acrylic acid, 1-(p-chlorobenzenesulfonamido)- 2-hydroxy-2,3,3a,8b-tetrahydro- 1H-cyclopenta[b]benzofuran-5-acrylic acid, 1-(p-bromobenzenesulfonamido)-2-hydroxy-2,3,3a,8b-tetrahydro- 1H-cyclopenta[b]benzofuran-5-acrylic acid, 1-(p-fluorobenzenesulfonamido)-2-hydroxy-2,3,3a,8b-tetrahydro- 1H-cyclopenta[b]benzofuran-5-acrylic acid, 1-(p-iodobenzenesulfonamido)-2-hydroxy-2,3,3a,8b-tetrahydro- 1H-cyclopenta[b]benzofuran-5-acrylic acid, 1-(p-trifluoromethylbenzenesulfonamido)-2-hydroxy-2,3,3a,8b-tetrahydro-1H-cyclopenta[b]benzofuran-5-acrylic acid, 1-(p-nitrobenzenesulfonamido)-2-hydroxy-2,3,3a,8b-tetrahydro-1H-cyclopenta[b]benzofuran-5-acrylic acid, 1-(p-cyanobenzenesulfonamido)-2-hydroxy-2,3,3a,8b-tetrahydro-1H-cyclopenta[b]benzofuran-5-acrylic acid, 1-(4-biphenylsulfonamido)-2-hydroxy-2,3,3a,8b-tetrahydro-1H-cyclopenta[b]benzofuran-5-acrylic acid, 1-(p-phenoxybenzenesulfonamido)-2-hydroxy- 2,3,3a, 8b-tetrahydro-1H-cyclopenta[b]benzofuran- 5-acrylic acid, 2-hydroxy-1-phenylmethanesulfonamido- 2,3,3a, 8b-tetrahydro-1H-cyclopenta[b]benzofuran- 5-acrylic acid, 2-hydroxy-1-(2-phenylethanesulfonamido)-2,3,3a,8b-tetrahydro-1H-cyclopenta[b]benzofuran-5-acrylic acid, 1-(1-naphthalenesulfonamido)-2-hydroxy-2,3,3a,8b-tetrahydro-1H-cyclopenta[b]benzofuran-5-acrylic acid, 1-(2-naphthalenesulfonamido)-2-hydroxy-2,3,3a,8b-tetrahydro-1H-cyclopenta[b]benzofuran-5-acrylic acid, 1-((benzenesulfonamido)methyl)-2-hydroxy- 2,3,3a, 8b-tetrahydro-1H-cyclopenta[b]benzofuran- 5-acrylic acid, 2-hydroxy-1((phenylmethanesulfonamido)methyl)- 2,3,3a,8b-tetrahydro- 1H-cyclopenta[b]benzofuran-5-acrylic acid, 2-hydroxy -1-((2-phenylethanesulfonamido)methyl)-2,3,3a,8b-tetrahydro-1H-cyclopenta[b]benzofuran-5-acrylic acid, 1-benzenesulfonamido-2-hydroxy-2,3,3a,8b-tetrahydro-1H-cyclopenta[b]benzofuran-5-butyric acid, 2-hydroxy-1-phenylmethanesulfonamido-2,3,3a,8b-tetrahydro-1H-cyclopenta[b]benzofuran-5-butyric acid, 2-hydroxy-1-(2-phenylethanesulfonamido)- 2,3,3a,8b-tetrahydro-1H-cyclopenta[b]benzofuran-5butyric acid, 1-((benzenesulfonamido)methyl)-2-hydroxy- 2,3,3a, 8b-tetrahydro-1H-cyclopenta[b]benzofuran- 5-butyric acid, 2-hydroxy-1-((phenylmethanesulfonamido)methyl)- 2,3,3a,8b-tetrahydro- 1H-cyclopenta[b]benzofuran-5-butyric acid, 2-hydroxy-1-((2-phenylethanesulfonamido)methyl)-2,3,3a,8b-tetrahydro-1H-cyclopenta[b]benzofuran-5-butyric acid, 2-benzenesulfonamido-1-hydroxy-2,3,3a,8b-tetrahydro-1H-cyclopenta[b]benzofuran-5-yloxyacetic acid, 2-benzenesulfonamido-2,3,3a,8b-tetrahydro- 1H-cyclopenta [b]benzofuran-5-yloxyacetic acid, 2-(p-chlorobenzenesulfonamido)-1-hydroxy-2,3,3a,8b-tetrahydro-1H-cyclopenta[b]benzofuran-5-yloxyacetic acid, 2-(p-chlorobenzenesulfonamido)-2,3,3a,8b-tetrahydro-1H-cyclopenta[b]benzofuran-5-yloxyacetic acid, 2-benzenesulfonamido-1-hydroxy-2,3,3a,8b-tetrahydro-1H-cyclopenta[b]benzofuran-5-carboxylic acid, 2-benzenesulfonamido-2,3,3a,8b-tetrahydro-1H-cyclopenta [b]benzofuran- 5-carboxylic acid, 2-benzenesulfonamido- 1-hydroxy-2,3,3a,8b-tetrahydro-1H-cyclopenta[b]benzofuran- 5-acetic acid, 2-benzenesulfonamido-2,3,3a,8b-tetrahydro-1H-cyclopenta[b]benzofuran-5-acetic acid, 2-benzenesulfonamido- 1-hydroxy-2,3, 3a,8b-tetrahydro-1H-cyclopenta[b]benzofuran- 5-propionic acid, 2-benzenesulfonamido- 2,3,3a,8b-tetrahydro-1H-cyclopenta[b]benzofuran- 5-propionic acid, 2-benzenesulfonamido- 1-hydroxy-2,3,3a,8b-tetrahydro-1H-cyclopenta[b]benzofuran- 5-acrylic acid, 2-benzenesulfonamido- 2,3,3a,8b-tetrahydro-1H-cyclopenta [b]benzofuran-5-acrylic acid, 2-benzenesulfonamido- 1-hydroxy-2,3,3a,8b-tetrahydro-1H-cyclopenta[b]benzofuran- 5-butyric acid, 2-benzenesulfonamido- 2,3,3a,8b-tetrahydro-1H-cyclopenta[b]benzofuran- 5-butyric acid, 1-benzenesulfonamido- 2-chloro-2,3,3a,8b-tetrahydro-1H-cyclopenta[b]benzofuran- 5-yl-oxyacetic acid, 1-benzenesulfonamido- 2-piperidyl-2,3,3a,8b-tetrahydro-1H-cyclopenta[b]benzofuran- 5-yl-oxyacetic acid, 1-benzenesulfonamido- 2-(4-phenylpiperidyl)-2,3,3a, 8b-tetrahydro- 1H-cyclopenta[b ]benzofuran-5-yl-oxyacetic acid, 1-benzenesulfonamido-2-cyano-2,3,3a,8b-tetrahydro- 1H-cyclopenta[b]benzofuran-5-yl-oxyacetic acid and their methyl esters, ethyl esters, propyl esters, isopropyl esters, butyl esters, pentyl esters, hexyl esters, heptyl esters, octyl esters, and decyl esters, etc.

Specific examples of the compounds of the present invention represented by the formula (I') include:

1-(phenylsulfonyloxy)-2,3,3a,8b-tetrahydro-1H-cyclopenta[b]benzofuran- 5-yloxyacetic acid, 1-((p-tolyl)sulfonyloxy)- 2,3,3a,8b-tetrahydro-1H-cyclopenta[b]benzofuran- 5-yloxyacetic acid, 1-((m-tolyl)sulfonyloxy)- 2,3,3a,8b-tetrahydro-1H-cyclopenta[b]benzofuran- 5-yloxyacetic acid, 1-((o-tolyl)sulfonyloxy)- 2,3,3a,8b-tetrahydro-1H-cyclopenta[b]benzofuran- 5-yloxyacetic acid, 1-))p-ethylphenyl)sulfonyloxy)-2,3,3a,8b-tetrahydro-1H-cyclopenta[b]benzofuran- 5-yloxyacetic acid, 1-((p-propylphenyl)sulfonyloxy)- 2,3,3a,8b-tetrahydro-1H-cyclopenta [b]benzofuran-5-yloxyacetic acid, 1-((p-butylphenyl)sulfonyloxy)- 2,3,3a,8b-tetrahydro-1H-cyclopenta[b]benzofuran- 5-yloxyacetic acid, 1-((p-methoxyphenyl)sulfonyloxy)- 2,3,3a,8b-tetrahydro-1H-cyclopenta[b]benzofuran- 5-yloxyacetic acid, 1-((p-chlorophenyl)sulfonyloxy)-2,3,3a,8b-tetrahydro-1H-cyclopenta[b]benzofuran- 5-yloxyacetic acid, 1-((m-chlorophenyl)sulfonyloxy)- 2,3,3a,8b-tetrahydro-1H-cyclopenta[b]benzofuran- 5-yloxyacetic acid, 1-((o-chlorophenyl)sulfonyloxy)- 2,3,3a,8b-tetrahydro-1H-cyclopenta[b]benzofuran- 5-yloxyacetic acid, 1-((p-bromophenyl) sulfonyloxy)-2,3,3a,8b-tetrahydro-1H-cyclopenta[b]benzofuran- 5-yloxyacetic acid, 1-((p-fluorophenyl)sulfonyloxy)- 2,3,3a,8b-tetrahydro-1H-cyclopenta[b]benzofuran- 5-yloxyacetic acid, 1-((m-fluorophenyl)sulfonyloxy)- 2,3,3a,8b-tetrahydro-1H-cyclopenta[b]benzofuran- 5-yloxyacetic acid, 1-((o-fluorophenyl)sulfonyloxy)- 2,3,3a,8b-tetrahydro-1H-cyclopenta[b]benzofuran- 5-yloxyacetic acid, 1-((p-iodophenyl)sulfonyloxy)- 2,3,3a,8b-tetrahydro-1H-cyclopenta[b]benzofuran- 5-yloxyacetic acid, 1-((p-trifluoromethylphenyl)sulfonyloxy)- 2,3,3a,8b-tetrahydro- 1H-cyclopenta[b]benzofuran-5-yloxyacetic acid, 1-((p-nitrophenyl)sulfonyloxy)-2,3,3a,8b-tetrahydro-1H-cyclopenta[b]benzofuran-5-yloxyacetic acid, 1-((p-cyanophenyl)sulfonyloxy)-2,3,3a,8b-tetrahydro-1H-cyclopenta[b]benzofuran-5-yloxyacetic acid, 1-((4-biphenylyl)sulfonyloxy)-2,3,3a,8b-tetrahydro- 1H-cyclopenta[b]benzofuran-5-yloxyacetic acid, 1-((p-phenoxyphenyl)sulfonyloxy)-2,3,3a,8b-tetrahydro-1H-cyclopenta[b]benzofuran-5-yloxyacetic acid, 1-((3, 4-dimethylphenyl)sulfonyloxy)-2,3,3a,8b-tetrahydro-1H-cyclopenta[b ]benzofuran-5-yloxyacetic acid, 1-((2,5-dichlorophenyl)sulfonyloxy)-2,3,3a,8b-tetrahydro- 1H-cyclopenta[b]benzofuran-5-yloxyacetic acid, 1-((2,6-dichlorophenyl)sulfonyloxy)-2,3,3a,8b-tetrahydro- 1H-cyclopenta[b]benzofuran-5-yloxyacetic acid, 1-((3,4-dichlorophenyl)sulfonyloxy)-2,3,3a,8b-tetrahydro- 1H-cyclopenta[b]benzofuran-5-yloxyacetic acid, 1-((3,5-dichlorophenyl)sulfonyloxy)-2,3,3a,8b-tetrahydro- 1H-cyclopenta[b]benzofuran-5-yloxyacetic acid, 1-((2-chloro-4-fluorophenyl)sulfonyloxy)-2,3,3a, 8b-tetrahydro-1H-cyclopenta[b]benzofuran-5-yloxyacetic acid, 1-((3-chloro-4-methylphenyl)sulfonyloxy)- 2,3,3a,8b-tetrahydro-1H cyclopenta[b]benzofuran-5-yloxyacetic acid, 1-((1-naphthyl)sulfonyloxy)- 2,3, 3a,8b-tetrahydro-1H-cyclopenta[b]benzofuran-5-yloxyacetic acid, 1-((2-naphthyl)sulfonyloxy)- 2,3, 3a,8b-tetrahydro-1H-cyclopenta[b]benzofuran-5-yloxyacetic acid, 1-(benzylsulfonyloxy)- 2,3,3a,8b-tetrahydro-1H-cyclopenta[b]benzofuran- 5-yloxyacetic acid, 1-(phenethylsulfonyloxy)- 2,3,3a,8b-tetrahydro-1H-cyclopenta[b]benzofuran- 5-yloxyacetic acid and their methyl esters, ethyl esters, propyl esters, isopropyl esters, pentyl esters, hexyl esters, heptyl esters, octyl esters and decyl esters, etc.

Among those compounds included in the present invention, those compounds in which B is represented by the general formula (II) or general formula (III) (wherein, $R_6$ is OH, $R_7$ is hydrogen and Y is a valence bond), and $R_1$ is COOMe can be produced according to the process indicated in step A.

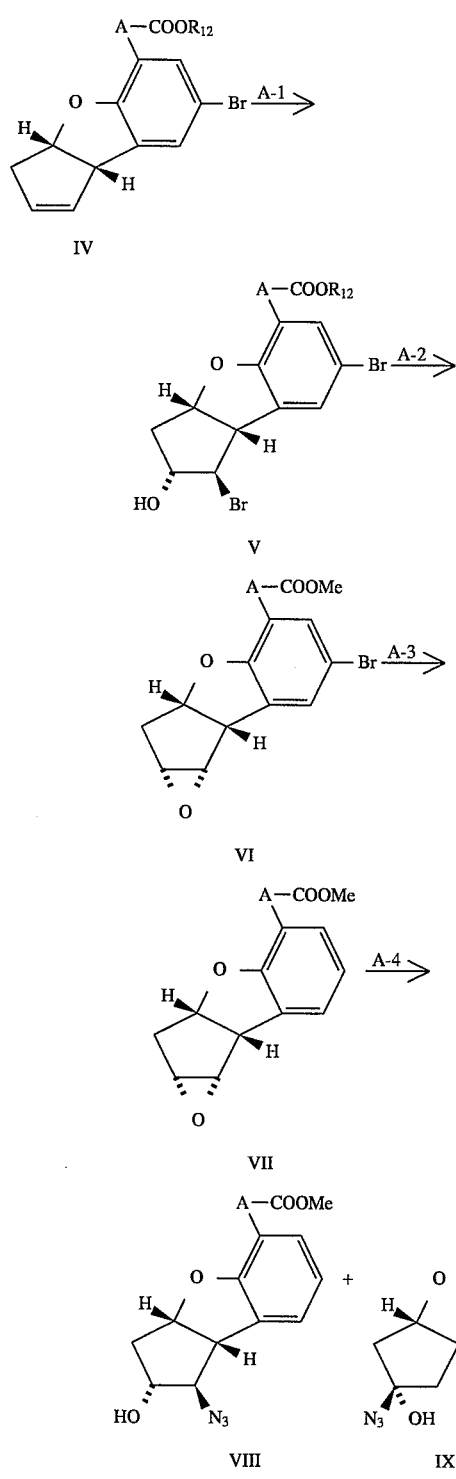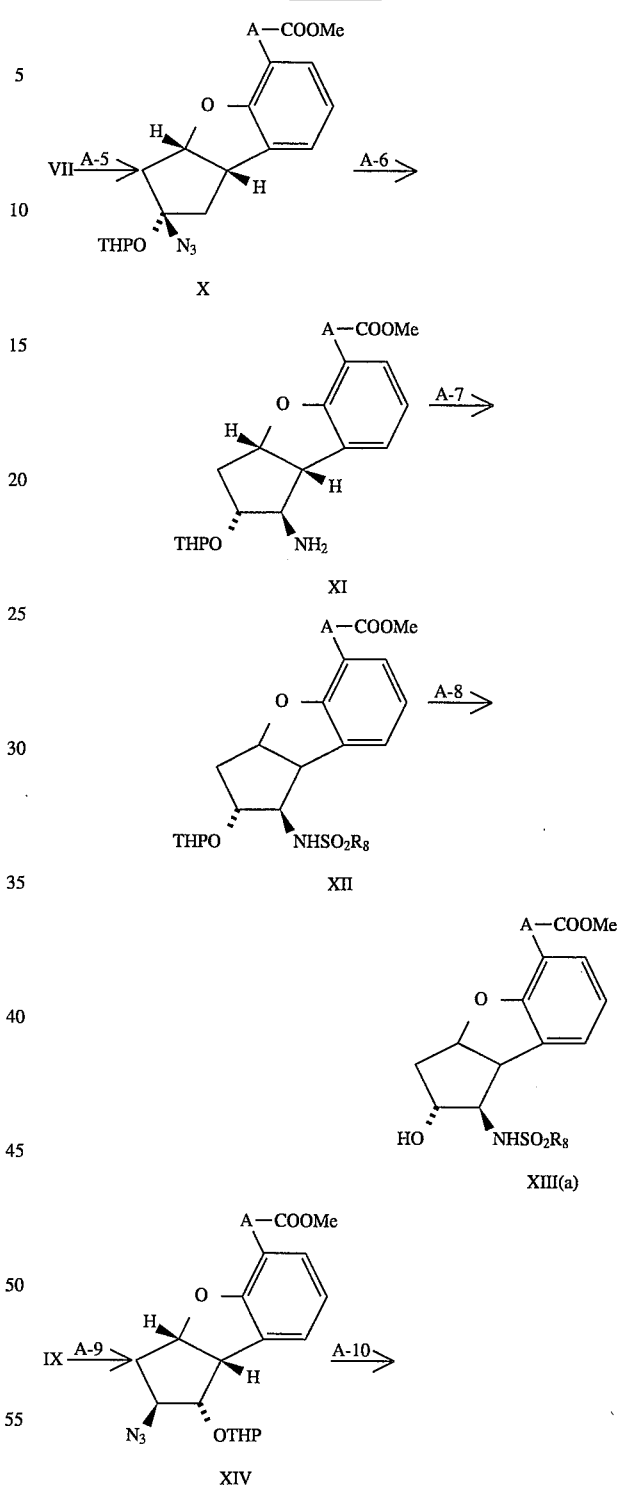

-continued

Step A

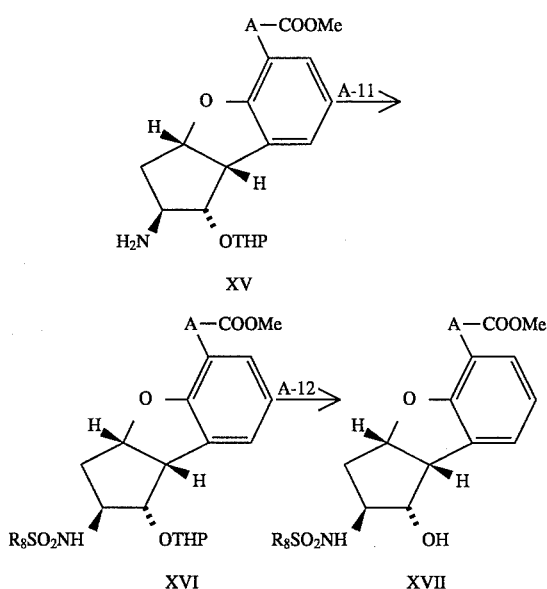

In these formulas, A and $R_8$ are as previously defined, and $R_{12}$ is a methyl or ethyl group.

Step A-1 is an addition reaction wherein bromohydrin is added to a double bond. This step is carried out by dissolving compound IV in a mixed solvent of dimethylsulfoxide and water followed by the action of N-bromosuccinimide (NBS).

Step A-2 involves epoxidation of bromohydrin. This step is carried out by using potassium carbonate, sodium carbonate and so forth for the base. Methanol is used for the solvent. In the case $R_{12}$ represents an ethyl group, $R_{12}$ is converted to a methyl group in this step.

Step A-3 is a debromination step. This step is carried out in a hydrogen atmosphere at normal pressure to 10 atmospheres using a catalyst such as palladium-carbon, palladium-barium sulfate or Rainey nickel in the presence of alkali such as potassium acetate or sodium acetate. In the case A represents —CH=CH—, A is converted to —CH$_2$CH$_2$— in this step. An example of a production process for those compounds of compound VII obtained in step A-3 wherein A is —CH$_2$CH$_2$CH$_2$— is described in Japanese Unexamined Patent Publication No. 57-144276.

Step A-4 is a step wherein an epoxide ring is opened with azide. This step is carried out by reacting sodium azide at the refluxing temperature in a mixed solvent of methanol and water. Although a methylethyl group is hydrolyzed to form a carboxylic acid in this step, carboxylic acid is converted to methylester by addition of diazomethane in a solvent such as methanol, ethanol, tetrahydrofuran or ethyl acetate. The compound obtained in step A-4 is obtained in the form of a mixture of the 1-azide form VIII and the 2-azide form IX. The 1-azide form VIII and 2-azide form IX are separated by a column chromatography technique (preferable separation is normally achieved using normal phase silica gel and a mixed solvent of ethyl acetate and cyclohexane for the developer).

Step A-5 is a step wherein the alcohol group of compound VIII is protected with tetrahydropyranyl ether. This step is carried out by reacting 2,3-dihydrofuran at a temperature of −78° C. to room temperature using p-toluene sulfonic acid as catalyst. Solvents such as ether and tetrahydrofuran are preferably used for the solvent.

Step A-6 is a step wherein amine is obtained by reducing azide, and is carried out according to the conditions of normal so-called hydrogenation. Namely, this step is carried out in a hydrogen atmosphere at normal pressure to 10 atmospheres using a catalyst such as palladium-carbon, palladium-barium sulfate or Rainey nickel. Examples of solvents used include methanol, tetrahydrofuran and benzene. Compound XI can also be produced from compound VI by carrying out a similar series of operations from step A-4 through step A-6 while omitting step A-3.

Step A-7 is a step wherein amine XI is converted to sulfonamide. This step is carried out by reacting amine XI with $R_8SO_2Cl$ (wherein, $R_8$ is the same as previously defined) in the presence of base such as triethylamine, diisopropylethylamine or pyridine. Although examples of solvents that are used include tetrahydrofuran, dimethoxyethane, dioxane, benzene, toluene, methylene chloride and chloroform, the product can also be achieved if bases such as triethylamine, diisopropylamine or pyridine are used as solvent. The reaction temperature is selected from between −78° C. to 100° C.

Step A-8 is a step wherein compound XIII(a) is obtained by removing a tetrahydropyranyl group from compound XII. This step is carried out in a solvent such as methanol, ethanol, aqueous tetrahydrofuran or aqueous dioxane. Examples of catalytic acid used include p-toluene sulfonic acid, hydrochloric acid and sulfuric acid.

Steps A-9 through A-12 are steps wherein sulfonamide XVII is produced from azide IX, and are carried out in the same manner as step A-5 through step A-8. Compound XV obtained in step A-10 can also be produced from compound VI by carrying out a similar series of operations as those of step A-4, step A-9 and step A-10 while omitting step A-3. Compound XIII(a) can also be produced by carrying out a similar series of operations as those of steps A-6 and A-7 without protecting the alcohol group of compound VIII. Compound XVII can also be produced by carrying out a similar series of operations as those of steps A-10 and A-11 without protecting the alcohol group of compound IX.

Those compounds included in the present invention wherein B is a compound for formula [II] (wherein, $R_7$ is a hydrogen and Y is a valence bond) and $R_1$ is COOMe can be produced by the process indicated in step B.

Step B

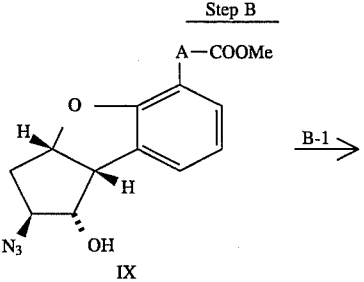

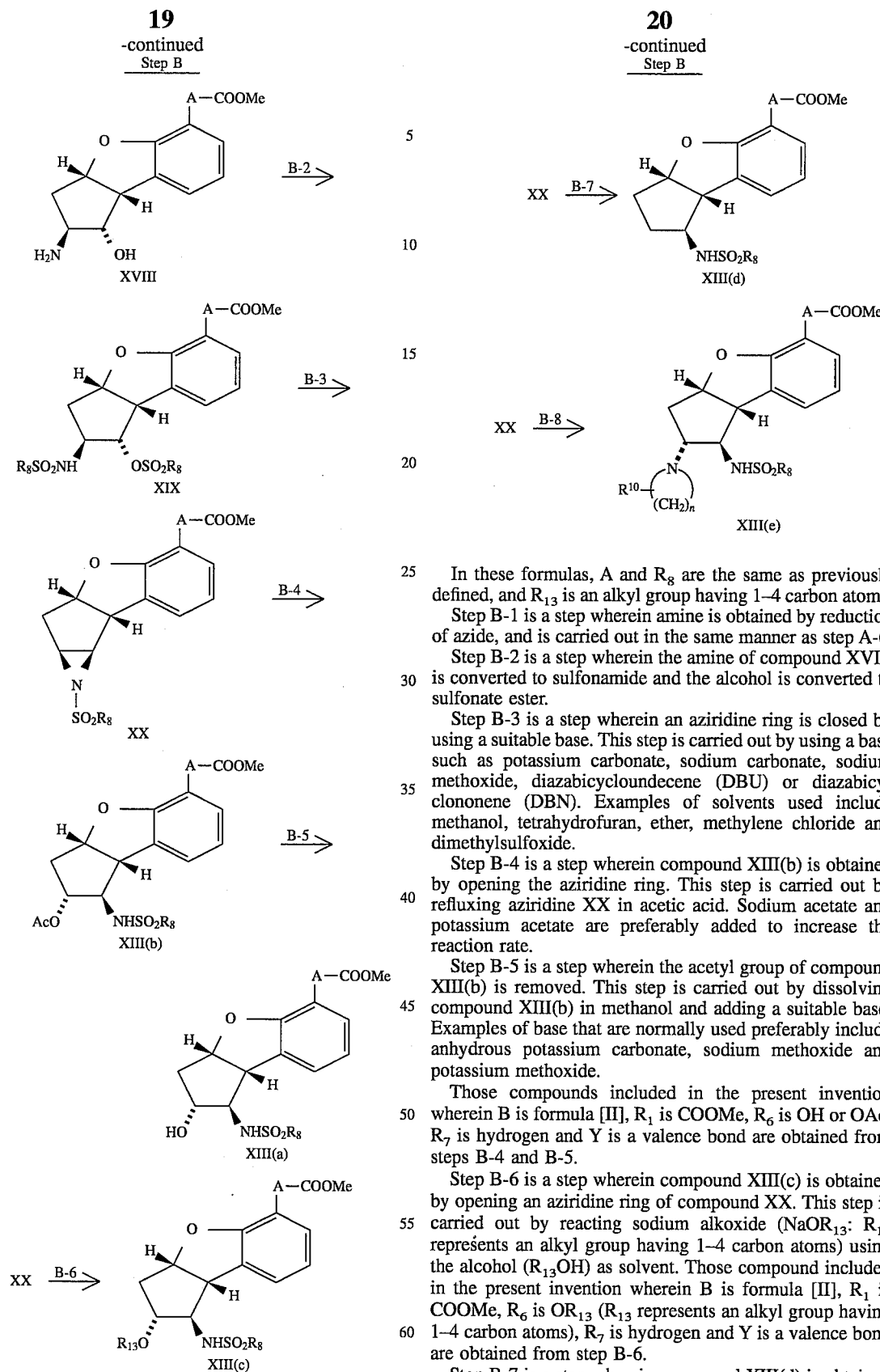

In these formulas, A and $R_8$ are the same as previously defined, and $R_{13}$ is an alkyl group having 1–4 carbon atoms.

Step B-1 is a step wherein amine is obtained by reduction of azide, and is carried out in the same manner as step A-6.

Step B-2 is a step wherein the amine of compound XVIII is converted to sulfonamide and the alcohol is converted to sulfonate ester.

Step B-3 is a step wherein an aziridine ring is closed by using a suitable base. This step is carried out by using a base such as potassium carbonate, sodium carbonate, sodium methoxide, diazabicycloundecene (DBU) or diazabicyclononene (DBN). Examples of solvents used include methanol, tetrahydrofuran, ether, methylene chloride and dimethylsulfoxide.

Step B-4 is a step wherein compound XIII(b) is obtained by opening the aziridine ring. This step is carried out by refluxing aziridine XX in acetic acid. Sodium acetate and potassium acetate are preferably added to increase the reaction rate.

Step B-5 is a step wherein the acetyl group of compound XIII(b) is removed. This step is carried out by dissolving compound XIII(b) in methanol and adding a suitable base. Examples of base that are normally used preferably include anhydrous potassium carbonate, sodium methoxide and potassium methoxide.

Those compounds included in the present invention wherein B is formula [II], $R_1$ is COOMe, $R_6$ is OH or OAc, $R_7$ is hydrogen and Y is a valence bond are obtained from steps B-4 and B-5.

Step B-6 is a step wherein compound XIII(c) is obtained by opening an aziridine ring of compound XX. This step is carried out by reacting sodium alkoxide (NaOR$_{13}$: $R_{13}$ represents an alkyl group having 1–4 carbon atoms) using the alcohol ($R_{13}$OH) as solvent. Those compound included in the present invention wherein B is formula [II], $R_1$ is COOMe, $R_6$ is OR$_{13}$ ($R_{13}$ represents an alkyl group having 1–4 carbon atoms), $R_7$ is hydrogen and Y is a valence bond are obtained from step B-6.

Step B-7 is a step wherein compound XIII(d) is obtained by opening an aziridine ring of compound XX. This step is carried out by reacting sodium borohydride and sodium borocyanohydride with aziridine XX in dimethylsulfoxide and hexamethylphosphoric triamide. Although the reaction is carried out at a temperature of room temperature to 150° C., a temperature of 50°–100° C. is preferable. Those compounds included in the present invention wherein B is formula [II] (wherein, $R_6$ is hydrogen, $R_7$ is hydrogen and Y is a valence bond) and $R_1$ is COOMe are obtained from step B-7.

Step B-8 is a step wherein compound XIII(e) is obtained by opening an aziridine ring of compound XX. This step is carried out by heating aziridine with cyclic secondary amine. Although examples of preferable solvents include methanol and ethanol, the product can also be achieved by heating aziridine XX and amine in the absence of solvent. Those compounds included in the present invention wherein B is formula [II], $R_6$ is cyclic amine and $R_7$ is hydrogen are obtained from step B-8.

Those compounds included in the present invention wherein B is formula [II] (wherein, $R_6$ is OH or OAc, $R_7$ is hydrogen and Y is $-CH_2-$) and $R_1$ is COOMe can be produced by the process indicated in step C.

Examples of production processes for starting material XXI of step C are described in Japanese Unexamined Patent Publication No. 58-124778, Japanese Unexamined Patent Publication No. 62-265279, Japanese Patent Application No. 62-262021 and Japanese Patent Application No. 2-64870.

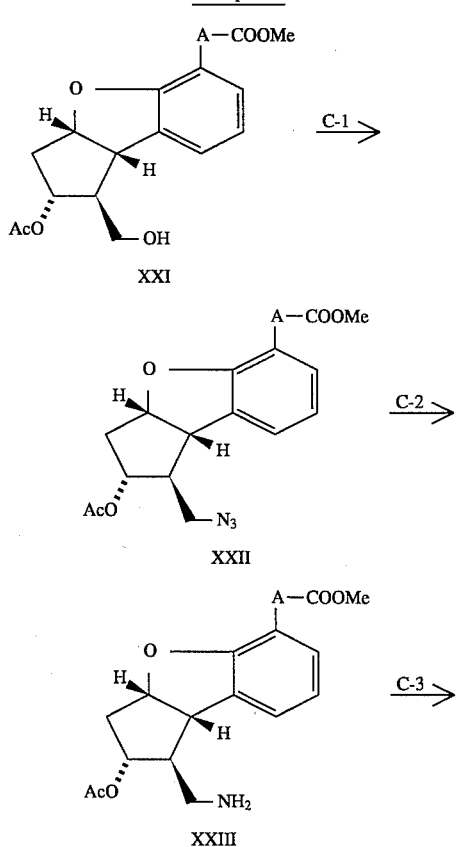

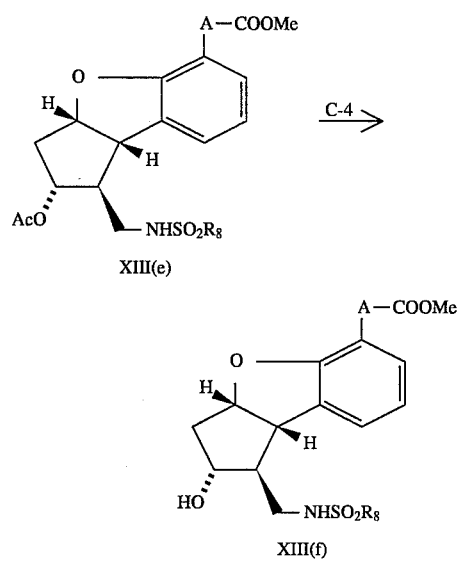

In these formulas, A and $R_8$ are the same as previously defined.

Step C-1 is a step wherein the hydroxyl group of compound XXI is converted to methanesulfonate ester followed by conversion to azide by a substitution reaction. The methanesulfonate esterification reaction is carried out by reacting with methanesulfonyl chloride in the presence of a base such as triethylamine, diisopropylamine or pyridine. Examples of solvents used include tetrahydrofuran, dimethoxyethane, dioxane, benzene, toluene, methylene chloride and chloroform. Although the reaction temperature is selected from between –100° C. to 50° C., it is preferably between –50° C. and room temperature. The following substitution reaction is carried out by reacting sodium azide at the refluxing temperature in a mixed solvent of methanol and water.

Step C-2 is a step wherein amine is obtained by reduction of azide, and is carried out in the same manner as step A-6.

Step C-3 is a step wherein amine is converted to sulfonamide, and is carried out in the same manner as step A-7.

Step C-4 is a step wherein the acetyl group of compound XIII(e) is removed, and is carried out in the same manner as step B-5.

Those compounds included in the present invention wherein B is formula [II] (wherein, $R_6$ is OH), A is $-CH=CH-$ and $R_1$ is COOMe can be produced by the process indicated in step D.

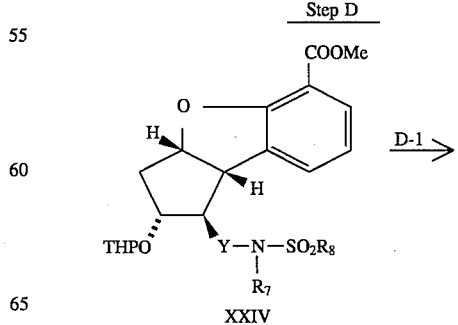

5,496,849

-continued
Step D

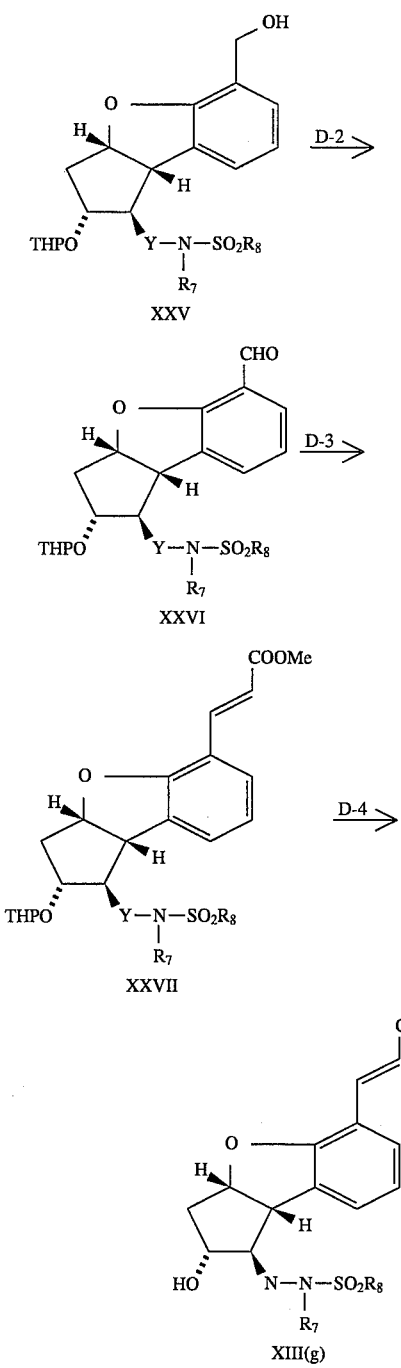

In these formulas, Y, $R_7$ and $R_8$ are the same as previously defined.

An example of a process for producing starting material XXIV of step D is described in step A.

Step D-1 is a step wherein ester is reduced to alcohol. This step is carried out, for example, by reduction by aluminum lithium hydride or catalytic hydrogenation by copper chromite catalyst. In the case of using aluminum lithium hydride for the reducing agent, examples of solvents used include tetrahydrofuran, dimethoxyethane and ether.

Step D-2 is a step wherein alcohol is oxidized to aldehyde, and various oxidizing agents can be used for this purpose. Examples of oxidizing agents used preferably in this step include chromic anhydride-pyridine complex, dimethylsulfoxide-dicyclohexylcarbodiimide and manganese dioxide.

Step D-3 is a step wherein aldehyde is converted to α,β-unsaturated ester having two long carbon chains. This step is carried out by adding salt, formed from carboalkoxymethylenetriphenylphosphorane or trialkylphosphonoacetate and metal hydride (such as sodium hydride or potassium hydride), to aldehyde XXVI.

Step D-4 is a step wherein the tetrahydropyranyl group of compound XXVII is removed, and is carried out in the same manner as step A-8.

Those compounds included in the present invention wherein B is formula [II] (wherein, $R_6$ is OH and $R_7$ is an alkyl group having 1–4 carbon atoms) and $R_1$ is COOMe can be produced by the process indicated in step E.

Step E

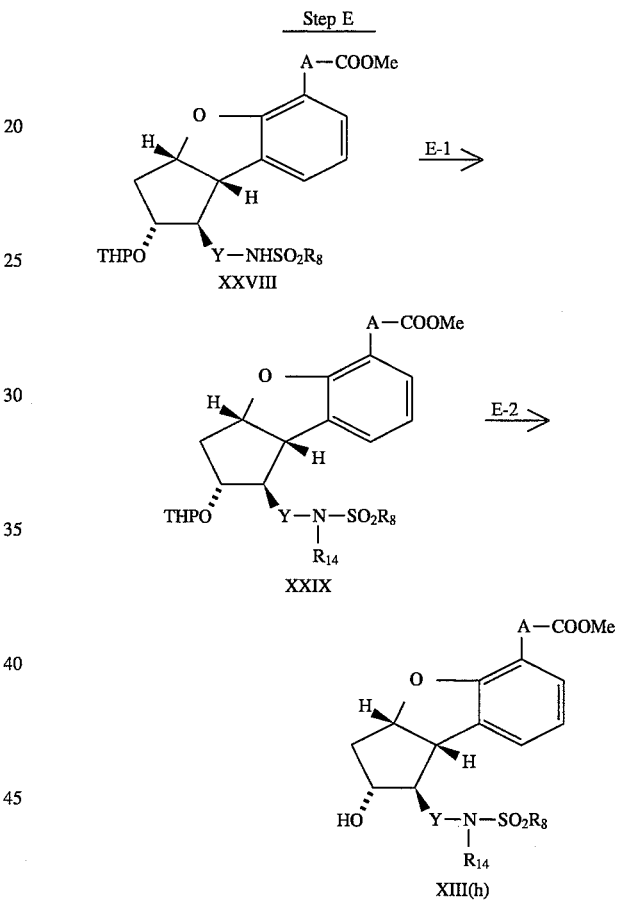

In these formulas, A, Y and $R_8$ are the same as previously defined, while $R_{14}$ is an alkyl group having 1–4 carbon atoms.

An example of a process for producing starting material XXVIII of step E is described in step A.

Step E-1 is a step wherein the amide hydrogen of compound XXVIII is converted to an alkyl group. This step is carried out by reacting with $R_{14}$-X (wherein, $R_{14}$ represents an alkyl group having 1–4 carbon atoms and X represents iodine, bromine or chlorine) in the presence of a suitable base. Examples of base used include potassium carbonate, sodium carbonate, lithium diisopropylamide, triethylamine, sodium hydride and silver oxide, while examples of solvents used include methanol, ethanol, tetrahydrofuran, dimethoxyethane, dimethylformamide and dimethylsulfoxide. Step E-2 is a step wherein the tetrahydropyranyl group of compound XXIX is removed, and is carried out in the same manner as step A-8.

Those compounds included in the present invention wherein B is formula [II], $R_1$ is —C(=O)Me and $R_6$ is OH can be produced by the process indicated in step F.

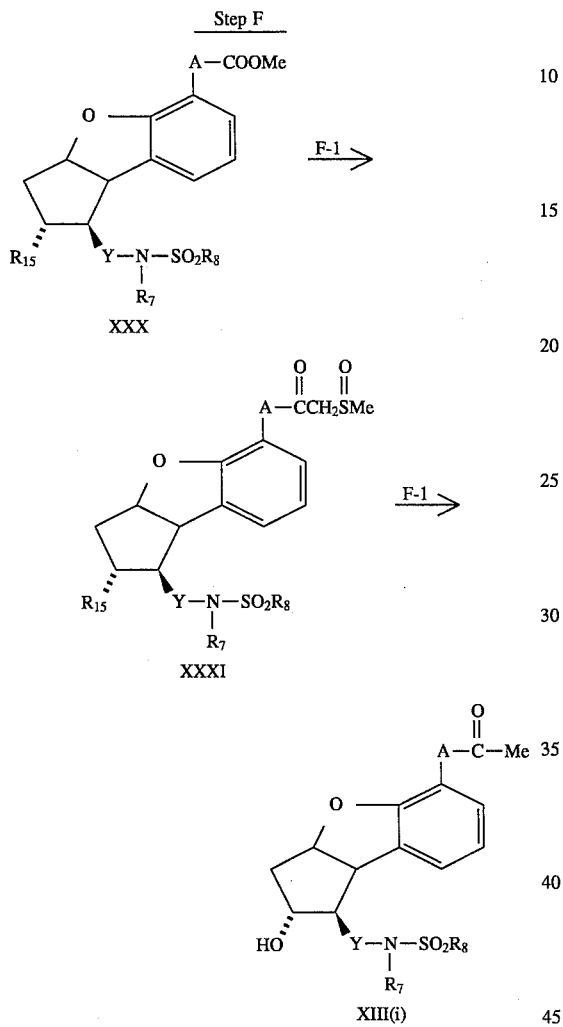

In these formulas, A, Y, $R_7$ and $R_8$ are the same as previously defined, while $R_{15}$ is either OH or OTHP.

An example of a process for producing starting material XXX of step F is described in step A.

Step F-1 is a step wherein dimucyl anion is added to ester XXX. This process is carried out by reacting dimucyl anion, formed from dimethylsulfoxide and a base such as or sodium hydride, with ester XXX in a solvent such as dimethoxyethane.

Step F-2 is a step wherein the carbon-sulfur bond of compound XXXI is cleaved. Although various reducing agents are used for the reducing agent of this step, zinc is normally used preferably. This reaction is carried out in an acid such as acetic acid. Examples of solvents used include acetic acid, ethanol and methanol. In the case $R_{15}$ is an OTHP group in this step, together with a reduction reaction occurring, the tetrahydropyranyl group is removed resulting in conversion of $R_{15}$ to OH.

Those compounds included in the present invention wherein B is formula [II], $R_1$ is COOMe and A is —OCH$_2$— can be produced by the process indicated in step G.

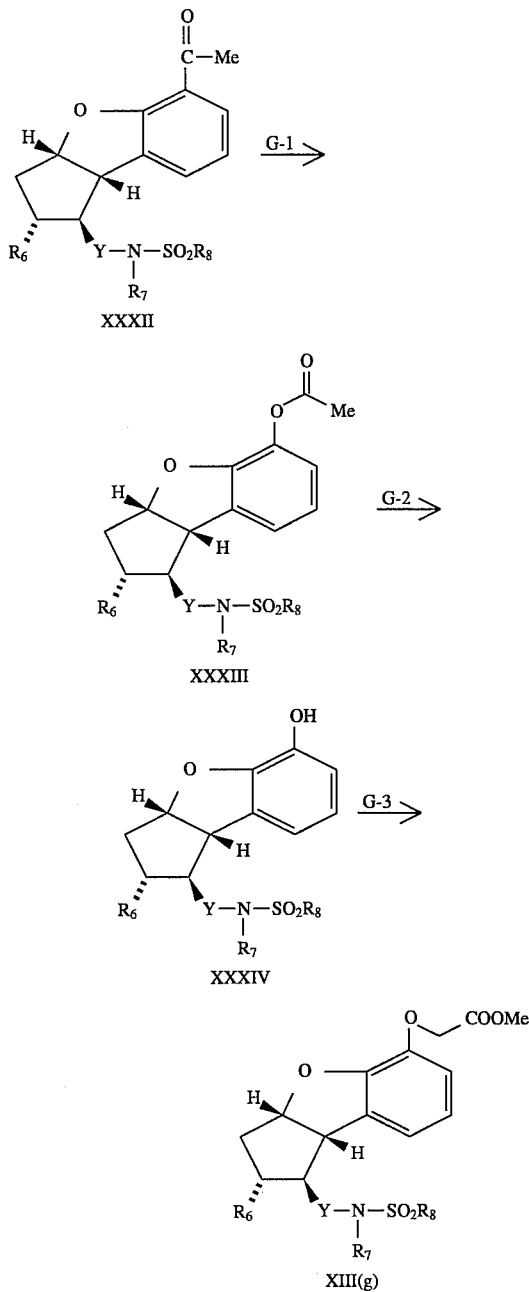

In these formulas, Y, $R_6$, $R_7$ and $R_8$ are the same as previously defined.

An example of a process for producing starting material XXXII of step G is described in step F.

Step G-1 is a step wherein methylketone is converted to acetate. This step is carried out by reacting a peracid such as m-chloroperbenzoic acid or peracetic acid with methylketone XXXII. Examples of preferably used solvents include dichloromethane and chloroform. Base such as sodium hydrogencarbonate may also be added to promote the reaction.

Step G-2 is a step wherein acetate is hydrolyzed and converted to phenol. Although this step is carried out at −30° C. to 70° C. by dissolving compound XXXIII in methanol and adding a suitable base, preferably results can normally be obtained at 0° C. to room temperature. Examples of base used preferably include potassium carbonate, sodium methoxide, sodium hydroxide and potassium hydroxide.

Step G-3 is a step wherein the phenol group of compound XXXIV is etherified. This step is carried out by extracting the phenolic hydrogen of compound XXXIV with a suitable base, and then reacting with methylbromoacetate. Examples of base used include potassium hydroxide, sodium hydroxide, sodium hydride, potassium hydride and potassium carbonate, while examples of solvents used include methanol, ethanol, dimethylformamide, dimethylsulfoxide, tetrahydrofuran and dimethoxyethane.

Although the diastereomers of compounds XIII(a) through XIII(j) of the compounds included in the present invention can be produced by various processes, one example of a process by which they can be produced is indicated in step H.

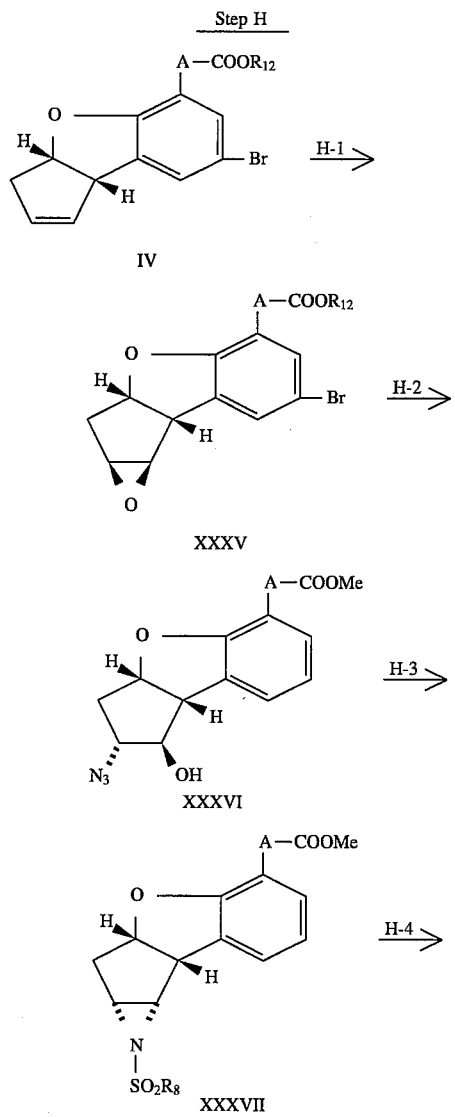

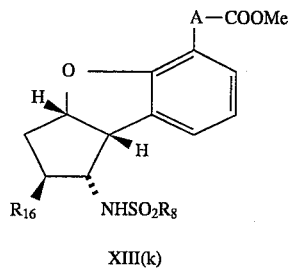

In these formulas, A and $R_8$ are the same as previously defined, while $R_{16}$ is hydrogen or $OR_{17}$ (where $R_{17}$ represents an alkyl group or acetyl group having 1–4 carbon atoms), and $R_{12}$ is a methyl or ethyl group.

Step H-1 is a step wherein the double bond of compound IV is epoxidated. This step is carried out using a peracid such as peracetic acid, perbenzoic acid or m-chloroperbenzoic acid. Examples of solvents used include methylene chloride and chloroform. In this step, epoxide XXXV is obtained wherein the oxygen of the epoxide and the benzofuran ring are oriented in the trans configuration.

Step H-2 is a step wherein compound XXXV is debrominated followed by opening of the epoxide ring with azide, and is carried out by a similar series of operations as steps A-3 and A-4.

Step H-3 is a step wherein compound XXXVII is obtained by reducing the azide of compound XXXVI to amine, converting the resulting amine of the aminoalcohol to sulfonamide, converting the alcohol to sulfonate ester and opening the aziridine ring in the presence of base. This step is carried out by a similar series of operations as steps A-6, A-7 and B-3.

Step H-4 is a step wherein the aziridine ring of compound XXXVII is opened, and is carried out in the same manner as step B-4, step B-6 or step B-7. Compound XIII(k)

(wherein $R_{16}$ is OH) can be produced by removing an acetyl group in the same manner as step B-5 from compound XIII(k)

(wherein $R_{16}$ is OAc) obtained by carrying out production of compound XXXVII in the same manner as step B-4.

Those compounds included in the present invention wherein B is formula [II] and $R_1$ is COOH can be produced by the process indicated in step I.

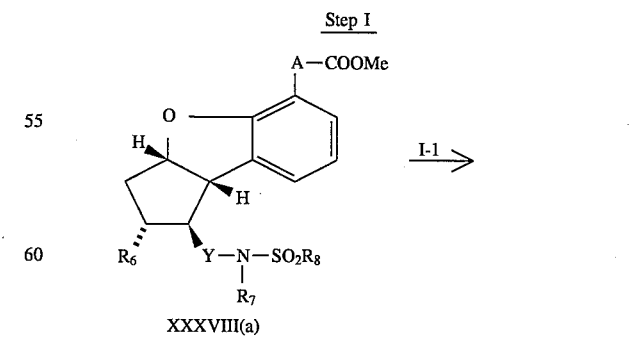

Step I

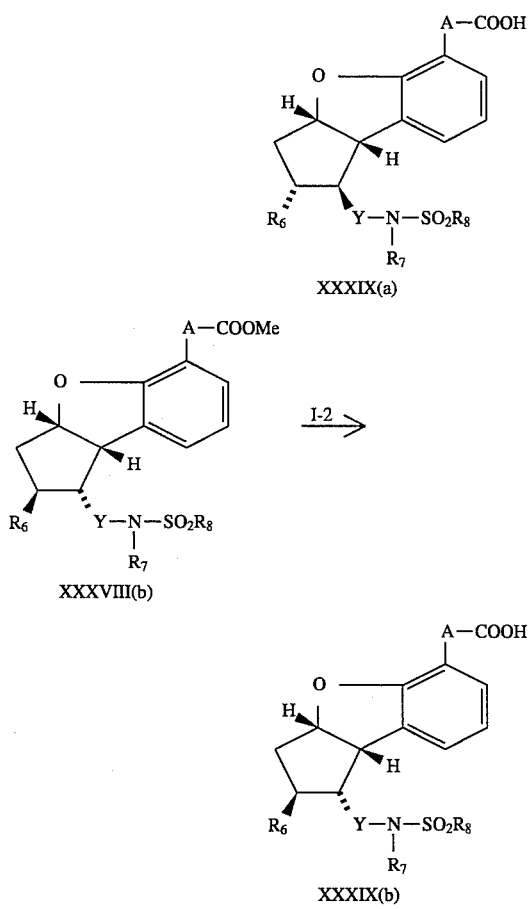

Step I-1 is a step involving hydrolysis of methylester. This process is carried out by reacting with base in a solvent such as aqueous ethanol, aqueous methanol, aqueous dioxane or aqueous tetrahydrofuran. Examples of base used preferably include inorganic bases like sodium hydroxide, potassium hydroxide, sodium carbonate and potassium carbonate. Although the reaction temperature is selected from a range of −20° C. to 150° C., a preferable reaction rate is normally obtained at room temperature. Step I-2 is carried out in the same manner as step I-1.

Those compounds included in the present invention wherein B is formula [III] and $R_1$ is COOH can be produced in the same manner as step I-1 by using compound I (where B is formula [III] and $R_1$ is COOMe).

Although an example of a process for production of compound Iv of step A and step H is described in Japanese Unexamined Patent Publication No. 57-144277, it can also be produced by the process indicated in step J.

In these formulas, A, Y, $R_6$, $R_7$ and $R_8$ are the same as previously defined.

Step J

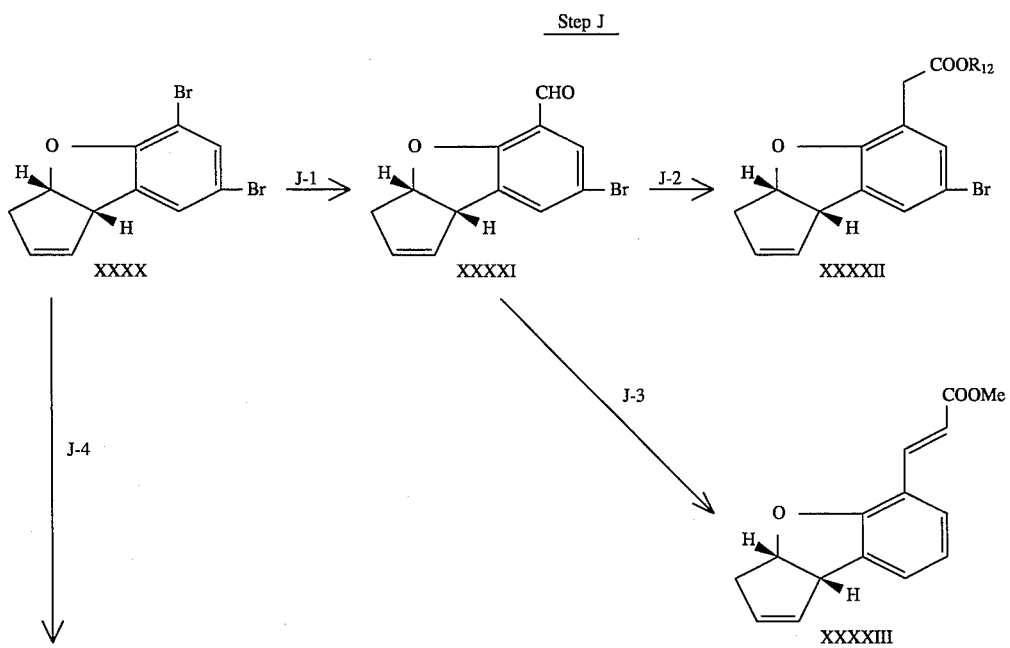

-continued
Step J

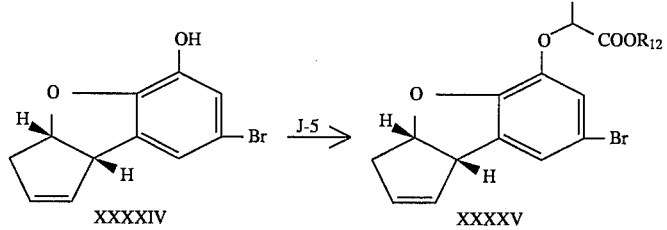 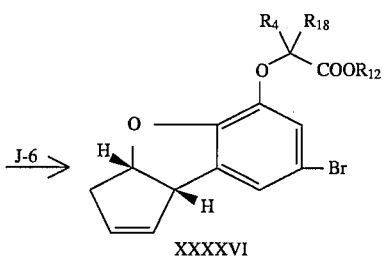

In the above-formula, $R_4$ is the same as previously defined, $R_{12}$ is methyl or ethyl, and $R_{18}$ is an alkyl having 1–4 carbon atoms.

An example of a process for producing starting material XXXX of step J is described in Japanese Unexamined Patent Publication No. 57-144277.

Step J-1 is a step wherein the bromine of compound XXXX is substituted with a formyl group. This step is carried out by extracting the bromine at the ortho position of oxygen using a suitable base, converting it to the corresponding phenyl anion and reacting with dimethylformamide. Examples of base used to extract the bromine include butyl lithium, phenyl lithium and cyclohexyl magnesium chloride. Examples of solvents used include tetrahydrofuran and dimethoxyethane. The extraction reaction is carried out at −78° C. to 100° C., while formylation is carried out at 0° C. to 50° C.

Step J-2 is a step wherein the formyl group of compound XXXXI is converted to an ester having one long carbon chain. This step is carried out by adding methyl methylsulfinylmethyl sulfide (FAMSO) in the presence of a suitable base followed by production of ester by acid treatment. The initial addition reaction is carried out using N-benzyltrimethylamine and so forth for the base in a solvent such as tetrahydrofuran or dimethoxyethane. Acid treatment is carried out using hydrochloric acid and sulfuric acid in a solvent such as methanol or ethanol.

Step J-3 is a step wherein aldehyde is converted to α,β-unsaturated ester having two long carbon chains, and is carried out in the same manner as step D-3.

Step J-4 is a step wherein the bromine of compound XXXX is substituted with a hydroxyl group. This step is carried out by extracting the bromine at the ortho position of oxygen in the same manner as step J-1, converting to the corresponding phenyl anion, treating with trimethyl boric acid to derive to the aryl boronic acid derivative, and oxidizing with hydrogen peroxide. This step can also be carried out by oxidizing the corresponding phenyl anion oxygen, t-butylperbenzoic acid, t-butylhydroperoxide or molybdenum pentoxide-pyridine-HMPA complex.

Step J-5 is a step wherein the phenol group of compound XXXXIV is etherified. This step is carried out by extracting the phenolic hydrogen of compound XXXXIV with a suitable base, and reacting with $$\text{R}_4\text{CHCOOR}_{12}$$
$$\vert$$
$$\text{Br}$$

(wherein, $R_4$ is the same as previously defined, and $R_{12}$ represents a methyl or ethyl group). Examples of base used include potassium hydroxide, sodium hydroxide, sodium hydride, potassium hydride and potassium carbonate, while examples of solvents used include methanol, ethanol, dimethylformamide, dimethylsulfoxide, tetrahydrofuran and dimethoxyethane.

Step J-6 is a step wherein an alkyl group is introduced at the α-position of an ester. This step is carried out by extracting the hydrogen at the α-position of the ester with a suitable base and reacting with $$R_{18}\text{-X}$$

(wherein, $R_{18}$ is an alkyl group having 1–4 carbon atoms, and X is iodine, bromine or chlorine). Examples of base used include sodium amide, lithium amide and lithium diisopropylamide. Examples of solvents used preferably include tetrahydrofuran and dimethoxyethane.

Those compounds of the present invention in the case $R_1$ is $COOR_2$ and $R_2$ is not hydrogen or a cation, namely in the case $R_1$ is an ester radical, can be produced by esterification of the carboxylic acid wherein the corresponding $R_2$ is hydrogen. Although various methods are known for esterification, a process which utilizes the action of a diazoalkane and a mixed acid anhydride process are used particularly preferably for production of the compounds of the present invention. In the process using diazoalkane, the target substance can be easily obtained by allowing a carboxylic acid and diazoalkane to come in contact in the presence of a solvent. Although examples of the diazoalkane include diazomethane, diazoethane, diazopropane and diazodecane, it is naturally not limited to these. The second mixed acid anhydride process has the broadest application range, and the majority of the ester compounds of the present invention are produced by this process. This process involves first reacting ethylchlorocarbonate, pivaloyl chloride and p-toluenesulfonyl acid chloride with a salt of a carboxylic acid to form a mixed acid anhydride, followed by addition of an excess amount of $R'_2OH$ (where, $R'_2$ is an alkyl group having 1–14 carbon atoms) and heating. Although specific examples of alcohol include methanol, ethanol, propanol, butanol, octanol, decanol, isopropanol and 2-ethylhexanol, it is not limited to these examples.

Although the compounds of steps A–J are indicated using the structural formulas of their optically active forms, these structures are used to represent the d form, l form and dl form. Steps A–J can be applied in exactly the same manner for the d, l and dl forms.

The details of a production example of optically active forms are described in reference examples 38–43 and working examples 67–74. Examples production methods for the raw materials of reference examples 38 and 39 are described in Japanese Unexamined Patent Publication No. 58-124778 and Japanese Unexamined Patent Publication No. 59-161371.

In the case steps A–H are carried out with the dl form, the racemic compound represented with general formula [I] can be easily separated into its d and l forms by optically active column chromatography technology.

In general formula (I), those compounds wherein B represents formula (II) and W is —O— can be produced by reacting the compound wherein B is represented with formula (II'):

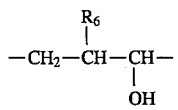

with the compound represented by the following formula:

R₄SO₂Cl (wherein, R₄ is the same as previously defined).

The production of compounds represented with formula (I') can, in particular, be produced in the following manner.

Those compounds of formula (I') wherein $R_{60}$ is a methyl (Me) group can be produced by the process shown in step A'. In the formulas, $R_{20}$, $R_{30}$ and $R_{40}$ are the same as previously defined.

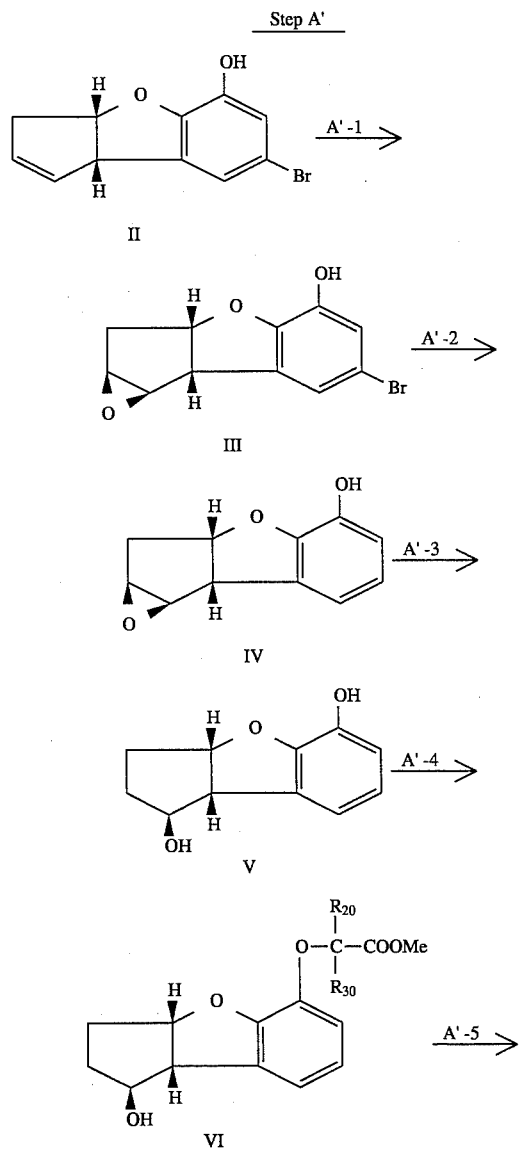

-continued
Step A'

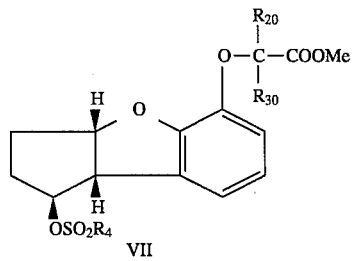

Step A'-1 is a step wherein the double bond of compound II is epoxidated. This step is carried out using a peracid such as peracetic acid, perbenzoic acid or m-chloroperbenzoic acid. Examples of solvents used preferably include methylene chloride and chloroform. In this step, epoxide III is obtained wherein the oxygen of the epoxide and the benzofuran ring are in the trans configuration.

Step A'-2 is a debromination step. This step is carried out in a hydrogen atmosphere at normal pressure to atmospheres using a catalyst such as palladium-carbon, palladium-barium sulfate or Rainey nickel in the presence of alkali such as potassium acetate or sodium acetate.

Step A'-3 is a step wherein the epoxide ring is opened and reduced to alcohol. Various hydride reagents are used for the reducing agent, examples of which include lithium aluminum hydride, lithium borohydride, sodium bis-methoxyethoxyaluminum hydride and diisobutylaluminum hydride.

Step A'-4 is a step wherein the phenol group of compound IV is etherified. This step is carried out by extracting the phenolic hydrogen of compound III with a suitable base and reacting with

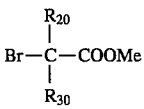

(wherein, $R_{20}$ and $R_{30}$ are the same as previously defined). Examples of base used include potassium hydroxide, sodium hydroxide, sodium hydride, potassium hydride and potassium carbonate, while examples of solvent used include methanol, ethanol, dimethylformamide, dimethylsulfoxide, tetrahydrofuran and dimethoxyethane.

Step A'-5 is a step wherein compound VI is converted to sulfonate ester. This step is carried out by reacting with R₄₀SO₂Cl (wherein, $R_{40}$ is the same as previously defined) in the presence of base such as triethylamine diisopropylethylamine or pyridine. Although examples of solvent used include tetrahydrofuran, dimethoxyethane, dioxane, benzene, toluene, methylene chloride and chloroform, base such as triethylamine, diisopropylethylamine and pyridine can also be used as solvent.

Those compounds of the present invention wherein $R_{60}$ is hydrogen can be produced by the process indicated in step B'. In these formulas, $R_{20}$, $R_{30}$ and $R_{40}$ are the same as previously defined.

Step B'

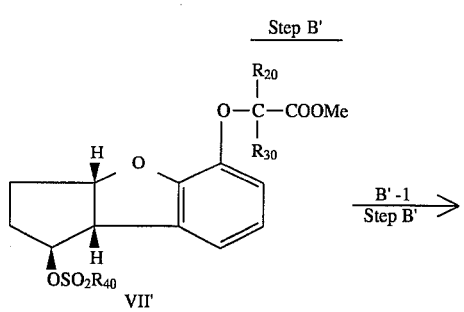

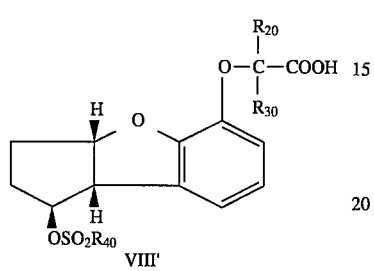

Step B'-1 is a step wherein a methyl ester is hydrolyzed. This step is carried out by reacting with base in a solvent such as aqueous ethanol, aqueous methanol, aqueous dioxane or aqueous tetrahydrofuran. Examples of base used preferably include inorganic bases such as sodium hydroxide, potassium hydroxide, sodium carbonate and potassium carbonate. Although the reaction temperature is selected from a range of −20° C. to 150° C., a preferable reaction rate is normally obtained at room temperature.

An example of the production process for compound II of step A' is described in Japanese Patent Application No. 4-249288. Those compounds of the present invention in the case $R_1$ is not hydrogen or a cation, namely in the case $R_1$ is an ester radical, can be produced by esterification of the carboxylic acid wherein the corresponding $R_1$ is hydrogen. Although various processes for esterification are known, the process which utilizes the action of diazoalkane and the mixed acid anhydride process are used particularly preferably for production of the compounds of the present invention. In the process using diazoalkane, the target substance can be easily obtained by allowing a carboxylic acid and diazoalkane to come in contact in a solvent. Although examples of diazoalkane include diazomethane, diazoethane, diazopropane and diazodecane, it is not limited to these. The second mixed acid anhydride process has the broadest application range, and the majority of the ester compounds of the present invention are produced by this process. This process involves first reacting ethylchlorocarbonate, pivaloyl chloride and p-toluenesulfonyl chloride with a salt of a carboxylic acid to form a mixed acid anhydride, followed by addition of an excess amount of $R_{60}OH$ (where, $R_{60}$ is the same as previously defined but not hydrogen or a cation) and heating. Although specific examples of alcohol include methanol, ethanol, propanol, butanol, octanol, decanol, isopropanol and 2-ethylhexanol, it is not limited to these examples.

Although the compounds of the present invention are indicated using the structural formulas of their optically active forms, these structures are used to represent the d form, l form and dl form. Steps A'–B' can be applied in exactly the same manner for the dl, and dl forms.

In the case steps A'–B' are carried out with the dl form, the racemic compound represented with general formula [I] can be easily separated into its d and l forms by optically active column chromatography technology.

The compound of the present invention has powerful pharmacological action such as platelet coagulation inhibitory action, vascular constriction inhibitory action and bronchial muscle contraction inhibitory action as a result of having thromboxane A2 antagonistic action. It is therefore effective in the treatment and prevention of hypertension, myocardial infarction, angina pectoris, post-PTCA thrombus formation, cerebral infarction, transient ischemic attack, peripheral circulatory disorders (Baillarger's disease, Raynaud's disease, Paget's disease, thrombotic thrombocytopenic purpura, liver disease, kidney disease, etc.), arteriosclerosis, platelet functional diseases concomitant to diabetes, retinal vessel occlusion, hyperlipemia, lupus nephritis, migraine headache, concussion, bronchial asthma, allergic diseases and so forth.

The compound of the present invention can normally be administered by intravenous injection, arterial injection, intramuscular injection, percutaneously, subcutaneously or orally for this purpose. When given orally or rectally, it is normally administered divided over 1–4 administrations within a range of 1 μg/kg/day to 100 mg/kg/day. In the case of intravenous drip or arterial injection, preferable effects are obtained if given within a range of 1 ng/kg/min. to 100 μg/kg/min. In the case of normal intravenous injection, intramuscular injection or subcutaneous injection, it is given divided into 1–4 administrations within a range of 0.1 μg/kg/day to 100 mg/kg/day. In the case of administration by these means, the dose is selected from the above ranges in consideration of the age, sex and general condition of the patient as well as the number of administrations of the drug.

The compound of the present invention my be administered orally in the form of a solid preparation containing vehicles such as starch, lactose, saccharose, glucose, microcrystalline cellulose and certain types of clay, as well as coloring agents, lubricants, binders, decomposing agents and coating agents. In addition, the compound of the present invention may also be administered non-orally in the form of these sterilized solutions, and may also contain other solutes, such as an adequate amount of sodium chloride or glucose and so forth, to make the liquid isotonic. Since the compound of the present invention has stability in terms of its chemical structure, there are no difficulties in terms of its preparation and it can be applied to a wide range of administration methods, including the above-mentioned oral preparations (tablets, powders and granules) as well as various injection preparations, suppositories, ointment, lotion or plasters.

EXAMPLES

The following provides a detailed explanation of examples of the present invention.

REFERENCE EXAMPLE 1

(1SR, 2RS, 3aSR, 8bRS)-7-bromo-1,2-epoxy-2,3,3a,8b-tetrahydro-1H-cyclopenta[b]benzofuran-5-carboxylic acid methyl ester (1)

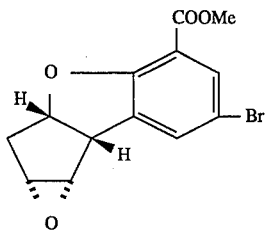
(1)

(3aSR, 8bSR)-7-bromo-3a,8b-dihydro-3H-cyclopenta[b]benzofuran-5-carboxylic acid methyl ester (12 g), produced according to the process described in Japanese Unexamined Patent Publication No. 57-144277, was dissolved in 150 ml of DMSO-water (18:1), followed by the addition of N-bromosuccinoimide (NBS, 10.2 g) at 0° C. and stirring for 1 hour. A saturated aqueous solution of sodium hydrogencarbonate (15 ml) and water (80 ml) were added to the reaction mixture followed by extraction with ethyl acetate (300 ml, 100 ml). The organic layer was concentrated after washing the organic layer with water (100 ml×2) and saturated brine (100 ml) and drying with anhydrous magnesium sulfate. The residue was dissolved in anhydrous THF (100 ml) and anhydrous methanol (100 ml) followed by the addition of potassium carbonate (8.3 g) and stirring overnight at room temperature. An aqueous solution of ammonium chloride (solution obtained by dissolving 8 g in 300 ml of water) was added to the reaction mixture followed by distilling off the THF and methanol. The residue was extracted with methylene chloride (300 ml, 100 ml) and concentrated after drying with magnesium sulfate. The resulting residue was then purified with column chromatography (silica gel: ethyl acetate/cyclohexane 8/1) to obtain the target compound (10.4 g, 82%).

M.P.: 175.5°–176.0° C. (recrystallized by ethyl acetate)

IR (KBr method): 3094, 3028, 2994, 2942, 1711, 1603, 1446, 1419, 1330, 1303, 1274, 1210, 1156, 1108, 1062, 1033, 1002, 978, 953, 884, 845, 824, 783, 712, 644, 619, 532, 437 cm$^{-1}$ NMR (90 MHZ, CDCl$_3$,δ): 2.16–2.35 (1H, m), 2.52 (1H, d, J=16.3 Hz), 3.87 (3H, s), 3.65–3.95 (3H, m), 5.40–5.60 (1H, m), 7.50–7.55 (1H, m), 7.85–7.95 (1H, m)

MASS (EI method, m/e): 310 (M$^+$)

REFERENCE EXAMPLE 2

(1RS, 2RS, 3aSR, 8bRS)-1-azido-2-hydroxy-2,3,3a,8b-tetrahydro-1H-cyclopenta[b]benzofuran-5-carboxylic acid methyl ester (2)

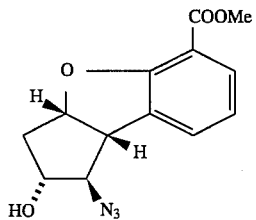
(2)

(1SR, 2RS, 3aSR, 8bSR)-7-bromo-1,2-epoxy-2,3,3a,8b-tetrahydro-1H-cyclopenta[b]benzofuran-5-carboxylate methyl ester (1) (9.4 g) was dissolved in methanol (300 ml) followed by addition of 10% palladium activated carbon (800 mg) and sodium acetate (3.7 g), stirring for 3 hours at room temperature in a hydrogen atmosphere and concentrating the reaction mixture after filtration. A solution containing the resulting residue dissolved in methanol (200 ml) was added to an aqueous solution (40 ml) of sodium azide (5.9 g) and refluxed for 24 hours. The reaction mixture was cooled to 0° C. followed by addition of 1N hydrochloric acid (92 ml) and saturated brine (100 ml) and extraction with methylene chloride (200 ml×3). The organic layers were combined and cooled to 0° C. followed by addition of an ether solution of diazomethane and esterification of the formed carboxylic acid. This solution was washed with a saturated aqueous solution of sodium hydrogencarbonate (100 ml) and saturated brine (100 ml) and concentrated after drying with anhydrous magnesium sulfate. When the resulting residue was separated and purified with column chromatography (silica gel: ethyl acetate/cyclohexane 1/8–1/4), (1SR, 2SR, 3aSR, 8bSR)-2-azido- 1-hydroxy-2,3,3a,8b-tetrahydro-1H-cyclopenta[b]benzofuran- 5-carboxylic acid methyl ester was obtained as the low polarity fraction, while the target compound was obtained as the high polarity fraction (2.55 g, 30.6%).

M.P.: 150.5°–151.5° C. (recrystallized by ethyl acetate)

IR (KBr method): 3496, 3004, 2960, 2936, 2922, 2114, 1707, 1613, 1454, 1325, 1257, 1222, 1185, 1141, 1087, 1056, 1035, 1013, 982, 959, 932, 876, 851, 828, 810, 789, 754, 692, 650, 617, 491 cm$^{-1}$ NMR (90 MHz, CDCl$_3$, δ): 1.90–2.10 (1H, m), 2.28–2.60 (1H, m), 3.60–4.00 (2H, m), 3.88 (3H, s), 4.10–4.30 (1H, m), 5.30–5.55 (1H, m), 6.92 (1H, s, J=7.7 Hz), 7.25–7.50 (1H, m), 7.70–7.85 (1H, m)

MASS (EI method, m/e): 275 (M$^+$)

REFERENCE EXAMPLE 3

(1RS, 2RS, 3aSR, 8bRS)-1-azido-2-tetrahydropyranyloxy-2,3,3a,8b-tetrahydro-1H -cyclopenta[b]benzofuran-5-carboxylic acid methyl ester (3)

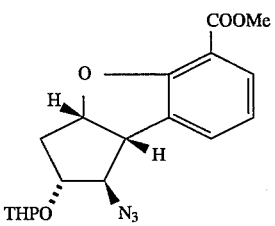
(3)

(1RS, 2RS, 3aSR, 8bRS)-1-azido-2-hydroxy-2,3,3a,8b-tetrahydro- 1H-cyclopenta[b]benzofuran-5-carboxylic acid methyl ester (2) (2.5 g) was dissolved in anhydrous THF (40 ml) followed by addition of a catalytic amount of p-toluenesulfonic acid and 2,3-dihydropyrane (1.64 ml) and stirring for 16 hours at room temperature. A saturated aqueous solution of sodium hydrogencarbonate (50 ml) was added to the reaction mixture followed by extraction with ethyl acetate (150 ml, 100 ml), combining of the organic layers, washing with water (50 ml) and saturated brine (50 ml) and concentration after drying with magnesium sulfate. The resulting residue was purified with column chromatography (silica gel: ethyl acetate/cyclohexane 1/10) to obtain the target confound (3.2 g, 98%).

IR (liquid film method): 2950, 2875, 2854, 2666, 2494, 232, 2109, 1717, 1609, 1452, 1354, 1325, 1294, 1272, 1214, 1189, 1137, 1077, 1036, 1006, 965, 938, 913, 870, 816, 758, 694, 617 cm$^{-1}$ NMR (400 Hz, CDCl$_3$, δ): 1.10–1.55 (6H, m), 2.20–2.35 (1H, m), 2.45, 2.57 (1H, ddd, J=5.5, 7.3, 14.7

Hz), 3.40–3.50 (1H, m), 3.61–3.65, 3.78–3.82 (1H, m), 3.67, 3.71 (1H, dd, J=4.3, 8.5 Hz), 3.88, 3.89 (3H, s), 3.90, 4.00 (1H, t, J=4.3 Hz), 4.07, 4.20 (1H, q, J=5.5 Hz), 4.60–4.70 (1H, m), 5.40 (1H, ddd, J=3.6, 7.3, 9.1 Hz), 6.88–6.91 (1H, m), 7.37–7.42 (1H, m), 7.73–7.77 (1H, m)

MASS (EI method, m/e): 359 (M$^+$)

REFERENCE EXAMPLE 4

(1RS, 2RS, 3aSR, 8bRS)-1-benzenesulfonamide-2-tetrahydropyranyloxy- 2,3,3a,8b-tetrahydro-1H-cyclopenta[b]benzofuran-5-carboxylic acid methyl ester (4)

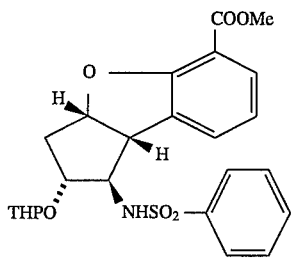

(1RS, 2RS, 3aSR, 8bRS)-1-azido-2-tetrahydropyranyloxy-2,3,3a,8b-tetrahydro-1H-cyclopenta[b]benzofuran-5-carboxylic acid methyl ester (3) (1.63 g) was dissolved in methanol (20 ml) followed by addition of 10% palladium activated carbon (160 mg) and stirring for 2 hours at room temperature in a hydrogen atmosphere. The reaction mixture was filtered and the filtrate was concentrated. The resulting residue was dissolved in methylene chloride (12 ml) followed by addition of triethylamine (2.52 ml) and benzenesulfonylchloride (1.16 ml) and stirring for 1 hour at room temperature. 1N hydrochloric acid (13.6 ml) and water (10 ml) were added to the reaction solution followed by extraction with ethyl acetate (60 ml, 20 ml). The organic layers were combined, washed with a saturated aqueous solution of sodium hydrogencarbonate (20 ml), water (20 ml×2) and saturated brine (20 ml), and concentrated. The resulting residue was then purified with column chromatography (silica gel: ethyl acetate/cyclohexane) to obtain the target compound (1.91 g) at a yield of 89%.

IR (liquid film method): 3264, 2952, 1711, 1611, 1452, 1325, 1278, 1214, 1164, 1071, 1036, 1007, 973, 913, 870, 56, 731, 690, 646 cm$^{-1}$ NMR (90 MHz, CDCl$_3$, δ): 0.7–2.2 (8H, m), 3.2–4.5 (6H, m), 3.86 (3H, s), 5.2–5.8 (2H, m), 6.7–7.0 (1H, m), 7.2–8.0 (7H, m)

MASS (EI method, m/e): 473 (M$^+$)

REFERENCE EXAMPLE 5

(3aSR, 8bSR)-7-bromo-3a,8b-dihydro-5-(2-methyl-sulfinyl- 2-methylthioethenyl)-3H-cyclopenta[b]benzofuran (5)

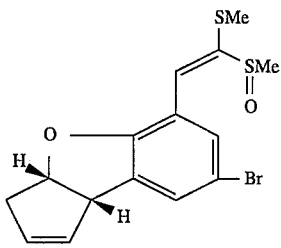

(3aSR, 8bSR )-5,7-dibromo-3a,8b-dihydro-3H-cyclopenta[[b]benzofuran (20 g), produced according to the process described in Japanese unexamined Patent Publication No. 57-144277, was dissolved in anhydrous THF (80 ml) followed by addition of a THF solution of cyclohexylmagnesium chloride (1.90N, 40 ml, 76 mmol) in the presence of argon and stirring for 2 hours at 40° C. After returning this reaction solution to room temperature, N,N-dimethylformamide (DMF, 14.6 ml) was dropped in followed by stirring for 1 hour. The reaction solution was neutralized with 6N hydrochloric acid (100 ml) while cooling with ice and extracted with ethyl acetate (400 ml, 200 ml×2). The organic layers were combined, washed with saturated brine (200 ml) and dried with anhydrous magnesium sulfate to obtain the aldehyde form of the crude product. Next, the residue was dissolved in anhydrous THF (100 ml) followed by the addition of methylmethylsulfinylmethyl sulfide (FAMSO, 9.9 ml) and N-benzyltrimethylammonium hydroxide (40% aqueous solution: Triton B, 4.0 ml) followed by refluxing for 2 hours. Water (100 ml) was added to the reaction solution followed by distilling off the THF. After extracting the residue with ethyl acetate (150 ml×2) and washing with water (50 ml) and brine (50 ml), it was dried with anhydrous magnesium sulfate and concentrated. The residue was then purified with column chromatography (silica gel: ethyl acetate/cyclohexane 1/20) to obtain the target compound (14.7 g, 63%).

IR (liquid film method): 3464, 3064, 3000, 2924, 2838, 2114, 1713, 1591, 1441, 1354, 1325, 1299, 1270, 1247, 1187, 1065, 998, 980, 948, 909, 878, 833, 775, 748, 714, 669 cm$^{-1}$ NMR (90 MHz, CDCl$_3$, δ): 2.34 (3H, s), 2.75 (3H, s), 2.80–2.95 (2H, m), 4.30–4.50 (1H, m), 5.40–5.60 (1H, m), 5.60–5.90 (2H, m), 7.29–7.32 (1H, d), 7.70 (1H, s), 8.20–8.25 (1H, m)

MASS (EI method, m/e): 370 (M$^+$)

REFERENCE EXAMPLE 6

(3aSR, 8bSR)-7-bromo-3a,8b-dihydro-3H-cyclopenta[b]benzofuran-5-acetic acid methyl ester (6)

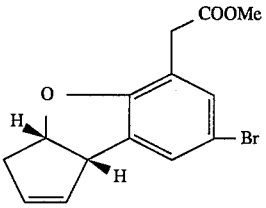

(3aSR, 8bSR)-7-bromo-3a,8b-dihydro-5-(2-methylsulfinyl- 2-methylthioethenyl)-3H-cyclopenta[b]benzofuran (5) (14.6 g) was dissolved in methanol (400 ml) followed by addition of a 5.24 N methanol hydrochloric acid solution (56 ml) while cooling with ice and stirring for 2 hours. Saturated sodium hydrogencarbonate solution was added to the reaction solution to neutralize followed by concentration. After extracting the residue with ethyl acetate (300 ml×2) and washing with water (50 ml) and brine (50 ml), it was dried with anhydrous magnesium sulfate and concentrated. The residue was then purified with column chromatography (silica gel: ethyl acetate/cyclohexane 1/20) to obtain the target compound (12.1 g, 99%).

IR (liquid film method): 2968, 2920, 1738, 1462, 1435, 1350, 1305, 1203, 1160, 1102, 1058, 998, 980, 951, 911, 880, 866, 832, 762, 721, 704, 630, 584, 567, 516, 412 cm$^{-1}$ NMR (90 MHz, CDCl$_3$, δ): 2.70–2.90 (1H, m), 3.53 (1H, bs), 3.69 (1H, s), 4.30–4.50 (1H, m), 5.40–5.60 (1H, m), 5.65–5.90 (2H, m), 7.10–7.30 (2H, m)

MASS (EI method, m/e): 308 (M⁺)

REFERENCE EXAMPLE 7

(1SR, 2RS, 3aSR, 8bRS)-7-bromo-1,2-epoxy-2,3, 3a,8b-tetrahydro- 1H-cyclopenta[b]benzofuran-5-acetic acid methyl ester (7)

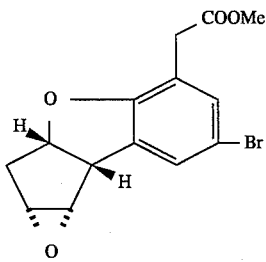

(7)

The target compound (9.7 g) was obtained from (3aSR, 8bSR)-7-bromo-3a,8b-dihydro-3H-cyclopenta[b]benzofuran-5-acetic acid methyl ester (11.2 g) in the same manner as Reference Example 1.

M.P.: 166.0°–167.5° C. (recrystallized by ethyl acetate)

IR (KBr method): 3040, 2962, 2928, 1736, 1464, 1431, 1394, 1346, 1311, 1263, 1224, 1199, 1158, 1069, 1046, 1033, 1009, 977, 915, 884, 874, 841, 828, 774, 743, 721, 669, 636, 594, 580, 557, 518, 429 cm⁻¹ NMR (90 MHz, CDCl₃, δ): 2.10–2.40 (1H, m), 2.45–2.75 (1H, m), 3.45–3.60 (2H, m), 3.68 (3H, s), 3.60– 3.90 (3H, m), 5.35–5.50 (1H, m), 7.15–7.40 (2H, m)

MASS (EI method, m/e):324 (M⁺)

REFERENCE EXAMPLE 8

(1RS, 2RS, 3aSR, 8bRS)-1-azido-2-hydroxy-2,3,3a, 8b-tetrahydro- 1H-cyclopenta[b]benzofuran-5-acetic acid methyl ester (8)

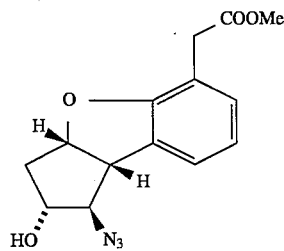

(8)

(1SR, 2SR, 3aSR, 8bRS)-2-azido-1-hydroxy-2,3,3a,8b-tetrahydro- 1H-cyclopenta[b]benzofuran-5-acetic acid methyl ester and the target compound (2.31 g, 31%) were obtained from (1SR, 2RS, 3aSR, 8bRS)-7-bromo-1,2-epoxy-2,3,3a,8b-tetrahydro- 1H-cyclopenta[b]benzofuran-5-acetic acid methyl ester (7) (8.7 g) in the same manner as Reference Example 2.

IR (liquid film method): 3428, 2956, 2498, 2230, 2108, 1738, 1622, 1601, 1483, 1458, 1348, 1257, 1160, 1087, 1062, 1040, 1013, 955, 864, 750 cm⁻¹ NMR (500 MHz, CDCl₃, δ): 2.17–2.25 (1H, m), 2.39–2.46 (1H, m), 3.52 (1H, d, J=16.0 Hz), 3.65 (1H, d, J=16.0 Hz), 3.68 (3H, s), 3.74 (1H, dd, J=3.0, 8.5 Hz), 3.90–3.95 (1H, m), 4.15 (1H, bs), 5.29 (1H, ddd, J=2.4, 6.7, 8.5 Hz), 6.87 (1H, t, J=7.4 Hz), 7.01 (1H, d, J=7.4 Hz), 7.19 (1H, d, J=7.4 Hz)

MASS (EI method, m/e): 289 (M⁺)

REFERENCE EXAMPLE 9

(1RS, 2RS, 3aSR, 8bRS)-1-azido-2-tetrahydropyranyloxy-2,3,3a,8b-tetrahydro-1H-cyclopenta[b]benzofuran-5-acetic acid methyl ester (9)

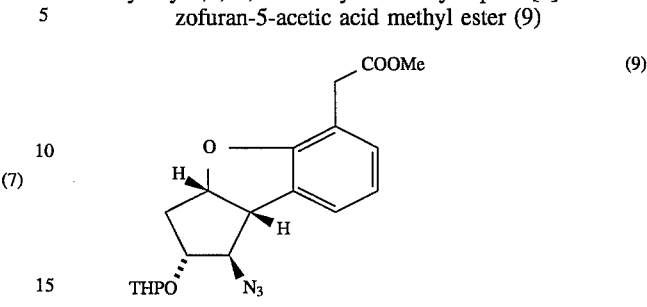

(9)

The target compound (2.75 g, 99.0%) was obtained from (1RS, 2RS, 3aSR, 8bRS)-1-azido-2-hydroxy-2,3,3a,8b-tetrahydro- 1H-cyclopenta[b]benzofuran-5-acetic acid methyl ester (8) (2.15 g) in the same manner as Reference Example 3.

M.P.: 107.0°–108.0° C.

IR (KBr method): 2954, 2108, 1748, 1597, 1464, 1433, 1400, 1352, 1257, 1212, 1189, 1158, 1120, 1083, 1029, 1011, 949, 909, 855, 812, 746 cm⁻¹ NMR (500 MHz, CDCl₃, δ): 1.20–1.60 (6H, m), 2.02–2.15 (1H, m), 2.45–2.62 (1H, m), 3.45–3.53 (1H, m), 3.69, 3.70 (3H, s), 3.53–3.85 (4H, m), 3.89, 3.97 (1H, t, J=5.5 Hz), 4.04, 4.14 (1H, q, J=6.1 Hz), 4.65 (1H, m), 5.20 (1H, ddd, J=4.3, 7.3, 9.1 Hz), 6.83, 6.84 (1H, t, J=7.4 Hz), 7.04 (1H, d, J=7.4 Hz), 7.14, 7.18 (1H, d, J=7.4 Hz)

MASS (EI method, m/e): 373 (M⁺)

REFERENCE EXAMPLE 10

(3aSR, 8bSR)-7-bromo-3a,8b-dihydro-3H-cyclopenta[b]benzofuran-5-acetic acid methyl ester (10)

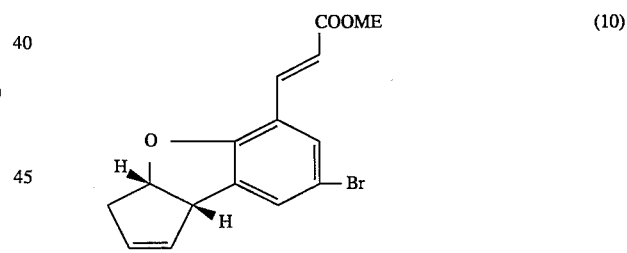

(10)

(3aSR, 8bSR)-5,7-dibromo-3a,8b-dihydro-3H-cyclopenta [b]benzofuran (10 g), produced according to the process described in Japanese Unexamined Patent Publication No. 57-144277, was dissolved in anhydrous THF (40 ml) followed by addition of a THF solution of cyclohexylmagnesium chloride (1.90N, 20 ml) in the presence of argon followed by stirring for 2 hours at 40° C. After returning this reaction solution to room temperature, N,N-dimethylformamide (DMF, 7.3 ml) was dropped in followed by stirring for 1 hour. The reaction solution was neutralized with hydrochloric acid (50 ml) while cooling with ice and extracted with ethyl acetate (200 ml, 100 ml× 2). The organic layers were combined, washed with saturated brine (100 ml) and dried with anhydrous magnesium sulfate to obtain the aldehyde form of the crude product. Next, an anhydrous THF solution (40 ml) of trimethylphosphonoacetate (9.78 g) was dropped into a suspension of sodium hydride (60% mineral oil dispersion, 2.15 g) in anhydrous THF (40 ml) and anhydrous DMSO (70 ml) at 0° C. followed by stirring for 30 minutes. Acetic acid (3.3 ml) was added to the reaction solution followed by concentration. After extracting the residue with ethyl acetate (200 ml×2) and washing with water (100 ml) and brine (100 ml), it was dried with anhydrous magnesium sulfate and concentrated. The residue was then purified with column chromatography (silica gel: ethyl acetate/cyclohexane 1/20) to obtain the target compound (8.93 g, 88.0%).

M.P.: 143.0°–144.0° C. (recrystallized by ethyl acetate)

IR (KBr method): 3386, 3064, 2992, 2946, 1818, 1777, 1707, 1632, 1582, 1437, 1354, 1340, 1328, 1305, 1238, 1174, 1112, 1069, 1031, 1002, 984, 946, 899, 866, 835, 777, 723, 708, 632, 609, 592, 565, 542, 485, 455, 420 cm$^{-1}$ NMR (90 MHz, CDCl$_3$, δ): 2.80–3.00 (2H, m), 3.79 (3H, s), 4.30–4.45 (1H, m), 5.50–5.85 (3H, m), 6.65 (1H, d, J=16.0 Hz), 7.20–7.30 (2H, m), 7.56 (1H, d, J=16.0 Hz)

MASS (EI method, m/e):320 (M$^+$)

REFERENCE EXAMPLE 11

(1SR, 2RS, 3aSR, 8bRS)-7-bromo-1,2-epoxy-2,3, 3a,8b-tetrahydro- 1H-cyclopenta[b]benzofuran-5-acetic acid methyl ester (11)

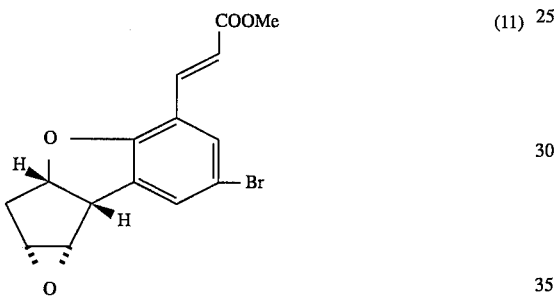

(11)

The target compound (3.7 g, 58.8%) was obtained from (3aSR, 8bSR)-7-bromo-3a,8b-dihydro-3H-cyclopenta[b]benzofuran-5-acetic acid methyl ester (10) (6.0 g) in the same manner as Reference Example 1.

M.P.: 167.5°–168.5° C. (recrystallized by ethyl acetate)

IR (KBr method): 2956, 1717, 1638, 1454, 1336, 1305, 1280, 1243, 1203, 1176, 1015, 980, 909, 884, 862, 841, 716, 669, 642, 427 cm$^{-1}$ NMR (90 MHz, CDCl$_3$, δ): 2.15–2.45 (1H, m), 2.50–2.75 (1H, m), 3.78 (3H, s), 3.65–3.95 (3H, m), 5.35–5.60 (1H, m), 6.61 (1H, d, J=16.0 Hz), 7.23–7.36 (2H, m), 7.55 (1H, d, J=16.0 Hz)

MASS (EI method, m/e): 336 (M$^+$)

REFERENCE EXAMPLE 12

(1RS, 2RS, 3aSR, 8bRS)-1-azido-2-hydroxy-2,3,3a, 8b-tetrahydro- 1H-cyclopenta[b]benzofuran-5-propionic acid methyl ester (12)

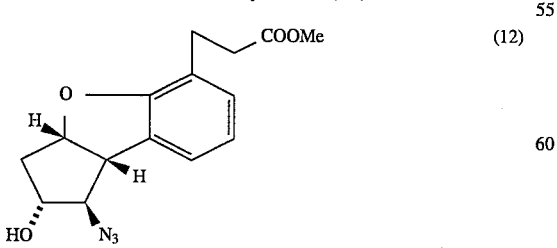

(12)

(1SR, 2SR, 3aSR, 8bRS)-2-azido-1-hydroxy-2,3,3a,8b-tetrahydro- 1H-cyclopenta[b]benzofuran-5-propionic acid methyl ester and the target compound (0.87 g, 26.9%) were obtained from (1SR, 2RS, 3aSR, 8bRS)-7-bromo-1,2-epoxy-2,3,3a,8b-tetrahydro-1H-cyclopenta[b]benzofuran-5-acrylic acid methyl ester (11) (3.6 g) in the same manner as Reference Example 2.

M.P.: 62.5°–63.5° C. (recrystallized from ethyl acetate)

IR (KBr method): 3526, 2996, 2950, 2904, 2238, 2112, 1715, 1599, 1481, 1458, 1421, 1375, 1352, 1336, 1307, 1263, 1209, 1191, 1106, 1067, 1042, 1011, 971, 953, 895, 861, 837, 787, 748, 640, 619, 592, 514, 484 cm$^{-1}$ NMR (500 MHz, CDCl$_3$, δ): 1.97 (1H, d, J=6.1 Hz), 2.18 (1H, dt, J=3.6, 14.7 Hz), 2.49 (1H, dt, J=6.1, 14.7 Hz), 2.56–2.70 (2H, m), 2.80–2.95 (2H, m), 3.63 (3H, s), 3.74 (1H, dd, J=4.3, 8.5 Hz), 3.90 (1H, t, J=3.6 Hz), 4.15–4.20 (1H, m), 5.25–5.28 (1H, m), 6.83 (1H, t, J=7.3 Hz), 6.99 (1H, d, J=7.3 Hz), 7.13 (1H, d, J=7.3 Hz)

MASS (EI method, m/e): 303 (M$^+$)

REFERENCE EXAMPLE 13

(1RS, 2RS, 3aSR, 8bRS)-1-azido-2-tetrahydropyranyloxy-2,3,3a,8b-tetrahydro-1H-cyclopenta[b]benzofuran-5-propionic acid methyl ester (13)

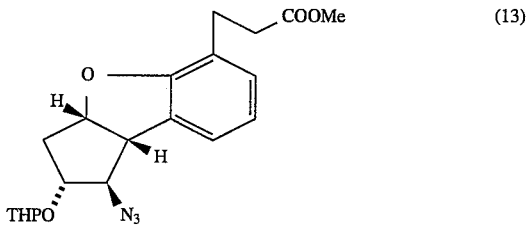

(13)

The target compound (1.01 g) was obtained from (1RS, 2RS, 3aSR, 8bRS)-1-azido-2-hydroxy-2,3,3a,8b-tetrahydro-1H-cyclopenta[b]benzofuran-5-propionic acid methyl ester (12) (0.87 g) in the same manner as Reference Example 3.

IR (liquid film method): 2934, 2110, 1740, 1562, 1510, 1460, 1359, 1257, 1193, 1131, 1071, 1038, 1023, 982, 965, 915, 870, 793, 754 cm$^{-1}$ NMR (400 MHz, CDCl$_3$, δ): 1.15–1.55 (6H, m), 2.00–2.20 (1H, m), 2.45–2.70 (3H, m), 2.80–2.90 (2H, m), 3.45–3.53 (1H, m), 3.67 (3H, s), 3.60–3.85 (2H, m), 3.89, 3.97 (1H, t, J=4.9 Hz), 4.06, 4.14 (1H, q, J=5.9 Hz), 4.61–4.65, 4.67–4.71 (1H, m), 5.20 (1H, ddd, J=4.4, 7.3, 8.8 Hz), 6.78, 6.79 (1H, t, J=7.3 Hz), 6.97 (1H, d, J=7.3 Hz), 7.08, 7.12 (1H, d, J=7.3 Hz)

MASS (EI method, m/e): 387 (M$^+$)

REFERENCE EXAMPLE 14

(1RS, 2RS, 3aSR, 8bRS)-1-azido-2-hydroxy-2,3,3a, 8b-tetrahydro- 1H-cyclopenta [b]benzofuran-5-bytyric acid methyl ester (14)

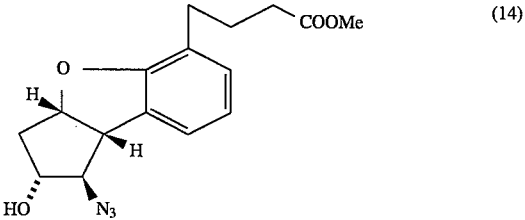

(14)

A methanol solution (50 ml) of (1SR, 2RS, 3aSR, 8bRS)-1,2-epoxy-2,3,3a,8b-tetrahydro-1H-cyclopenta[b]benzofuran-5-butyric acid methyl ester (1.65 g), produced according to the process described in Japanese Unexamined Patent Publication No. 57-144276, was added to a solution containing sodium azide (1.17 g, 18.0 mmol) dissolved in water (10 ml) and refluxed for 24 hours. After cooling the reaction mixture to 0° C., 1N hydrochloric acid (19 ml) was added followed by the addition of saturated brine (25 ml) and extraction with methylene chloride (50 ml×3). The organic layers were combined and cooled to 0° C. followed by addition of an ether solution of diazomethane to esterify the carboxylic acid formed. This solution was washed with a saturated aqueous solution of sodium hydrogencarbonate (20 ml) and saturated brine (20 ml) and concentrated after drying with anhydrous magnesium sulfate. When the resulting residue was purified with column chromatography (silica gel: ethyl acetate/cyclohexane 1/8–1/4), (1SR, 2SR, 3aSR, 8bRS)-2-azido-1-hydroxy-2,3,3a,8b-tetrahydro-1H-cyclopenta[b]benzofuran-5-butyric acid methyl ester was obtained as the low polarity fraction, while the target compound was obtained as the high polarity fraction (0.57 g, 30.0%).

IR (liquid film method): 3388, 2938, 2496, 2364, 2230, 2106, 1736, 1599, 1560, 1541, 1481, 1456, 1375, 1257, 1193, 1151, 1089, 1029, 957, 864, 764, 745 cm$^{-1}$ NMR (400 MHz, CDCl$_3$, δ): 1.81–2.05 (2H, m), 2.15–2.23 (2H, m), 2.25–2.33 (2H, m), 2.43–2.52 (1H, m), 2.53–2.69 (2H, m), 3.64 (3H, s), 3.74 (1H, dd, J=3.9, 8.3 Hz), 3.90 (1H, t, J=3.4 Hz), 4.17–4.20 (1H, bs), 5.25 (1H, ddd, J=2.9, 6.8, 8.8 Hz), 6.83 (1H, t, J=7.8 Hz), 6.97 (1H, d, J=7.8 Hz), 7.11 (1H, d, J=7.8 Hz)

MASS (EI method, m/e): 317 (M$^+$)

REFERENCE EXAMPLE 15

(1RS, 2RS, 3aSR, 8bRS)-1-azido-2-tetrahydropyranyloxy-2,3,3a,8b-tetrahydro-1H-cyclopenta[b]benzofuran-5-butyric acid methyl ester (15)

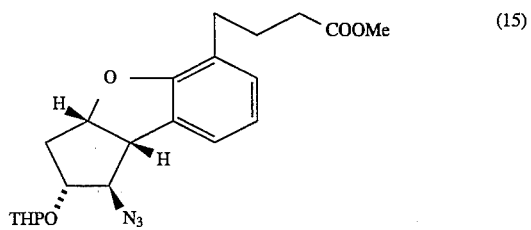

The target compound (695 mg, 98%) was obtained from (1RS, 2RS, 3aSR, 8bRS)-1-azido-2-hydroxy-2,3,3a,8b-tetrahydro-1H-cyclopenta[b]benzofuran-5-butyric acid methyl ester (14) (560 mg) in the same manner as Reference Example 3.

IR (liquid film method): 3338, 2932, 2854, 2662, 2492, 2232, 2108, 1742, 1599, 1481, 1456, 1354, 1325, 1259, 1201, 1135, 1079, 1036, 965, 913, 870, 818, 764, 745, 710 cm$^{-1}$ NMR (400 MHz, CDCl$_3$, δ): 1.15–1.60 (6H, m), 1.88–1.97 (2H, m), 2.00–2.18 (1H, m), 2.31–2.37 (2H, m), 2.46–2.61 (2H, m), 3.45–3.53 (1H, m), 3.66 (3H, s), 3.60–3.85 (2H, m), 3.89, 3.97 (1H, t, J=5.4 Hz), 4.06, 4.14 (1H, q, J=5.9 Hz), 4.63–4.68 (1H, m), 5.18 (1H, ddd, J=3.9, 7.3, 8.8 Hz), 6.79, 6.80 (1H, t, J=7.8 Hz), 6.95 (1H, d, J=7.8 Hz), 7.07, 7.11 (1H, d, J=7.8 Hz)

MASS (EI method, m/e): 401 (M$^+$)

REFERENCE EXAMPLE 16

(3aSR, 8bSR)-7-bromo-5-hydroxy-3a,8b-dihydro-3H-cyclopenta[b]benzofuran (16)

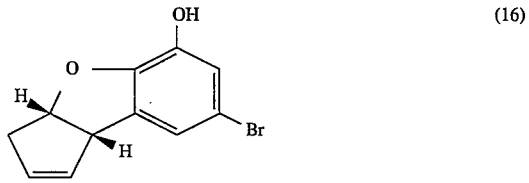

(3aSR, 8bSR)-5,7-dibromo-3a,8b-dihydro-3H-cyclopenta[b]benzofuran (42.7 g), produced according to the process described in Japanese Unexamined Patent Publication No. 57-144277, was dissolved in anhydrous THF (120 ml) followed by addition of a THF solution of cyclohexylmagnesium chloride (1.52N, 107 ml) in the presence of argon followed by stirring for 1.5 hours at 40° C. A THF solution (50 ml) of trimethyl boric acid (19.9 ml) was added at −10° C. After stirring for 1 hour at that temperature, a solution of acetic acid (10 ml) and 35% hydrogen peroxide (23.6 ml) diluted with water (25 ml) was added. After returning the reaction mixture to room temperature and stirring for 18 hours, a solution containing sodium hydrogensulfite (41 g) dissolved in water (200 ml) was added slowly while stirring at 0° C. followed by filtration. The THF of the filtrate was removed by distillation under reduced pressure and the residue was extracted with ethyl acetate (600 ml, 200 ml). The organic layers were washed with saturated brine (200 ml) and dried with anhydrous magnesium sulfate. After concentrating, the residue was purified with column chromatography (silica gel: ethyl acetate/cyclohexane 1/10) to obtain the target compound (28.9 g, 84 %).

M.P.: 110°–111° C. (recrystallized from ethyl acetate/n-hexane)

IR (KBr method): 3430, 2900, 1600, 1460, 1420, 1360, 1300, 1280, 1260, 1220, 1160, 1150, 1050, 97 0, 940, 890, 840, 810, 760, 740, 720, 700, 600 cm$^{-1}$ NMR (90 MHz, CDCl$_3$, δ): 2.6–3.1 (2H, m), 4.38 (1H, br.d, J=8 Hz), 5.02 (1H, br.s), 5.4–5.9 (3H, m), 6.8–7.0 (2H, m)

MASS (EI method, m/e): 252 (M$^+$)

REFERENCE EXAMPLE 17

(3aSR, 8bSR)-7-bromo-3a,8b-dihydro-3H-cyclopenta[b]benzofuran-5-yloxyacetic acid methyl ester (17)

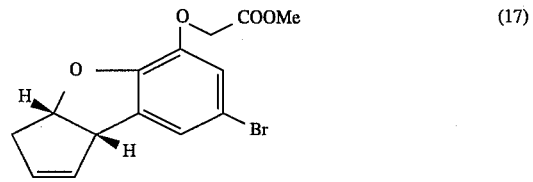

Sodium hydride (60% mineral oil dispersion, 3.95 g) was suspended in anhydrous THF (50 ml) followed by slowly adding a solution of anhydrous THF (100 ml) of (3aSR, 8bSR)-7-bromo-5-hydroxy-3a,8b-dihydro-3H-cyclopenta[b]benzofuran (16) (25.0 g) at 0° C. and stirring for 15 minutes at 0° C. Methylbromoacetate (18.7 ml) was added to this reaction solution followed by stirring for 18 hours at room temperature. A solution containing ammonium chloride (18 g) dissolved in water (200 ml) was added to the resulting reaction mixture at 0° C. followed by extraction with ethyl acetate (400 ml). The organic phase was washed with water (200 ml) and saturated brine (200 ml) and concentrated after drying with anhydrous magnesium sulfate. The resulting residue was recrystallized with ethyl acetate/n-hexane to obtain the target compound in the form of a white crystal (27.6 g, 86%). After then concentrating the mother liquor, the residue was purified with column chromatography (silica gel: ethyl acetate/cyclohexane 1/5) to obtain the target compound (3.9 g, 12%).

M.P.: 96°–96.5° C. (recrystallized from ethyl acetate/n-hexane)

IR (KBr method): 2920, 1730, 1620, 1580, 1490, 1430, 1330, 1290, 1240, 1200, 1180, 1110, 1100, 1010, 1000, 980, 940, 900, 840, 830, 790, 740, 710 cm$^{-1}$ NMR (90 MHz, CDCl$_3$, δ): 2.7–3.0 (2H, m), 3.79 (3H, s), 4.47 (1H, br.d, J=8 Hz), 4.68 (2H, s), 5.4–5.9 (3H, m), 6.81 (1H, d, J=1.8 Hz), 6.9–7.05 (1H, m)

MASS (EI method, m/e): 324 (M$^+$)

REFERENCE EXAMPLE 18

(1SR, 2RS, 3aSR, 8bRS)-7-bromo-1,2-epoxy-2,3,3a,8b-tetrahydro- 1H-cyclopenta[b]benzofuran-5-yloxyacetic acid methyl ester (18)

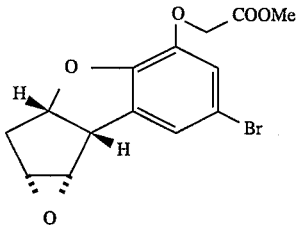

(18)

The target compound (13.8 g, 72%) was obtained from (3aSR, 8bSR)-7-bromo-3a,8b-dihydro-3H-cyclopenta[b]benzofuran-5-yloxyacetic acid methyl ester (17) (18.4 g) in the same manner as Reference Example 1.

M.P.: 160.5°–161° C. (recrystallized from ethyl acetate)

IR (KBr method): 2950, 1770, 1730, 1610, 1580, 1480, 420, 1390, 1290, 1280, 1200, 1110, 1020, 1000, 960, 920, 900, 860, 840, 820, 790, 760, 730, 640, 590, 500, 420 cm$^{-1}$ NMR (400 MHz, CDCl$_3$, δ): 2.28 (1H, ddd, J=1.7, 7.6, 16.1 Hz), 2.59 (1H, d, J=16.1 Hz), 3.66 (1H, br.s), 3.71 (1H, br.s), 3.75–3.85 (1H, m), 3.79 (3H, s), 4.64 (1H, d, J=16.2 Hz), 4.69 (1H, d, J=16.2 Hz), 5.40 (1H, t, J=7.6 Hz), 6.87 (1H, d, J=1.8 Hz), 7.05–7.1 (1H, m)

MASS (EI method, m/e): 340 (M$^+$)

REFERENCE EXAMPLE 19

(1SR, 2RS, 3aSR, 8bRS)-1,2-epoxy-2,3,3a,8b-tetrahydro-1H-cyclopenta[b]benzofuran-5-yloxyacetic acid methyl ester (19)

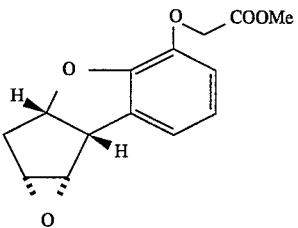

(19)

(1SR, 2RS, 3aSR, 8bRS)-7-bromo-1,2-epoxy-2,3,3a,8b-tetrahydro- 1H-cyclopenta[b]benzofuran-5-yloxyacetic acid methyl ester (18) (31.4 g) was dissolved in ethanol (1.5 l) followed by addition of 10% palladium activated carbon (3.17 g) and sodium acetate (11.3 g) followed by stirring for 5 hours in a hydrogen atmosphere. After filtering the reaction mixture using selite, the ethanol was removed by distillation under reduced pressure. The residue was dissolved in ethyl acetate (1 l), washed with 1N hydrochloric acid (200 ml) and saturated brine (150 ml) and concentrated after drying with magnesium sulfate. The residue was then purified with column chromatography (silica gel: cyclohexane/ethyl acetate 1/1–1/2) to obtain the target compound (20.04 g) at a yield of 83%.

M.P.: 111°–112° C. (recrystallized from cyclohexane/chloroform)

IR (KBr method): 2940, 1760, 1620, 1597, 1491, 1466, 1431, 1381, 1338, 1307, 1286, 1270, 1228, 1191, 1118, 1033, 994, 971, 897, 849, 772, 741, 719, 704 cm$^{-1}$ NMR (90 MHz, CDCl$_3$, δ): 6.73–7.00 (3H, m), 5.37 (1H, brt, J=7.7 Hz), 4.68 (2H, s), 3.76 (3H, s), 3.66–3.83 (3H, m), 2.59 (1H, brd, J=15.9 Hz), 2.24 (1H, dd, J=7.0, 16.0 Hz)

MASS (EI method, m/e): 262 (M$^+$)

REFERENCE EXAMPLE 20

(1RS, 2RS, 3aSR, 8bRS)-1-azido-7-bromo-2-hydroxy-2,3,3a,8b-tetrahydro-1H-cyclopenta[b]benzofuran-5-yloxyacetic acid methyl ester (20) and
(1SR, 2SR, 3aSR, 8bRS)-2-azido-7-bromo-1-hydroxy-2,3,3a,8b-tetrahydro-1H-cyclopenta [b]benzofuran-5-yloxyacetic acid methyl ester (20')

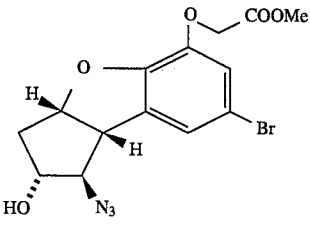

(20)

and

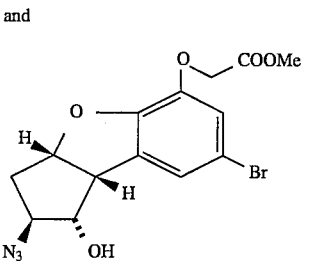

(20')

(1SR, 2RS, 3aSR, 8bRS)-7-bromo-1,2-epoxy-2,3,3a,8b-tetrahydro- 1H-cyclopenta[b]benzofuran-5-yloxyacetic acid methyl ester (18) (4.35 g) was added to a solution containing sodium azide (2.50 g) dissolved in water (25 ml) and methanol (80 ml) and refluxed for 24 hours. After cooling the reaction mixture to 0° C., 1N hydrochloric acid (40 ml) was added followed by the addition of saturated brine (50 ml) and extraction with methylene chloride (300 ml, 100 ml×2). After combining the organic layers and cooling to 0° C., an ether solution of diazomethane was added to esterify the carboxylic acid formed. This solution was then washed with a mixed solution of saturated aqueous solution of sodium hydrogencarbonate (20 ml) and saturated brine (80 ml) and concentrated after drying with anhydrous magnesium sulfate. When the resulting residue was separated and purified with column chromatography (silica gel: ethyl acetate/cyclohexane 1/5–1/2.5), (1SR, 2SR, 3aSR, 8bRS)-2-azido-7-bromo-1-hydroxy-2,3,3a,8b-tetrahydro-1H-cyclopenta [b]benzofuran-5-yloxyacetic acid methyl ester (20') (3.28 g, yield: 67%) was obtained as the low polarity fraction, while (1RS, 2RS, 3aSR, 8bRS)-1-azido-7-bromo-2-hydroxy- 2,3,3a,8b-tetrahydro-1H-cyclopenta[b]benzofuran-5-yloxyacetic acid methyl ester (20) was obtained as the high polarity fraction (1.56 g, yield: 32%).

1-azide form (20)

M.P.: 107°–107.5° C. (recrystallized from ethyl acetate/n-hexane)

IR (KBr method): 3450, 2880, 2100, 1750, 1610, 1590, 1480, 1430, 1400, 1290, 1250, 1230, 1200, 1110, 1080, 1020, 970, 940, 920, 880, 860, 850, 830, 820, 760, 730, 650, 600, 500 cm$^{-1}$ NMR (400 MHz, CDCl$_3$, δ): 1.85–2.0 (1H, m), 2.23 (1H, dt, J=3.2, 15.0 Hz), 2.47 (1H, ddd, J=5.5, 6.5, 15.0 Hz), 3.72 (1H, dd, J=3.5, 8.7 Hz), 3.79 (3H, s), 3.91 (1H, t, J=3.5 Hz), 4.15–4.25 (1H, m), 4.68 (1H, d, J=16.1 Hz), 4.71 (1H, d, J=16.1 Hz), 5.35 (1H, ddd, J=3.2, 6.5, 8.7 Hz), 6.88 (1H, d, J=1.8 Hz), 7.05–7.1 (1H, m)

MASS (EI method, m/e): 383 (M$^+$)

2-azide form (20')

IR (liquid film method): 3480, 2950, 2100, 1750, 1610, 1590, 1480, 1430, 1190, 1120, 1000, 940, 880, 860, 750 cm$^{-1}$ NMR (400 MHz, CDCl$_3$, δ): 1.85–2.0 (2H, m), 2.46 (1H, dd, J=6.4, 14.3 Hz), 3.68 (1H, ddd, J=6.4, 8.4, 11.0 Hz), 3.81 (3H, s), 3.97 (1H, t, J=8.3 Hz), 4.1–4.25 (1H, m), 4.70 (2H, s), 5.75–5.85 (1H, m), 6.89 (1H, d, J=1.8 Hz), 7.05–7.1 (1H, m)

MASS (EI method, m/e): 383 (M$^+$)

REFERENCE EXAMPLE 21

(1RS, 2RS, 3aSR, 8bRS)-1-azido-2-hydroxy-2,3,3a, 8b-tetrahydro- 1H-cyclopenta[b]benzofuran-5-yloxyacetic acid methyl ester (21) and (1SR, 2SR, 3aSR, 8bRS)-2-azido-1-hydroxy- 2,3,3a,8b-tetrahydro-1H-cyclopenta[b]benzofuran-5-yloxyacetic acid methyl ester (21')

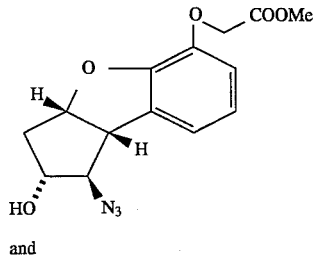

and

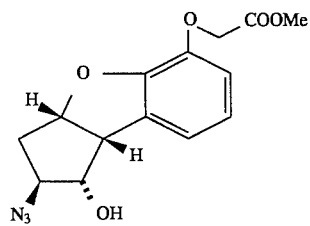

(1RS, 2RS, 3aSR, 8bRS)-1-azido-2-hydroxy-2,3,3a,8b-tetrahydro- 1H-cyclopenta[b]benzofuran-5-yloxyacetic acid methyl ester (21) (4.44 g) and (1SR, 2SR, 3aSR, 8bRS)-2-azido-      1-hydroxy-2,3,3a,8b-tetrahydro-1H-cyclopenta [b]benzofuran-5-yloxyacetic acid methyl ester (21') (6.33 g) were obtained from (1SR, 2RS, 3aSR, 8bRS)-1,2-epoxy-2, 3,3a,8b-tetrahydro-1H-cyclopenta[b]benzofuran-5-yloxyacetic acid methyl ester (19) (10.0 g) in the same manner as Reference Example 20.

1-azide form (21)

IR (liquid film method): 3472, 2956, 2105, 1760, 1622, 1597, 1491, 1464, 1439, 1379, 1296, 1224, 1195, 1116, 1035, 951, 762, 729 cm$^{-1}$ NMR (400 MHz, CDCl$_3$, δ): 6.94 (1H, dd, J=1.0, 7.3 Hz), 6.84 (1H, t, J=7.3 Hz), 6.75 (1H, brd, J=7.8 Hz), 5.33 (1H, ddd, J=3.0, 6.9, 8.8 Hz), 4.73, 4.69 (each 1H, ABq, J=16.1 Hz), 4.17 (1H, m), 3.90 (1H, brt, J=3.9 Hz), 3.78 (3H, s), 3.74 (1H, dd, J=3.9, 8.3 Hz), 2.47 (1H, ddd, J=5.9, 6.8, 14.6 Hz), 2.23 (1H, m), 2.01 (1H, brd, J=5.4 Hz)

MASS (EI method, m/e): 305 (M$^+$)

1-azide form (21 ')

M.P.: 85°–86° C. (recrystallized from cyclohexane/ethyl acetate)

IR (KBr method): 3366, 2092, 1775, 1620, 1491, 1466, 1454, 1439, 1315, 1290, 1249, 1236, 1203, 1185, 1166, 1125, 1104, 1060, 1009, 963, 777, 741 cm$^{-1}$ NMR (400 MHz, CDCl$_3$, δ): 6.94 (1H, d, J=7.3 Hz), 6.82 (1H, t, J=7.3 Hz), 6.76 (1H, dd, J=1.0, 7.3 Hz), 5.28 (1H, m), 4.72 (2H, s), 4.17 (1H, q, J=8.3 Hz), 4.00 (1H, t, J=8.3 Hz), 3.80 (3H, s), 3.66 (1H, ddd, J=6.4, 8.3, 10.7 Hz), 2.46 (1H, dd, J=6.3, 14.6 Hz), 1.87–1.96 (2H, m)

MASS (EI method, m/e): 305 (M$^+$)

REFERENCE EXAMPLE 22

(1RS, 2RS, 3aSR, 8bRS)-1-azido-7-bromo-2-tetrahydropyranyloxy- 2,3,3a,8b-tetrahydro-1H-cyclopenta[b]benzofuran-5-yloxyacetic acid methyl ester (22)

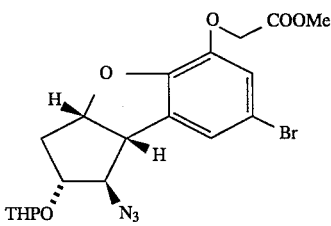

The target compound (1.67 g) was obtained from (1RS, 2RS, 3aSR, 8bRS)-1-azido-7-bromo-2-hydroxy-2,3,3a,8b-tetrahydro- 1H-cyclopenta[b]benzofuran-5-yloxyacetic acid methyl ester (20) (1.41 g) in the same manner as Reference Example 3.

IR (liquid film method): 2950, 2100, 1760, 1620, 1580, 1480, 1430, 1350, 1190, 1120, 1070, 1030, 960, 900, 860, 750 cm$^{-1}$ NMR (90 MHz, CDCl$_3$, δ): 1.15–1.65 (6H, m), 2.1–2.3 (1H, m), 2.4–2.6 (1H, m), 3.45–3.55 (1H, m), 3.6–3.75 (5H, m), 3.9–4.2 (2H, m), 4.6–4.7 (3H, m), 5.25–5.35 (1H, m), 6.85–6.9 (1H, m), 7.0–7.1 (1H, m)

MASS (EI method, m/e): 467 (M$^+$)

REFERENCE EXAMPLE 23

(1SR, 2SR, 3aSR, 8bSR)-2-azido-7-bromo-1-tetrahydropyranyloxy- 2,3,3a,8b-tetrahydro-1H-cyclopenta[b]benzofuran-5-yloxyacetic acid methyl ester (23)

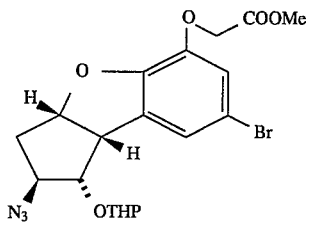

The target compound (3.08 g) was obtained from (1SR, 2SR, 3aSR, 8bRS)-2-azido-7-bromo-1-hydroxy-2,3,3a,8b-tetrahydro- 1H-cyclopenta[b]benzofuran-5-yloxyacetic acid methyl ester (20') (2.79 g) in the same manner as Reference Example 3.

IR (liquid film method): 2950, 2100, 1760, 1620, 1480, 1440, 1360, 1260, 1200, 1120, 1100, 1080, 1040, 960, 900, 860, 820, 760 cm$^{-1}$ NMR (90 MHz, CDCl$_3$, δ): 1.4–2.1 (7H, m), 2.2–2.6 (1H, m), 3.4–4.4 (5H, m), 3.80 (3H, s), 4.6–5.0 (3H, m), 5.1–5.4 (1H, m), 6.8–6.9 (1H, m), 7.2–7.3 (1H, m)

MASS (EI method, m/e): 467 (M$^+$)

REFERENCE EXAMPLE 24

(1RS, 2RS, 3aSR, 8bRS)-1-azido-2-tetrahydropyranyloxy-2,3,3a,8b-tetrahydro-1H-cyclopenta[b]benzofuran-5-yloxyacetic acid methyl ester (24)

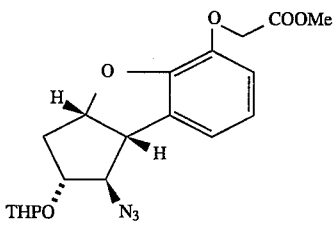

The target compound (4.87 g) was obtained from (1RS, 2RS, 3aSR, 8bRS)-1-azido-2-hydroxy-2,3,3a,8b-tetrahydro-1H-cyclopenta [b]benzofuran-5-yloxyacetic acid methyl ester (21) (4.44 g) in the same manner as Reference Example 3.

IR (liquid film method): 2950, 2876, 2106, 1767, 1620, 1597, 1487, 1461, 1441, 1354, 1261, 1197, 1120, 1079, 1038, 1006, 967, 913, 870, 789, 764, 729 cm$^{-1}$ NMR (90 MHz, CDCl$_3$, δ): 6.73–6.98 (3H,m), 5.16–5.38 (1H, m), 4.66 (2H, s), 3.78 (3H, s), 3.37–4.23 (6H, m), 2.03–2.71 (2H, m), 1.23–1.62 (6H, m)

MASS (EI method, m/e): 389 (M$^+$)

REFERENCE EXAMPLE 25

(1RS, 2RS, 3aSR, 8bRS)-1-benzenesulfonamide-2-tetrahydropyranyloxy- 2,3,3a,8b-tetrahydro-1H-cyclopenta [b]benzofuran-5-yloxyacetic acid methyl ester (25)

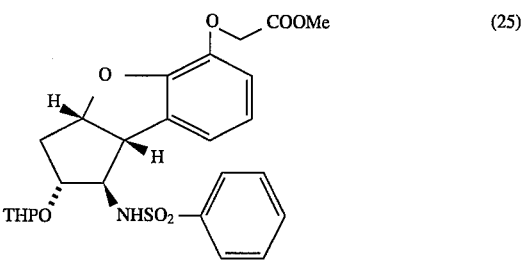

(1RS, 2RS, 3aSR, 8bRS)-1-azido-7-bromo-2-tetrahydropyranyloxy- 2,3,3a,8b-tetrahydro-1H-cyclopenta [b]benzofuran-5-yloxyacetic acid methyl ester (22) (908 mg) was dissolved in methanol (20 ml) followed by the addition of sodium acetate (318 mg) and 10% palladium activated carbon (100 mg) and stirring for 18 hours at room temperature in a hydrogen atmosphere. Triethylamine (1 ml) was added to the reaction mixture followed by filtering and concentration. Water (50 ml) was added to the residue followed by extraction with methylene chloride (100 ml, 50 ml×3). The organic layers were combined and washed with saturated brine (50 ml) followed by concentration after drying with magnesium sulfate. The residue was dissolved in methylene chloride (8 ml) followed by the addition of triethylamine (0.81 ml) and benzenesulfonyl chloride (0.50 ml) and stirring for 3 hours at room temperature. 1N hydrochloric acid (8 ml) and water (15 ml) were added to the reaction solution and separated. The aqueous layer was re-extracted with methylene chloride (50 ml×2) followed by combining of the organic layers, washing with a saturated aqueous solution of sodium hydrogencarbonate (25 ml), water (25 ml) and saturated brine (25 ml) and concentrating after drying with anhydrous magnesium sulfate. The resulting residue was then separated and purified with column chromatography (silica gel: methylene chloride/acetonitrile 5/1) to obtain the target compound (725 mg) at a yield of 74%.

IR (liquid film method): 3276, 3026, 2952, 1756, 1622, 1599, 1491, 1466, 1441, 1381, 1325, 1220, 1195, 1164, 1118, 1094, 1073, 1035, 1007, 971, 893, 868, 851, 756, 690, 667, 584 cm$^{-1}$ NMR (90 MHz, CDCl$_3$, δ): 1.0–1.8 (6H, m), 1.9–2.6 (2H, m), 3.2–4.1 (5H, m), 3.77 (3H, s), 4.2–4.5 (1H, m), 4.66 (2H, s), 5.1–5.4 (1H, m), 6.6–7.1 (3H, m), 7.4–8.1 (5H, m)

MASS (EI method, m/e): 503 (M$^+$)

REFERENCE EXAMPLE 26

2-((3aSR, 8bSR)-7-bromo-3a,8b-dihydro-3H-cyclopenta [b]benzofuran-5-yloxy)-propionic acid ethyl ester (26)

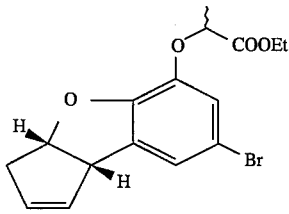
(26)

A methanol solution (30 ml) of potassium hydroxide (1.37 g) was added to a solution of (3aSR, 8bSR)-7-bromo-5-hydroxy- 3a,8b-dihydro-3H-cyclopenta[b]benzofuran (16) (5.2 g) dissolved in methanol (50 ml) followed by stirring for 1 hour. The methanol was distilled off followed by azeotropic distillation with ethanol. An N,N-dimethylformamide (DMF) (10 ml) solution of ethyl 2-bromopropionic acid (5.42 ml) was dropped into a solution of the residue dissolved in DMF (80 ml) followed by stirring for 2 hours. After removing the DMF of the reaction solution by distillation under reduced pressure, the residue was extracted with ethyl acetate (200 ml×2). The organic layers were combined, washed with water (50 ml ×2) and saturated brine (50 ml), and concentrated after drying with anhydrous magnesium sulfate. The residue was then purified with column chromatography (silica gel: ethyl acetate/cyclohexane 1/10) to obtain the target compound (17.2 g, 98%).

IR (liquid film method): 2988, 2942, 1752, 1605, 1466, 1377, 1338, 1290, 1236, 1193, 1133, 1104, 1075, 1046, 1002, 911, 859, 832, 733, 710 cm$^{-1}$ NMR (90 MHz, CDCl$_3$, δ): 1.25 (3H, t, J=7.0 Hz), 1.59 (3H, d, J=6.8 Hz), 2.80–3.00 (2H, m), 4.21 (2H, q, J=7.0 Hz), 4.10–4.50 (1H, m), 4.83 (1H, q, J=6.8 Hz), 5.40–5.70 (1H, m), 5.60–5.90 (2H, m), 6.80–6.90 (1H, m), 6.95–7.00 (1H, m)

MASS (EI method, m/e): 352 (M$^+$)

REFERENCE EXAMPLE 27

2-((3aSR, 8bSR)-7-bromo-3a,8b-dihydro-3H-cyclopenta[b]benzofuran-5-yloxy)-2-methylpropionic acid ethyl ester (27)

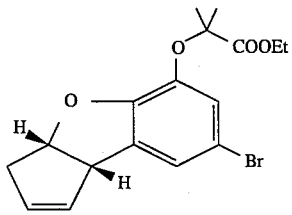
(27)

A 1.62 N n-butyllithium solution (18.8 ml) was added to an anhydrous THF solution (30 ml) of diisopropylamine (4.29 ml) cooled to 0° C. and stirred for 30 minutes. Next, after cooling the reaction solution to −78° C., an anhydrous THF solution (20 ml) of 2-((3aSR, 8bSR)-7-bromo-3a,8b-dihydro- 3H-cyclopenta[b]benzofuran-5-yloxy) -propionate ethyl ester (26) (7.15 g) was added followed by stirring for 30 minutes. Hexamethylphosphoric triamide (HMPA: 5.3 ml) was then added followed by dropping in an anhydrous THF solution (10 ml) of methyl iodide (3.8 ml) and stirring for hours. After neutralizing the reaction solution with an aqueous solution of ammonium chloride, the reaction solution was extracted with ethyl acetate (200 ml×2). After combining the organic layers and washing with water (50 ml) and brine (50 ml), the organic layers were dried with anhydrous magnesium sulfate and concentrated. The residue was then separated and purified with column chromatography (silica gel: ethyl acetate/cyclohexane 1/20) to obtain the target compound (4.6 g, 57.1%).

IR (liquid film method): 3064, 2988, 2942, 1738, 1603, 1466, 1419, 1383, 1367, 1338, 1292, 1238, 1191, 1139, 1071, 1025, 1002, 988, 948, 911, 861, 833, 762, 712 cm$^{-1}$ NMR (90 MHz, CDCl$_3$, δ): 1.32 (3H, t, J=7.0 Hz), 1.56 (3H, s), 2.80–2.85 (2H, m), 4.24 (2H, q, J=7.0 Hz), 4.20–4.45 (1H, m), 5.40–5.60 (1H, m), 5.60–5.85 (2H, m), 6.80–6.83 (1H, m), 6.85–7.03 (1H, m)

MASS (EI method, m/e): 368 (M$^+$)

REFERENCE EXAMPLE 28

2-((1SR, 2RS, 3aSR, 8bRS)-7-bromo-1,2-epoxy-2, 3,3a,8b-tetrahydro- 1H-cyclopenta[b]benzofuran-5-yloxy)-2-methylpropionic acid methyl ester (28)

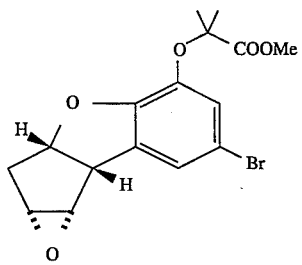
(28)

The target compound (2.78 g, 74.0%) was obtained from 2-((3aSR, 8bSR)-7-bromo-3a,8b-dihydro-3H-cyclopenta[b] benzofuran-5-yloxy)-2-methylpropionate ethyl ester (27) (3.74 g) in the same manner as Reference Example 1.

IR (liquid film method): 3462, 2994, 2952, 2846, 1742, 1605, 1593, 1468, 1423, 1386, 1367, 1336, 1299, 1234, 1195, 1141, 1102, 1075, 1038, 1017, 975, 940, 911, 868, 845, 830, 804, 758, 656 cm$^{-1}$ NMR (90 MHz, CDCl$_3$, δ): 1.55 (3H, s), 1.56 (3H, s), 2.10–2.20 (1H, m), 2.40–2.70 (1H, m), 3.60–3.90 (3H, m), 3.77 (3H, s), 5.20–5.50 (1H, m), 6.90–7.00 (1H, m), 7.02–7.10 (1H, m)

MASS (EI method, m/e): 368 (M$^+$)

REFERENCE EXAMPLE 29

2-((1RS, 2RS, 3aSR, 8bRS)-1-azido-2-hydroxy-2,3, 3a,8b-tetrahydro- 1H-cyclopenta[b]benzofuran-5-yloxy)-2-methylpropionic acid methyl ester (29)

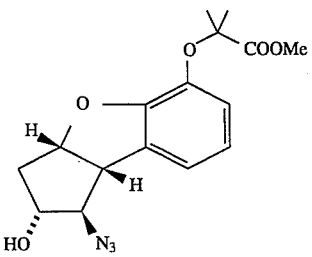
(29)

2-((1SR, 2SR, 3aSR,8bRS)-2-azido-1-hydroxy-2,3,3a, 8b-tetrahydro- 1H-cyclopenta[b]benzofuran-5-yloxy)-2-methylpropionic acid methyl ester and the target compound (820 mg, 33%) were obtained from 2-((1SR, 2RS, 3aSR, 8bRS)-7-bromo-1,2-epoxy-2,3,3a,8b-tetrahydro-1H-cyclopenta [b]benzofuran-5-yloxy)-2-methylpropionic acid methyl ester (28) (2.74 g) in the same manner as Reference Example 2.

IR (liquid film method): 3480, 2992, 2952, 2504, 2230, 2108, 1740, 1609, 1481, 1462, 1383, 1367, 1270, 1197, 1174, 1141, 1091, 1044, 1013, 957, 932, 870, 847, 814, 764, 737 cm$^{-1}$ NMR (400 MHz, CDCl$_3$, δ): 1.52 (3H, s), 1.58 (3H, s), 1.97 (1H, bs), 2.20 (1H, dt, J=3.7, 14.7 Hz), 2.45 (1H, ddd, J=5.4, 6.3, 14.7 Hz), 3.73 (1H, dd, J=3.7, 8.8 Hz), 3.78 (3H, s), 3.74 (1H, dd, J=3.0, 8.5 Hz), 3.91 (1H, t, J=3.7 Hz), 4.15– 4.25 (1H, m), 5.27–5.30 (1H, m), 6.73–6.80 (1H, m), 6.96–7.00 (1H, m)

MASS (EI method, m/e): 333 (M$^+$)

REFERENCE EXAMPLE 30

2-((1RS, 2RS, 3aSR, 8bRS)-1-azido-2-tetrahydropyranyl oxy-2,3,3a,8b-tetrahydro-1H-cyclopenta[b] benzofuran-5-yloxy)- 2-methylpropionic acid methyl ester (30)

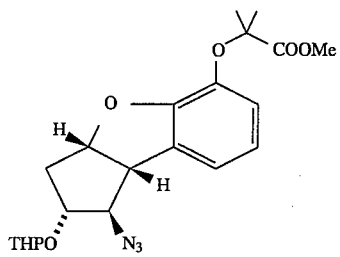
(30)

The target compound (850 mg, 83%) was obtained from 2-(( 1RS, 2RS, 3aSR, 8bRS)-1-azido-2-hydroxy-2,3,3a,8b-tetrahydro- 1H-cyclopenta[b]benzofuran-5-yloxy)-2-methylpropionic acid methyl ester (29) (817 mg) in the same manner as Reference Example 3.

IR (liquid film method): 3338, 2948, 2874, 2106, 1740, 1609, 1597, 1481, 1460, 1383, 1367, 1265, 1197, 1174, 1137, 1081, 1038, 1021, 1006, 965, 913, 870, 847, 814, 764, 737 cm$^{-1}$ NMR (400 MHz, CDCl$_3$, δ): 1,56, 1.58 (3H, s), 1.57, 1.59 (3H, s), 2.04, 2.15 (1H, ddd, J=4.4, 6.8, 14.3 Hz), 2.48–2.62 (1H, m), 3.47–3.52 (1H, m) 3.61–3.84 (2H, m), 3.76, 3.77 (3H, s), 3.89–3.97 (1H, t, J=5.4 Hz), 4.03–4.15 (1H, m), 4.63–4.68 (1H, m), 5.20 (1H, ddd, J=4.4, 7.3, 9.3 Hz), 6.67–6.76 (1H, m), 6.90–6.96 (1H, m)

MASS (EI method, m/e): 417 (M$^+$)

REFERENCE EXAMPLE 31

(1RS, 2SR, 3aSR, 8bRS)-1,2-(N-benzenesulfonylimino)-2,3,3a,8b-tetrahydro-1H-cyclopenta[b] benzofuran-5-yloxyacetic acid methyl ester (31)

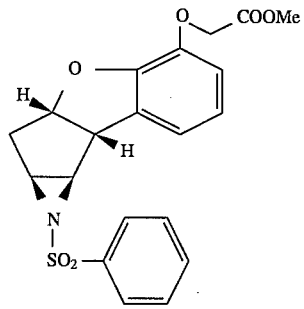
(31)

(1SR, 2SR, 3aSR, 8bRS)-2-azido-1-hydroxy-2,3,3a,8b-tetrahydro- 1H-cyclopenta[b]benzofuran-5-yloxyacetic acid methyl ester (21") (10.0 g) was dissolved in methanol (100 ml) and tetrahydrofuran (150 ml) followed by the addition of 10% palladium activated carbon (670 mg) and stirring for hours at room temperature in a hydrogen atmosphere. The reaction mixture was then concentrated after filtering. The residue was dissolved in pyridine (150 ml) followed by the addition of benzenesulfonyl chloride (16.8 ml) and stirring for 4 hours at 80° C. After distilling off the pyridine under reduced pressure, ethyl acetate (300 ml) was added to the residue which was then washed with 1N hydrochloric acid (100 ml). The organic layer was washed with a saturated aqueous solution of sodium hydrogencarbonate (100 ml), water (100 ml) and saturated brine (100 ml) and concentrated after drying with anhydrous magnesium sulfate. The residue was dissolved in methanol (150 ml) and tetrahydrofuran (150 ml) followed by the addition of anhydrous potassium carbonate (5.89 g) and stirring for 3 hours at room temperature. Acetic acid (5.3 ml) and water (150 ml) were added to the reaction mixture followed by extraction with ethyl acetate (200 ml×2). The organic layers were washed with water (150 ml) and saturated brine (150 ml) and concentrated after drying with magnesium sulfate. The resulting residue was then purified with column chromatography (silica gel: ethyl acetate/cyclohexane) to obtain the target compound (10.11 g) at a yield of 77%.

M.P.: 103°–104° C. (recrystallized from ethyl acetate/n-hexane)

IR (liquid film method): 3260, 2954, 1771, 1620, 1595, 1493, 1448, 1392, 1352, 1323, 1309, 1294, 1220, 1201, 1170, 1154, 1114, 1098, 1087, 1050, 1023, 998, 949, 903, 878, 864, 847, 758, 721, 690, 611, 580, 563 cm$^{-1}$ NMR (90 MHz, CDCl$_3$, δ): 2.14 (1H, dt, J=4.9, 15.3 Hz), 2.61 (1H, dd, J=7.7, 15.3 Hz), 3.43 (1H, t, J=4.9 Hz), 3.70 (1H, d, J=4.9 Hz), 3.77 (3H, s), 4.16 (1H, d, J=7.7 Hz), 4.69 (2H, s), 5.07 (1H, dt, J=4.9, 7.7 Hz), 6.7–7.0 (3H, m), 7.5–7.8 (3H, m), 7.9–8.1 (2H, m)

MASS (EI method, m/e): 401 (M$^+$)

REFERENCE EXAMPLE 32

(1RS, 2SR, 3aSR, 8bRS)-7-bromo-1,2-epoxy-2,3, 3a,8b-tetrahydro- 1H-cyclopenta[b]benzofuran-5-yloxyacetic acid methyl ester (32)

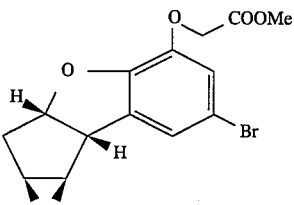
(32)

(3aSR, 8bSR)-7-bromo-3a,8b-dihydro-3H-cyclopenta[b] benzofuran-5-yloxyacetic acid methyl ester (17) (11.0 g) was dissolved in methylene chloride (150 ml) followed by the addition of m-chloroperbenzoic acid (14.6 g) and stirring for 22 hours at room temperature. A solution of sodium thiosulfate dissolved in water (100 ml) was slowly added to the reaction mixture at 0° C. The resulting mixture was extracted with methylene chloride (150 ml×2) and the organic layers were washed with a saturated aqueous solution of sodium hydrogen carbonate (150 ml), water (150 ml) and saturated brine (150 ml) and concentrated after drying with magnesium sulfate. The resulting residue was purified with column chromatography to obtain the target compound (9.26 g).

M.P.: 111°–112° C. (recrystallized from ethyl acetate/n-hexane)

IR (KBr method): 2960, 1736, 1620, 1584, 1491, 1423, 1325, 1290, 1265, 1199, 1122, 1102, 1033, 1013, 1002, 973, 938, 868, 835, 816, 785, 648 cm$^{-1}$ NMR (90 MHz, CDCl$_3$, δ): 1.9–1.2 (1H, m), 2.70 (1H, d, J=7.6, 15.8 Hz), 3.5–3.7 (2H, m), 3.79 (3H, s), 4.15 (1H, br.d, J=8 Hz), 4.63 (2H, s), 5.10 (1H, d, J=3.5, 7.6 Hz), 6.8–6.9 (1H, m), 7.0–7.1 (1H, m)

MASS (EI method, m/e): 340 (M$^+$)

REFERENCE EXAMPLE 33

(1RS, 2SR, 3aSR, 8bRS)-1,2-epoxy-2,3,3a,8b-tetrahydro-1H-cyclopenta[b]benzofuran-5-yloxyacetic acid methyl ester (33)

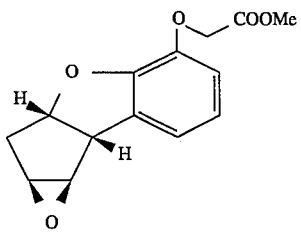

The target compound (288 mg) was obtained from (1RS, 2SR, 3aSR, 8bRS)-7-bromo-1,2-epoxy-2,3,3a,8b-tetrahydro-1H-cyclopenta [b]benzofuran-5-yloxyacetic acid methyl ester (32) (421 mg) in the same manner as Reference Example 19.

M.P.: 76°–77° C. (recrystallized from ethyl acetate/n-hexane)

IR (KBr method): 2996, 1748, 1620, 1591, 1491, 1468, 1437, 1386, 1286, 1226, 1191, 1123, 1104, 1042, 977, 955, 940, 835, 806, 791, 764, 725, 708 cm$^{-1}$ NMR (90 MHz, CDCl$_3$, δ): 1.9–2.2 (1H, m), 2.70 (1H, dd, J=7.3, 15.5 Hz), 3.56 (1H, t, J=2.4 Hz), 3.70 (1H, d, J=2.4 Hz), 3.78 (3H, s), 4.17 (1H, d, J=7.9 Hz), 4.71 (2H, s), 4.9–5.2 (1H, m), 6.7–7.0 (3H, m)

MASS (EI method, m/e): 262 (M$^+$)

REFERENCE EXAMPLE 34

(1RS, 2RS, 3aSR, 8bRS)-2-azido-1-hydroxy-2,3,3a, 8b-tetrahydro- 1H-cyclopenta[b]benzofuran-5-yloxyacetic acid methyl ester (34)

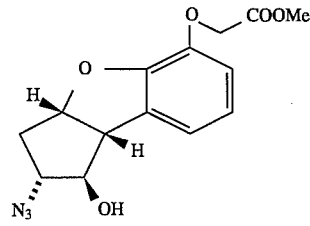

The target compound (2.30 g) was obtained from (1RS, 2SR, 3aSR, 8bRS)-1,2-epoxy-2,3,3a,8b-tetrahydro-1H-cyclopenta [b]benzofuran-5-yloxyacetic acid methyl ester (33) (2.00 g) in the same manner as Reference Example 20.

IR (liquid film method): 3494, 2958, 2110, 1742, 1622, 1597, 1491, 1464, 1439, 1377, 1193, 1114, 1040, 961, 847, 766, 727 cm$^{-1}$ NMR (400 MHz, CDCl$_3$, δ): 2.19 (1H, ddd, J=3.5, 6.1, 14.6 Hz), 2.22 (1H, d, J=3.9 Hz), 2.60 (1H, dt, J=6.7, 14.6 Hz), 3.74 (1H, dd, J=3.9, 8.8 Hz), 3.78 (3H, s), 3.8–3.9 (1H, m), 4.1–4.2 (1H, m), 4.71 (1H, d, J=16.4 Hz), 4.73 (1H, d, J=16.4 Hz), 5.36 (1H, ddd, J=3.5, 6.7, 8.8 Hz), 6.75–6.85 (2H, m), 6.9–6.95 (1H, m)

MASS (EI method, m/e): 305 (M$^+$)

REFERENCE EXAMPLE 35

(1RS, 2RS, 3aSR, 8bSR)-2-benzenesulfonamido-1-benzenesulfonyloxy- 2,3,3a,8b-tetrahydro-1H-cyclopenta [b]benzofuran-5-yloxyacetic acid methyl ester (35)

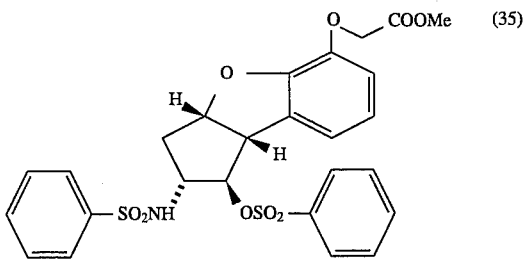

(1RS, 2RS, 3aSR, 8bRS)-2-azido-1-hydroxy-2,3,3a,8b-tetrahydro- 1H-cyclopenta[b]benzofuran-5-yloxyacetic acid methyl ester (34) (185 mg) was dissolved in methanol (6 ml) followed by addition of 10% palladium activated carbon (20 mg) and stirring for 2 hours at room temperature in a hydrogen atmosphere. The reaction mixture was filtered and the filtrate was concentrated. The resulting residue was dissolved in pyridine (6 ml) followed by addition of benzenesulfonyl chloride (0.38 ml) and stirring for 3 hours at 80° C. 1N hydrochloric acid (25 ml) was added at 0° C. to the reaction mixture followed by extraction with ethyl acetate (50 ml×2). The organic layers were washed with a saturated aqueous solution of sodium hydrogencarbonate (25 ml), water (25 ml) and saturated brine (25 ml), and concentrated after drying with anhydrous magnesium sulfate. The resulting residue was then purified with column chromatography (silica gel: ethyl acetate/cyclohexane 1/5–1/2) to obtain the target compound (164 mg) at a yield of 48%.

IR (liquid film method): 3292, 3030, 2958, 1756, 1622, 1597, 1491, 1464, 1450, 1367, 1340, 1299, 1224, 1189, 1096, 951, 855, 754, 688 cm$^{-1}$ NMR (90 MHz, CDCl$_3$, δ): 1.9–2.6 (2H, m), 3.75 (3H, s), 3.7–4.0 (2H, m), 4.5–4.9 (3H,m), 5.1–5.5 (2H, m), 6.4–6.8 (3H, m), 7.2–8.0 (10H, m)

MASS (EI method, m/e): 559 (M$^+$)

REFERENCE EXAMPLE 36

(1SR, 2RS, 3aSR, 8bRS)-1,2-(N-benzenesulfo-nylimino)-2,3,3a,8b-tetrahydro-1H-cyclopenta[b]benzofuran-5-yloxyacetic acid methyl ester (36)

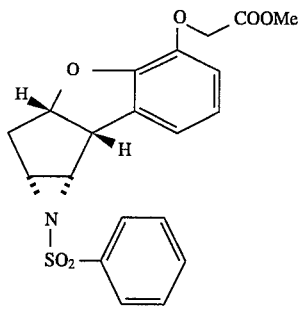

(1RS, 2RS, 3aSR, 8bSR)-2-benzenesulfonamido-1benzenesulfonyloxy- 2,3,3a,8b-tetrahydro-1H-cyclopenta [b]benzofuran-5-yloxyacetic acid methyl ester (35) (1.25 g) was dissolved in dimethylsulfoxide (20 ml) followed by addition of diazabicycloundecene (DBU, 0.67 ml) and stirring for 2 hours at room temperature. 0.2N hydrochloric acid (25 ml) was added to the reaction mixture followed by extraction with ethyl acetate (50 ml×2). The organic layers were washed with water (25 ml) and saturated brine (25 ml) and concentrated after drying with magnesium sulfate. The resulting residue was purified with column chromatography (silica gel: ethyl acetate/cyclohexane) to obtain the target compound (764 mg) at a yield of 85%.

M.P.: 133°–134° C. (recrystallized from ethyl acetate/n-hexane)

IR (KBr method): 2958, 1773, 1622, 1597, 1493, 1435, 1319, 1294, 1197, 1156, 1120, 1091, 1013, 1000, 967, 870, 799, 733, 688, 600, 555 cm$^{-1}$ NMR (400 MHz, CDCl$_3$, δ): 2.41 (1H, ddd, J=3.2, 7.3, 16.1 Hz), 2.69 (1H, d, J=16.1 Hz), 3.35–3.45 (1H, m), 3.75–3.85 (2H, m), 3.80 (3H, s), 4.69 (2H, s) 5.33 (1H, t, J=7.3 Hz), 6.37 (1H, d, J=7.3 Hz), 6.43 (1H, d, J=7.3 Hz), 6.65–6.7 (1H, m), 7.2–7.3 (2H, m), 7.4–7.5 (3H, m)

MASS (EI method, m/e): 401 (M$^+$)

REFERENCE EXAMPLE 37

(1SR, 2RS, 3aSR, 8bSR)-2-acetoxy-1-azidomethyl-2,3,3a,8b-tetrahydro-1H-cyclopenta[b]benzofuran-5-yloxyacetic acid methyl ester (37)

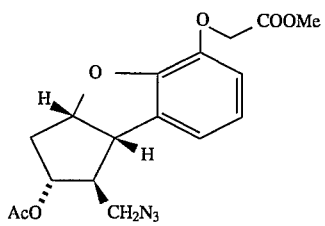

(1SR, 2RS, 3aSR, 8bSR)-2-acetoxy-1-hydroxymethyl-2,3,3a,8b-tetrahydro-1H-cyclopenta[b]benzofuran-5-yloxyacetic acid methyl ester (567 mg), produced according to the process described in Japanese Unexamined Patent Publication No. 62-265279, was dissolved in methylene chloride (5 ml) and cooled to −78° C. Triethylamine (0.4 ml) and methanesulfonyl chloride (0.16 ml) were added to this solution followed by stirring for 1.5 hours at −78° C. in an argon atmosphere. The reaction solution was poured into water (50 ml) and extracted with ethyl acetate (30 ml ×2). The organic layers were combined and washed with saturated brine (20 ml) and concentrated after drying with sodium sulfate. The residue was dissolved in a mixed solution of water and methanol (4:1, 5 ml) followed by the addition of sodium azide (270 mg) and refluxing for 5.5 hours in an argon atmosphere. After cooling the reaction solution to room temperature, the reaction solution was poured into water (50 ml) and extracted with ethyl acetate (30 ml×2). The organic layers were combined and washed with saturated brine (20 ml) followed by concentration after drying with sodium sulfate. The resulting residue was then purified with column chromatography (silica gel: cyclohexane/ethyl acetate 2/1) to obtain the target compound (534 mg) at a yield of 88%.

IR (liquid film method): 2958, 2106, 1734, 1620, 1597, 1491, 1464, 1371, 1243, 1193, 1098, 1058, 847, 764, 729 cm$^{-1}$ NMR (90 MHz, CDCl$_3$, δ): 6.68–6.93 (3H, m), 5.09–5.42 (1H, m), 4.98 (1H, q, J=5.5 Hz), 4.72 (2H, s), 3.78 (3H, s), 3.42–3.75 (3H, m), 2.24–2.76 (3H, m), 1.82 (3H, s)

MASS (EI method, m/e): 361 (M$^+$)

WORKING EXAMPLE 1

(1RS, 2RS, 3aSR, 8bRS)-1-benzenesulfonamido-2-hydroxy-2,3,3a,8b-tetrahydro-1H-cyclopenta[b]benzofuran-5-carboxylic acid methyl ester (38)

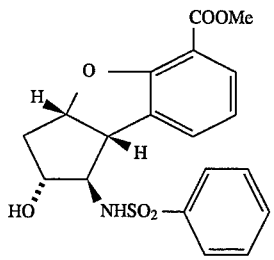

(1RS, 2RS, 3aSR, 8bRS)-1-azido-2-tetrahydropyranyloxy-2,3,3a,8b-tetrahydro-1H-cyclopenta[b]benzofuran-5-carboxylic acid methyl ester (3) (1.08 g) was dissolved in methanol (15 ml) and anhydrous THF (15 ml) followed by the addition of 10% palladium activated carbon (100 mg) and stirring for 3 hours at room temperature in a hydrogen atmosphere. The reaction solution was filtered and concentrated, and the residue was dissolved in methylene chloride (20 ml) followed by the addition of triethylamine (1.69 ml) and benzenesulfonyl chloride (0.77 ml) and stirring for 3 hours at room temperature. 1N hydrochloric acid (13 ml) and water (15 ml) were added to the reaction solution to separate. The aqueous layer was re-extracted with methylene chloride (50 ml) and combined with the organic layer, washed with a saturated aqueous solution of sodium hydrogencarbonate (30 ml), water (30 ml) and saturated brine (30 ml) and concentrated after drying with anhydrous magnesium sulfate. The residue was dissolved in methanol (100 ml) followed by the addition of a catalytic amount of p-toluenesulfonic acid and stirring for 15 hours at room temperature. Water (40 ml) was added to the reaction solution followed by neutralization with a saturated aqueous solution of sodium hydrogencarbonate followed by concentration with methanol. The residue was extracted twice with methylene chloride (60 ml), the organic layers were washed with water (40 ml) and saturated brine (40 ml) followed by concentration after drying with anhydrous sodium sulfate. The resulting residue was then purified with the Merk Rover Column (ethyl acetate/cyclohexane 2/1) to obtain the target compound (1.03 g) at a yield of 88%.

M.P.: 139.0°–134.0° C.

IR (KBr method): 3434, 3166, 2956, 1665, 1603, 1437, 1296, 1214, 1145, 1035, 919, 890, 861, 754, 716, 687, 549 cm$^{-1}$ NMR (500 MHz, CDCl$_3$, δ): 2.13 (1H, ddd, J=4.3, 7.3, 14.6 Hz), 2.54 (1H, dt, J=7.3, 14.6 Hz), 2.71 (1H, d, J=3.6 Hz), 3.46 (1H, q, J=5.5 Hz), 3.62 (1H, dd, J=5.5, 9.1 Hz), 3.85 (3H, s), 4.08–4.12 (1H, m), 5.30 (1H, ddd, J=4.3, 7.3, 9.1 Hz), 5.48–5.50 (1H, m), 6.70–6.73 (1H, m), 6.92–6.94 (1H, m), 7.52–7.56 (2H, m), 7.60–7.64 (1H, m), 7.67–7.69 (1H, m), 7.79–7.93 (2H, m)

MASS (EI method, m/e): 389 (M$^+$)

Elementary Analysis: (as C$_{19}$H$_{19}$NO$_6$S) Calculated values: C: 58.60, H: 4.92, N: 3.60, S: 8.23 Measured values: C: 58.49, H: 5.05, N: 3.74, S: 8.33

WORKING EXAMPLE 2

(1RS, 2RS, 3aSR, 8bRS)-1-benzenesulfonamido-2-hydroxy-2,3,3a,8b-tetrahydro-1H-cyclopenta[b]benzofuran-5-carboxylic acid (39)

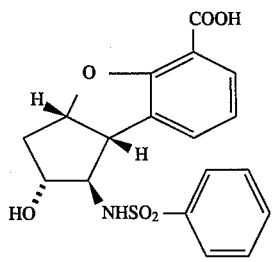
(39)

(1RS, 2RS, 3aSR, 8bRS)-1-benzenesulfonamido-2-hydroxy-2,3,3a,8b-tetrahydro-1H-cyclopenta[b]benzofuran-5-carboxylic acid methyl ester (38) (700 mg) was dissolved in methanol (40 ml) followed by the addition of 2N sodium hydroxide (1 ml) and stirring for 15 hours at room temperatures. The reaction solution was concentrated and water (10 ml) was added to the residue followed by neutralization with 1N hydrochloric acid (1.1 ml). The resulting liquid was extracted twice with methylene chloride (50 ml), the organic layers were washed with water (40 ml) and saturated brine (40 ml) and concentrated after drying with anhydrous sodium sulfate. The resulting residue was then recrystallized with ethyl acetate to obtain the target compound in the form of a white crystal (623 mg) at a yield of 93%.

M.P.: 177.5°–178.5° C.

IR (KBr method): 3496, 3188, 1684, 1615, 1454, 1311, 1218, 1160, 1069, 936, 882, 853, 754, 721, 688, 594, 542 cm$^{-1}$ NMR (400 MHz, CDCl$_3$, -DMSO, δ): 2.04–2.11 (1H, m), 2.50–2.52 (1H, m), 3.37–3.40 (1H, m), 3.68–3.70 (2H, m), 4.06–4.08 (1H, m), 5.32–5.36 (1H, m), 6.70–6.73 (1H, m), 7.01–7.03 (1H, m), 7.50–7.53 (2H, m), 7.56–7.59 (1H, m), 7.68–7.70 (2H, m), 7.91–7.93 (1H, m), 11.0–12.5 (1H, BS)

MASS (EI method, m/e): 375 (M$^+$)

Elementary Analysis: (as C$_{18}$H$_{17}$NO$_6$S) Calculated values: C: 57.59, H: 4.56, N: 3.73, S: 8.54 Measured values: C: 57.50, H: 4.69, N: 3.87, S: 8.60

WORKING EXAMPLE 3

(1RS, 2RS, 3aSR, 8bRS)-1-benzenesulfonamido-2-hydroxy-2,3,3a,8b-tetrahydro-1H-cyclopenta[b]benzofuran-5-acetic acid methyl ester (40)

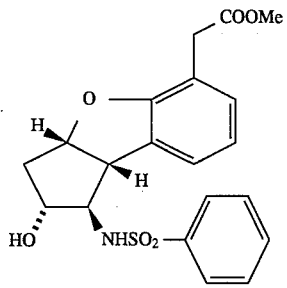
(40)

The target compound (1.01 g) was obtained at a yield of 86% from (1RS, 2RS, 3aSR, 8bRS)-1-azido-2-tetrahydropyranyloxy- 2,3,3a,8b-tetrahydro-1H-cyclopenta [b]benzofuran-5-acetic acid methyl ester (9) (1.08 g) in the same manner as Working Example 1.

M.P.: 183.5°–184.5° C.

IR (KBr method): 3516, 3252, 2976, 2956, 1721, 1599, 1481, 1456, 1437, 1408, 1390, 1365, 1313, 1290, 1274, 1220, 1199, 1178, 1151, 1127, 1096, 1073, 1044, 1011, 965, 926, 876, 861, 830, 793, 756, 719, 690, 623, 584, 559, 518, 422 cm$^{-1}$ NMR (500 MHz, CDCl$_3$, δ): 2.05 (1H, ddd, J=4.3, 6.1, 14.7 Hz), 2.46 (1H, dt, J=6.1, 14.1 Hz), 2.85 (1H, d, J=4.9 Hz), 3.45 (1H, q, J=5.3 Hz), 3.52 (1H, d, J=16.5 Hz), 3.57 (1H, d, J=16.5 Hz), 3.57–3.59 (1H, m), 3.67 (3H, m), 4.01–4.05 (1H, m), 5.12–5.16 (1H, m), 6.66–6.67 (2H, m), 6.93– 6.95 (1H, m), 7.53–7.56 (2H, m), 7.60–7.63 (1H, m), 7.91–7.93 (2H, m)

MASS (EI method, m/e): 403 (M$^+$)

Elementary Analysis: (as C$_{20}$H$_{21}$NO$_6$S) Calculated values: C: 59.54, H: 5.25, N: 3.47, S: 7.95 Measured values: C: 59.57, H: 5.35, N: 3.64, S: 7.96

WORKING EXAMPLE 4

(1RS, 2RS, 3aSR, 8bRS)-1-benzenesulfonamido-2-hydroxy-2,3,3a,8b-tetrahydro-1H-cyclopenta[b]benzofuran-5-acetic acid (41)

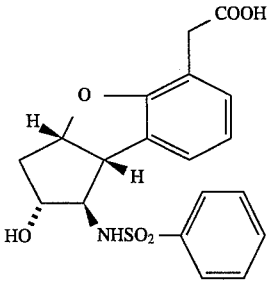
(41)

The target compound (540 mg) was obtained from (1RS, 2RS, 3aSR, 8bRS)-1-benzenesulfonamido-2-hydroxy-2,3, 3a,8b-tetrahydro- 1H-cyclopenta[b]benzofuran-5-acetic acid methyl ester (40) (620 mg) in the same manner as Working Example 2.

M.P.: 165.0°–166.0° C. (recrystallized by ethyl acetate)

IR (KBr method): 3274, 1715, 1597, 1450, 1398, 1309, 1276, 1222, 1166, 1083, 1040, 961, 915, 859, 789,758, 719, 687, 569 cm$^{-1}$ NMR (400 MHz, CDCl$_3$, δ): 1.95–2.01 (1H, m), 2.45 (1H, dt, J=5.8, 14.6 Hz), 2.0–3.0 (1H, bs), 3.39 (1H, q, J=5.4 Hz), 3.47 (1H, d, J=16.6 Hz), 3.52 (1H, d, J=16.6 Hz), 3.69 (1H, dd, J=4.4, 8.8 Hz), 4.03 (1H, q, J=5.8 Hz), 3.0–4.0 (1H, m), 5.16 (1H, ddd, 4.4, 6.8, 8.8 Hz), 6.64 (1H, t, J=7.3 Hz), 6.73 (1H, d, J=7.3 Hz), 6.94 (1H, d, 7.3 Hz), 7.49–7.53 (3H, m), 7.91–7.93 (2H, m)

MASS (EI method, m/e): 389 (M$^+$)

Elementary Analysis: (as $C_{19}H_{19}NO_6S$) Calculated values: C: 58.60, H: 4.92, N: 3.60, S: 8.23 Measured values: C: 58.59, H: 5.07, N: 3.72, S: 8.35

WORKING EXAMPLE 5

(1RS, 2RS, 3aSR, 8bRS)-1-benzenesulfonamido-2-hydroxy-2,3,3a,8b-tetrahydro-1H-cyclopenta[b]benzofuran-5-propionic acid methyl ester (42)

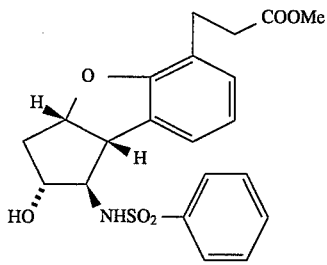
(42)

The target compound (885 mg) was obtained at a yield of 83% from (1RS, 2RS, 3aSR, 8bRS)-1-azido-2-tetrahydropyranyloxy- 2,3,3a,8b-tetrahydro-1H-cyclopenta [b]benzofuran-5-propionic acid methyl ester (13) (0.99 g) in the same manner as Working Example 1.

M.P.: 157.5°–158.5° C.

IR (KBr method): 3520, 3268, 2942, 2904, 1729, 1597, 1450, 1307, 1278, 1201, 1154, 1091, 1062, 1023, 938, 888, 849, 804, 760, 737, 721, 694, 623, 584, 559 cm$^{-1}$ NMR (500 MHz, CDCl$_3$, δ): 2.00–2.06 (1H, m), 2.50–2.63 (3H, m), 2.74 (1H, d, J=3.0 Hz), 2.77–2.87 (2H, m), 3.44 (1H, q, J=5.5 Hz), 3.57 (1H, dd, J=5.5, 9.1 Hz), 3.62 (3H, s), 4.08–4.11 (1H, m), 5.09 (1H, d, J=6.7 Hz), 5.13–5.18 (1H, ddd, 4.9, 7.3, 8.5 Hz), 6.55 (1H, d, J=7.3 Hz), 6.60 (1H, t, J=7.3 Hz), 6.90 (1H, d, J=7.3 Hz), 7.52–7.56 (1H, m), 7.60–7.64 (1H, m), 7.91–7.94 (1H, m)

MASS (EI method, m/e): 417 (M$^+$)

Elementary Analysis: (as $C_{21}H_{23}NO_6S$) Calculated values: C: 60.42, H: 5.55, N: 3.36, S: 7.68 Measured values: C: 60.44, H: 5.58, N: 3.45, S: 7.70

WORKING EXAMPLE 6

(1RS, 2RS, 3aSR, 8bRS)-1-benzenesulfonamido-2-hydroxy-2,3,3a,8b-tetrahydro-1H-cyclopenta[b]benzofuran-5-propionic acid (43)

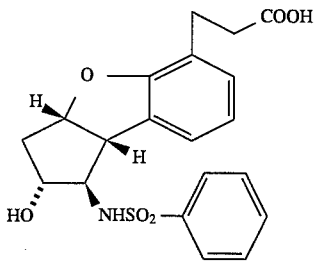
(43)

The target compound (540 mg) was obtained from (1RS, 2RS, 3aSR, 8bRS)-1-benzenesulfonamido-2-hydroxy-2,3, 3a,8b-tetrahydro- 1H-cyclopenta[b]benzofuran-5-propionic acid methyl ester (42) (730 mg) in the same manner as Working Example 2.

M.P.: 150.5°–151.5° C. (recrystallized by ethyl acetate)

IR (KBr method): 3442, 3202, 3062, 2970, 2934, 1698, 1597, 1462, 1421, 1344, 1309, 1249, 1214, 1199, 1172, 1149, 1087, 1069, 1040, 1027, 987, 967, 940, 897, 849, 824, 787, 756, 745, 719, 687, 619, 584, 553, 470, 414 cm$^{-1}$ NMR (500 MHz, CDCl$_3$, δ): 1.95 (1H, ddd, J=4.9, 7.3, 13.4 Hz), 1.8–2.5 (1H, bs), 2.41–2.61 (3H, m), 2.76–2.87 (2H, m), 3.0–3.4 (1H, bs), 3.35 (1H, q, J=5.5 Hz), 3.64 (1H, dd, J=5.6, 9.1 Hz), 4.03–4.07 (1H, m), 5.12 (1H, ddd, 4.9, 6.7, 9.1 Hz), 6.58 (1H, t, J=7.3 Hz), 6.64 (1H, d, J=7.3 Hz), 6.90 (1H, d, J=7.3 Hz), 7.49–7.52 (2H, m), 7.55–7.58 (1H, m), 7.91–7.93 (2H, m)

MASS (EI method, m/e): 403 (M$^+$)

Elementary Analysis: (as $C_{20}H_{21}NO_6S$) Calculated values: C: 59.54, H: 5.25, N: 3.47, S: 7.95 Measured values: C: 59.53, H: 5.23, N: 3.60, S: 7.94

WORKING EXAMPLE 7

(1RS, 2RS, 3aSR, 8bRS)-1-benzenesulfonamido-2-hydroxy-2,3,3a,8b-tetrahydro-1H-cyclopenta[b]-benzofuran-5-butyric acid methyl ester (44)

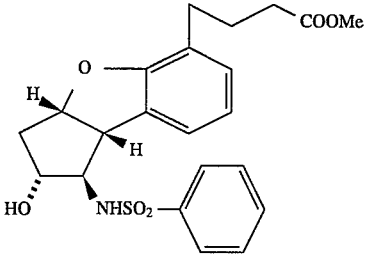
(44)

The target compound (570 mg) was obtained at a yield of 77% from (1RS, 2RS, 3aSR, 8bRS)-1-azido-2-tetrahydropyranyloxy- 2,3,3a,8b-tetrahydro-1H-cyclopenta [b]benzofuran-5-butyric acid methyl ester (15) (685 mg) in the same manner as Working Example 1.

M.P.: 113.0°–114.0° C.

IR (KBr method): 3442, 3200, 1742, 1595, 1452, 1344, 1309, 1265, 1193, 1168, 1100, 1067, 1035, 940, 903, 843, 824, 785, 758, 745, 719, 690, 619, 580, 561 cm$^{-1}$ NMR (400 MHz, CDCl$_3$, δ): 1.80–1.97 (2H, m), 2.01–2.07 (1H, m), 2.18–2.30 (2H, m), 2.49–2.82 (3H, m), 2.84 (1H, d, J=3.5 Hz), 3.45 (1H, q, J=5.3 Hz), 3.57 (1H, dd, 5.3, 8.8 Hz), 3.63 (3H, s), 4.07–4.12 (1H, m), 5.00 (1H, d, J=6.9 Hz), 5.14 (1H, ddd, J=4.4, 7.3, 8.8 Hz), 6.53 (1H, d, J=7.3 Hz), 6.60 (1H, t, J=7.3 Hz), 6.88 (1H, d, J=7.3 Hz), 7.52–7.57 (1H, m), 7.60–7.65 (1H, m), 7.91–7.94 (1H, m)

MASS (EI method, m/e): 431 (M$^+$)

Elementary Analysis: (as $C_{22}H_{25}NO_6S$) Calculated values: C: 61.24, H: 5.84, N: 3.25, S: 7.43 Measured values: C: 61.12, H: 5.92, N: 3.41, S: 7.56

WORKING EXAMPLE 8

(1RS, 2RS, 3aSR, 8bRS)-1-benzenesulfonamido-2-hydroxy-2,3,3a,8b-tetrahydro-1H-cyclopenta[b]benzofuran-5-butyric acid (45)

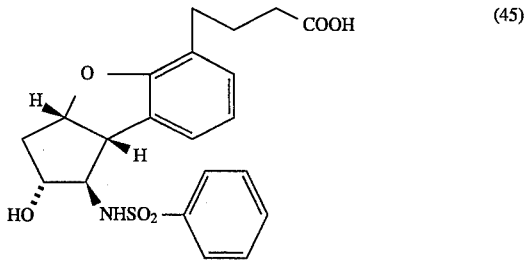

The target compound (360 mg) was obtained from (1RS, 2RS, 3aSR, 8bRS)-1-benzenesulfonamido-2-hydroxy-2,3, 3a,8b-tetrahydro- 1H-cyclopenta[b]-benzofuran-5-butyric acid methyl ester (44) (30 mg) in the same manner as Working Example 2.

M.P.: 145.0°–146.0° C. (recrystallized by ethyl acetate)

IR (KBr method): 3333, 2938, 2640, 1715, 1593, 1452, 1398, 1334, 1261, 1191, 1149, 1125, 1085, 1085, 1025, 922, 866, 799, 758, 717, 688, 594, 576, 553, 478, 499 cm$^{-1}$ NMR (400 MHz, CDCl$_3$, δ): 1.76–2.02 (4H, m), 2.15–2.28 (2H, m), 2.40–2.59 (1H, m), 3.37 (1H, q, J=5.4 Hz), 3.65 (1H, dd, J=4.8, 9.2 Hz), 4.04–4.09 (1H, m), 5.12 (1H, ddd, J=4.9, 6.8, 8.8 Hz), 6.57–6.64 (2H, m), 6.85–6.87 (1H, m), 7.45–7.59 (4H, m), 7.91–7.94 (2H, m)

MASS (EI method, m/e): 417 (M$^+$)

WORKING EXAMPLE 9

(1RS, 2RS, 3aSR, 8bRS)-1-benzenesulfonamido-2-hydroxy-2,3,3a,8b-tetrahydro-1H-cyclopenta[b]benzofuran-5-yloxyacetic acid methyl ester (46)

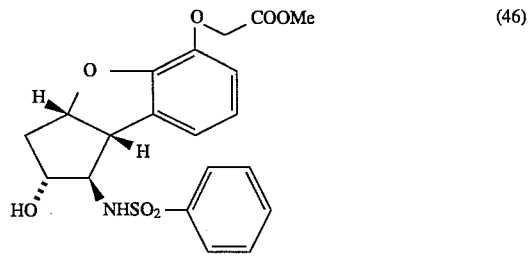

(1RS, 2RS, 3aSR, 8bRS)-1-azido-7-bromo-2-tetrahydropyranyloxy- 2,3,3a,8b-tetrahydro-1H-cyclopenta[b]benzofuran-5-yloxyacetic acid methyl ester (22) (1.64 g) was dissolved in methanol. (25 ml) followed by the addition of sodium acetate (561 mg) and 10% palladium activated carbon (250 mg) and stirring for 15 hours at room temperature in a hydrogen atmosphere. Triethylamine (1.4 ml) was added to the reaction mixture followed by filtration and concentration. Water (50 ml) was added to the residue followed by extraction with methylene chloride (100 ml×3). The organic layers were combined and washed with saturated brine (50 ml) followed by concentration after drying with magnesium sulfate. The residue was dissolved in pyridine (15 ml) followed by the addition of benzenesulfonyl chloride (1.31 ml) and stirring for 1 hour at room temperature. Methylene chloride (120 ml) was added to the reaction solution followed by addition of 3N hydrochloric acid (70 ml) to separate. The aqueous phase was re-extracted with methylene chloride (70 ml), combined with the organic phase, washed with a saturated aqueous solution of sodium hydrogencarbonate (50 ml), water (30 ml) and saturated brine (50 ml) followed by concentration after drying with anhydrous magnesium sulfate. The residue was dissolved in methanol (80 ml) followed by the addition of a catalytic amount of p-toluenesulfonic acid and stirring for 2 hours at room temperature. A saturated aqueous solution of sodium hydrogencarbonate (50 ml) and water (80 ml) were added to the reaction mixture followed by extraction with methylene chloride (100 ml, 80 ml×2). The organic layers were combined, washed with water (80 ml) and saturated brine (50 ml) followed by concentration after drying with magnesium sulfate. The resulting residue was then purified with column chromatography (silica gel: methylene chloride/acetonitrile 20/1–5/1) to obtain the target compound (1.13 g) at a yield of 79%.

M.P.: 149°–149.5° C. (recrystallized from ethyl acetate)

IR (KBr method): 3460, 3220, 3020, 1750, 1620, 1600, 1490, 1440, 1390, 1340, 1310, 1290, 1220, 1200, 1160, 1150, 1110, 1060, 1030, 1010, 930, 890, 750, 740, 720, 680, 580, 560 cm$^{-1}$ NMR (400 MHz, CDCl$_3$, δ): 2.10 (1H, ddd, J=4.7, 7.1, 14.8 Hz), 2.53 (1H, dt, J=6.7, 14.8 Hz), 2.55–2.65 (1H, m), 3.47 (1H, q, J=5.9 Hz), 3.58 (1H, dd, J=5.9 Hz, 8.8 Hz), 3.76 (3H, s), 4.05–4.15 (1H, m), 4.66 (1H, d, J=16.2 Hz), 4.68 (1H, d, J=16.2 Hz), 4.82 (1H, d, J=5.9 Hz), 5.21 (1H, ddd, J=4.7, 6.7, 8.8 Hz), 6.35–6.45 (1H, m), 6.62 (1H, t, J=7.8 Hz), 6.65–6.75 (1H, m), 7.5–7.7 (3H, m), 7.85–7.95 (2H, m)

MASS (EI method, m/e): 419 (M$^+$)

Elementary Analysis: (as C$_{20}$H$_{21}$NO$_7$S) Calculated values: C: 57.27, H: 5.05, N: 3.34, S: 7.64 Measured values: C: 57.23, H: 5.05, N: 3.44, S: 7.73

WORKING EXAMPLE 10

(1RS, 2RS, 3aSR, 8bRS)-1-benzenesulfonamido-2-hydroxy-2,3,3a,8b-tetrahydro-1H-cyclopenta[b]benzofuran-5-yloxyacetic acid (47)

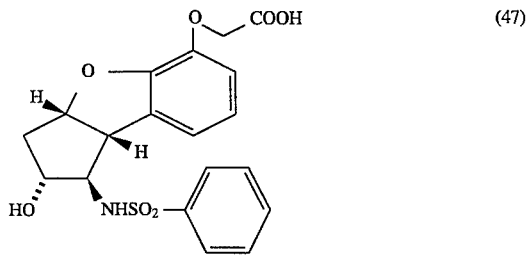

The target compound (1.56 g) was obtained from (1RS, 2RS, 3aSR, 8bRS)-1-benzenesulfonamido-2-hydroxy-2,3, 3a,8b-tetrahydro- 1H-cyclopenta[b]benzofuran-5-yloxyacetic acid methyl ester (1.83 g) in the same manner as Working Example 2.

M.P.: 195°–196° C. (recrystallized from ethyl acetate)

IR (KBr method): 3490, 3160, 2900, 1720, 1620, 1590, 1480, 1460, 1430, 1330, 1310, 1290, 1270, 1200, 1150, 1120, 1090, 1060, 970, 940, 900, 770, 760, 720, 690, 620, 600, 560 cm$^{-1}$ NMR (400 MHz, CDCl$_3$,+DMSO-d$_6$, δ): 2.03 (1H, ddd, J=4.8, 7.3, 13.8 Hz), 2.48 (1H, dt, J=6.8, 13.8 Hz), 3.39 (1H, q, J=4.9 Hz), 3.68 (1H, dd, J=4.9, 8.9 Hz), 4.0–4.1 (1H, m), 4.59 (1H, d, J=16.4 Hz), 4.61 (1H, d, J=16.4 Hz), 5.21 (1H, ddd, J=4.8, 6.8, 8.9 Hz), 6.45–6.55 (1H, m), 6.60 (1H, t, J=7.6 Hz), 6.65–6.70 (1H, m), 7.45–7.65 (4H, m), 7.9–7.95 (2H, m)

MASS (EI method, m/e): 405 (M$^+$)

Elementary Analysis: (as $C_{19}H_{19}NO_7S$) Calculated values: C: 56.29, H: 4.72, N: 3.45, S: 7.91 Measured values: C: 56.24, H: 4.75, N: 3.61, S: 8.05

WORKING EXAMPLE 11

(1RS, 2RS, 3aSR, 8bRS)-1-(p-toluenesulfonamido)-2-hydroxy- 2,3,3a,8b-tetrahydro-1H-cyclopenta[b]benzofuran-5-yloxyacetic acid methyl ester (48)

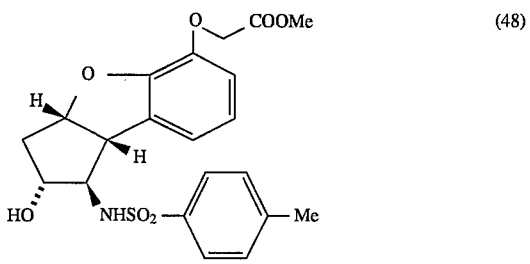

The target compound (425 mg) was obtained in the same manner as Working Example 9 from (1RS, 2RS, 3aSR, 8bRS)-1azido- 7-bromo-2-tetrahydropyranyloxy-2,3,3a,8b-tetrahydro-1H-cyclopenta[b]benzofuran-5-yloxyacetic acid methyl ester (22) (625 mg) with the exception of using p-toluenesulfonyl chloride (771 mg) instead of benzenesulfonyl chloride.

M.P.: 131.5°–132.5° C. (recrystallized by ethyl acetate/n-hexane)

IR (KBr method): 3430, 3188, 1734, 1597, 1495, 1470, 1435, 1350, 1307, 1288, 1267, 1203, 1193, 1166, 1149, 1108, 1087, 1064, 1033, 1006, 940, 895, 864, 818, 760, 725, 663, 559, 547 cm$^{-1}$ NMR (500MHz, CDCl$_3$, δ): 2.09 (1H, ddd, J=4.8, 7.0, 14.7 Hz), 2.44 (3H, s), 2.52 (1H, dt, J=7.0, 14.7 Hz), 2.73 (1H, d, J=3.7 Hz), 3.42 (1H, q, J=5.8 Hz), 3.59 (1H, dd, J=5.8, 9.1 Hz), 3.77 (3H, s), 4.05–4.1 (1H, m), 4.67 (1H, d, J=15.9 Hz), 4.68 (1H, d, J=15.9 Hz), 5.09 (1H, d, J=5.8 Hz), 5.20 (1H, ddd, J=4.8, 7.0, 9.1 Hz), 6.43 (1H, d, J=7.3 Hz), 6.62 (1H, t, J=7.3 Hz), 6.67 (1H, d, J=7.3 Hz), 7.32 (2H, d, J=8.3 Hz), 7.79 (2H, d, J=8.3 Hz)

MASS (EI method, m/e): 433 (M$^+$)

Elementary Analysis: (as $C_{21}H_{23}NO_7S$) Calculated values: C: 58.19, H: 5.35, N: 3.23, S: 7.40 Measured values: C: 58.18, H: 5.37, N: 3.16, S: 7.44

WORKING EXAMPLE 12

(1RS, 2RS, 3aSR, 8bRS)-1-(p-toluenesulfonamido)-2-hydroxy- 2,3,3a,8b-tetrahydro-1H-cyclopenta[b]benzofuran-5-yloxyacetatic acid (49)

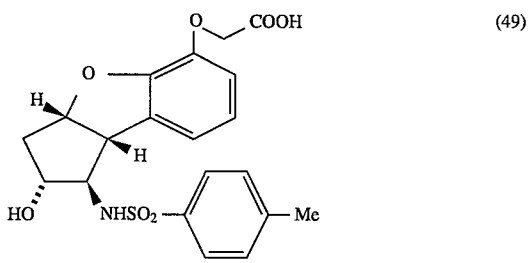

The target compound (183 mg) was obtained from (1RS, 2RS, 3aSR, 8bRS)-1-(p-toluenesulfonamido)-2-hydroxy-2,3,3a,8b-tetrahydro-1H-cyclopenta[b]benzofuran-5-yloxyacetic acid methyl ester (48) (235 mg) in the same manner as Working Example 2.

M.P.: 201°–202° C. (recrystallized by ethyl acetate/methanol/n-hexane)

IR (KBr method): 3500, 3196, 2924, 1723, 1624, 1599, 1491, 1462, 1435, 1334, 1305, 1274, 1199, 1160, 1118, 1098, 1064, 973, 938, 897, 814, 727, 708, 671, 567, 530 cm$^{-1}$ NMR (500 MHz, DMSO-d$_6$, δ): 2.02 (1H, ddd, J=4.9, 7.3, 14.0 Hz), 2.4–2.5 (1H, m), 2.42 (3H, s), 3.3–3.4 (1H, m), 3.68 (1H, dd, J=4.9, 9.2 Hz), 4.0–4.1 (1H, m), 4.59 (1H, d, J=16.5 Hz), 4.61 (1H, d, J=16.5 Hz), 5.15–5.25 (1H, m), 6.53 (1H, d, J=7.6 Hz), 6.60 (1H, t, J=7.6 Hz), 6.65 (1H, d, J=7.6 Hz), 7.30 (2H, d, J=8.3 Hz), 7.4–7.6 (1H, m), 7.79 (2H, d, J=8.3 Hz)

MASS (EI method, m/e): 419 (M$^+$)

Elementary Analysis: (as $C_{20}H_{21}NO_7S$) Calculated values: C: 57.27, H: 5.05, N: 3.34, S: 7.64 Measured values: C: 57.51, H: 5.12, N: 3.22, S: 7.65

WORKING EXAMPLE 13

(1RS, 2RS, 3aSR, 8bRS)-1-(p-methoxybenzenesulfonamido)- 2-hydroxy-2,3,3a,8b-tetrahydro-1H-cyclopenta[b]benzofuran-5-yloxyacetic acid methyl ester (50)

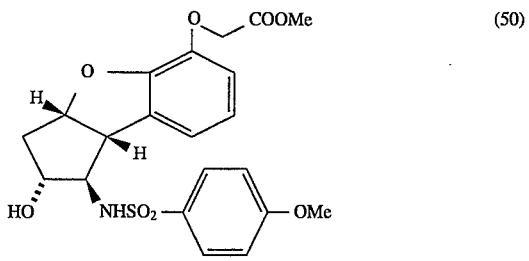

The target compound (395 mg) was obtained in the same manner as Working Example 9 from (1RS, 2RS, 3aSR, 8bRS)-1-azido- 7-bromo-2-tetrahydropyranyloxy-2,3,3a, 8b-tetrahydro-1H-cyclopenta[b]benzofuran-5-yloxyacetic acid methyl ester (22) (620 mg) with the exception of using p-methoxybenzenesulfonyl chloride (818 mg) instead of benzenesulfonyl chloride.

M.P.: 147°–148° C. (recrystallized by ethyl acetate/n-hexane)

IR (KBr method): 3534, 3274, 1742, 1597, 1495, 1468, 1446, 1299, 1265, 1203, 1154, 1106, 1067, 1025, 936, 895, 835, 725, 669, 563 cm$^{-1}$ NMR (500 MHz, CDCl$_3$, δ): 2.08 (1H, ddd, J=4.9, 7.3, 14.7 Hz), 2.54 (1H, dt, J=7.1, 14.7 Hz), 2.78 (1H, d, J=5.5 Hz), 3.35–3.45 (1H, m), 3.58 (1H, dd, J=5.5, 8.9 Hz), 3.77 (3H, s), 3.88 (3H, s), 4.05–4.15 (1H, m), 4.67 (1H, d, J=16.1 Hz), 4.69 (1H, d, J=16.1 Hz), 5.05 (1H, br.d, J=6 Hz), 5.20 (1H, ddd, J=4.9, 7.1, 8.9 Hz), 6.46 (1H, d, J=7.3 Hz), 6.6–6.7 (2H, m), 6.98 (2H, d, J=9.2 Hz), 7.84 (2H, d, J=9.2 Hz)

MASS (EI method, m/e): 449 (M$^+$)

Elementary Analysis: (as $C_{21}H_{23}NO_8S$) Calculated values: C: 56.12, H: 5.16, N: 3.12, S: 7.13 Measured values: C: 56.47, H: 5.15, N: 3.29, S: 7.20

WORKING EXAMPLE 14

(1RS, 2RS, 3aSR, 8bRS)-1-(p-methoxybenzenesulfonamido)- 2-hydroxy-2,3,3a,8b-tetrahydro-1H-cyclopenta[b]benzofuran-5-yloxyacetic acid (51)

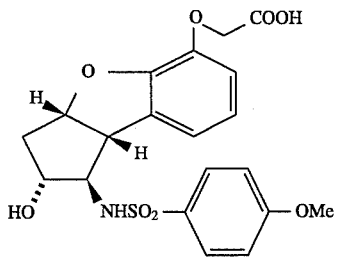

The target compound (198 mg) was obtained from (1RS, 2RS, 3aSR, 8bRS)-1-(p-methoxybenzenesulfonamido)-2-hydroxy- 2,3,3a,8b-tetrahydro-1H-cyclopenta[b]benzofuran-5-yloxyacetic acid methyl ester (50) (276 mg) in the same manner as Working Example 2.

M.P.: 195°–196° C. (recrystallized by methanol/ethyl acetate/n-hexane)

IR (KBr method): 3480, 3182, 1725, 1626, 1599, 1491, 1460, 1435, 1330, 1299, 1263, 1197, 1154, 1118, 1100, 1067, 1031, 975, 938, 901, 837, 804, 770, 727, 700, 669, 574 cm$^{-1}$ NMR (500 MHz, DMSO-d$_6$, δ): 1.85–2.0 (1H, m), 2.2–2.25 (1H, m), 3.55–3.6 (1H, m), 3.84 (3H, s), 3.9–3.95 (1H, m), 4.56 (1H, d, J=16.5 Hz), 4.57 (1H, d, J=16.5 Hz), 4.6–4.65 (1H, m), 5.15–5.25 (1H, m), 6.4–6.45 (1H, m), 6.6–6.65 (1H, m), 7.15 (2H, d, J=9.2 Hz), 7.75–7.85 (3H, m)

MASS (EI method, m/e): 435 (M$^+$)

Elementary Analysis: (as C$_{20}$H$_{21}$NO$_8$S) Calculated values: C: 55.17, H: 4.86, N: 3.22, S: 7.36 Measured values: C: 55.21, H: 4.88, N: 3.24, S: 7.35

WORKING EXAMPLE 15

(1RS, 2RS, 3aSR, 8bRS)-1-(p-fluorobenzenesulfonamido)- 2-hydroxy-2,3,3a,8b-tetrahydro-1H-cyclopenta[b]benzofuran-5-yloxyacetic acid methyl ester (52)

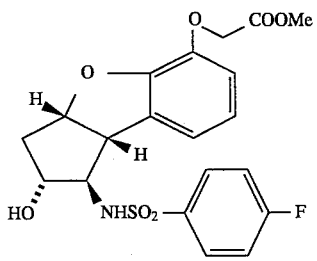

The target compound (363 mg) was obtained in the same manner as Working Example 9 from (1RS, 2RS, 3aSR, 8bRS)-1-azido- 7-bromo-2-tetrahydropyranyloxy-2,3,3a, 8b-tetrahydro-1H-cyclopenta[b]benzofuran-5-yloxyacetate methyl ester (22) (616 mg) with the exception of using p-fluorobenzenesulfonyl chloride (771 mg) instead of benzenesulfonyl chloride.

M.P.: 118°–119° C. (recrystallized by ethyl acetate/n-hexane)

IR (KBr method): 3530, 3270, 1738, 1622, 1595, 1493, 1468, 1444, 1332, 1296, 1282, 1265, 1238, 1201, 1170, 1158, 1108, 1075, 1013, 938, 901, 839, 762, 727, 669, 547 cm$^{-1}$ NMR (500 MHz, CDCl$_3$, δ): 2.10 (1H, ddd, J=4.9, 7.3, 14.7 HZ), 2.54 (1H, dt, J=7.0, 14.7 Hz), 2.7–2.75 (1H, br.s), 3.43 (1H, q, J=5.8 Hz), 3.57 (1H, dd, J=5.8, 8.9 Hz), 3.77 (3H, s), 4.05–4.1 (1H, m), 4.67 (1H, d, J=16.5 Hz), 4.69 (1H, d, J=16.5 Hz), 5.1–5.15 (1H, m), 5.20 (1H, ddd, J=4.9, 7.0, 8.9 Hz), 6.44 (1H, d, J=6.7 Hz), 6.6–6.7 (2H, m), 7.15–7.25 (2H, m), 7.9–7.95 (2H, m)

MASS (EI method, m/e): 437 (M$^+$)

Elementary Analysis: (as C$_{20}$H$_{20}$FNO$_7$S) Calculated values: C: 54.92, H: 4.61, N: 3.20, S: 7.33 Measured values: C: 55.11, H: 4.64, N: 3.11, S: 7.41

WORKING EXAMPLE 16

(1RS, 2RS, 3aSR, 8bRS)-1-(p-fluorobenzenesulfonamido)- 2-hydroxy-2,3,3a,8b-tetrahydro-1H-cyclopenta[b]benzofuran-5-yloxyacetic acid (53)

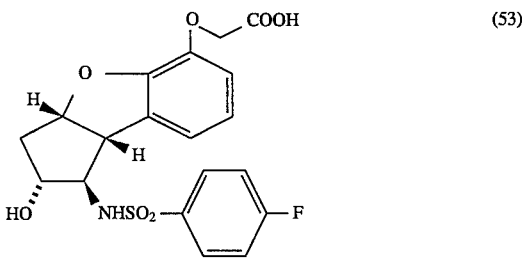

The target compound (200 mg) was obtained from (1RS, 2RS, 3aSR, 8bRS)-1-(p-fluorobenzenesulfonamido)-2-hydroxy-2,3,3a,8b-tetrahydro-1H-cyclopenta[b]benzofuran-5-yloxyacetic acid methyl ester (52) (280 mg) in the same manner as Working Example 2.

M.P.: 222°–223° C. (recrystallized by methanol/ethyl acetate/n-hexane)

IR (KBr method): 3496, 3186, 1725, 1595, 1491, 1462, 1435, 1334, 1294, 1276, 1238, 1199, 1166, 1154, 1120, 1096, 1065, 975, 938, 899, 843, 727, 673, 567, 542, 530 cm$^{-1}$ NMR (500 MHz, DMSO-d$_6$, δ) : 2.0–2.1 (1H, m), 2.4–2.5 (1H, m), 3.35–3.45 (1H, m), 3.68 (1H, dd, J=4.9, 9.1 Hz), 4.0–4.1 (1H, m), 4.59 (1H, d, J=16.5 Hz), 4.60 (1H, d, J=16.5 Hz), 5.21 (1H, ddd, J=4.3, 7.3, 9.1 Hz), 6.55–6.7 (3H, m), 7.15–7.25 (2H, m), 7.78 (1H, d, J=6.7 Hz), 7.9–8.0 (2H, m)

MASS (EI method, m/e): 423 (M$^+$)

Elementary Analysis: (as C$_{19}$H$_{18}$FN$_7$OS) Calculated values: C: 53.90, H: 4.28, N: 3.31, S: 7.57 Measured values: C: 53.96, H: 4.25, N: 3.08, S: 7.66

WORKING EXAMPLE 17

(1RS, 2RS, 3aSR, 8bRS)-1-(p-chlorobenzenesulfonamido)-2-hydroxy-2,3,3a,8b-tetrahydro-1H-cyclopenta[b]benzofuran-5-yloxyacetic acid methyl ester (54)

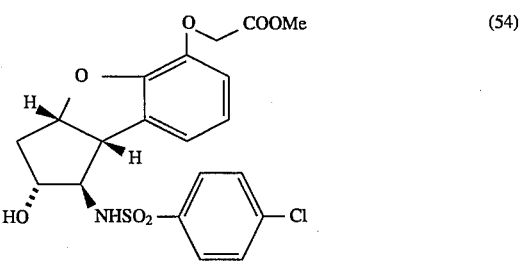

The target compound (400 mg) was obtained in the same manner as Working Example 9 from (1RS, 2RS, 3aSR, 8bRS)-1-azide- 7-bromo-2-tetrahydropyranyloxy-2,3,3a,8b-tetrahydro-1H-cyclopenta[b]benzofuran-5-yloxyacetic acid methyl ester (22) (609 mg) with the exception of using p-chlorobenzenesulfonyl chloride (823 mg) instead of benzenesulfonyl chloride.

M.P.: 128°–129° C. (recrystallized by ethyl acetate/n-hexane)

IR (KBr method): 3570, 3534, 3330, 1760, 1620, 1597, 1491, 1468, 1437, 1396, 1379, 1338, 1282, 1226, 1193, 1162, 1110, 1029, 1015, 973, 955, 924, 861, 837, 766, 752, 729, 611, 559, 482 cm$^{-1}$ NMR (500 MHz, CDCl$_3$, δ): 2.09 (1H, ddd, J=4.9, 7.3, 14.7 Hz), 3.54 (1H, dt, J=6.9, 14.7 Hz), 2.7 (1H, br.s,), 3.4–3.45 (1H, m), 3.55–3.6 (1H, m), 3.78 (3H, s), 4.0–4.1 (1H, m), 4.68 (1H, d, J=16.5 Hz), 4.69 (1H, d, J=16.5 Hz), 5.1–5.25 (2H, m), 6.41 (1H, d, J=7.3 Hz), 6.6–6.75 (2H, m), 7.49 (2H, d, J=8.9 Hz), 7.83 (2H, d, J=8.9 Hz)

MASS (EI method, m/e): 453 (M$^+$)

Elementary Analysis: (as C$_{20}$H$_{20}$ClNO$_7$S) Calculated values: C: 52.91, H: 4.44, N: 3.09, S: 7.06 Measured values: C: 53.01, H: 4.57, N: 3.17, S: 7.32

WORKING EXAMPLE 18

(1RS, 2RS, 3aSR, 8bRS)-1-(p-chlorobenzenesulfonamido)-2-hydroxy-2,3,3a,8b-tetrahydro-1H-cyclopenta[b]benzofuran-5-yloxy acetic acid (55)

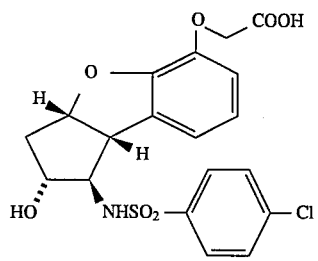

(55)

The target compound (221 mg) was obtained from (1RS, 2RS, 3aSR, 8bRS)-1-(p-chlorobenzenesulfonamido)-2-hydroxy-2,3,3a,8b-tetrahydro-1H-cyclopenta[b]benzofuran-5-yloxyacetic acid methyl ester (54) (304 mg) in the same manner as Working Example 2.

M.P.: 219°–220° C. (recrystallized by methanol/ethyl acetate/n-hexane)

IR (KBr method): 3494, 3184, 1723, 1620, 1595, 1491, 1462, 1435, 1336, 1276, 1199, 1162, 1118, 1096, 1065, 973, 938, 899, 822, 758, 729, 638, 557, 542 cm$^{-1}$ NMR (500 MHz, DMSO-d$_6$, δ): 1.8–1.9 (1H, m), 2.2–2.3 (1H, m), 3.55–3.6 (1H, m), 3.85–3.9 (1H, m), 4.58 (2H, s), 4.65–4.7 (1H, m), 5.15–5.2 (1H, m), 6.45–6.5 (1H, m), 6.6–6.65 (2H, m), 7.70 (2H, d, J=8.5 Hz), 7.87 (2H, d, J=8.5 Hz), 8.12 (1H, d, J=7.3 Hz)

MASS (EI method, m/e): 439 (M$^+$)

Elementary Analysis: (as C$_{19}$H$_{18}$ClNO$_7$S) Calculated values: C: 51.88, H: 4.12, N: 3.18, S: 7.29 Measured values: C: 51.82, H: 4.18, N: 3.23, S: 7.45

WORKING EXAMPLE 19

(1RS, 2RS, 3aSR, 8bRS)-1-(m-chlorobenzenesulfonamido)-2-hydroxy-2,3,3a,8b-tetrahydro-1H-cyclopenta[b]benzofuran- 5-yloxyacetic acid methyl ester (56)

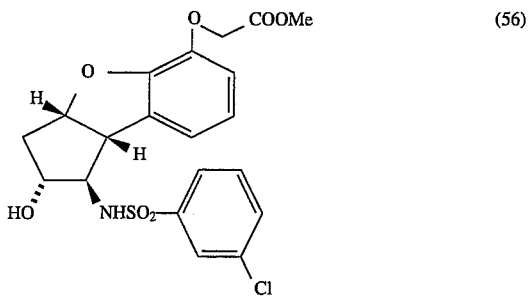

(56)

The target compound (455 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta[b]benzofuran-5-yloxyacetic acid methyl ester (24) (436 mg) with the exception of using m-chlorobenzenesulfonyl chloride (473 mg) instead of benzenesulfonyl chloride.

M.P.: 110.0°–110.5° C. IR (KBr method): 3496, 3152, 2914, 1740, 1622, 1597, 1491, 1468, 1435, 1419, 1325, 1294, 1232, 1199, 1160, 1108, 1067, 1027, 1002, 975, 938, 895, 857, 843, 785, 766, 725, 681, 671, 619, 596, 555, 536, 499, 416 cm$^{-1}$ NMR (400 MHz, CDCl$_3$, δ): 2.06–2.13 (1H, m), 2.49–2.56 (1H, m), 2.66 (1H, d, J=3.9 Hz), 3.43–3.49 (1H, m), 3.55–3.59 (1H, m), 3.77 (3H, s), 4.04–4.10 (1H, m), 4.68 (2H, s), 5.17–5.22 (1H, m), 5.24 (1H, d, J=7.3 Hz), 6.45–6.47 (1H, m), 6.63–6.68 (2H, m), 7.44–7.48 (1H, m), 7.56–7.58 (1H, m), 7.77–7.79 (1H, m), 7.89–7.90 (1H, m)

MASS (EI method, m/e): 453 (M$^+$)

Elementary Analysis: (as C$_{20}$H$_{20}$ClNO$_7$S) Calculated values: C: 52.92, H: 4.44, N: 3.09, S: 7.06, Cl: 7.81 Measured values: C: 52.66, H: 4.46, N: 3.13, S: 7.29, Cl: 7.79

WORKING EXAMPLE 20

(1RS, 2RS, 3aSR, 8bRS)-1-(m-chlorobenzenesulfonamido)-2-hydroxy-2,3,3a,8b-tetrahydro-1H-cyclopenta[b]benzofuran-5-yloxyacetic acid (57)

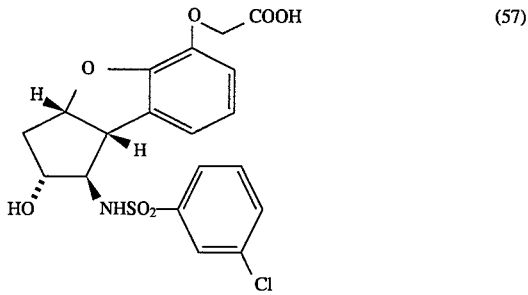

(57)

The target compound (230 mg) was obtained from (1RS, 2RS, 3aSR, 8bRS)-1(m-chlorobenzenesulfonamido)-2-hydroxy-2,3,3a,8b-tetrahydro-1H-cyclopenta[b]benzofuran-5-yloxyacetic acid methyl ester (56) (298 mg) in the same manner as Working Example 2.

M.P.: 219.0–°220.0° C. (recrystallized by ethyl acetate)

IR (KBr method): 3488, 3178, 2898, 2598, 1723, 1657, 1626, 1597, 1578, 1562, 1543, 1491, 1464, 1435, 1359, 1336, 1296, 1276, 1199, 1162, 1118, 1067, 1040, 1009, 975, 938, 901, 843, 787, 772, 727, 700, 679, 671, 644, 619, 598, 574, 534, 501, 466, 445, 433, 422 cm$^{-1}$ NMR (400 MHz, CDCl$_3$, δ): 2.00–2.06 (1H, m), 2.38–2.45 (1H, m), 3.43–3.47 (1H, m), 3.65–3.68 (1H, m), 4.00–4.04 (1H, m), 2.8–4.0 (2H, bs), 4.59 (2H, s), 5.19–5.23 (1H, m), 6.58–6.67 (3H, m), 7.45–7.49 (1H, m), 7.53–7.55 (1H, m), 7.80–7.83 (1H, m), 7.90–7.93 (2H, m)

MASS (EI method, m/e): 439 (M$^+$)

WORKING EXAMPLE 21

(1RS, 2RS, 3aSR, 8bRS)-1-(o-chlorobenzene-sulfonamido)- 2-hydroxy-2,3,3a,8b-tetrahydro-1-cyclopenta[b]benzofuran-5-yloxyacetic acid methyl ester (58)

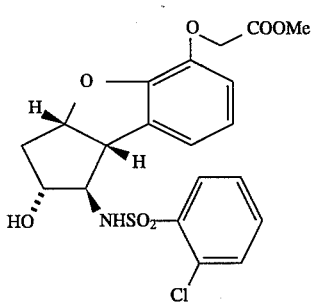
(58)

The target compound (438 mg) was obtained in the same manner as Working Example 1 from (1RS, 2RS, 3aSR, 8bRS)-1azido- 2-tetrahydropyranyloxy-2,3,3a,8b-tetrahydro-1H-cyclopenta[b]benzofuran-5-yloxyacetic acid methyl ester (24) (412 mg) with the exception of using o-chlorobenzenesulfonyl chloride (447 mg) instead of benzenesulfonyl chloride.

M.P.: 139.0°–140.0° C.

IR (KBr method): 3528, 3268, 3192, 2988, 2962, 1748, 1601, 1576, 1487, 1448, 1392, 1325, 1247, 1193, 1168, 1096, 1040, 961, 938, 899, 862, 760, 710, 665, 586, 567, 474 cm$^{-1}$ NMR (400 MHz, CDCl$_3$, δ): 2.04–2.15 (1H, m), 2.40 (1H, d, J=4.5 Hz), 2.47–2.54 (1H, m), 3.40–3.44 (1H, m), 3.68–3.71 (1H, m), 3.75 (3H, s), 4.11–4.15 (1H, m), 4.64 (1H, d, J=16.6 Hz), 4.69 (1H, d, J=16.6 Hz), 5.25–5.30 (1H, m), 5.38 (1H, d, J=6.4 Hz), 6.50–6.53 (1H, m), 6.62–6.68 (2H, m), 7.42–7.46 (1H, m), 7.54–7.60 (2H, m), 8.11–8.13 (1H, m)

MASS (EI method, m/e):453 (M$^+$)

Elementary Analysis: (as C$_{20}$H$_{20}$NO$_7$S) Calculated values: C: 52.92, H: 4.44, N: 3.09, S: 7.06, Cl: 7.81 Measured values: C: 52.92, H: 4.46, N: 2.99, S: 7.15, Cl: 7.71

WORKING EXAMPLE 22

(1RS, 2RS, 3aSR, 8bRS)-1-(o-chlorobenzene-sulfonamido)-2-hydroxy-2,3,3a,8b-tetrahydro-1-cyclopenta[b]benzofuran-5-yloxyacetic acid (59)

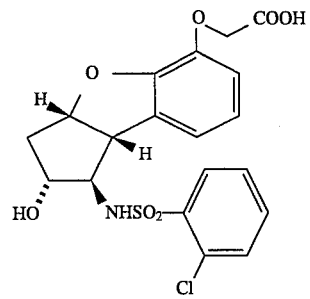
(59)

The target compound (285 mg) was obtained from (1RS, 2RS, 3aSR, 8bRS)-1-(o-chlorobenzenesulfonamido)-2-hydroxy-2,3,3a,8b-tetrahydro-1-cyclopenta[b]benzofuran-5-yloxyacetic acid methyl ester (58) (324 mg) in the same manner as Working Example 2.

M.P.: 210.5°–212.0° C. (recrystallized by ethyl acetate)
IR (KBr method): 3502, 1727, 1626, 1597, 1491, 1460, 1435, 1336, 1263, 1197, 1166, 1116, 1071, 1046, 938, 903, 843, 756, 727, 710, 667, 588, 559, 472, 439 cm$^{-1}$ NMR (400 MHz, CDCl$_3$, δ): 2.02–2.08 (1H, m), 2.46–2.53 (1H, m), 2.4–3.2 (2H, bs), 3.41–3.45 (1H, m), 3.72–3.76 (1H, m), 4.06–4.10 (1H, m), 4.58 (1H, d, J=16.4 Hz), 4.62 (1H, d, J=16.4 Hz), 5.21–5.26 (1H, m), 6.49–6.51 (1H, m), 6.58–6.66 (2H, m), 7.31–7.34 (1H, m), 7.38–7.42 (1H, m), 7.49–7.57 (2H, m), 8.09–8.12 (1H, m) MASS (EI method, m/e): 439 (M$^+$)

WORKING EXAMPLE 23

(1RS, 2RS, 3aSR, 8bRS)-1-(p-bromobenzene-sulfonamido)-2-hydroxy-2,3,3a,8b-tetrahydro-1H-cyclopenta[b]benzofuran-5-yloxyacetic acid methyl ester (60)

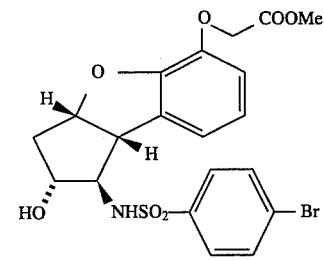
(60)

The target compound (350 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta[b]benzofuran-5-yloxyacetic acid methyl ester (24) (480 mg) with the exception of using p-bromobenzenesulfonyl chloride (361mg) instead of benzenesulfonyl chloride.

IR (liquid film method): 3280, 1736, 1624, 1576, 1560, 1543, 1491, 1460, 1392, 1218, 1193, 1164, 1093, 1069, cfd1011, 824, 756 cm$^{-1}$ IR (400 MHz, CDCl$_3$, δ): 2.05–2.1 (1H, m), 2.4–2.5 (1H, m), 2.7 (1H, bs), 3.42 (1H, q, J=6.3 Hz), 3.5–3.6 (1H, m), 3 78 (3H, s), 4.0–4.15 (1H, m), 4.68 (2H, s), 5.1–5.2 (1H, m), 5.25 (1H, d, J=6.8 Hz), 6.3–6.4 (1H, m), 6.6–6.7 (2H, m), 7.64–7.67 (2H, m), 7.74–7.76 (2H, m)

MASS (EI method, m/e): 497 (M+)

WORKING EXAMPLE 24

(1RS, 2RS, 3aSR, 8bRS)-1-(p-bromobenzenesulfonamido)-2-hydroxy-2,3,3a,8b-tetrahydro-1H-cyclopenta[b]benzofuran-5-yloxyacetic acid (61)

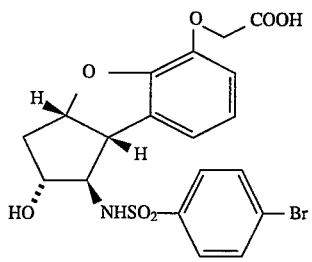

(61)

The target compound (108 mg) was obtained from (1RS, 2RS, 3aSR, 8bRS)-1-(p-bromobenzenesulfonamido)-2-hydroxy-2,3,3a,8b-tetrahydro-1H-cyclopenta[b]benzofuran-5-yloxyacetic acid methyl ester (60) (139.7 mg) in the same manner as working Example 2.

M.P.: 223.0°–223.5° C. (recrystallized by ethyl acetate)

IR (KBr method): 3492, 3196, 2920, 2604, 1725, 1624, 1599, 1576, 1491, 1462, 1435, 1392, 1336, 1323, 1274, 1199, 1164, 1118, 1094, 1067, 1009, 973, 938, 897, 841, 820, 785, 770, 758, 741, 725, 704, 629, 603, 557, 540, 420 cm$^{-1}$ NMR (400 MHz, CDCl$_3$, δ): 2.0–2.1 (1H, m), 2.4–2.45 (1H, m), 2.6–3.0 (1H, bs), 3.40–3.45 (1H, m), 3.65–3.7 (1H, m), 3.96–4.05 (2H, m), 4.59 (2H, s), 5.15–5.25 (1H, m), 6.55–6.6 (1H, m), 6.6–6.7 (2H, m), 7.62–7.65 (2H, m), 7.77–7.80 (2H, m), 7.85 (1H, d, J=6.5 Hz)

MASS (EI method, m/e): 483 (M+)

Elementary Analysis: (as $C_{19}H_{18}BrNO_7S$) Calculated values: C: 47.12, H: 3.75, N: 2.89, S: 6.62, Br: 16.50 Measured values: C: 46.75, H: 3.84, H: 2.84, S: 6.90, Br: 16.25

WORKING EXAMPLE 25

(1RS, 2RS, 3aSR, 8bRS)-1-(p-iodobenzenesulfonamido)-2-hydroxy- 2,3,3a,8b-tetrahydro-1H-cyclopenta[b]benzofuran-5-yloxyacetic acid methyl ester (62)

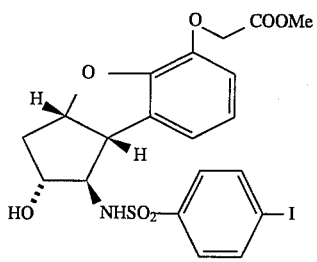

(62)

The target compound (542 mg) was obtained in the same manner as Working Example 1 from (1RS, 2RS, 3aSR, 8bRS)-1-azido- 2-tetrahydropyranyloxy-2,3,3a,8b-tetrahydro-1H -cyclopenta[b]benzofuran-5-yloxyacetic acid methyl ester (24) (424 mg) with the exception of using p-iodobenzenesulfonyl chloride (659 mg) instead of benzenesulfonyl chloride.

M.P.: 159.5°–160.5° C.

IR (KBr method): 3502, 3274, 2924, 1744, 1620, 1597, 1570, 1493, 1444, 1386, 1330, 1294, 1241, 1203, 1164, 1112, 1056, 1009, 944, 893, 843, 822, 754, 731, 596, 555 cm$^{-1}$ NMR (400 MHz, CDCl$_3$, δ): 2.01–2.04 (1H, m), 2.45–2.52 (1H, m), 3.34–3.38 (1H, m), 3.55 (1H, bs), 3.65–3.68 (1H, m), 3.76 (3H, s), 4.00–4.05 (1H, m), 4.67 (2H, s), 5.17–5.22 (1H, m), 6.55–6.57 (1H, m), 6.62–6.72 (2H, m), 7.61–7.63 (2H, m), 7.67–7.69 (1H, m), 7.83–7.85 (2H, m)

MASS (EI method, m/e):545 (M+)

Elementary Analysis: (as $C_{20}H_{20}INO_7S$) Calculated values: C: 44.05, H: 3.70, N: 2.57, S: 5.88, I: 23.27 Measured values: C: 43.89, H: 3.72, N: 2.52, S: 5.87, I: 22.94

WORKING EXAMPLE 26

(1RS, 2RS, 3aSR, 8bRS)-1-(p-iodobenzenesulfonamido)-2-hydroxy- 2,3,3a,8b-tetrahydro-1H-cyclopenta[b]benzofuran-5-yloxyacetic acid (63)

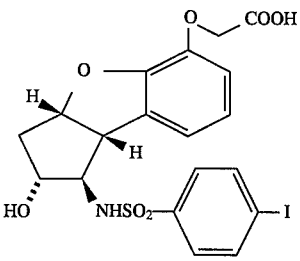

(63)

The target compound (293 mg) was obtained from (1RS, 2RS, 3aSR, 8bRS)-1-(p-iodobenzenesulfonamido)-2-hydroxy-2,3,3a,8b-tetrahydro-1H-cyclopenta[b]benzofuran-5-yloxyacetic acid methyl ester (62) (337 mg) in the same manner as Working Example 2.

M.P.: 219.5°–221.0° C. (recrystallized by ethyl acetate)

IR (KBr method): 3486, 3152, 2916, 2604, 1939, 1723, 1624, 1599, 1572, 1491, 1462, 1435, 1386, 1323, 1263, 1199, 1160, 1118, 1093, 1064, 1006, 973, 936, 897, 841, 785, 772, 733, 702, 625, 603, 557, 538, 458 cm$^{-1}$ NMR (400 MHz, CDCl$_3$, δ): 1.99–2.04 (1H, m), 2.35–2.41 (1H, m), 3.41–3.45 (1H, m), 3.64–3.67 (1H, m), 3.97–4.01 (1H, m), 2.8–3.8 (2H, bs), 4.58 (2H, s), 5.18–5.23 (1H, m), 6.54–6.56 (1H, m), 6.62–6.67 (2H, m), 7.63–7.65 (2H, m), 7.85–7.91 (3H, m)

MASS (EI method, m/e): 531 (M+)

Elementary Analysis: (as $C_{19}H_{18}INO_7S$) Calculated values: C: 42.95, H: 3.41, N: 2.64, S: 6.03, I: 23.88 Measured values: C: 42.72, H: 3.42, N: 2.64, S: 6.02, I: 23.87

WORKING EXAMPLE 27

(1RS, 2RS, 3aSR, 8bRS)-1-(p-trifluoromethylbenzenesulfonamido)-2-hydroxy-2,3,3a,8b-tetrahydro-1H-cyclopenta[b]benzofuran-5-yloxyacetic acid methyl ester (64)

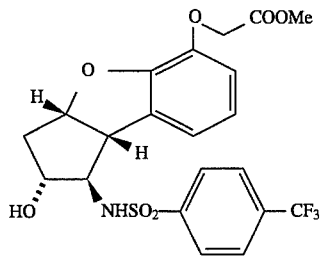

The target compound (420 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta[b]benzofuran-5-yloxyacetic acid methyl ester (24) (490 mg) with the exception of using p-trifluoromethyl-benzenesulfonyl chloride (616 mg) instead of benzenesulfonyl chloride.

M.P.: 139.5°–141.0° C.

IR (KBr method): 3562, 3518, 3280, 3106, 3050, 2968, 2928, 1937, 1763, 1620, 1597, 1493, 1468, 1439, 1406, 1325, 1296, 1230, 1203, 1168, 1110, 1064, 1033, 1017, 963, 938, 895, 841, 822, 785, 758, 725, 712, 623, 598, 549, 472, 429, 410 cm$^{-1}$ NMR (400 MHz, CDCl$_3$, δ): 2.04–2.11 (1H, m), 2.50–2.56 (1H, m), 2.7 (1H, bs), 3.44–3.55 (2H, m), 3.78 (3H, s), 4.04–4.06 (1H, m), 4.65–4.67 (2H, m), 5.12–5.17 (1H, m), 5.40 (1H, d, J=7.3 Hz), 6.29–6.31 (1H, m), 6.55–6.59 (1H, m), 6.63–6.65 (1H, m), 7.78 (2H, d, J=8.0 Hz), 8.02 (2H, d, J=8.0 Hz)

MASS (EI method, m/e): 487 (M$^+$)

Elementary Analysis: (as $C_{21}H_{20}F_3NO_7S$) Calculated values: C: 51.75, H: 4.14, N: 2.87, S: 6.58, F: 11.69 Measured values: C: 51.67, H: 4.18, N: 2.94, S: 6.55, F: 11.65

WORKING EXAMPLE 28

(1RS, 2RS, 3aSR, 8bRS)-1-(p-trifluoromethylbenzenesulfonamido)-2-hydroxy-2,3,3a,8b-tetrahydro-1H-cyclopenta [b]benzofuran-5-yloxyacetic acid (65)

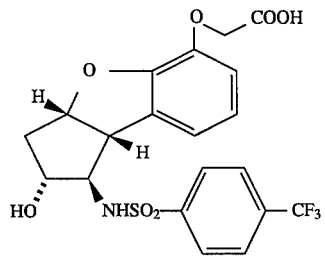

The target compound (203 mg) was obtained from (1RS, 2RS, 3aSR, 8bRS)-1-(p-trifluoromethylbenzenesulfonamido)-2-hydroxy- 2,3,3a,8b-tetrahydro-1H-cyclopenta[b]benzofuran-5-yloxyacetic acid methyl ester (64) (240 mg) in the same manner as Working Example 2.

M.P.: 225.0°–226.0° C. (recrystallized by ethyl acetate)

IR (KBr method): 3632, 3196, 1721, 1657, 1638, 1626, 1562, 1510, 1491, 1462, 1435, 1406, 1330, 1274, 1145, 1098, 1064, 716, 623, 594, 538, 507, 456, 412 cm$^{-1}$ NMR (400 MHz, CDCl$_3$, δ): 1.99–2.05 (1H, m), 2.42–2.49 (1H, m), 2.6–3.1 (1H, bs), 3.41–3.45 (1H, m), 3.63–3.69 (1H, m), 3.86 (1H, bs), 3.99–4.02 (1H, m), 4.59 (2H, s), 5.17–5.22 (1H, m), 6.52–6.54 (1H, m), 6.58–6.67 (2H, m), 7.75–7.77 (2H, m), 8.00 (1H, d, J=6.8 Hz), 8.05–8.07 (2H, m)

MASS (EI method m/e): 473 (M$^+$)

WORKING EXAMPLE 29

(1RS, 2RS, 3aSR, 8bRS)-1-(p-cyanobenzenesulfonamido)-2-hydroxy-2,3,3a,8b-tetrahydro-1H-cyclopenta[b]benzofuran-5-yloxyacetic acid methyl ester (66 )

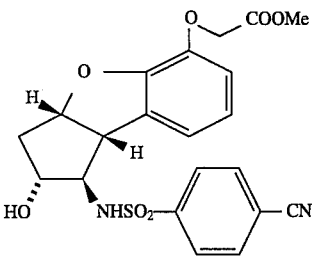

The target compound (362 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (455 mg) with the exception of using p-cyanobenzenesulfonyl chloride (472 mg) instead of benzenesulfonyl chloride.

M.P.: 146.0°–147.0° C.

IR (KBr method): 3500, 2234, 1769, 1657, 1618, 1562, 1491, 1462, 1435, 1402, 1342, 1284, 1228, 1203, 1164, 1114, 1031, 957, 919, 849, 774, 725, 632, 572, 516, 443, 431, 414 cm$^{-1}$ NMR (400 MHz, CDCl$_3$, δ): 2.01 (1H, ddd, J=4.9 Hz), 7.3, 14.0 Hz), 2.48 (1H, dt, J=6.7, 14.0 Hz), 3.40 (1H, t, J=6.1 Hz), 3.52 (1H, d, J=3.6 Hz), 3.66 (1H, dd, J=5.5, 9.1 Hz), 3.76 (3H, s), 3.96–4.01 (1H, m), 4.65 (1H, d, J=16.4 Hz), 4.68 (1H, d, J=16.4 Hz), 5.19 (1H, ddd, J=4.9, 7.3, 9.1 Hz), 6.62–6.69 (3H, m), 7.76–7.79 (2H, m), 7.93 (1H, bs), 8.02–8.04 (2H, m)

MASS (FAB method, m/e): 443 (M–H)–

Elementary Analysis: (as $C_{21}H_{20}NO_7S$) Calculated values: C: 56.75, H: 4.54, N: 6.30, S: 7.21 Measured values: C: 56.75, H: 4.68, N: 6.29, S: 6.93

WORKING EXAMPLE 30

(1RS, 2RS, 3aSR, 8bRS)-1-(p-nitrobenzenesulfonamido)-2-hydroxy-2,3,3a,8b-tetrahydro-1H-cyclopenta[b]benzofuran-5-yloxyacetic acid methyl ester (67)

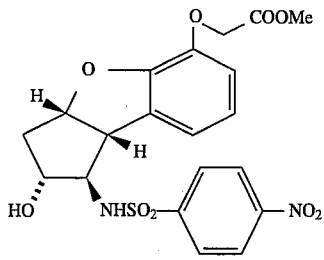

The target compound (379 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (447 mg) with the exception of using p-nitrobenzenesulfonyl chloride (510 mg) instead of benzenesulfonyl chloride.

M.P.: 87.0°–88.5° C.

IR (KBr method): 3554, 1771, 1698, 1620, 1524, 1491, 1435, 1352, 1284, 1222, 1197, 1166, 1120, 922, 855, 777, 739, 609, 547 cm$^{-1}$ NMR (400 MHz, CDCl$_3$, δ): 1.94 (1H, ddd, J=4.9, 7.9, 13.4 Hz), 2.40–2.46 (1H, m), 3.33–3.37 (2H, m), 3.60 (1H, dd, J=5.4, 8.5 Hz), 3.69 (3H, s), 3.92–3.95 (1H, m), 4.57–4.62 (2H, m), 5.09–5.14 (1H, m), 6.54–6.62 (3H, m), 7.88 (1H, d, J=6.7 Hz), 8.01–8.03 (2H, m), 8.22–8.24 (2H, m)

MASS (FAB method, m/e): 463 (M–H)–

Elementary Analysis: (as C$_{20}$H$_{19}$N$_2$O$_9$S) Calculated values: C: 51.72, H: 4.34, N: 6.03, S: 6.90 Measured values: C: 51.68, H: 4.64, N: 5.80, S: 6.77

WORKING EXAMPLE 31

(1RS, 2RS, 3aSR, 8bRS)-1-(p-nitrobenzenesulfonamido)-2-hydroxy-2,3,3a,8b-tetrahydro-1H-cyclopenta[b]benzofuran-5-yloxyacetic acid (68)

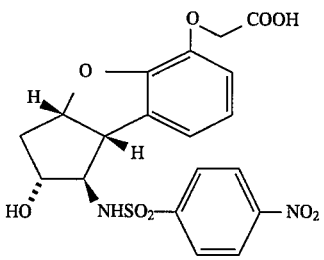

The target compound (139 mg) was obtained from (1RS, 2RS, 3aSR, 8bRS)-1-(p-nitrobenzenesulfonamido)-2 -hydroxy2,3,3a,8b-tetrahydro-1H-cyclopenta[b]benzofuran-5-yloxyacetic acid methyl ester (67) (180 mg) in the same manner as Working Example 2.

M.P.: 208.5°–210.0° C. (recrystallized by ethyl acetate)

IR (Far method): 3502, 1750, 1599, 1531, 1491, 1462, 1435, 1354, 1263, 1199, 1166, 1118, 1065, 938, 899, 855, 739, 685, 605, 534,431 cm$^{-1}$ NMR (400 MHz, CDCl$_3$, δ): 1.98–2.04 (1H, m), 2.41–2.48 (1H, m), 2.60–3.20 (2H, bs), 3.47 (1H, q, J=6.4 Hz), 3.67 (1H, dd, J=5.4, 9.3 Hz), 3.98 (1H, q, J=5.9 Hz), 4.68 (1H, d, J=16.6 Hz), 4.63 (1H, d, J=16.6 Hz), 5.17–5.22 (1H, m), 6.61–6.70 (3H, m), 8.10–8.13 (2H, m), 8.15–8.16 (1H, 8.30–8.34 (2H, m), MASS (FAB method, m/e): 449 (M"H)–

WORKING EXAMPLE 32

(1RS, 2RS, 3aSR, 8bRS)-1-(2,4-difluorobenzenesulfonamido)-2-hydroxy-2,3,3a,8b-tetrahydro-1H-cyclopenta[b]benzofuran-5-yloxyacetic acid methyl ester (69)

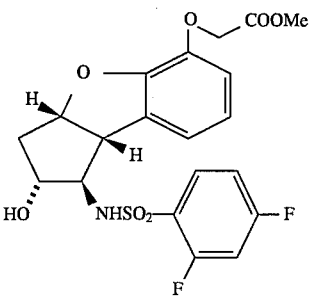

The target compound (406 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (431 mg) with the exception of using difluorobenzene-sulfonyl chloride (472 mg) instead of benzenesulfonyl chloride.

M.P.: 120.0°–121.0° C.

IR (KBr method): 3494, 3130, 2966, 2920, 1773, 1740, 1543, 1491, 1466, 1433, 1336, 1280, 1224, 1197, 1166, 1120, 1069, 1002, 969, 940, 897, 849, 826, 787, 729, 671, 619, 590, 559, 540, 522, 472, 455, 416 cm$^{-1}$ (400 MHZ, CDCl$_3$, δ): 2.08–2.14 (1H, m), 2.48 (1H, d, J=4.4 Hz), 2.49–2.56 (1H, m), 3.42–3.46 (1H, m), 3.63–3.66 (1H, m), 3.77 (3H, s), 4.08–4.12 (1H, m), 4.66 (1H, d, J=6.1 Hz), 4.70 (1H, d, J=6.1 Hz), 5.22–5.27 (2H, m), 6.62–6.64 (1H, m), 6.67–6.73 (2H, m), 6.97–7.03 (2H, m), 7.90–7.95 (1H, m)

MASS (EI method, m/e): 455 (M$^+$)

Elementary Analysis: (as C$_{20}$H$_{19}$F$_2$NO$_7$S) Calculated values: C: 52.75, H: 4.20, N: 3.08, S: 7.04, F: 8.34 Measured values: C: 52.75, H: 4.23, N: 3.06, S: 7.13, F: 8.36

WORKING EXAMPLE 33

(1RS, 2RS, 3aSR, 8bRS)-1-(2,4-difluorobenzenesulfonamido)-2-hydroxy-2,3,3a,8b-tetrahydro-1H-cyclopenta[b]benzofuran-5-yloxyacetic acid (70)

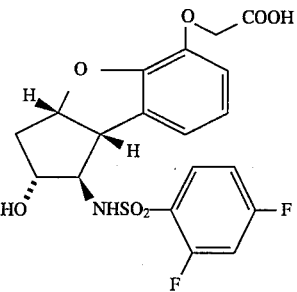

The target compound (230 mg) was obtained from (1RS, 2RS, 3aSR, 8bRS)-1-(2,4-difluorobenzenesulfonamido)-2-hydroxy- 2,3,3a,8b-tetrahydro-1H-cyclopenta[b]benzofuran-5-yloxyacetic acid methyl ester (69) (283 mg) in the same manner as Working Example 2.

M.P.: 203.0°–204.0° C. (recrystallized by ethyl acetate)

IR (KBr method): 3496, 3172, 1725, 1607, 1491, 1466, 1433, 1336, 1276, 1199, 1166, 1120, 1069, 971, 940, 903, 849, 770, 727, 671, 619, 524, 435 cm$^{-1}$ NMR (400 MHz, CDCl$_3$, δ): 1.99–2.05 (1H, m), 2.46–2.53 (1H, m), 2.57–2.60 (1H, m), 2.4–3.03 (1H, bs), 3.40–3.44 (1H, m), 3.70–3.74 (1H, m), 4.02–4.07 (1H, m), 4.58–4.63 (2H, m), 5.18–5.22 (1H, m), 6.66–6.68 (3H, m), 6.93–6.99 (2H, m), 7.89–7.95 (2H, m)

MASS (EI method, m/e): 441 (M$^+$)

Elementary Analysis: (as C$_{19}$H$_{17}$N$_2$O$_7$S) Calculated values: C: 51.70, H: 3.88, N: 3.17, S: 7.26, F: 8.61 Measured values: C: 51.58, H: 3.82, N: 3.12, S: 7.35, F: 8.64

WORKING EXAMPLE 34

(1RS, 2RS, 3aSR, 8bRS)-1-(3,4-dichlorobenzene-sulfonamido)- 2-hydroxy-2,3,3a,8b-tetrahydro-1H-cyclopenta[b]benzofuran-5-yloxyacetic acid methyl ester (71)

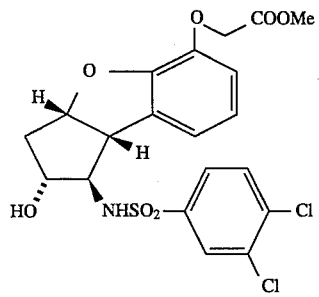

(71)

The target compound (480 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (506 mg) with the exception of using dichlorobenzenesulfonyl chloride (638 mg) instead of benzenesulfonyl chloride.

M.P.: 135.5°–136.5° C.

IR (KBr method): 3500, 3148, 2368, 1738, 1657, 1620, 1599, 1562, 1543, 1510, 1491, 1460, 1373, 1323, 1292, 1241, 1199, 1164, 1100, 1067, 1033, 1002, 975, 886, 818, 764, 679, 638, 605, 532, 462, 420, 410 cm$^{-1}$ NMR (400 MHz, CDCl$_3$, δ): 2.09–2.15 (1H, m), 2.52–2.59 (1H, m), 2.61 (1H, d, J=3.9 Hz), 3.44–3.50 (1H, m), 3.55–3.58 (1H, m), 3.78 (3H, s), 4.05–4.14 (1H, m), 4.66–4.70 (2H, m), 5.03 (1H, d J=6.8 Hz), 5.18–5.23 (1H, m), 6.49–6.51 (1H, m), 6.65–6.71 (2H, m), 7.57–7.59 (1H, m), 7.69–7.72 (1H, m), 7.97–7.98 (1H, m)

MASS (EI method, m/e: 4 87 (M$^+$)

Elementary Analysis: (as C$_{20}$H$_{19}$Cl$_2$NO$_7$S) Calculated values: C: 49.19, H: 3.92, N: 2.87, S: 6.57, Cl: 14.52 Measured values: C: 49.38, H: 3.93, N: 3.09, S: 6.66, Cl: 14.43

WORKING EXAMPLE 35

(1RS, 2RS, 3aSR, 8bRS)-1-(3,4-dichlorobenzene-sulfonamido)-2-hydroxy-2,3,3a,8b-tetrahydro-1H-cyclopenta[b]benzofuran-5-yloxyacetic acid (72)

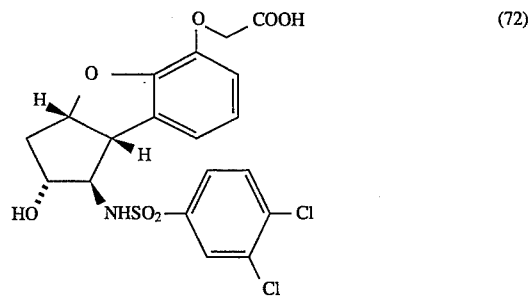

(72)

The target compound (153 mg) was obtained from (1RS, 2RS, 3aSR, 8bRS)-1-(3,4-dichlorobenzenesulfonamido)-2-hydroxy- 2,3,3a,8b-tetrahydro-1H-cyclopenta[b]benzofuran-5-yloxyacetic acid methyl ester (71) (202 mg) in the same manner as Working Example 2.

M.P.: 239.0°–240.0° C, (recrystallized by ethyl acetate)

IR (KBr method): 3492, 3180, 2914, 1721, 1657, 1626, 1599, 1562, 1543, 1510, 1491, 1460, 1435, 1373, 1336, 1276, 1199, 1164, 1118, 1100, 1067, 1035, 975, 938, 901, 818, 758, 772, 727, 702, 679, 640, 578, 528, 511, 458, 414 cm$^{-1}$ NMR (400 MHz, CDCl$_3$, δ): 1.99–2.05 (1H, m), 2.41–2.48 (1H, m), 2.7–3.2 (1H, bs), 3.4–3.45 (1H, m), 3.64–3.68 (1H, m), 3.8–3.9 (1H, bs), 3.98–4.02 (1H, m), 4.60 (2H, s), 5.17–5.22 (1H, m), 6.65–6.69 (3H, m), 7.57 (1H, d, J=8.3 Hz), 7.75 (1H, dd, J=8.3, 1.9 Hz), 7.93 (1H, d, J=6.8 Hz), 8.02 (1H, d, J=1.9 Hz)

MASS (FAB method, m/e): 472 (M–H)–

WORKING EXAMPLE 36

(1RS, 2RS, 3aSR, 8bRS)-1-phenylmethanesulfona-mido-2-hydroxy- 2,3,3a,8b-tetrahydro-1H-cyclopenta[b]benzofuran-5-yloxyacetic acid methyl ester (73)

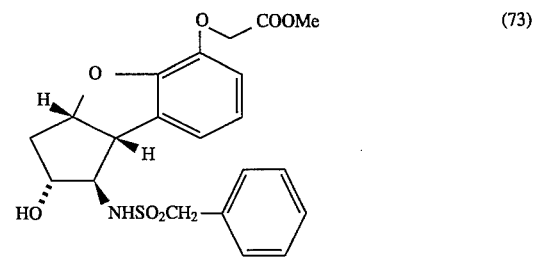

(73)

The target compound (395 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (480 mg) with the exception of using benzylsulfonyl chloride (468 mg) instead of benzenesulfonyl chloride.

M.P.: 157.5°–158.0° C.

IR (KBr method): 3516, 3314, 1754, 1657, 1620, 1562, 1543, 1491, 1437, 1377, 1315, 1294, 1274, 1228, 1193, 1166, 1114, 1075, 942, 774, 725, 700, 601, 549 cm$^{-1}$ NMR (400 MHz, CDCl$_3$, δ): 2.10–2.20 (1H, m), 2.50–2.60 (1H, m), 3.56–3.59 (1H, m), 3.61–3.66 (1H, m), 3.77 (3H, s), 4.05–4.10 (1H, m), 4.35 (1H, d, J=14.0 Hz), 4.38 (1H, d, J=14.0 Hz), 4.45 (1H, d, J=6.8 Hz), 4.65–4.75 (2H, m), 5.18–5.23 (1H, m), 6.74–6.76 (1H, m), 6.80–6.84 (1H, m), 6.9–6.92 (1H, m), 7.37–7.43 (5H, m)

MASS (EI method, m/e): 433 (M+)

Elementary Analysis: (as $C_{21}H_{23}NO_7S$) Calculated values: C: 58.19, H: 5.35, N: 3.23, S: 7.40 Measured values: C: 58.17, H: 5.37, N: 3.13, S: 7.45

WORKING EXAMPLE 37

(1RS, 2RS, 3aSR, 8bRS)-1-phenylmethanesulfonamido-2-hydroxy- 2,3,3a,8b-tetrahydro-1H-cyclopenta[b]benzofuran-5-yloxyacetic acid (74)

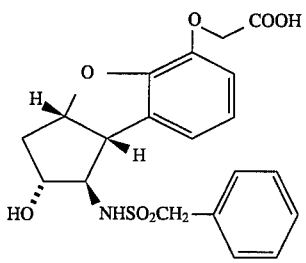

The target compound (101 mg) was obtained from (1RS, 2RS, 3aSR, 8bRS)-1-phenylmethanesulfonamido-2-hydroxy-2,3,3a,8b-tetrahydro-1H-cyclopenta[b]benzofuran-5-yloxyacetic acid methyl ester (73) (144 mg) in the same manner as Working Example 2.

M.P.: 223.5°–225.0° C. (recrystallized from ethyl acetate)

IR (KBr method): 3464, 3150, 2910, 2608, 2364, 1725, 1626, 1595, 1491, 1460, 1433, 1361, 1307, 1294, 1272, 1199, 1172, 1143, 1120, 1067, 1035, 971, 940, 903, 845, 772, 727, 698, 623, 605, 545, 518 cm$^{-1}$ NMR (400 MHz, CDCl$_3$, δ): 2.00–2.08 (1H, m), 2.50–2.80 (3H, m), 3.65–3.70 (2H, m), 4.03–4.10 (1H, m), 4.34 (1H, d, J=13.7 Hz), 4.38 (1H, d, J=13.7 Hz), 4.62 (1H, d, J=6.8 Hz), 4.67 (1H, d, J=6.8 Hz), 5.15–5.20 (1H, m), 6.72–6.80 (2H, m), 6.96–6.98 (1H, m), 7.04–7.06 (1H, m), 7.34–7.38 (3H, m), 7.42–7.48 (2H, m)

MASS (EI method, m/e):419 (M+)

WORKING EXAMPLE 38

(1RS, 2RS, 3aSR, 8bRS)-1-(2-phenylethanesulfonamido)- 2-hydroxy-2,3,3a,8b-tetrahydro-1H-cyclopenta[b]benzofuran-5-yloxyacetic acid methyl ester (75)

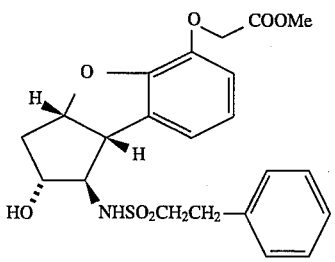

The target compound (450 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (470 mg) with the exception of using phenethylsulfonyl chloride (494 mg) instead of benzenesulfonyl chloride.

M.P.: 142.5°–143.0° C.

IR (KBr method): 3528, 3308, 2954, 1756, 1618, 1491, 1433, 1311, 1274, 1222, 1189, 1151, 1110, 1067, 975, 924, 758, 729, 702, 601, 513, 424 cm$^{-1}$ NMR (400 MHz, CDCl$_3$, δ): 2.08 (1H, ddd, J=5.4, 8.3, 13.7 Hz), 2.55 (1H, dt, J=6.8, 13.7 Hz), 2.61 (1H, d, J=4.9 Hz), 3.13–3.17 (2H, m), 3.34–3.46 (2H, m), 3.52–3.62 (2H, m), 3.78 (3H, s), 3.92–3.98 (1H, m), 4.54 (1H, d, J=7.8 Hz), 4.68–4.75 (2H, m), 5.18 (1H, ddd, J=4.9, 7.4, 8.8 Hz), 6.72–6.81 (2H, m), 6.98–7.00 (1H, m), 7.20–7.22 (2H, m), 7.24–7.27 (1H, m), 7.32–7.34 (2H, m)

MASS (FAB method, m/e): 446 (M–H)–

Elementary Analysis: (as $C_{22}H_{25}NO_7S$) Calculated values: C: 59.05, H: 5.63, N: 3.13, S: 7.16 Measured values: C: 58.70, H: 5.41, N: 3.28, S: 7.11

WORKING EXAMPLE 39

(1RS, 2RS, 3aSR, 8bRS)-1-(2-phenylethanesulfonamido)-2-hydroxy-2,3,3a,8b-tetrahydro-1H-cyclopenta[b]benzofuran-5-yloxyacetic acid (76)

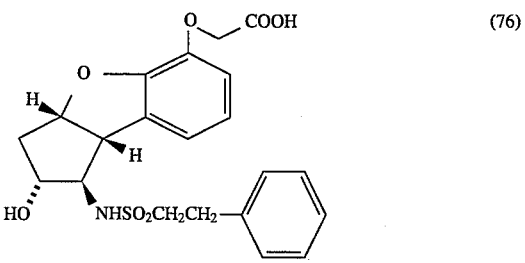

The target compound (130 mg) was obtained from (1RS, 2RS, 3aSR, 8bRS)-1-(2-phenylethanesulfonamido)-2-hydroxy-2,3,3a,8b-tetrahydro-1H-cyclopenta[b]benzofuran-5-yloxyacetic acid methyl ester (75) (158 mg) in the same manner as Working Example 2.

M.P.: 193.0°–194.0° C. (recrystallized from ethyl acetate)

IR (KBr method): 3458, 1723, 1624, 1597, 1491, 1460, 1435, 1265, 1199, 1135, 1118, 1067, 940, 845, 772, 727, 698, 542 cm$^{-1}$ NMR (500 MHz, DMSO, δ): 1.97–2.03 (1H, m), 2.55–2.60 (2H, m), 2.0–3.4 (2H, bs), 3.08–3.20 (2H, m), 3.31–3.45 (2H, m), 3.60 (1H, q, J=7.3 Hz), 3.68 (1H, dd, J=6.1, 9.1 Hz), 4.01–4.04 (1H, m), 4.64 (1H, d, J=16.3 Hz), 4.65 (1H, d, J=16.3 Hz), 5.15–5.20 (1H, m), 6.72–6.78 (2H, m), 7.10–7.13 (2H, m), 7.19–7.23 (3H, m), 7.27–7.30 (2H, m)

MASS (EI method, m/e): 433 (M+)

Elementary Analysis: (as $C_{21}H_{23}NO_7S$) Calculated values: C: 58.19, H: 5.35, N: 3.23, S: 7.40 Measured values: C: 58.06, H: 5.28, N: 3.46, S: 7.56

WORKING EXAMPLE 40

(1RS, 2RS, 3aSR, 8bRS)-1-(2-naphthalenesulfonamido)-2-hydroxy- 2,3,3a,8b-tetrahydro-1H-cyclopenta[b]benzofuran-5-yloxyacetic acid methyl ester (77)

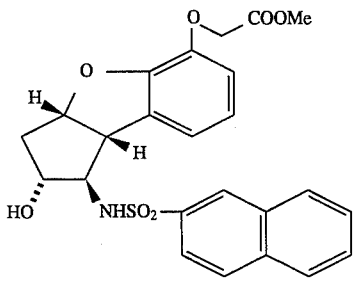

The target compound (380 mg) was obtained in the same manner as Working Example 1 from (1RS, 9.RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (417 mg) with the exception of using naphthalenesulfonyl chloride (548 mg) instead of benzenesulfonyl chloride.

M.P.: 112.5°–114.0° C.

IR (KBr method): 3490, 3142, 1740, 1622, 1597, 1491, 1468, 1435, 1294, 1232, 1199, 1156, 1131, 1108, 1067, 1027, 1002, 961, 897, 816, 783, 667, 644, 621, 538, 476 cm$^{-1}$ NMR (400 MHz, CDCl$_3$, δ): 2.05–2.10 (1H, m), 2.50–2.5 (1H, m), 3.50–3.55 (2H, m), 3.56–3.60 (1H, m), 3.74 (3H, m), 4.07–4.19. (1H, m), 4.63 (2H, s), 5.08 (1H, d, J=6.9 Hz), 5.17–5.22 (1H, m), 6.26–6.28 (1H, m), 6.39–6.36 (1H, m), 6.54–6.56 (1H, m), 7.61–7.69 (2H, m), 7.86–8.01 (4H, m), 8.46 (1H, s)

MASS (EI method, m/e): 469 (M$^+$)

Elementary Analysis: (as C$_{24}$H$_{23}$NO$_7$S) Calculated values: C: 61.40, H: 4.94, N: 2.98, S: 6.83 Measured values: C: 61 45, H: 5.00, N: 2 97, S: 6.95

WORKING EXAMPLE 41

(1RS, 2RS, 3aSR, 8bRS)-1-(2-naphthalenesulfonamido)-2-hydroxy- 2,3,3a,8b-tetrahydro-1H-cyclopenta[b]benzofuran-5-yloxyacetic acid (78)

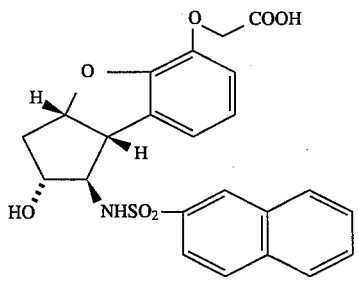

The target compound (102 mg) was obtained from (1RS, 2RS, 3aSR, 8bRS)-1-(2-naphthalenesulfonamido)-2-hydroxy-2,3,3a,8b-tetrahydro-1H-cyclopenta[b]benzofuran-5-yloxyacetic acid methyl ester (77) (153 mg) in the same manner as Working Example 2.

M.P.: 215.0°–216.0° C. (recrystallized from ethyl acetate)

IR (KBr method): 3482, 1721, 1626, 1597, 1491, 1462, 1433, 1263, 1199, 1158, 1120, 1067, 901, 841, 814, 750, 725, 667,621, 534, 478 cm$^{-1}$ NMR (400 MHz, CDCl$_3$, δ): 1.98–2.04 (1H, m), 2.40–2.60 (1H, m), 2.80–3.20 (1H, bs), 3.45–3.50 (1H, m), 3.67–3.70 (1H, m), 3.80 (1H, bs), 4.03–4.07 (1H, m), 4.55 (2H, s), 5.17–5.22 (1H, m), 6.37–6.44 (2H, m), 6.55–6.57 (1H, m), 7.58–7.67 (2H, m), 7.79 (1H, d, J=6.8 Hz), 7.91–8.00 (4H, m), 8.45 (1H, s)

MASS (FAB method, m/e): 454 (M–H)–

WORKING EXAMPLE 42

(1RS, 2RS, 3aSR, 8bRS)-1-methanesulfonamido-2-hydroxy-2,3,3a,8b-tetrahydro-1H-cyclopenta[b]benzofuran-5-yloxyacetic acid methyl ester (79)

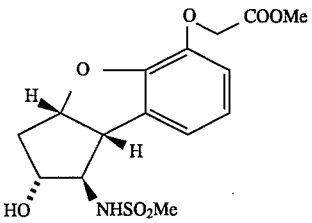

The target compound (219 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (485 mg) with the exception of using methanesulfonyl chloride (0.19 ml) instead of benzenesulfonyl chloride.

M.P.: 119.0°–120.0° C.

IR (KBr method): 3444, 3254, 3030, 2974, 2938, 1775, 1622, 1593, 1562, 1543, 1491, 1464, 1398, 1350, 1299, 1247, 1220, 1197, 1147, 1114, 1033, 975, 951, 917, 886, 855, 781, 766, 737, 598, 534, 511, 420 cm$^{-1}$ NMR (400 MHz, CDCl$_3$, δ): 2.05–2.20 (1H, m), 2.60–2.7 (1H, m), 2.83 (1H, d, J=4.4 Hz), 3.05 (3H, s), 3.60–3.65 (2H, m), 3.79 (3H, s), 4.05–4.10 (1H, m), 4.71 (1H, d, J=16.2 Hz), 4.74 (1H, d, J=16.2 Hz), 4.92 (1H, d, J=7.0 Hz), 5.20–5.25 (1H, m), 6.75–6.77 (1H, m), 6.81–6.84 (1H, m), 7.00–7.05 (1H, m)

MASS (EI method, m/e): 357 (M$^+$)

Elementary Analysis: (as C$_{15}$H$_{19}$NO$_7$S) Calculated values: C: 50.41, H: 5.36, N: 3.92, S: 8.97 Measured values: C: 50.39, H: 5.37, N: 3.92, S: 9.15

WORKING EXAMPLE 43

(1RS, 2RS, 3aSR, 8bRS)-1-methanesulfonamido-2-hydroxy-2,3,3a,8b-tetrahydro-1H-cyclopenta[b]benzofuran-5-yloxyacetic acid (80)

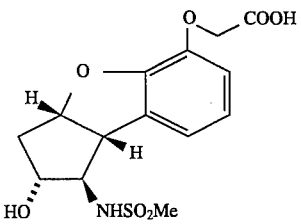

The target compound (142 mg) was obtained from (1RS, 2RS, 3aSR, 8bRS)-1-methanesulfonamido-2-hydroxy-2,3, 3a,8b-tetrahydro- 1H-cyclopenta[b]benzofuran-5-yloxyacetic acid methyl ester (79) (167 mg) in the same manner as Working Example 2.

M.P.: 228.5°–230.0° C. (recrystallized from ethyl acetate)

WORKING EXAMPLE 44

(1RS, 2RS, 3aSR, 8bRS)-1-butanesulfonamido-2-hydroxy-2,3,3a,8b-tetrahydro-1H-cyclopenta[b]benzofuran-5-yloxyacetic acid methyl ester (81)

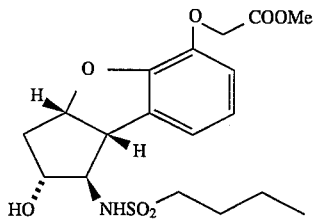
(81)

The target compound (312 mg) was obtained in the same manner as Working Example 1 from (1RS, 2RS, 3aSR, 8bRS)-1-azido- 2-tetrahydropyranyloxy-2,3,3a,8b-tetrahydro-1H -cyclopenta [b]benzofuran-5-yloxyacetic acid methyl ester (24) (480 mg) with the exception of using butanesulfonyl chloride (0.32 ml) instead of benzenesulfonyl chloride.

M.P.: 131.0°–132.0° C.

IR (KBr method): 3518, 3318, 2966, 2936, 2876, 1760, 1618, 1591, 1562, 1543, 1489, 1466, 1429, 1377, 1292, 1226, 1183, 1145, 1120, 1069, 1029, 986, 971, 932, 859, 830, 766, 731, 706, 679, 600, 540, 499, 422 Cm$^{-1}$ NMR (400 MHz, CDCl$_3$, δ): 0.94 (3H, t, J=7. Hz), 1.4–1.5 (2H, m), 1.75–1.85 (2H, m), 2.05–2.20 (1H, m), 2.60–2.70 (1H, m), 2.86 (1H, d, J=4.0 Hz), 3.05–3.15 (2H, m), 3.55–3.65 (2H, m), 3.79 (3H, s), 4.05–4.10 (1H, m), 4.64 (1H, d, J=6.2 Hz), 4.70 (1H, d, J=16.0 Hz), 4.74 (1H, d, J=16.0 Hz), 5.2–5.25 (1H, m), 6.75–6.78 (1H, m), 6.80–6.83 (1H, m), 6.97–6.99 (1H, m)

MASS (EI method, m/e):399 (M$^+$)

Elementary Analysis: (as C$_{18}$H$_{25}$NO$_7$S) Calculated values: C: 54.12, H: 6.31, N: 3.51, S: 8.03 Measured values: C: 54.06, H: 6.33, N: 3.54, S: 8.13

WORKING EXAMPLE 45

(1RS, 2RS, 3aSR, 8bRS)-1-butanesulfonamido-2-hydroxy-2,3,3a,8b-tetrahydro-1H-cyclopenta[b]benzofuran-5-yloxyacetic acid (82)

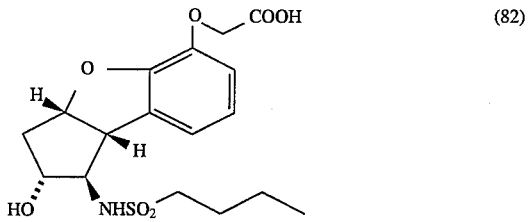
(82)

The target compound (203 mg) was obtained from (1RS, 2RS, 3aSR, 8bRS)-1-butanesulfonamido-2-hydroxy-2,3,3a, 8b-tetrahydro- 1H-cyclopenta[b]benzofuran-5-yloxyacetic acid methyl ester (81) (2.49 mg) in the same manner as Working Example 2.

M.P.: 191.0°–191.5° C. (recrystallized from ethyl acetate)

IR (KBr method): 3450, 3t66, 2876, 2606, 1725, 1624, 1597, 1491, 1460, 1435, 1363, 1272, 1197, 1118, 1050, 973, 940, 899, 843, 772, 727, 700, 615, 578, 528 cm$^{-1}$ NMR (400 MHz, CDCl$_3$, δ): 0.94 (3H, t, J=7.4 Hz), 1.4–1.5 (2H, m), 1.75–1.85 (2H, m), 1.95–2.05 (1H, m), 2.50–2.60 (2H, m), 3.0–3.15 (2H, m), 3.50–3.60 (1H, m), 3.65–3.70 (1H, m), 4.0–4.05 (1H, m), 4.3 (1H, bs), 4.62 (1H, d, J=16.5 Hz), 4.65 (1H, d, J=16.5 Hz), 5.15–5.20 (1H, m), 6.7–6.8 (2H, m), 7.05–7.10 (1H, m), 7.15 (1H, d, J=7.7 Hz)

MASS (EI method, m/e):385 (M$^+$)

Elementary Analysis: (as C$_{17}$H$_{23}$NO$_7$S) Calculated values: C: 52.98, H: 6.01, N: 3.63, S: 8.32 Measured values: C: 52.96, H: 6.02, N: 3.43, S: 8.52

WORKING EXAMPLE 46

(1RS, 2RS, 3aSR, 8bRS)-1-octanesulfonamido-2-hydroxy-2,3,3a,8b-tetrahydro-1H-cyclopenta[b]benzofuran-5-yloxyacetic acid methyl ester (83)

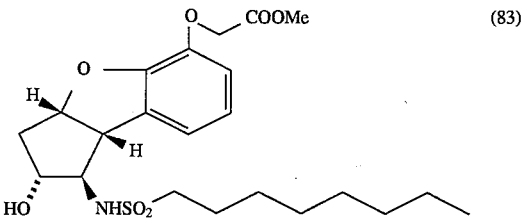
(83)

The target compound (370 mg) was obtained in the same manner as Working Example 1 from (1RS, 2RS, 3aSR, 8bRS)-1-azido- 2-tetrahydropyranyloxy-2,3,3a,8b-tetrahydro-1H-cyclopenta [b]benzofuran-5-yloxyacetic acid methyl ester (24) (428 mg) with the exception of using octanesulfonyl chloride (0.43 ml) instead of benzenesulfonyl chloride.

M.P.: 60.5°–61.5° C.

IR (KBr method): 3558, 3472, 3348, 3190, 2922, 2860, 1748, 1649, 1620, 1597, 1495, 1466, 1398, 1352, 1311, 1241, 1191, 1176, 1139, 1114, 1056, 1031, 1015, 971, 938, 890, 843, 789, 758, 721, 569, 526, 466 cm$^{-1}$ NMR (400 MHz, CDCl$_3$, δ): 0.86–0.90 (3H, m), 1.2–1.35 (8H, m), 1.38–1.48 (2H, m), 1.78–1.86 (2H, m), 2.08–2.14 (1H, m), 2.59–2.66 (1H, m), 2.90 (1H, d, J=3.9 Hz), 3.06–3.10 (2H, m), 3.58–3.62 (2H, m), 3.78 (3H, s), 4.05–4.15 (1H, m), 4.72

WORKING EXAMPLE 47

(1RS, 2RS, 3aSR, 8bRS)-1-octanesulfonamido-2-hydroxy-2,3,3a,8b-tetrahydro-1H-cyclopenta[b]benzofuran-5-yloxyacetic acid (84)

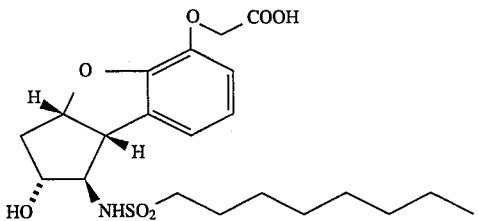
(84)

The target compound (210 mg) was obtained from (1RS, 2RS, 3aSR, 8bRS)-1-octanesulfonamido-2-hydroxy-2,3,3a,8b-tetrahydro-1H-cyclopenta[b]benzofuran-5-yloxyacetic acid methyl ester (83) (250 mg) in the same manner as Working Example 2.

M.P.: 196.0°–197.5° C. (recrystallized from ethyl acetate)
IR (KBr method): 3478, 3278, 2922, 2858, 1736, 1622, 1595, 1491, 1462, 1433, 1263, 1197, 1151, 1122, 913, 777, 725, 636, 600, 433 cm$^{-1}$ NMR (400 MHz, CDCl$_3$, δ): 0.86–0.89 (3H, m), 1.2–1.35 (8H, m), 1.36–1.45 (2H, m), 1.78–1.86 (2H, m), 2.00–2.07 (1H, m), 2.55–2.62 (1H, m), 3.04–3.08 (2H, m), 3.51–3.56 (1H, m), 3.66–3.70 (1H, m), 3.99–4.05 (1H, m), 3.2–4.2 (2H, bs), 4.63 (1H, d, J=16.4 Hz), 4.68 (1H, d, J=16.4 Hz), 5.16–5.22 (1H, m), 6.74–6.80 (3H, m), 7.07 (1H, m)

MASS (EI method, m/e): 441 (M$^+$)

Elementary Analysis: (as $C_{22}H_{31}NO_7S$) Calculated values.: C: 55.93, H: 7.27, N: 3.26, S: 7.46 Measured values: C: 55.67, H: 7.01, N: 3.43, S: 7.36

WORKING EXAMPLE 48

2-((1RS, 2RS, 3aSR, 8bRS)-1-benzenesulfonamido-2-hydroxy- 2,3,3a,8b-tetrahydro-1H-cyclopenta[b] benzofuran-5-yloxy)- 2-methylpropionic acid methyl ester (85)

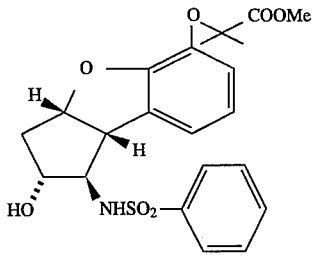
(85)

The target compound (370 mg) was obtained from 2-((1RS, 2RS, 3aSR, 8bRS)-1-azido-2-tetrahydropyranyloxy-2,3,3a,8b-tetrahydro-1H-cyclopenta[b]benzofuran-5-yloxy)-2-methylpropionic acid methyl ester (30) (460 mg) in the same manner as Working Example 1.

IR (liquid film method): 3506, 3276, 2998, 2954, 1736, 1609, 1481, 1460, 1386, 1367, 1292, 1145, 1075, 907, 866, 754, 690, 667 cm$^{-1}$ NMR (400 MHz, CDCl$_3$, δ): 1.50 (3H, s), 1.53 (3H, s), 2.0–2.10 (1H, m), 2.49 (1H, dt, J=6.3, 14.2 Hz), 2.72 (1H, d, J=3.9 Hz), 3.42–3.48 (1H, m), 3.58 (1H, dd, J=4.9, 8.8 Hz), 3.76 (3H, s), 4.05–4.11 (1H, m), 5.05 (1H, d, J=6.9 Hz), 5.17 (1H, ddd, J=4.4, 7.3, 8.8 Hz), 6.41 (1H, d, J=7.8 Hz), 6.56 (1H, t, J=7.8 Hz), 6.65 (1H, d, J=7.8 Hz), 7.52–7.55 (2H, m), 7.59–7.63 (1H, m), 7.90–7.92 (2H, m)

MASS (EI method, m/e): 447 (M$^+$)

WORKING EXAMPLE 49

2-((1RS, 2RS, 3aSR, 8bRS)-1-benzenesulfonamido-2-hydroxy- 2,3,3a,8b-tetrahydro-1H-cyclopenta[b] benzofuran-5-yloxy)- 2-methylpropionic acid (86)

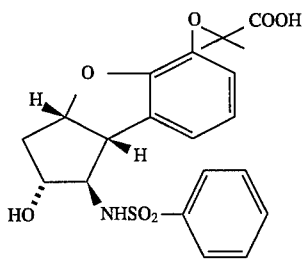
(86)

The target compound (315 mg) was obtained from 2-((1S, 2RS, 3aSR, 8bRS)-1-benzenesulfonamido-2-hydroxy-2,3,3a,8b-tetrahydro-1H-cyclopenta[b]benzofuran-5-yloxy)-2-methylpropionic acid methyl ester (85) (350 mg) in the same manner as Working Example 2.

IR (KBr method): 3398, 2352, 1717, 1549, 1560, 1543, 1508, 1460, 1261, 1160, 1044, 909, 864, 754, 690 cm$^{-1}$ NMR (400 MHz, CDCl$_3$, –DMSO, δ): 1.49 (3H, s), 1.53 (3H, s), 2.00–2.06 (1H, m), 2.40–2.47 (1H, dt, J=5.9, 14.6 Hz), 2.70–3.40 (1H, bs), 3.44–3.50 (1H, m), 3.60–3.67 (1H, m), 4.07–4.14 (2H, m), 5.18 (1H, ddd, J=3.9, 6.8, 8.3 Hz), 5.46 (1H, d, J=6.8 Hz), 6.50 (1H, d, J=7.3 Hz), 6.61 (1H, t, J=7.3 Hz), 6.75 (1H, d, J=7.3 Hz), 7.52–7.56 (2H, m), 7.60–7.64 (1H, m), 7.90–7.93 (1H, m)

MASS (EI method, m/e): 433 (M$^+$)

WORKING EXAMPLE 50

(1RS, 2RS, 3aSR, 8bRS)-1-benzenesulfonamido-2-hydroxy-2,3,3a,8b-tetrahydro-1H-cyclopenta[b]benzofuran-5-(E)-acrylic acid methyl ester (87)

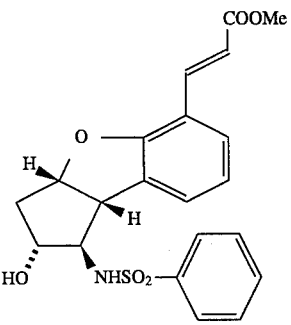
(87)

(1RS, 2RS, 3aSR, 8bRS)-1-benzenesulfonamido-2-tetrahydropyranyloxy- 2,3,3a,8b-tetrahydro-1H-cyclopenta[b]benzofuran-5-carboxylic acid methyl ester (4) (853 mg) was dissolved in anhydrous THF (10 ml) followed by the addition of lithium aluminum hydride (137 mg) at −20° C. and stirring for 15 minutes. Water (10 ml) was slowly added to the reaction mixture followed by the addition of 1N hydrochloric acid (15 ml) and extraction with ethyl acetate (50 ml, 20 ml). The organic layers were washed with a saturated aqueous solution of sodium hydrogencarbonate (20 ml), water (20 ml) and saturated brine (20 ml) and concentrated after drying with magnesium sulfate. The resulting residue was dissolved in methylene chloride (10 ml) followed by the addition of manganese dioxide (782 mg) and stirring for 6 hours at room temperature. Manganese dioxide (469 mg) was further added three times at 12 hour intervals. The reaction mixture was then stirred for 12 hours after the final addition of manganese dioxide and the reaction mixture was filtered. The crystals were washed with THF (20 ml×3) and the filtrates were combined followed by concentration. Next, sodium hydride (60% mineral oil dispersion, 201 mg) was suspended in anhydrous THF followed by the addition of DMSO (8 ml) and cooling to 0° C. Dimethoxyphosphoryl methyl acetate (0.874 ml) was added to this mixture followed by stirring for 30 minutes at 0° C. A THF solution (6 ml) of the aldehyde synthesized above was added to this reaction mixture at 0° C. and stirred for 20 minutes at the same temperature. The resulting reaction solution was neutralized with acetic acid and concentrated. Water (30 ml) was then added to the residue followed by extraction with ethyl acetate (40 ml×2). The organic layers were washed with water (30 ml×2) and saturated brine (30 ml) and concentrated after drying with anhydrous sodium sulfate. The resulting residue was dissolved in methanol (20 ml) followed by the addition of 3 drops of concentrated hydrochloric acid and stirring for 1 hour at room temperature. The resulting reaction mixture was neutralized by addition of sodium hydrogencarbonate followed by concentration. Water (30 ml) was added to the residue followed by extraction with ethyl acetate (40 ml×2). The organic layers were washed with water (30 ml) and saturated brine (30 ml) and concentrated after drying with anhydrous magnesium sulfate. The resulting residue was separated and purified with column chromatography (silica gel: ethyl acetate/cyclohexane) to obtain the target compound (602 mg) at a yield of 81%.

M.P.: 220.0°–221.0° C. (recrystallized from THF/n-hexane)

IR (KBr method): 3420, 3132, 2916, 1628, 1607, 1589, 1483, 1450, 1330, 1296, 1261, 1201, 1162, 1096, 1075, 1027, 982, 909, 870, 849, 793, 750, 721, 690, 617, 586, 555 cm$^{-1}$ NMR (400 MHz, DMSO, δ): 1.97 (1H, br.d, J=15.0 Hz), 2.2–2.3 (1H, m), 3.35–3.45, 3.55–3.65 (1H, m), 3.69 (3H, s), 3.90–3.95 (1H, m), 4.65 (1H, d, J=2.9 Hz), 5.3–5.4 (1H, m), 6.60 (1H, d, J=16.1 Hz), 6.7–6.8 (2H, m), 7.3–7.4 (1H, m), 7.55 (1H, d, J=16.1 Hz), 7.6–7.7 (3H, m), 7.85–7.95 (2H, m), 8.00–8.05 (1H, m)

MASS (EI method, m/e): 415 (M$^+$)

Elementary Analysis: (as $C_{21}H_{21}NO_6S$) Calculated values: C: 60.71, H: 5.09, N: 3.37, S: 7.72 Measured values: C: 60.80, H: 5.32, N: 3.60, S: 7.77

WORKING EXAMPLE 51

(1RS, 2RS, 3aSR, 8bRS)-1-benzenesulfonamido-2-hydroxy-2,3,3a,8b-tetrahydro-1H-cyclopenta[b]benzofuran-5-(E)-acrylic acid (88)

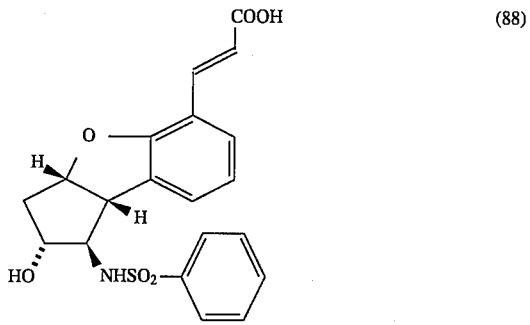

The target compound (166 mg) was obtained from (1RS, 2RS, 3aSR, 8bRS)-1-benzenesulfonamido-2-hydroxy-2,3,3a,8b-tetrahydro-1H-cyclopenta[b]benzofuran-5-(E)-acrylic acid methyl ester (87) (250 mg) in the same manner as Working Example 2.

M.P.: 231°–232° C. (recrystallized from methanol/ethyl acetate/n-hexane)

IR (KBr method): 3432, 3190, 2978, 1680, 1628, 1607, 1589, 1452, 1421, 1311, 1216, 1203, 1172, 1087, 1069, 1029, 988, 940, 909, 750, 719, 688, 588, 559 cm$^{-1}$ NMR (400 MHz, DMSO, δ): 1.96 (1H, br.d, J=15.0 Hz), 2.2–2.3 (1H, m), 3.35–3.45 (1H, m), 3.55–3.65 (1H, m), 3.90–3.95 (1H, m), 4.66 (1H, d, J=3.4 Hz), 5.3–5.4 (1H, m), 6.51 (1H, d, J=16.1 Hz), 6.7–6.8 (2H, m), 7.25–7.35 (1H, m), 7.48 (1H, d, J=16.1 Hz), 7.6–7.75 (3H, m), 7.85–7.95 (2H, m), 8.03 (1H, d, J=7.3 Hz), 12.26 (1H, br.s)

MASS (EI method, m/e): 401 (M$^+$)

Elementary Analysis: (as $C_{20}H_{19}NO_6S$) Calculated values: C: 59.84, H: 4.77, N: 3.49, S: 7.99 Measured values: C: 59.82, H: 4.81, N: 3.54, S: 8.10

WORKING EXAMPLE 52

(1RS, 2RS, 3aSR, 8bRS)-1-benzenesulfonamido-2-hydroxy-2,3,3a,8b-tetrahydro-1H-cyclopenta[b]benzofuran-5-yloxyacetic acid methyl ester (46)

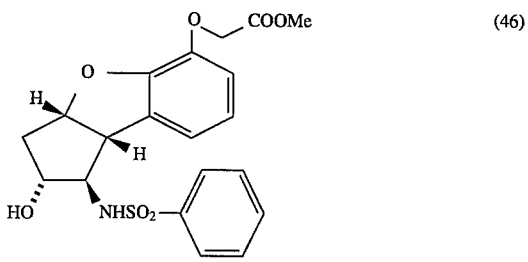

(1RS, 2SR, 3aSR, 8bRS)-1,2-(N-benzenesulfonylimino)-2,3,3a,8b-tetrahydro-1H-cyclopenta[b]benzofuran-5-yloxyacetic acid methyl ester (31) (155 mg) was dissolved in acetic acid (2 ml) followed by the addition of sodium acetate (95 mg) and refluxing for 3 hours. The reaction solution was cooled followed by the addition of ethyl acetate (50 ml) and water (30 ml). Sodium hydrogencarbonate (3.5 g) was then slowly added to this mixture at 0° C. to separate. The aqueous layer was re-extracted with ethyl acetate (30 ml) followed by combining of the organic layers, washing with water (30 ml) and saturated brine (30 ml) and concentrating after drying with anhydrous magnesium sulfate. The residue was dissolved in methanol (4 ml) followed by the addition of a methanol solution of sodium methoxide (5.22N, 0.03 ml) and stirring for 3 hours at room temperature. The reaction solution was neutralized with acetic acid and concentrated. Water (25 ml) was added to the residue followed by extraction with ethyl acetate (50 ml, 20 ml). The organic layers were combined and washed with water (20 ml) and saturated brine (20 ml). The organic layers were dried with anhydrous magnesium sulfate and concentrated, and the resulting residue was purified with column chromatography (silica gel: ethyl acetate/cyclohexane 1/1–2/1) to obtain the target compound (141 mg) at a yield of 87%.

Spectral data is the same as that of compound (48) produced in Working Example 9.

WORKING EXAMPLE 53

(1SR, 3aSR, 8bRS)-1-benzenesulfonamido-2,3,3a, 8b-tetrahydro- 1H-cyclopenta[b]benzofuran-5-yloxyacetic acid methyl ester (89)

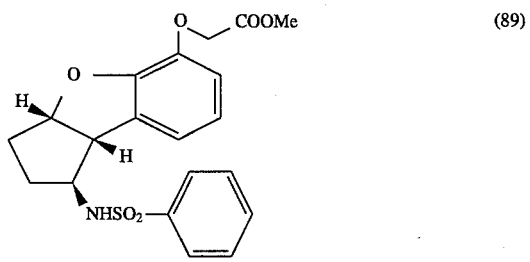

(89)

(1RS, 2SR, 3aSR, 8bRS)-1,2-(N-benzenesulfonylimino)-2,3,3a,8b-tetrahydro-1H-cyclopenta[b]benzofuran-5-yloxyacetic acid methyl ester (31) (1.00 g) was dissolved in HMPA (8 ml) followed by the addition of NaCNBH$_3$ (626 mg) and stirring for 4.5 hours at 70° C. Ethyl acetate (100 ml) was added to the reaction solution and washed with water (40 ml). The aqueous layer was re-extracted with ethyl acetate (40 ml), the organic layer was combined and washed twice with a mixed solvent of water (30 ml) and saturated brine (10 ml) and once with saturated brine (40 ml). The organic layer was dried with anhydrous magnesium sulfate followed by concentration. The residue was purified with column chromatography (silica gel: ethyl acetate/cyclohexane 1/1) to obtain the target compound (595 mg) at a yield of 59%.

M P.: 129°–130° C. (recrystallized from ethyl acetate/n-hexane)

IR (KBr method): 3260, 2954, 1771, 1620, 1595, 1493, 1448, 1392, 1352, 1323, 1309, 1294, 1220, 1201, 1170, 1154, 1114, 1098, 1087, 1050, 1023, 998, 949, 903, 878, 864, 847, 758, 721, 690, 611, 580, 563 cm$^{-1}$ NMR (500 MHz, CDCl$_3$, δ): 1.55–1.6 (1H, m), 1.65–1.7 (1H, m), 2.0–2.1 (1H, m), 2.15–2.2 (1H, m), 3.65–3.7 (1H, m), 3.77 (3H, s), 3.85 (1H, d, J=7.9 Hz), 4.67 (1H, d, J=16.5 Hz), 4.68 (1H, d, J=16.5 Hz), 4.77 (1H, d, J=6.1 Hz), 5.3–5.35 (1H, m), 6.65–6.75 (3H, m), 7.55–7.65 (3H, m), 7.9–7.95 (2H, m)

MASS (EI method, m/e): 403 (M$^+$)

Elementary Analysis: (as C$_{20}$H$_{21}$NO$_6$S) Calculated values: C: 59.54, H: 5.25, N: 3.47, S: 7.95 Measured values: C: 59.61, H: 5.28, N: 3.61, S: 8.14

WORKING EXAMPLE 54

(1SR, 3aSR, 8bRS)-1-benzenesulfonamido-2,3,3a, 8b-tetrahydro- 1H-cyclopenta[b]benzofuran-5-yloxyacetic acid (90)

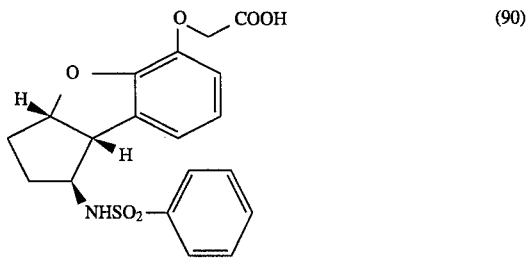

(90)

The target compound (206 mg) was obtained from (1SR, 3aSR, 8bRS)-1-benzenesulfonamido-2,3,3a,8b-tetrahydro-1H-cyclopenta [b]benzofuran-5-yloxyacetic acid methyl ester (89) (260 mg) in the same manner as Working Example 2.

M.P.: 148°–149° C. (recrystallized from ethyl acetate/n-hexane)

IR (KBr method): 3250, 2972, 2934, 1738, 1620, 1595, 1493, 1468, 1454, 1437, 1350, 1317, 1296, 1249, 1205, 1154, 1114, 1085, 1017, 990, 948, 936, 905, 878, 760, 727, 692, 613, 578, 563 cm$^{-1}$ NMR (400 MHz, CDCl$_3$, δ): 1.5–1.6 (1H, m), 1.7–1.8 (1H, m), 1.95–2.2 (2H, m), 3.6–3.7 (1H, m), 3.85 (1H, d, J=7.8 Hz), 4.69 (1H, d, J=16.6 Hz), 4.71 (1H, d, J=16.6 Hz), 4.73 (1H, d, J=6.4 Hz), 5.3– 5.35 (1H, m), 6.7–6.8 (3H, m), 7.5–7.65 (3H, m), 7.85–7.95 (2H, m)

MASS (EI method, m/e): 389 (M$^+$)

Elementary Analysis: (as C$_{19}$H$_{19}$NO$_6$S) Calculated values: C: 58.60, H: 4.92, N: 3.60, S: 8.23 Measured values: C: 58.59, H: 4.92, N: 3.51, S: 8.43

WORKING EXAMPLE 55

(1RS, 2RS, 3aSR, 8bRS)-1-benzenesulfonamido-2-methoxy-2,3,3a,8b-tetrahydro-1H-cyclopenta [b]benzofuran-5-yloxyacetic acid methyl ester (91)

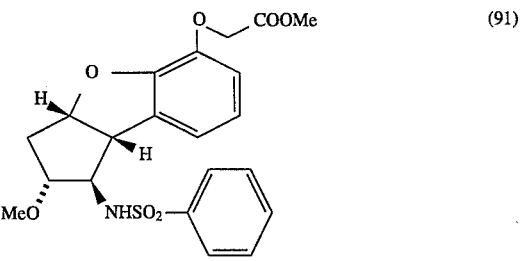

(91)

(1RS, 2SR, 3aSR, 8bRS)-1,2 -(N-benzenesulfonylimino)-2,3,3a,8b-tetrahydro-1H-cyclopenta [b]benzofuran-5-yloxyacetic acid methyl ester (31) (500 mg) was dissolved in methanol (5 ml) followed by the addition of a methanol solution of sodium hydroxide (5.22N, 0.60 ml) and refluxing for 6 hours. The reaction mixture was neutralized with acetic acid followed by the addition of water (20 ml) and extraction with ethyl acetate (60 ml×2). The organic layers were washed with water (20 ml) and saturated brine (20 ml) and concentrated after drying with anhydrous magnesium sulfate. The resulting residue was purified with column chromatography (silica gel: ethyl acetate/cyclohexane 1/1) to obtain the target compound (474 mg).

M.P.: 140°–141° C. (recrystallized by ethyl acetate/n-hexane)

IR (KBr method): 3268, 2930, 1773, 1620, 1597, 1493, 1450, 1394, 1373, 1319, 1294, 1203, 1158, 1114, 1027, 893, 762, 719, 688, 582 cm$^{-1}$ NMR (400 MHz, CDCl$_3$, δ): 2.15–2.2 (1H, m), 2.26 (1H, ddd, J=5.4, 6.8, 14.7 Hz), 2.94 (3H, s), 3.6–3.75 (3H, m), 3.76 (3H, s), 4.66 (2H, s), 4.98 (1H, d, J=6.8 Hz), 5.2–5.3 (1H, m), 6.65–6.75 (3H, m), 7.55–7.65 (3H, m), 7.9–7.95 (2H, m)

MASS (EI method, m/e): 433 (M$^+$)

Elementary Analysis: (as C$_{21}$H$_{23}$NO$_7$S) Calculated values: C: 58.19, H: 5.35, N: 3.23, S: 7.40 Measured values: C: 58.09, H: 5.51, N: 3.28, S: 7.37

WORKING EXAMPLE 56

(1RS, 2RS, 3aSR, 8bRS)-1-benzenesulfonamido-2-methoxy-2,3,3a,8b-tetrahydro-1H-cyclopenta[b]benzofuran-5-yloxyacetic acid (92)

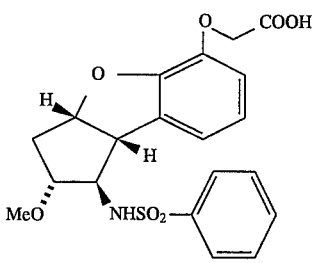

The target compound (154 mg) was obtained from (1RS, 2RS, 3aSR, 8bRS)-1-benzenesulfonamido-2-methoxy-2,3, 3a,8b-tetrahydro- 1H-cyclopenta[b]benzofuran-5-yloxyacetic acid methyl ester (91) (190 mg) in the same manner as Working Example 2.

M.P.: 177°–178° C. (recrystallized by ethyl acetate/n-hexane)

IR (KBr method): 3268, 2928, 1771, 1626, 1595, 1493, 1435, 1371, 1321, 1294, 1193, 1166, 1114, 1093, 1067, 1046, 977, 946, 920, 895, 841, 764, 721, 694, 679, 617, 582, 561 cm$^{-1}$ NMR (400 MHz, DMSO-d$_6$, δ): 1.95–2.05 (1H, m), 2.2–2.3 (1H, m), 2.79 (3H, s), 3.45–3.5 (1H, m), 3.55–3.6 (2H, m), 4.56 (2H, s), 5.2–5.25 (1H, m), 6.34 (1H, d, J=7.3 Hz), 6.6–6.65 (2H, m), 7.6–7.7 (3H, m), 7.85–7.95 (2H, m), 8.11 (1H, d, J=7.3 Hz)

MASS (EI method, m/e): 419 (M$^+$)

Elementary Analysis: (as C$_{20}$H$_{21}$NO$_7$S) Calculated values: C: 57.27, H: 5.05, N: 3.34, S: 7.64 Measured values: C: 56.96, H: 5.34, N: 3.68, S: 7.62

WORKING EXAMPLE 57

(1RS, 3aSR, 8bRS)-1-benzenesulfonamido-2,3,3a, 8b-tetrahydro- 1H-cyclopenta[b]benzofuran-5-yloxyacetic acid methyl ester (93)

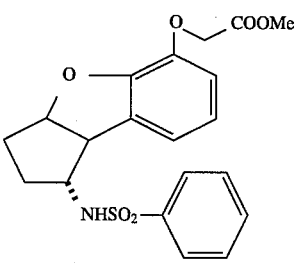

The target compound (75 mg) was obtained from (1SR, 2RS, 3aSR, 8bRS)-1,2 -(N-benzenesulfonylimino) -2,3,3a, 8b-tetrahydro- 1H-cyclopenta[b]benzofuran-5-yloxyacetic acid methyl ester (36) (200 mg) in the same manner as Working Example 53.

M.P.: 133°–134° C. (recrystallized by ethyl acetate/n-hexane)

IR (KBr method): 3284, 2978, 2958, 1750, 1622, 1591, 1491, 1462, 1446, 1361, 1319, 1292, 1226, 1197, 1123, 1091, 969, 940, 922, 760, 733, 719, 690, 594, 563, 538 cm$^{-1}$ NMR (400 MHz, CDCl$_3$, δ): 1.25–1.35 (1H, m), 1.65–1.75 (2H, m), 2.1–2.2 (1H, m), 3.78 (3H, s), 3.85–4.0 (2H, m), 4.33 (1H, d, J=9.8 Hz), 4.69 (1H, d, J=16.4 Hz), 4.71 (1H, d, J=16.4 Hz), 5.25–5.3 (1H, m), 6.7–6.85 (3H, m), 7.5–7.6 (3H, m), 7.85–7.9 (2H, m)

MASS (EI method, m/e): 403 (M$^+$)

Elementary Analysis: (as C$_{20}$H$_{21}$NO$_6$S) Calculated values: C: 59.54, H: 5.25, N: 3.47, S: 7.95 Measured values: C: 59.33, H: 5.29, N: 3.51, S: 7.76

WORKING EXAMPLE 58

(1RS, 3aSR, 8bRS)-1-benzenesulfonamido-2,3,3a, 8b-tetrahydro- 1H-cyclopenta[b]benzofuran-5-yloxyacetic acid (94)

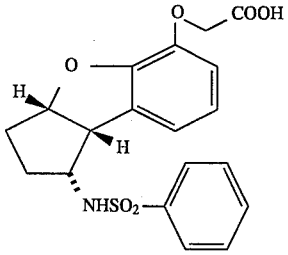

The target compound (67 mg) was obtained from ( 1RS, 3aSR, 8bRS)-1-benzenesulfonamido-2,3,3a,8b-tetrahydro-1H-cyclopenta [b]benzofuran-5-yloxyacetic acid methyl ester (93) (100 mg) in the same manner as Working Example 2.

M.P.: 188°–189° C. (recrystallized by ethyl acetate/n-hexane)

IR (KBr method): 3288, 2956, 1717, 1624, 1591, 1491, 1450, 1359, 1319, 1286, 1236, 1199, 1156, 1123, 1091, 938, 920, 890, 760, 735, 719, 690, 594 cm$^{-1}$ NMR (400 MHz, DMSO-d$_6$, δ): 1.2–1.4 (2H, m), 1.65–1.75 (1H, m), 1.8–1.9 (1H, m), 3.6–3.7 (1H, m), 3.82 (1H, t, J=7.5 Hz), 4.61 (2H, s), 5.17 (1H, dd, J=5.4, 7.5 Hz), 6.7–6.8 (2H, m), 6.91 (1H, d, J=6.8 Hz), 7.5–7.7 (4H, m), 7.8–7.85 (2H, m)

MASS (EI method, m/e): 389 (M$^+$)

Elementary Analysis: (as C$_{19}$H$_{19}$NO$_6$S) Calculated values: C: 58.60, H: 4.92, N: 3.60, S: 8.23 Measured values: C: 58.42, H: 4.85, N: 3.61, S: 8.27

WORKING EXAMPLE 59

(1SR, 2RS, 3aSR, 8bSR)-2-acetoxy-1-((benzenesulfonamido)methyl)- 2,3,3a,8b-tetrahydro-1H-cyclopenta[b]benzofuran-5-yloxyacetic acid methyl ester (95)

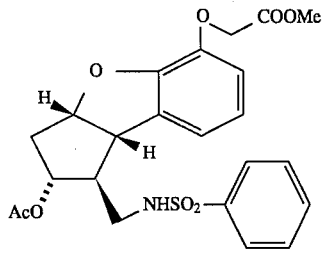

(1SR, 2RS, 3aSR, 8bSR)-2-acetoxy-1-azidomethyl-2,3,3a,8b-tetrahydro-1H-cyclopenta[b]benzofuran-5-yloxyacetic acid methyl ester (37) (390 mg) was dissolved in methanol (5 ml) followed by the addition of 10% palladium activated carbon (40 mg) and stirring for 4 hours at room temperature in a hydrogen atmosphere. The reaction mixture was concentrated after filtering using selite. The residue was dissolved in methylene chloride (5 ml) followed by the addition of triethylamine (0.15 ml, 1.06 mmol) and benzenesulfonyl chloride (0.10 ml) and stirring for 17 hours at room temperature. The reaction solution was poured into water (50 ml) and extracted with ethyl acetate (30 ml×2). The organic layers were combined, washed with 1N hydrochloric acid (20 ml), a saturated aqueous solution of sodium hydrogen carbonate (20 ml) and saturated brine (20 ml), and concentrated after drying with sodium sulfate. The resulting residue was purified with column chromatography (silica gel: cyclohexane/ethyl acetate 1/1) to obtain the target compound (160 mg) at a yield of 31%. NMR (90 MHz, CDCl$_3$, δ): 6.63–7.95 (8H, m), 4.79–5.61 (3H, m), 4.69 (2H, s), 3.78 (3H, s), 3.60–3.75 (2H, m), 2.92–3.14 (2H, m), 2.00–2.50 (2H, m), 1.76 (3H, s)

MASS (EI method, m/e):475 (M$^+$)

WORKING EXAMPLE 60

(1SR, 2RS, 3aSR, 8bSR)-1-((benzenesulfonamido)methyl)-2-hydroxy-2,3,3a,8b-tetrahydro-1H-cyclopenta[b]benzofuran-5-yloxyacetic acid methyl ester (96)

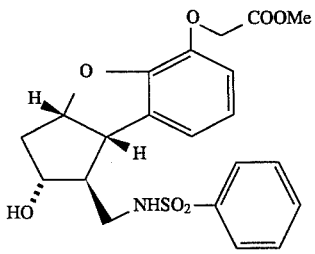

(1SR, 2RS, 3aSR, 8bSR)-2-acetoxy-1((benzenesulfonamido)methyl)- 2,3,3a,8b-tetrahydro-1H-cyclopenta [b]benzofuran-5-yloxyacetic acid methyl ester (95) (160 mg) was dissolved in methanol (2 ml) followed by the addition of a 5.92N methanol solution of sodium methoxide (0.05 ml) and stirring for 2.5 hours at room temperature in an argon atmosphere. After neutralizing the reaction solution with acetic acid, water (50 ml) was poured in followed by extraction with ethyl acetate (30 ml ×3). The organic layers were combined, washed with a saturated aqueous solution of sodium hydrogencarbonate (30 ml) and concentrated after drying with sodium sulfate. The residue was purified with column chromatography (silica gel: chloroform/methanol 95/5) to obtain the target compound (94 mg) at a yield of 64%.

M.P.: 126° C. (recrystallized from ethyl acetate/cyclohexane)

IR (KBr method): 3466, 3174, 2958, 2930, 1758, 1731, 1620, 1593, 1510, 1491, 1466, 1450, 1325, 1309, 1272, 1253, 1193, 1166, 1098, 1079, 1038, 789, 758, 727, 690, 592, 540, 518, 501, 418 cm$^{-1}$ NMR (500 MHz, CDCl$_3$, δ): 7.87 (2H, m), 7.59 (1H, m), 7.52 (2H, m), 6.82 (1H, brd, J=6.7 Hz), 6.77 (1H, t, J=8.0 Hz), 6.72 (1H, dd, J=1.2, 7.9 Hz), 5.13 (1H, ddd, J=4.9, 6.7, 8.5 Hz), 5.02 (1H, brm), 4.72, 4.68 (each 1H, ABq, J=16.5 Hz), 3.97 (1H, m), 3.78 (3H, s), 3.35 (1H, t, J=8.6 Hz), 3.30 (1H, ddd, J=5.5, 7.9, 12.8 Hz), 3.08 (1H, ddd, J=4.9, 7.9, 12.8 Hz), 2.57 (1H, m), 1.93–2.07 (3H, m)

MASS (EI method, m/e): 433 (M$^+$)

Elementary Analysis: (as C$_{21}$H$_{23}$NO$_7$S) Calculated values: C: 58.21, H: 5.35, N: 3.23, S: 7.38 Measured values: C: 58.06, H: 5.33, N: 3.21, S: 7.46

WORKING EXAMPLE 61

(1RS, 2RS, 3aSR, 8bRS)-1-(N-methylbenzenesulfonamido)-2-hydroxy-2,3,3a,8b-tetrahydro-1H-cyclopenta[b]benzofuran-5-yloxyacetic acid methyl ester (97)

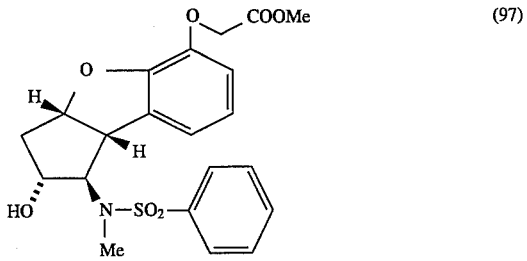

Potassium carbonate (154 mg) and methyl iodide (0.14 ml) were added to an acetone solution (8 ml) of (1RS, 2RS, 3aSR, 8bRS)-1-benzenesulfonamido-2-tetrahydropyranyloxy-2,3,3a,8b-tetrahydro-1H-cyclopenta[b]benzofuran-5-yloxyacetic acid methyl ester (25) (375 mg) followed by refluxing for 5 hours. After cooling the reaction mixture and adding acetic acid (0.15 ml), water (30 ml) was added followed by extraction with ethyl acetate (40 ml×2). The organic layers were combined, washed with saturated brine (30 ml) and concentrated after drying with anhydrous magnesia sulfate. The residue was dissolved in methanol (15 ml) followed by the addition of 3 drops of concentrated hydrochloric acid and stirring for 3 hours at room temperature. The reaction solution was then neutralized with sodium hydrogencarbonate and concentrated. The resulting residue was purified with column chromatography (silica gel: methylene chloride/acetonitrile 4/1) to obtain the target compound (300 mg) at a yield of 93%. IR (liquid film method): 3516, 3026, 2958, 1758, 1622, 1595, 1491, 1464, 1448, 1379, 1330, 1222, 1193, 1154, 1114, 1091, 1027, 1002, 946, 861, 832, 754, 690, 667, 586 cm$^{-1}$ NMR (400 MHz, CDCl$_3$, δ): 1.95–2.05 (3H, m), 2.25–2.35 (1H, m), 2.6–2.7 (1H, m), 2.96 (3H, s), 3.6–3.7 (1H, m), 3.78 (3H, s), 4.05–4.15 (2H, m), 4.70 (2H, s), 5.13 (1H, ddd, J=6.1, 7.6, 9.3 Hz), 6.32

(1H, d, J=7.8 Hz), 6.60 (1H, t, J=7.8 Hz), 6.68 (1H, d, J=7.8 Hz), 7.45–7.6 (3H, m), 7.8–7.85 (2H, m)

MASS (EI method, m/e): 433 (M⁺)

WORKING EXAMPLE 62

(1RS, 2RS, 3aSR, 8bRS)-1-(N-methylbenzenesulfonamido)-2-hydroxy-2,3,3a,8b-tetrahydro-1H-cyclopenta[b]benzofuran-5-yloxyacetic acid (98)

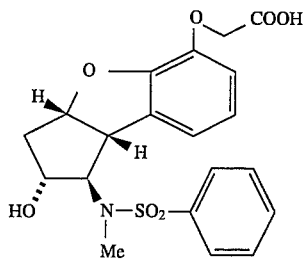

The target compound (101 mg) was obtained from (1RS, 2RS, 3aSR, 8bRS)-1-(N-methylbenzenesulfonamido)-2-hydroxy-2,3,3a,8b-tetrahydro-1H-cyclopenta[b]benzofuran-5-yloxyacetic acid methyl ester (97) (180 mg) in the same manner as Working Example 2.

M.P.: 194°–195° C. (recrystallized from methanol/water)

IR (KBr method): 3502, 2950, 1742, 1622, 1591, 1491, 1464, 1448, 1427, 1328, 1290, 1257, 1203, 1158, 1122, 1110, 1089, 1031, 969, 944, 891, 855, 833, 774, 748, 735, 719, 683, 590, 569 cm⁻¹ NMR (400 MHz, DMSO-d₆, δ): 1.69 (1H, ddd, J=6.3, 9.3, 13.2 Hz), 2.4–2.5 (1H, m), 2.78 (3H, s), 3.6–3.7 (1H, m), 3.9–4.0 (1H, m), 4.08 (1H, t, J=8.1 Hz), 4.65 (2H, S), 4.89 (1H, d, J=6.8 Hz), 5.05–5.15 (1H, m), 6.65–6.75 (3H, m), 7.5–7.7 (3H, m), 7.85–7.9 (2H, m), 12.9–13.0 (1H, m)

MASS (EI method, m/e): 419 (M⁺)

Elementary Analysis: (as $C_{20}H_{21}NO_7S$) Calculated values: C: 57.27, H: 5.05, N: 3.34, S: 7.64 Measured values: C: 57.30, H: 5.11, N: 3.43, S: 7.79

WORKING EXAMPLE 63

(1SR, 2SR, 3aSR, 8bRS)-2-benzenesulfonamido-1-hydroxy-2,3,3a,8b-tetrahydro-1H-cyclopenta[b]benzofuran-5-yloxyacetic acid methyl ester (99)

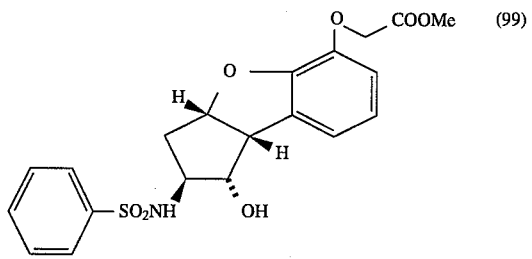

The target compound (2.15 g) was obtained from (1SR, 2SR, 3aSR, 8bSR)-2-azido-7-bromo-tetrahydropyranyloxy-2,3,3a,8b-tetrahydro-1H-cyclopenta[b]benzofuran-5-yloxyacetic acid methyl ester (23) (3.07 g) in the same manner as Working Example 9.

M.P.: 119°–120° C. (recrystallized from ethyl acetate)

IR (KBr method): 3420, 3280, 2930, 1760, 1730, 1620, 1590, 1490, 1440, 1330, 1290, 1200, 1150, 1120, 1090, 1000, 940, 770, 760, 740, 720, 690, 610, 600, 560 cm⁻¹ NMR (400 MHz, CDCl₃, δ): 1.74 (1H, ddd, J=5.5, 11.6, 14.3 Hz), 2.31 (1H, dd, J=6.6, 14.3 Hz), 2.55–2.65 (1H, m), 3.25–3.4 (1H, m), 3.79 (3H, s), 3.96 (1H, t, J=8.4 Hz), 4.1–4.2 (1H, m), 4.68 (1H, d, J=16.3 Hz), 4.70 (1H, d, J=16.3 Hz), 5.15–5.25 (2H, m), 6.7–6.75 (1H, m), 6.79 (1H, t, J=7.6 Hz), 6.94 (1H, d, J=7.6 Hz), 7.45–7.6 (3H, m), 7.8–7.9 (2H, m)

MASS (EI method, m/e): 419 (M⁺)

Elementary Analysis: (as $C_{20}H_{21}NO_7S$) Calculated values: C: 57.27, H: 5.05, N: 3.34, S: 7.64 Measured values: C: 57.38, H: 5.24, N: 3.16, S: 7.34

WORKING EXAMPLE 64

(1SR, 2SR, 3aSR, 8bRS)-2-benzenesulfonamido-1-hydroxy-2,3,3a,8b-tetrahydro-1H-cyclopenta[b]benzofuran-5-yloxyacetic acid (100)

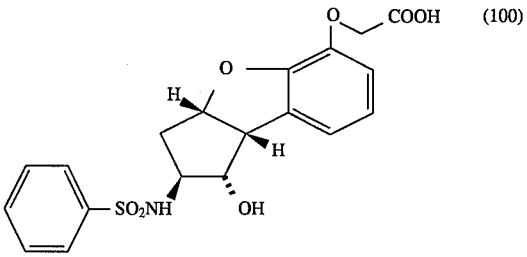

The target compound (287 mg) was obtained from (1SR, 2SR, 3aSR, 8bRS)-2-benzenesulfonamido-1-hydroxy-2,3,3a,8b-tetrahydro-1H-cyclopenta[b]benzofuran-5-yloxyacetic acid methyl ester (99) (500 g) in the same manner as Working Example 2.

M.P.: 181°–182° C. (recrystallized from ethyl acetate)

IR (KBr method): 3480, 3270, 2930, 1710, 1620, 1590, 1480, 1450, 1320, 1280, 1230, 1190, 1150, 1120, 1110, 1090, 1000, 940, 900, 850, 800, 770, 750, 730, 720, 690, 600, 560 cm⁻¹ NMR (400 MHz, CDCl₃, +DMSO-d₆, δ): 1.55–1.7 (1H, m), 1.75–1.9 (1H, m), 3.1–3.2 (1H, m), 3.78 (1H, t, J=8.5 Hz), 4.07 (1H, t, J=8.5 Hz), 4.58 (2H, s), 5.0–5.1 (1H, m), 6.6–6.7 (2H, m), 6.8–6.9 (1H, m), 7.5–7.6 (3H, m), 7.7–7.75 (1H, m), 7.8–7.85 (2H, m)

MASS (EI method, m/e): 405 (M⁺)

Elementary Analysis: (as $C_{19}H_{19}NO_7S$) Calculated values: C: 56.29, H: 4.72, N: 3.45, S: 7.91 Measured values: C: 56.34, H: 4.74, N: 3.37, S: 7.98

WORKING EXAMPLE 65

(1RS, 2RS, 3aSR, 8bRS)-1-benzenesulfonamido-2-hydroxy-2,3,3a,8b-tetrahydro-1H-cyclopenta[b]benzofuran-5-yloxymethyl methyl ketone (101)

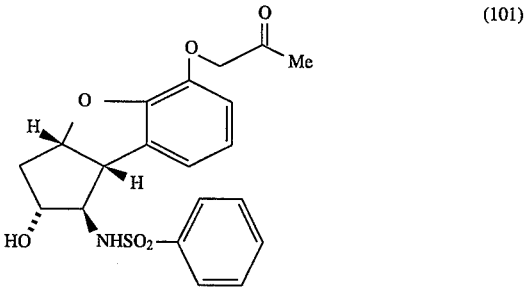

Sodium hydride (60% mineral oil dispersion, 162 mg) was added to anhydrous DMSO (2 ml) followed by stirring for 1 hour at 70° C. Anhydrous THF (2 ml) was added to the reaction mixture at 0° C. followed by the addition of an anhydrous THF solution (2 ml) of (1RS, 2RS, 3aSR, 8bRS)-1-benzenesulfonamido-2-tetrahydropyranyloxy-2,3,3a,8b-tetrahydro-1H-cyclopenta[b]benzofuran-5-yloxyacetic acid methyl ester (25) (510 mg) and stirring for 30 minutes at 0° C. The reaction solution was neutralized with 1N hydrochloric acid (4.3 ml) followed by the addition of water (40 ml) and extraction with ethyl acetate (100 ml×2). The organic layers were combined, washed with a saturated aqueous solution of sodium hydrogencarbonate (40 ml), water (40 ml×2) and saturated brine (40 ml), and then concentrated after drying with anhydrous magnesium sulfate. The residue was dissolved in acetic acid (8 ml) followed by the addition of zinc powder (659 mg) and refluxed for 10 minutes. The reaction solution was then cooled and filtered. Ethyl acetate (120 ml) and water (120 ml) were added to the filtrate followed by the slow addition of sodium hydrogencarbonate (14.1 g) to this mixture at 0° C. to separate. The aqueous layer was re-extracted with ethyl acetate (120 ml), and the organic layers were combined, washed with water (60 ml×2) and saturated brine (60 ml) and concentrated after drying with anhydrous magnesium sulfate. The resulting residue was purified with column chromatography (silica gel: ethyl acetate/cyclohexane 1/1–1/2) to obtain the target compound (211 mg) at a yield of 52 %.

M.P.: t79°–180° C. (recrystallized from methanol)

IR (KBr method): 3500, 3236, 2904, 1738, 1620, 1599, 1489, 1460, 1431, 1419, 1336, 1299, 1255, 1232, 1214, 1187, 1154, 1104, 1060, 969, 938, 886, 843, 774, 754, 743, 727, 683, 615, 584, 559, 545, 536 cm$^{-1}$ NMR (500 MHz, DMSO-d$_6$, δ): 1.85–1.9 (1H, m), 2.10 (3H, s), 2.2–2.3 (1H, m), 3.35–3.4 (1H, m), 3.55–3.6 (1H, m), 3.85–3.95 (1H, m), 4.6–4.65 (1H, m), 4.68 (2H, s), 5.25–5.35 (1H, m), 6.3–6.35 (1H, m), 6.55–6.65 (2H, m), 7.6–7.7 (3H, m), 7.85–7.9 (2H, m), 7.95–8.0 (1H, m)

MASS (EI method, m/e): 403 (M$^+$)

WORKING EXAMPLE 66

(1RS, 2RS, 3aSR, 8bRS)-1-benzenesulfonamido-2-hydroxy2,3,3a,8b-tetrahydro-1H-cyclopenta[b]benzofuran-5-yloxyacetic acid ethyl ester (102)

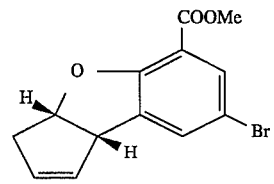

Triethylamine (0.051 ml) and ethyl chloroformate (0.035 ml) were added to a tetrahydrofuran solution (1.5 ml) of (1RS, 2RS, 3aSR, 8bRS)-1-benzenesulfonamido-2-hydroxy- 2,3,3a,8b-tetrahydro-1H-cyclopenta[b]benzofuran-5-yloxyacetic acid (47) (150 mg) followed by stirring for 30 minutes at room temperature. Ethanol (1.1 ml) and triethylamine (0.051 ml) were added to the reaction mixture followed by stirring for 1 hour at room temperature. The resulting solution was then extracted with ethyl acetate (50 ml). The organic layer was washed with water (20 ml) and saturated brine (20 ml) and concentrated after drying with anhydrous magnesium sulfate. The resulting residue was purified with column chromatography (silica gel: ethyl acetate/cyclohexane 1/1) to obtain the target compound (126 mg).

M.P.: 124.5v–125.5° C. (recrystallized by ethyl acetate/n-hexane

IR (KBr method): 3504, 3252, 2978, 1769, 1738, 1620, 1595, 1495, 1452, 1303, 1263, 1197, 1151, 1106, 1079, 1033, 940, 905, 864, 845, 756, 721, 690 cm$^{-1}$ NMR (400 MHz, CDCl$_3$, δ): 1.27 (3H, t, J=7.1 Hz), 2.08 (1H, ddd, J=4.9, 7.3, 14.2 Hz), 2.52 (1H, dt, J=6.6, 14.2 Hz), 2.74 (1H, d, J=3.9 Hz), 3.4–3.45 (1H, m), 3.58 (1H, dd, J=5.4, 8.8 Hz), 4.05–4.1 (1H, m), 4.23 (2H, q, J=7.1 Hz), 4.65 (2H, s), 5.05–5.15 (2H, m), 6.37 (1H, d, J=6.8 Hz), 6.55–6.7 (2H, m), 7.5–7.65 (3H, m), 7.9–7.95 (2H, m)

MASS (EI method, m/e): 433 (M$^+$)

Elementary Analysis: (as C$_{21}$H$_{23}$NO$_7$S) Calculated values: C: 58.19, H: 5.35, N: 3.23, S: 7.40 Measured values: C: 58.11, H: 5.42, N: 3.36, S: 7.45

REFERENCE EXAMPLE 38

(3aS, 8bS)-7-bromo-3a,8b-dihydro-3H-cyclopenta[b] benzofuran-5-carboxylic acid methyl ester (103)

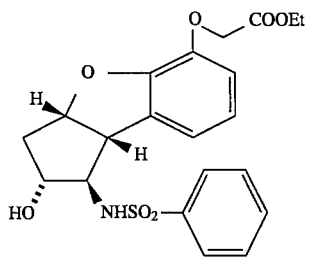

(3aS, 8bS)-7-bromo-3a,8b-dihydro-3H-cyclopenta[b] benzofuran-5-carboxylic acid (30 mg), produced according to the process described in Japanese Unexamined Patent Publication No. 59-161371, was dissolved in methanol (850 ml) followed by the addition of 95% sulfuric acid (1.1 ml) and refluxing for 15 minutes. The crystals that precipitated from the reaction mixture were collected by filtration. The crystals were dissolved in ethyl acetate (600 ml), washed with a 1% saturated aqueous solution of sodium hydrogencarbonate (200 ml) and saturated brine (200 ml), and concentrated to a solid after drying with anhydrous magnesium sulfate. The filtrate was concentrated under reduced pressure, and the residue was dissolved in methylene chloride followed by washing with a 1% saturated aqueous solution of sodium hydrogencarbonate (200 ml) and saturated brine (150 ml), and concentrated to a solid after drying with anhydrous magnesium sulfate. The resulting residues were combined and crystallized by ethyl acetate to obtain the target compound (25.8 mg) in the form of needle-shaped crystals. In addition, the mother liquor was purified with chromatography (silica gel: n-hexane/ethyl acetate/methylene chloride 10:1:2) to obtain the target compound (3.8 g) in the form of crystals (total: 29.6 g, yield: 94%).

M.P.: 155°–159° C. (recrystallized by ethyl acetate)

[α]D$^{25}$–168.64 (c 0.472, MeOH)

IR (KBr method): 2988, 2952, 1709, 1603, 1437, 1346, 1328, 1274, 1199, 1154, 1046, 1025, 998, 949, 897, 876, 828, 783, 739, 710, 621, 561, 516, 462 cm$^{-1}$ NMR (90 MHz, CDCl$_3$, δ): 2.91 (2H, m), 3.88 (3H, s), 4.37 (1H, br, d, J=7.5 Hz), 5.6–5.9 (3H, m), 7.4–7.5 (1H, m), 7.8–7.9 (1H, m)

MASS (EI method, m/e): 294 (M$^+$)

REFERENCE EXAMPLE 39

(3aR, 8bR)-7-bromo-3a,8b-dihydro-3H-cyclopenta[b]benzofuran-5-carboxylic acid methyl ester (104)

The target compound (29.0 g, yield: 92%) was obtained from (3aR, 8bR)-7-bromo-3a,8b-dihydro-3H-cyclopenta

[b]benzofuran-5-carboxylic acid (30 g), produced according to the process described in Japanese Unexamined Patent Publication No. 58-124778, in the same manner as Reference Example 38.

M.P.: 153°–158° C. (recrystallized by ethyl acetate)
$[\alpha]_D^{25}$+168.29 (c 0.492, MeOH)

IR (KBr method): 3088, 3054, 2988, 2952, 2914, 1771, 1711, 1603, 1437, 1346, 1330, 1274, 1212, 1199, 1154, 1046, 1025, 998, 949, 897, 876, 828, 783, 737, 710, 621, 561, 516, 464, 414 cm$^{-1}$ NMR (90 MHz, CDCl$_3$, δ): 2.91 (2H, m), 3.88 (3H, s), 4.37 (1H, d, br, J=7.3 Hz), 5.6–5.9 (3H, m), 7.4–7.5 (1H, m), 7.82 (1H, d, J=2.2 Hz)

MASS (EI method, m/e): 294 (M$^+$)

REFERENCE EXAMPLE 40

(1S, 2R, 3aS, 8bR)-7-bromo-1,2-epoxy-2,3,3a,8b-tetrahydro- 1H-cyclopenta[b]benzofuran-5-carboxylic acid methyl ester (105)

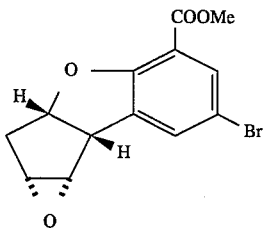
(105)

The target compound (12.5 g, yield: 51.3%) was obtained from (3aS, 8bS)-7-bromo-3a,8b-dihydro-3H-cyclopenta [b]benzofuran-5-carboxylic acid methyl ester (103) (23.0 g) in the same manner as Reference Example 1.

M.P.: 234°–236° C. (recrystallized by ethyl acetate)
$[\alpha]_D^{25}$–106.36 (c 0.440, CHCl$_3$)

IR (KBr method): 3086, 3028, 2990, 2950, 1709, 1603, 1450, 1419, 1332, 1307, 1274, 1212, 1156, 1100, 1064, 1029, 1004, 978, 953, 882, 843, 826, 785, 712, 640, 621, 534, 433 cm$^{-1}$ NMR (90 MHz, CDCl$_3$, δ): 2.30 (1H, ddd, J=1.3, 7.5, 15.8 Hz), 2.70 (1H, d, J=15.8 Hz), 3.71 (3H, br), 3.87 (3H, s), 5.50 (1H, t, J=7.7 Hz), 7.5–7.6 (1H, m), 7.90 (1H, d, J=2.2 Hz)

MASS (EI method, m/e): 310 (M$^+$)

REFERENCE EXAMPLE 41

(1R, 2S, 3aR, 8bS)-7-bromo-1,2-epoxy-2,3,3a,8b-tetrahydro- 1H-cyclopenta [b]benzofuran-5-carboxylic acid methyl ester (106)

The target compound (24.2 g, yield: 80.5%) was obtained from (3aR, 8bR)-7-bromo-3a,8b-dihydro-3H-cyclopenta [b]benzofuran-5-carboxylic acid methyl ester (104) (28.5 g) in the same manner as Reference Example 1.

M.P.: 233°–235° C. (recrystallized by ethyl acetate)
$[\alpha]_D^{25}$+106.52 (c 0.506, CHCl$_3$)

IR (KBr method): 3086, 3028, 2990, 2950, 1711, 1603, 1450, 1421, 1332, 1307, 1274, 1212, 1156, 1100, 1064, 1029, 1004, 978, 953, 882, 843, 826, 785, 712, 640, 621, 534, 435 cm$^{\pm 1}$ NMR (90 MHz, CDCl$_3$, δ): 2.30 (1H, ddd, J=1.3, 7.5, 16.3 Hz), 2.70 (1H, d, J=16.3 Hz), 3.70 (3H, br, s), 3.87 (3H, s), 5.49 (1H, t, J=7.5 Hz), 7.51 (1H, d, J=2.2 Hz), 7.90 (1H, d, J=2.2 Hz)

MASS (EI method, m/e):310 (M$^+$)

REFERENCE EXAMPLE 42

(1R, 2R, 3aS, 8bR)-1-azido-7-bromo-2-hydroxy-2, 3,3a,8b-tetrahydro-1H-cyclopenta[b]benzofuran-5-carboxylic acid methyl ester (107)

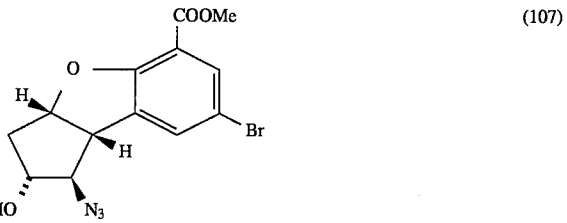
(107)

(1S, 2R, 3aS, 8bR)-7-bromo-1,2-epoxy-2,3,3a,8b-tetrahydro- 1H-cyclopenta[b]benzofuran-5-carboxylic acid methyl ester (105) (11.9 g) was dissolved in methanol (250 ml) followed by the addition of a 1.27M aqueous solution of sodium azide (0.114 mol) and refluxing for 4 hours. After concentrating the reaction mixture under reduced pressure and removing the methanol, 3N hydrochloric acid was added followed by extraction with ethyl acetate (400 ml 100 ml×2). The organic layer was then washed with water (150 ml×2) and saturated brine (150 ml). The resulting extract was cooled to 0° C. followed by the addition of diazomethane and stirring for 30 minutes. Moreover, acetic acid (0.1 ml) was added followed by concentration. The residue was purified with column chromatography (silica gel: n-hexane/ethyl acetate/methylene chloride 3:1:1) to obtain the target compound (4.2 g) after crystallizing by ethyl acetate/n-hexane.

M.P.: 114°–146° C. (recrystallized by ethyl acetate/n-hexane)

$[\alpha]_D^{25}$+60.90 (c 0.550, MeOH)

IR (KBr method): 3520, 3098, 2958, 2942, 2892, 2500, 2232, 2114, 1721, 1603, 1437, 1357, 1328, 1296, 1267, 1193, 1162, 1135, 1075, 1033, 1006, 973, 953, 926, 876, 851, 808, 787, 729, 700, 675, 609, 555, 516, 426, 412 cm$^{-1}$ NMR (90 MHz, CDCl$_3$, δ): 2.1–2.6 (3H, m), 3.6–3.9 (2H, m), 3.88 (3H, s), 4.24 (1H, m), 5.44 (1H, m), 7.5–7.6 (1H, m), 7.87 (1H, d, J=2.2 Hz)

MASS (EI method, m/e):353 (M$^+$)

REFERENCE EXAMPLE 43

(1S, 2S, 3aR, 8bS)-1-azido-7-bromo-2-hydroxy-2,3, 3a,8b-tetrahydro-1H-cyclopenta[b]benzofuran-5-carboxylic acid methyl ester (108)

The target compound (6.2 g) was obtained from (1R, 2S, 3aR, 8bS)-7-bromo-1,2-epoxy-2,3,3a,8b-tetrahydro-1H-cyclopenta [b]benzofuran-5-carboxylic acid methyl ester (106) (21.3 g) in the same manner as Reference Example 42.

M.P.: 144°–146° C. (recrystallized by ethyl acetate/n-hexane)

$[\alpha]_D^{25}$–60.91 (c 0.504, MeOH)

IR (KBr method): 3522, 2958, 2232, 2114, 1721, 1603, 452, 1357, 1328, 1296, 1267, 1234, 1193, 1162, 1075, 1033, 973, 953, 926, 876, 851, 789,729, 675, 555, 516 cm$^{-1}$ NMR (90 MHz, CDCl$_3$, δ): 2.24–2.47 (3H, m), 3.63 (2H, m), 3.88 (3H, s), 4.24 (1H, m), 5.44 (1H, ddd, J=3.1, 6.2, 8.6 Hz), 7.49 (1H, dd, J=1.1, 2.2 Hz), 7.87 (1H, m)

MASS (EI method, m/e): 353 (M$^+$)

WORKING EXAMPLE 67

(1R, 2R, 3aS, 8bR)-1-benzenesulfonamido-2-hydroxy-2,3,3a,8b-tetrahydro-1H-cyclopenta[b]benzofuran-5-carboxylic acid methyl ester (109)

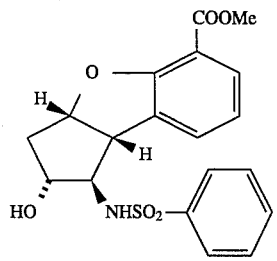
(109)

(1R, 2R, 3aS, 8bR)-1-azido-7-bromo-2-hydroxy-2,3,3a,8b-tetrahydro-1H-cyclopenta[b]benzofuran-5-carboxylic acid methyl ester (107) (3.9 g) was dissolved in methanol (50 ml) followed by the addition of sodium acetate (1.8 g) and 10% palladium activated carbon (400 mg) and stirring for 20 hours at room temperature in a hydrogen atmosphere. The reaction mixture was filtered with selite and the filtrate was concentrated. The residue was dissolved in water (60 ml) and extracted with ethyl acetate (100 ml+30 ml×2). The organic layer was washed with water (40 ml) and saturated brine (40 ml) and then concentrated after drying with anhydrous sodium sulfate. The resulting residue was dissolved in methylene chloride (70 ml) and cooled to −70° C. followed by the addition of triethylamine (6.0 ml) and benzenesulfonyl chloride (1.79 ml) and stirring for 3 hours at −70° C. in an argon atmosphere. Methanol (2.0 ml) was added to the reaction mixture followed by the addition of 1N hydrochloric acid (2.0 ml) after raising the temperature to room temperature. Moreover, after extracting with methylene chloride (100 ml +40 ml×2), the organic layer was washed with a saturated aqueous solution of sodium hydrogen carbonate (50 ml), water (50 ml) and saturated brine (50 ml), and concentrated after drying with anhydrous sodium sulfate. The residue was purified with column chromatography (silica gel: ethyl acetate/n-hexane 2:1) to obtain the target compound (3.38 g) at a yield of 79%.

$[\alpha]_D^{25}$+138.31 (c 0.582, MeOH)

IR (liquid film method): 3492, 3264, 3024, 2956, 1707, 1611, 1450, 1284, 1216, 1191, 1162, 1094, 1067, 1035, 928, 853, 806, 756, 721, 690, 667, 588, 445, 420, 404 cm$^{-1}$ NMR (90 MHz, CDCl$_3$, δ): 1.8–2.7 (2H, m), 2.85 (1H, br, s), 3.4–4.2 (3H, m), 3.85 (3H, s), 5.31 (1H, ddd, J=4.0, 6.5, 8.5 Hz), 5.76 (1H, br, s), 6.6–7.0 (2H, m), 7.4–7.75 (4H, m), 7.8–8.0 (2H, m)

MASS (EI method, m/e): 389 (M$^+$)

WORKING EXAMPLE 68

(1S, 2S, 3aR, 8bS)-1-benzenesulfonamido-2-hydroxy-2,3,3a,8b-tetrahydro-1H-cyclopenta[b]benzofuran-5-carboxylic acid methyl ester (110)

The target compound (3.36 g) was obtained at a yield of 76% from (1S, 2S, 3aR, 8bS)-1-azido-7-bromo-2-hydroxy-2,3,3a,8b-tetrahydro-1H-cyclopenta[b]benzofuran-5-carboxylic acid methyl ester (108) (4.0 g) in the same manner as Working Example 67.

$[\alpha]_D^{25}$−150.39 (c 0.508, MeOH)

IR (liquid film method): 3454, 3264, 3026, 2956, 1707, 1611, 1450, 1284, 1216, 1191, 1162, 1094, 1067, 1035, 928, 853, 808, 754, 721, 690, 667, 586, 451 cm$^{-1}$ NMR (90 MHz, CDCl$_3$, δ): 2.12 (1H, ddd, J=4.7, 6, 7, 14.7 Hz), 2.55 (1H, dt, J=6.4, 14.7 Hz), 2.75 (1H, s, br), 3.4–3.7 (2H, m), 3.85 (3H, s), 4.11 (1H, q, J=5.6 Hz), 5.30 (1H, ddd, J=4.1, 6.4, 8.8 Hz), 5.5–5.8 (1H, s, br), 6.70 (1H, t, J=7.5 Hz), 6.94 (1H, d, J=6.6 Hz), 7.5–7.75 m), 7.8–8.0 (2H, m)

MASS (EI method, m/e):389 (M$^+$)

WORKING EXAMPLE 69

(1R, 2R, 3aS, 8bR)-1-benzenesulfonamido-2-hydroxy-2,3,3a,8b-tetrahydro-1H-cyclopenta[b]benzofuran-5-yl methyl ketone (111)

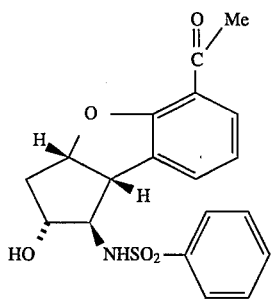
(111)

The target compound (330 mg) was obtained at a yield of 86% from (1R, 2R, 3aS, 8bR)-1-benzenesulfonamido-2-hydroxy- 2,3,3a,8b-tetrahydro-1H-cyclopenta[b]benzofuran-5-carboxylic acid methyl ester (109) (400 mg) in the same manner as Working Example 65.

$[\alpha]_D^{25}$+143.41 (c 0.516, MeOH)

IR (liquid film method): 3454, 3158, 3024, 2926, 1655, 1601, 1446, 1367, 1330, 1294, 1241, 1216, 1156, 1116, 1081, 1040, 1021, 967, 917, 882, 859, 828, 754, 688, 669, 466, 422, 412, 406 cm$^{-1}$ NMR (90 MHz, CDCl$_3$, δ): 2.0–3.0 (3H, m), 2.55 (3H, s), 3.4–3.8 (2H, m), 4.0–4.2 (1H, s), 5.27 (1H, ddd, J=4.6, 6.3, 8.6 Hz), 5.84 (1H, br, s), 6.6–6.95 (2H, m), 7.4–7.7 (4H, m), 7.8–8.0 (2H, m)

MASS (EI method, m/e): 373 (M$^+$)

WORKING EXAMPLE 70

(1S, 2S, 3aR, 8bS)-1-benzenesulfonamido-2-hydroxy-2,3,3a,8b-tetrahydro-1H-cyclopenta[b]benzofuran-5-yl methyl ketone (112)

The target compound (1.67 g) was obtained at a yield of 53.7% from (1S, 2S, 3aR, 8bS)-1-benzenesulfonamido-2-hydroxy- 2,3,3a,8b-tetrahydro-1H-cyclopenta[b]benzofuran-5-carboxylic acid methyl ester (110) (3.25 g) in the same manner as Working Example 65.

$[\alpha]_D^{25}$−1.45.52 (c 0.514, MeOH)

IR (liquid film method): 4216, 3268, 3024, 1671, 1605, 448, 1367, 1313, 1286, 1216, 1162, 1094, 1071, 928, 758, 688, 478, 464, 447, 439, 431, 412, 404 cm$^{-1}$ NMR (90 MHz, CDCl$_3$, δ): 2.07 (1H, ddd, J=4.6, 7.0, 14.3 Hz), 2.4–2.7, (1H, m), 2.55 (3H, s), 2.85 (1H, s, br), 3.4–3.75 (2H, m), 4.16 (1H, m), 5.27 (1H, ddd, J=4.4, 7.3, 8.4 Hz), 5.85 (1H, s), 6.6–6.9 (2H, m), 7.5–7.7 (4H, m), 7.8–8.0 (2H, m)

MASS (EI method, m/e): 373 (M$^+$)

WORKING EXAMPLE 71

(1R, 2R, 3aS, 8bR)-1-benzenesulfonamido-2-hydroxy-2,3,3a,8b-tetrahydro-1H-cyclopenta[b]benzofuran-5-yloxyacetic acid methyl ester (113)

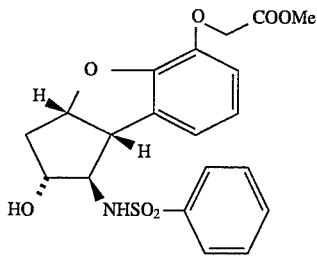
(113)

(1R, 2R, 3aS, 8bR)-1-benzenesulfonamido-2-hydroxy-2,3,3a,8b-tetrahydro-1H-cyclopenta[b]benzofuran-5-yl methyl ketone (111) (219 mg) was dissolved in methylene chloride (4 ml) followed by the addition of sodium hydrogencarbonate (197 mg, 2.3 mmol) and metachloroperbenzoic acid (potency: 70%, 289 mg) and stirring for 2 hours at room temperature. A 3% aqueous solution of sodium sulfite (15 ml) was added to the reaction mixture followed by extraction with methylene chloride (15 ml+10 ml×2). The organic layer was washed with water (15 ml) and saturated brine (15 ml) and concentrated after drying with anhydrous magnesium sulfate. The residue was purified with column chromatography (silica gel: cyclohexane/ethyl acetate 1:2) to obtain (1R, 2R, 3aS, 8bR)-1-benzenesulfonamido-2-hydroxy- 2,3,3a,8b-tetrahydro-1H-cyclopenta[b]benzofuran-5-yl acetate (190 mg).

The (1R, 2R, 3aS, 8bR)-1-benzenesulfonamido-2-hydroxy- 2,3,3a,8b-tetrahydro-1H-cyclopenta[b]benzofuran-5-yl acetate (448 mg), produced according to the process described above, was dissolved in methanol followed by the addition of 0.61N potassium hydroxide/methanol solution (1.9 ml) and stirring for 20 minutes at room temperature. The reaction mixture was added to a 5% aqueous solution of ammonium chloride and extracted with ethyl acetate (50 ml+30 ml×2). The organic layer was washed with saturated brine (30 ml) and concentrated after drying with anhydrous sodium sulfate. The residue was purified with column chromatography (silica gel: methylene chloride/methanol 20:1–7:1) to obtain (1R, 2R, 3aS, 8bR)-1-benzenesulfonamido- 2-hydroxy-2,3,3a,8b-tetrahydro-1H-cyclopenta[b]benzofuran-5-ol (376 mg).

The (1R, 2R, 3aS, 8bR)-1-benzenesulfonamido-2-hydroxy-2,3,3a,8b-tetrahydro-1H-cyclopenta[b]benzofuran-5-ol (342 mg), produced according to the process described above, was dissolved in N,N-dimethylformamide (6 ml) followed by dropping in a 5.2N solution of sodium methoxide and methanol (0.21 ml). Moreover, methyl bromoacetate (0.10 ml) was added followed by stirring for 2 hours at room temperature in an argon atmosphere. The reaction mixture was then added to a 1.5% aqueous solution of ammonium chloride (20 ml) and extracted with 20% n-hexane/ethyl acetate (40 ml+20 ml×2). The organic layer was washed with water (20 ml) and saturated brine (20 ml) and concentrated after drying with anhydrous magnesium sulfate. The residue was purified with column chromatography (silica gel: chloroform/methanol 15:1) and then crystallized by ethyl acetate/diethyl ether to obtain the target compound (209 mg).

M.P.: 105.5°–106.5° C. (recrystallized by ethyl acetate/diethyl ether)

$[\alpha]_D^{25}$+59.99° (c 0.495, MeOH)

IR (KBr method): 3498, 3232, 2348, 1756, 1620, 1599, 1491, 1334, 1294, 1222, 1193, 1156, 1108, 938, 886, 758, 727, 688, 584, 559, 424 cm$^{-1}$ NMR (400 MHz, CDCl$_3$, δ): 2.09 (1H, ddd, J=4.9, 7.3, 14.7 Hz), 2.53 (1H, dt, J=6.8, 14.7 Hz), 2.71 (1H, d, J=3.9 Hz), 3.46 (1H, q, J=6.8 Hz), 3.59 (1H, dd, J=5.4, 8.8 Hz), 3.77 (3H, s), 4.09 (1H, m), 4.64–4.71 (2H, m), 5.07 (1H, d, J=6.8 Hz), 5.23 (1H, ddd, J=4.9, 6.8, 8.8 Hz), 6.38 (1H, d, J=7.2 Hz), 6.59–6.68 (2H, m), 7.52–7.56 (2H, m), 7.59–7.64 (1H, m), 7.92 (2H, m)

MASS (EI method, m/e): 419 (M$^+$)

Elementary Analysis: (as C$_{20}$H$_{21}$NO$_7$S) Calculated values: C: 57.27, H: 5.05, N: 3.34, S: 7.64 Measured values: C: 57.17, H: 5.08, N: 3.35, S: 7.75

WORKING EXAMPLE 72

(1S, 2S, 3aR, 8bS)-1-benzenesulfonamido-2-hydroxy-2,3,3a,8b-tetrahydro-1H-cyclopenta[b]benzofuran-5-yloxyacetic acid methyl ester (114)

(1S, 2S, 3aR, 8bS)-1-benzenesulfonamido-2-hydroxy-2,3,3a,8b-tetrahydro-1H-cyclopenta[b]benzofuran-5-yl methyl ketone (112) (1.57 g) was dissolved in methylene chloride (30 ml) followed by the addition of sodium hydrogencarbonate (2.12 g) and metachloroperbenzoic acid (potency: 70%, 4.61) and stirring for 5 hours at room temperature. A 4% aqueous solution of sodium sulfite (100 ml) was added to the reaction mixture followed by extraction with methylene chloride (100 ml+50 ml×2). The organic layer was washed with saturated brine (50 ml×2) and concentrated to a solid after drying with anhydrous magnesium sulfate. The residue was purified with column chromatography (silica gel: n-hexane/ethyl acetate 1:1–1:2) to obtain (1S, 2S, 3aR, 8bS)-1-benzenesulfonamido-2-hydroxy- 2,3,3a,8b-tetrahydro-1H-cyclopenta[b]benzofuran-5-yl acetate (1.26 g).

The (1S, 2S, 3aR, 8bS)-1-benzenesulfonamido-2-hydroxy- 2,3,3a,8b-tetrahydro-1H-cyclopenta[b]benzofuran-5-yl acetate (1.14 g), produced according to the process described above, was dissolved in methanol (15 ml) followed by the addition of 0.61N potassium hydroxide/methanol solution (5.0 ml) and stirring for 30 minutes at room temperature. The reaction mixture was added to a 5% aqueous solution of ammonium chloride and extracted with ethyl acetate (60 ml+30 ml×2). The organic layer was washed with saturated brine (30 ml) and concentrated to a solid after drying with anhydrous sodium sulfate. The residue was purified with column chromatography (silica gel: chloroform/methanol 20:1–10:1) to obtain (1SR, 2S, 3aR, 8bS)-1-benzenesulfonamido-2-hydroxy-2,3,3a,8b-tetrahydro- 1H-cyclopenta[b]benzofuran-5-ol (940 mg).

The (1S, 2S, 3aR, 8bS)-1-benzenesulfonamido-2-hydroxy-2,3,3a,8b-tetrahydro-1H-cyclopenta[b]benzofuran-5-ol (846 mg), produced according to the process described above, was dissolved in N,N-dimethylformamide (12 ml) followed by dropping in a 5.2N solution of sodium methoxide and methanol (0.54 ml). Moreover, methyl bromoacetate (0.27 ml) was added followed by stirring for 2 hours at room temperature in an argon atmosphere. The reaction mixture was then added to a 5% aqueous solution of ammonium chloride (20 ml) and extracted with 15% n-hexane/ethyl acetate (80 ml+40 ml×2). The organic layer was washed with water (30 ml) and saturated brine (30 ml) and concentrated to a solid after drying with anhydrous magnesium sulfate. The residue was purified with column chromatography (silica gel: chloroform/methanol 20:1–10:1) and then crystallized by ethyl acetate/diethyl ether to obtain the target compound (640 mg).

M.P.: 106°–106.5° C. (recrystallized by ethyl acetate/diethyl ether)

[α]$_D^{25}$ −59.49 (c 0.474, MeOH)

IR (KBr method): 3498, 3234, 2906, 1756, 1620, 1599, 1489, 1450, 1334, 1294, 1222, 1193, 1156, 1108, 1056, 975, 938, 886, 841, 758, 727, 687, 619, 584, 557, 445 cm$^{-1}$ NMR (500 MHz, CDCl$_3$, γ): 2.08 (1H, ddd, J=4.9, 7.3, 14.0 Hz), 2.52 (1H, dt, J=6.7, 14.0 Hz), 2.68 (1H, d,J=4.3 Hz), 3.45 (1H, q, J=6.1 Hz), 3.58 (1H, dd, J=5.5, 9.2 Hz), 3.77 (3H, s), 4.05–4.12 (1H, m), 4.68 (2H, m), 5.19–5.24 (2H, m), 6.38 (1H, d, J=7.3 Hz), 6.60 (1H, t, J=7.3 Hz), 6.65 (1H, d, J=7.3 Hz), 7.54 (2H, t, J=7.3 Hz), 7.62 (1H, m), 7.92 (2H, m)

MASS (EI method, m/e): 419 (M$^+$)

Elementary Analysis: (as C$_{20}$H$_{21}$NO$_7$S) Calculated values: C: 57.27, H: 5.05, N: 3.34, S: 7.64 Measured values: C: 57.22, H: 5.10, N: 3.53, S: 7.50

WORKING EXAMPLE 73

(1R, 2R, 3aS, 8bR)-1-benzenesulfonamido-2-hydroxy-2,3,3a,8b-tetrahydro-1H-cyclopenta[b]benzofuran-5-yloxyacetic acid (115)

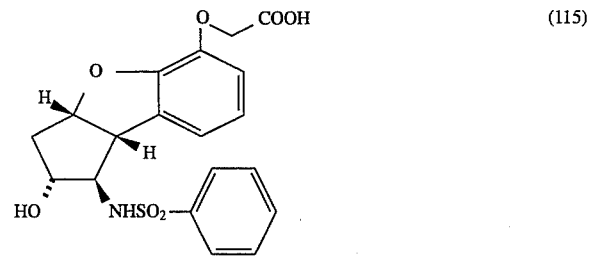

The target compound was quantitatively obtained from (1R, 2R, 3aS, 8bR)-1-benzenesulfonamido-2-hydroxy-2,3, 3a,8b-tetrahydro-1H-cyclopenta[b]benzofuran-5-yloxyacetic acid methyl ester (113) (250 mg) in the same manner as Working Example 2.

IR (liquid film method): 3260, 2938, 1734, 1624, 1597, 1491, 1466, 1448, 1294, 1193, 1162, 1096, 1035, 959, 897, 859, 756, 723, 690, 667, 584, 487, 474, 462, 445, 435, 426, 410 cm$^{-1}$ NMR (400 MHz, DMSO-d$_6$, δ): 7.98 (1H, dd, J=7.0 Hz), 7.89 (1H, dd, J=1.5, 7.8 Hz), 7.61–7.69 (3H, m), 6.57–6.63 (2H, m), 6.33 (1H, d, J=6.8 Hz), 5.20 (1H, m), 4.65 (1H, d, J=2.8 Hz), 4.55 (2H, s), 3.91 (1H, s, br), 3.56 (1H, dd, J=2.4, 8.8 Hz), 2.22 (1H, dt, J=6.3, 14.2 Hz), 1.88 (1H, d, br, J=14.2 Hz)

MASS (EI method, m/e): 405 (M$^+$)

WORKING EXAMPLE 74

(1S, 2S, 3aR, 8bS)-1-benzenesulfonamido-2-hydroxy-2,3,3a,8b-tetrahydro-1H-cyclopenta[b]benzofuran-5-yloxyacetic acid (116)

The target compound was quantitatively obtained from (1S, 2S, 3aR, 8bS)-1-benzenesulfonamido-2-hydroxy-2,3, 3a,8b-tetrahydro-1H-cyclopenta[b]benzofuran-5-yloxyacetic acid methyl ester (114) (250 mg) in the same manner as Working Example 2.

IR (KBr method): 3436, 3268, 3028, 2934, 1738, 1624, 1597, 1491, 1466, 1450, 1294, 1425, 1193, 1160, 1096, 1035, 1000, 959, 897, 859, 756, 723, 690, 667, 584, 553, 478, 449, 433, 416, 408 cm$^{-1}$ NMR (400 MHz, DMSO-d$_6$, δ): 7.98 (1H, d, J=6.8 Hz), 7.89 (1H, dd, J=1.5, 7.8 Hz), 7.61–7.69 (3H, m), 6.57–6.63 (2H, m), 6.33 (1H, d, J=6.8 Hz), 5.20 (1H, m), 4.65 (1H, s, br), 4.55 (2H, s), 3.90 (1H, s, br), 3.56 (1H, dd, J=2.4, 8.8 Hz), 2.22 (1H, dt, J=6.4, 14.2 Hz), 1.88 (1H, d, br, J=14.2 Hz)

MASS (EI method, m/e): 405 (M$^+$)

REFERENCE EXAMPLE 44

(1RS, 2 SR, 3aSR, 8bRS)-1,2-epoxy-5-hydroxy-2,3, 3a,8b-tetrahydro- 1H-cyclopenta[b]benzofuran (117)

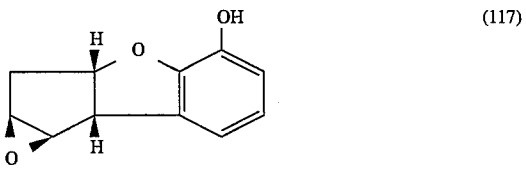

(3aSR, 8bSR)-7-bromo-3a,8b-dihydro-5-hydroxy-3H-cyclopenta[b]benzofuran (10.0 g) was dissolved in methylene chloride (150 ml) followed by the addition of m-chloroperbenzoic acid (25.2 g) and stirring for 2 hours at room temperature. A solution containing sodium thiosulfate (58.8 g) dissolved in water (200 ml) was slowly added to the reaction mixture at 0° C. The resulting mixture was extracted with methylene chloride (600 ml, 200 ml×2), the organic layer was washed with a saturated aqueous solution of sodium hydrogen carbonate (200 ml) and saturated brine (200 ml), and concentrated after drying with magnesium sulfate. The resulting residue was dissolved in tetrahydrofuran (20 ml) and methanol (80 ml) followed by the addition of sodium acetate (3.89 g) and 10% palladium activated carbon (1.00 g) to this solution and stirring for 24 hours at room temperature in a hydrogen atmosphere. After filtering the reaction mixture using selite, the solvent was removed under reduced pressure. Ethyl acetate (150 ml) was added to the residue followed by washing with water (80 ml) and saturated brine (80 ml) and concentration after drying with magnesium sulfate. The residue was then purified with column chromatography (silica gel: cyclohexane/ethyl acetate 10/1–2/1) to obtain the target compound (3.77 g) at a yield of 51%.

M.P.: 121°–122° C. (recrystallized by ethyl acetate/n-hexane)

IR (KBr method): 2900–3500, 1615, 1600, 1468, 1312, 1288, 1270, 1220, 1179, 1038, 963, 832, 814, 770, 722 cm$^{-1}$ NMR (90 MHz, CDCl$_3$, δ): 1.9–2.2 (1H, m), 2.71 (1H, dd, J=7.6, 15.8 Hz), 3.57 (1H, t, J=2.7 Hz), 3.72 (1H, d, J=2.7 Hz), 4.20 (1H, d, J=7.6 Hz), 5.0–5.2 (2H, m), 6.7–6.9 (3H, m)

MASS (EI method, m/e): 190 (M$^+$)

REFERENCE EXAMPLE 45

(1SR, 3aSR, 8bRS)-1,5-dihydroxy-2,3,3a,8b-tetrahydro-1H-cyclopenta[b]benzofuran (118)

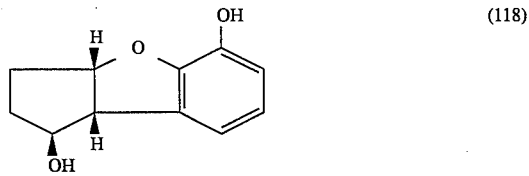

(1RS, 2SR, 3aSR, 8bRS)-1,2-epoxy-5-hydroxy-2,3,3a,8b-tetrahydro- 1H-cyclopenta[b]benzofuran (117) (2.40 g) was dissolved in anhydrous tetrahydrofuran (80 ml) followed by the addition of aluminum lithium hydride (717 mg) and refluxing for 2 hours. The reaction mixture was cooled to 0° C. and water (30 ml) was added slowly followed by the addition of 3N hydrochloric acid (40 ml). The resulting mixture was extracted with ethyl acetate (150 ml, 100 ml×2), the organic layer was washed with a saturated aqueous solution of sodium hydrogencarbonate (50 ml) and saturated brine (50 ml) and then concentrated after drying with anhydrous magnesium sulfate. The resulting residue was purified with column chromatography (silica gel: cyclohexane/ethyl acetate 3/1) to obtain the target compound (2.10 g) at a yield of 87%.

M.P.: 145°–146° C. (recrystallized by ethyl acetate/n-hexane)

IR (KBr method): 2000–3500, 1599, 1479, 1446, 1398, 1296, 1245, 1185, 1149, 1052, 1031, 977, 940, 861, 824, 772, 760, 725 cm$^{-1}$ $^{NMR}$ (90 MHz, CDCl$_3$, δ): 1.3–2.4 (4H, m), 3.63 (1H, d, J=8.0 Hz), 4.0–4.2 (1H, m), 4.8–5.0 (1H, m), 5.2–5.4 (1H, m), 6.5–6.8 (3H, m), 9.02 (1H, s)

MASS (EI method, m/e): 192 (M$^+$)

REFERENCE EXAMPLE 46

(1SR, 3aSR, 8bRS)-1-hydroxy-2,3,3a,8b-tetrahydro-1H-cyclopenta[b]benzofuran-5-yloxyacetic acid methyl ester (119)

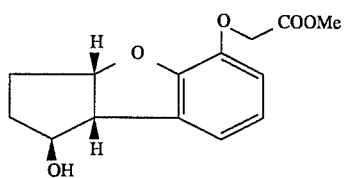

(1SR, 3aSR, 8bRS) -1,5-dihydroxy-2,3,3a,8b-tetrahydro-1H-cyclopenta[b]benzofuran (118) (1.62 g) was dissolved in methanol (20 ml) followed by the addition of potassium hydroxide (581 mg) and stirring for 30 minutes at room temperature. The reaction mixture was concentrated and the residue was suspended in dimethylformamide (30 ml) followed by the addition of methyl bromoacetate (1.44 ml) and stirring for 2 hours at room temperature. An aqueous solution of ammonium chloride (40 ml) was added to the resulting reaction mixture followed by extraction with ethyl acetate (100 ml×3). The organic layers were washed with water (50 ml×3) and saturated brine (50 ml) and then concentrated after drying with anhydrous magnesium sulfate. The resulting residue was then purified with column chromatography (silica gel: acetonitrile/methylene chloride 1/15) to obtain the target compound (2.04 g) at a yield of 92%.

IR (liquid film method): 3100–3700, 2960, 1742, 1620, 1597, 1491, 1464, 1439, 1377, 1296, 1226, 1195, 1114, 1006, 980, 965, 942, 859, 820, 768, 727 cm$^{-1}$ $^{NMR}$ (90 MHz, CDCl$_3$, δ): 1.6–1.95 (3H, m), 2.05–2.4 (2H, m), 3.7–3.9 (1H, m), 3.78 (3H, s), 4.2–4.4 (1H, m), 4.71 (2H, s), 5.3–5.6 (1H, m), 6.6–7.0 (3H, m)

MASS (EI method, m/e): 264 (M$^+$)

WORKING EXAMPLE 75

(1SR, 3aSR, 8bSR)-1-(phenylsulfonyloxy)-2,3,3a,8b-tetrahydro- 1H-cyclopenta[b]benzofuran-5-yloxyacetic acid methyl ester (120)

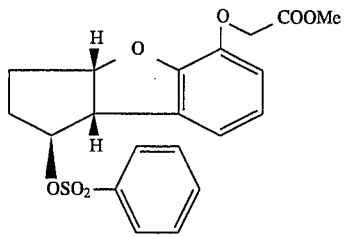

(1SR, 3aSR, 8bRS)-1-hydroxy-2,3,3a,8b-tetrahydro-1H-cyclopenta[b]benzofuran-5-yloxyacetic acid methyl ester (119) (492 mg) was dissolved in pyridine (5 ml) followed by the addition of benzenesulfonyl chloride (0.70 ml) and stirring for 17 hours at room temperature. The reaction liquid was dropped into 3N hydrochloric acid (30 ml) and extracted with ethyl acetate (100 ml, 50 ml). The organic layer was washed with a saturated aqueous solution of sodium hydrogencarbonate (30 ml), water (30 ml) and saturated brine (30 ml), and then concentrated after drying with anhydrous magnesium sulfate. The resulting residue was purified with column chromatography (silica gel: cyclohexane/ethyl acetate 2/1) to obtain the target compound (623 mg) at a yield of 83%.

M.P.: 90°–91° C. (recrystallized from ethyl acetate/n-hexane)

IR (KBr method): 2980, 1754, 1622, 1595, 1493, 1468, 1450, 1354, 1299, 1224, 1191, 1112, 1073, 949, 922, 895, 849, 828, 772, 758, 729, 714, 687, 607, 586, 547 cm$^{-1}$ NMR (400 MHz, CDCl$_3$, δ): 1.7–1.8 (1H, m), 1.85–1.95 (1H, m), 2.1–2.3 (2H, m), 3.77 (3H, s), 4.00 (1H, d, J=7.3 Hz), 4.67 (1H, d, J=16.1 Hz), 4.69 (1H, d, J=16.1 Hz), 4.85 (1H, d, J=3.9 Hz), 5.35–5.45 (1H, m), 6.65–6.8 (3H, m), 7.55–7.7 (3H, m), 7.95–8.0 (2H, m)

MASS (EI method, m/e): 404 (M$^+$)

Elementary Analysis: (as C$_{20}$H$_{20}$O$_7$S) Calculated values: C: 59.40, H: 4.98, S: 7.93 Measured values: C: 59.29, H: 5.22, S: 7.97

WORKING EXAMPLE 76

(1SR, 3aSR, 8bSR)-1-(phenylsulfonyloxy)-2,3,3a,8b-tetrahydro-1H-cyclopenta[b]benzofuran-5-yloxyacetic acid (121)

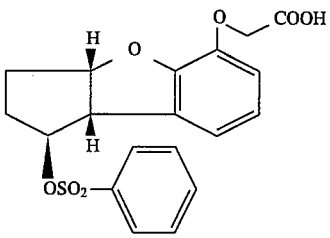

(1SR, 3aSR, 8bSR)-1-(phenylsulfonyloxy)-2,3,3a,8b-tetrahydro-1H-cyclopenta[b]benzofuran-5-yloxyacetic acid methyl ester (120) (200 mg) was dissolved in methanol (8 ml) and tetrahydrofuran (2 ml) followed by the addition of 1N sodium hydroxide (1.5 ml) and stirring for 3 hours at 0° C. The reaction mixture was concentrated and water (20 ml) was added to the residue followed by neutralization with 1N hydrochloric acid (1.5 ml). The resulting mixture was extracted with ethyl acetate (50 ml×2), the organic layer was washed with water (20 ml) and saturated brine (20 ml), and then concentrated after drying with anhydrous magnesium sulfate. The resulting residue was recrystallized with ethyl acetate/n-hexane to obtain the target compound (140 mg).

M.P.: 158°–159° C.

IR (KBr method): 2400–3400, 1734, 1622, 1593, 1491, 1435, 1367, 1261, 1185, 1116, 949, 913, 762, 725, 685, 594, 551, 511 cm$^{-1}$ $^{NMR}$ (400 MHz, CDCl$_3$, δ): 1.65–1.8 (1H, m), 1.85–1.95 (1H, m), 2.1–2.25 (2H, m), 4.01 (1H, d, J=7.3 Hz), 4.68 (1H, d, J=16.9 Hz), 4.71 (1H, d, J=16.9 Hz), 4.85 (1H, d, J=3.9 Hz), 5.35–5.45 (1H, m), 6.7–6.8 (3H, m), 7.55–7.7 (3H, m), 7.95–8.0 (2H, m)

MASS (EI method, m/e): 390 (M$^+$)

Elementary Analysis: (as C$_{19}$H$_{18}$O$_7$S) Calculated values: C: 58.45, H: 4.65, S: 8.21 Measured values: C: 58.35, H: 4.79, S: 8.23

WORKING EXAMPLE 77

(1SR, 3aSR, 8bSR)-1-((p-tolyl)sulfonyloxy)-2,3,3a, 8b-tetrahydro-1H-cyclopenta[b]benzofuran-5-yloxy-acetic acid methyl ester (122)

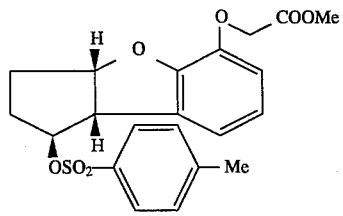

(122)

The target compound (270 mg) was obtained from (1SR, 3aSR, 8bRS)-1-hydroxy-2,3,3a,8b-tetrahydro-1H-cyclopenta[b]benzofuran-5-yloxyacetic acid methyl ester (119) (195 mg) in the same manner as Working Example 1 with the exception of using p-toluenesulfonyl chloride (423 mg) instead of benzenesulfonyl chloride.

M.P.: 101°–102° C. (recrystallized from ethyl acetate/n-hexane)

IR (KBr method): 2800–3000, 1754, 1620, 1597, 1493, 1468, 1437, 1354, 1296, 1226, 1193, 1178, 1114, 953, 919, 895, 874, 864, 818, 770, 727, 669, 551 cm$^{-1}$ $^{NMR}$ (400 MHz, CDCl$_3$, δ): 1.65–1.8 (1H, m), 1.85–1.9 (1H, m), 2.1–2.25 (2H, m), 2.47 (3H, s), 3.77 (3H, s), 3.99 (1H, d, J=7.3 Hz), 4.67 (1H, d, J=16.1 Hz), 4.69 (1H, d, J=16.1 Hz), 4.83 (1H, d, J=3.9 Hz), 5.35–5.45 (1H, m), 6.65–6.8 (3H, m), 7.38 (2H, d, J=8.1 Hz), 7.83 (2H, d, J=8.1 Hz)

MASS (EI method, m/e): 418 (M$^+$)

Elementary Analysis: (as C$_{20}$H$_{22}$O$_7$S) Calculated values: C: 60.28, H: 5.30, S: 7.66 Measured values: C: 60.26, H: 5.29, S: 7.64

WORKING EXAMPLE 78

(1SR, 3aSR, 8bSR)-1-((p-tolyl)sulfonyloxy)-2,3,3a, 8b-tetrahydro-1H-cyclopenta[b]benzofuran-5-yloxy-acetic acid (123)

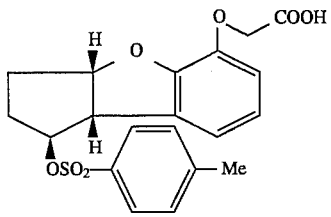

(123)

The target compound (116 mg) was obtained from (1SR, 3aSR, 8bSR)-1-((p-tolyl)sulfonyloxy)-2,3,3a,8b-tetrahydro-1H-cyclopenta[b]benzofuran-5-yloxyacetic acid methyl ester (122) (151 mg) in the same manner as Working Example 2.

M.P.: 165°–166° C. (recrystallized from methanol/ethyl acetate/n-hexane)

IR (KBr method): 2300–3300, 1744, 1715, 1620, 1595, 1493, 1429, 1369, 1294, 1261, 1172, 1118, 1096, 953, 922, 893, 874, 861, 810, 770, 729, 669, 551, 509 cm$^{-1}$ $^{NMR}$ (400 MHz, CDCl$_3$, δ): 1.65–1.75 (1H, m), 1.85–1.95 (1H, m), 2.1–2.25 (2H, m), 2.47 (3H, s), 4.01 (1H, d, J=7.8 Hz), 4.69 (1H, d, J=16.8 Hz), 4.71 (1H, d, J=16.8 Hz), 4.83 (1H, d, J=3.9 Hz), 5.35–5.45 (1H, m), 6.7–6.8 (3H, m), 7.38 (2H, d, J=8.3 Hz), 7.83 (2H, d, J=8.3 Hz)

MASS (EI method, m/e): 404 (M$^+$)

Elementary Analysis: (as C$_{20}$H$_{20}$O$_7$S) Calculated values: C: 59.40, H: 4.98, S: 7.93 Measured values: C: 59.32, H: 4.92, S: 7.81

WORKING EXAMPLE 79

(1SR, 3aSR, 8bSR)-1-((p-chlorophenyl)sulfonyloxy)-2,3,3a,8b-tetrahydro-1H-cyclopenta[b]benzofuran-5-yloxyacetic acid methyl ester (124)

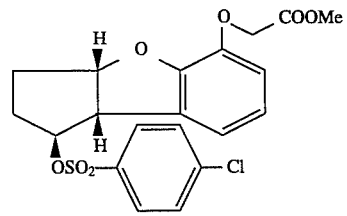

(124)

The target compound (455 mg) was obtained from (1SR, 3aSR, 8bRS)-1-hydroxy-2,3,3a,8b-tetrahydro-1H-cyclopenta[b]benzofuran-5-yloxyacetic acid methyl ester (119) (330 mg) in the same manner as Working Example 1 with the exception of using p-chlorobenzenesulfonyl chloride (660 mg) instead of benzenesulfonyl chloride.

M.P.: 123°–123.5° C. (recrystallized from ethyl acetate/n-hexane)

IR (KBr method): 2980, 1765, 1620, 1593, 1491, 1441, 1398, 1371, 1296, 1218, 1199, 1189, 1112, 1085, 949, 922, 897, 868, 835, 803, 752, 727, 658, 621, 567, 511, 484 cm$^{-1}$ $_{NMR}$ (400 MHz, CDCl$_3$, δ): 1.7–1.8 (1H, m), 1.85–1.95 (1H, m), 2.05–2.3 (2H, m), 3.77 (3H, s), 4.03 (1H, d, J=7.7 Hz), 4.70 (1H, d, J=16.1 Hz), 4.72 (1H, d, J=16.1 Hz), 4.87 (1H, d, J=3.9 Hz), 5.40 (1H, dd, J=5.1, 7.7 Hz), 6.65–6.85 (3H, m), 7.55–7.65 (2H, m), 7.85–7.95 (2H, m)

WORKING EXAMPLE 80

(1SR, 3aSR, 8bSR)-1-((p-chlorophenyl)sulfony-loxy)-2,3,3a,8b-tetrahydro-1H-cyclopenta[b]benzo-furan-5-yloxyacetic acid (125)

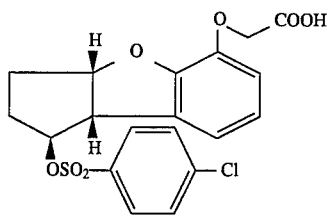

The target compound (194 mg) was obtained from (1SR, 3aSR, 8bSR)-1-((p-chlorophenyl)sulfonyloxy)-2,3,3a,8b-tetrahydro-1H-cyclopenta[b]benzofuran-5-yloxyacetic acid methyl ester (124) (230 mg) in the same manner as Working Example 2.

M.P.: 168°–169° C. (recrystallized from methanol/ethyl acetate/n-hexane)

IR (KBr method): 2700–3700, 1731, 1620, 1595, 1491, 1435, 1365, 1294, 1276, 1263, 1189, 1116, 1100, 948, 920, 897, 828, 764, 623, 557, 487 cm$^{-1}$ NMR (400 MHz, CDCl$_3$, δ): 1.65–1.8 (1H, m), 1.85–1.95 (1H, m), 2.1–2.3 (2H, m), 4.05 (1H, d, J=7.8 Hz), 4.69 (1H, d, J=16.6 Hz), 4.72 (1H, d, J=16.6 Hz), 4.87 (1H, d, J=4.4 Hz), 5.35–5.45 (1H, m), 6.7–6.85 (3H, m), 7.55–7.65 (2H, m), 7.85–7.95 (2H, m)

MASS (EI method, m/e): 424 (M$^+$)

Elementary Analysis: (as C$_{19}$H$_{17}$ClO$_7$S) Calculated values: C: 53.71, H: 4.03, S: 7.55 Measured values: C: 53.49, H: 4.05, S: 7.33

WORKING EXAMPLE 81

(1SR, 3aSR, 8bSR)-1-((p-fluorophenyl)sulfony-loxy)-2,3,3a,8b-tetrahydro-1H-cyclopenta[b]benzo-furan-5-yloxyacetic acid methyl ester (126)

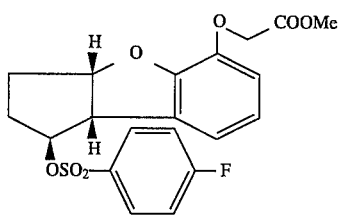

The target compound (275 mg) was obtained from (1SR, 3aSR, 8bRS)-1-hydroxy-2,3,3a,8b-tetrahydro-1H-cyclopenta[b]benzofuran-5-yloxyacetic acid methyl ester (119) (195 mg) in the same manner as Working Example 1 with the exception of using p-fluorobenzenesulfonyl chloride. (431 mg) instead of benzenesulfonyl chloride.

M.P.: 106°–107° C. (recrystallized from ethyl acetate/n-hexane)

IR (KBr method): 2800–3100, 1765, 1620, 1593, 1493, 1444, 1371, 1296, 1224, 1201, 1187, 1154, 1112, 973, 951, 938, 922, 851, 801, 729, 675, 569, 551 cm$^{-1}$ NMR (400 MHz, CDCl$_3$, δ) : 1.7–1.8 (1H, m),1.85–1.95 (1H, m), 2.1–2.3 (2H, m), 3.77 (3H, s), 4.03 (1H, d, J=7.8 Hz), 4.67 (1H, d, J=16.1 Hz), 4.70 (1H, d, J=16.1 Hz), 4.86 (1H, d, J=3.9 Hz), 5.35–5.45 (1H, m), 6.65–6.85 (3H, m), 7.25–7.35 (2H, m), 7.95–8.05 (2H, m)

MASS (EI method, m/e): 422 (M$^+$)

Elementary Analysis: (as C$_{20}$H$_{19}$FO$_7$S) Calculated values: C: 56.87, H: 4.53, S: 7.59 Measured values: C: 56.81, H: 4.55, S: 7.57

WORKING EXAMPLE 82

(1SR, 3aSR, 8bSR)-1-((p-fluorophenyl)sulfony-loxy)-2,3,3a,8b-tetrahydro-1H-cyclopenta[b]benzo-furan-5-yloxyacetic acid (127)

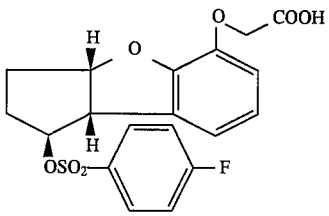

The target compound (124mg) was obtained from (1SR, 3aSR, 8bSR)-1-((p-fluorophenyl)sulfonyloxy)-2,3,3a,8b-tetrahydro-1H-cyclopenta[b]benzofuran-5-yloxyacetic acid methyl ester (126) (160 mg) in the same manner as Working Example 2.

M.P.: 162°–163° C. (recystallized from methanol/ethyl acetate/n-hexane)

IR (KBr method): 2300–3300, 1731, 1624, 1595, 1491, 1435, 1365, 1276, 1263, 1238, 1187, 1156, 1118, 1098, 946, 922, 895, 882, 839, 779, 557 cm$^{-1}$ NMR (400 MHz, CDCl$_3$, δ): 1.65–1.8 (1H, m), 1.85–1.95 (1H, m), 2.1–2.3 (2H, m), 4.04 (1H, d, J=7.3 Hz), 4.69 (1H, d, J=16.8 Hz), 4.72 (1H, d, J=16.8 Hz), 4.86 (1H, d, J=3.9 Hz), 5.35–5.45 (1H, m), 6.7–6.85 (3H, m), 7.2–7.35 (2H, m), 7.95–8.05 (2H, m)

MASS (EI method, m/e): 408 (M$^+$)

Elementary Analysis: (as C$_{19}$H$_{17}$FO$_7$S) Calculated values: C: 55.88, H: 4.20, S: 7.85 Measured values: C: 55.81, H: 4.20, S: 7.82

WORKING EXAMPLE 83

Platelet aggregation inhibitory action

Human whole blood drawn from the median cubital vein was centrifuged for 10 minutes at 800 rpm, and the upper portion was collected as platelet-rich plasma (PRP). The PRP was transferred to a small test tube followed by the addition of U-46619 (Funakoshi), a drug which demonstrates TXA2 action, to induce platelet aggregation. The size of the aggregates were measured with a platelet aggregate measuring instrument (Hematracer 1, Nikko Bioscience) as the change in turbidity. The compounds were added 1 minute before addition of U-46619, and the concentration which inhibits aggregation by 50% was calculated as the IC$_{50}$ value.

The results of evaluating the activity of the compounds of the present invention with this method are summarized in Table 1.

TABLE 1

| Compound | Platelet Aggregation Inhibitory Action IC$_{50}$ (mol/l) | Compound | Platelet Aggregation inhibitory Action IC$_{50}$ (mol/l) |
| --- | --- | --- | --- |
| (41) | 1.7 × 10$^{-6}$ | (74) | 5.3 × 10$^{-6}$ |

TABLE 1-continued

| Compound | Platelet Aggregation Inhibitory Action $IC_{50}$ (mol/l) | Compound | Platelet Aggregation inhibitory Action $IC_{50}$ (mol/l) |
|---|---|---|---|
| (43) | $5.1 \times 10^{-7}$ | (76) | $5.5 \times 10^{-7}$ |
| (45) | $4.3 \times 10^{-6}$ | (78) | $5.1 \times 10^{-8}$ |
| (46) | $6.8 \times 10^{-8}$ | (82) | $1.0 \times 10^{-6}$ |
| (47) | $1.8 \times 10^{-8}$ | (84) | $7.3 \times 10^{-6}$ |
| (49) | $2.2 \times 10^{-8}$ | (88) | $4.5 \times 10^{-7}$ |
| (51) | $6.8 \times 10^{-8}$ | (90) | $9.9 \times 10^{-8}$ |
| (53) | $3.3 \times 10^{-8}$ | (92) | $1.0 \times 10^{-7}$ |
| (55) | $1.7 \times 10^{-8}$ | (94) | $6.8 \times 10^{-8}$ |
| (57) | $4.1 \times 10^{-8}$ | (96) | $6.7 \times 10^{-7}$ |
| (59) | $6.9 \times 10^{-8}$ | (102) | $2.2 \times 10^{-7}$ |
| (61) | $4.4 \times 10^{-8}$ | (121) | $1.3 \times 10^{-7}$ |
| (63) | $5.8 \times 10^{-8}$ | (123) | $9.3 \times 10^{-8}$ |
| (65) | $2.7 \times 10^{-7}$ | (125) | $9.4 \times 10^{-8}$ |
| (68) | $1.4 \times 10^{-7}$ | (127) | $1.0 \times 10^{-7}$ |
| (70) | $2.9 \times 10^{-8}$ | Control | $5.0 \times 10^{-6}$ |
| (72) | $1.2 \times 10^{-7}$ | | |

Control: 4-(2-benzenesulfonamido)ethyl)-phenoxyacetic acid (compound described in Japanese Unexamined Patent Publication No. 54-122250)

As is clear from Table 1, the compounds of the present invention has platelet aggregation inhibitory action equal to or greater than that of the control compound.

WORKING EXAMPLE 84

Vasoconstriction Inhibitory Action

Male and female long Evans rats having body weights of 150–200 g were used in this example. After sacrificing the animals by decapitation, the thoracic aorta was removed, and the outer membrane was peeled off to obtain I2 spiral specimens roughly 2 cm in length. Blood vessel specimens were warmed to 37° C. and preserved in a Magnus tube containing 10 ml of a nutrient solution aerated with 95% oxygen+5% carbon dioxide gas. The nutrient solution contained 118.3 mmol of NaCl, 4.7 mmol of KCl, 22.5 mmol of CaCl, 1.2 mmol of $MgSO_4$, 1.2 mmol of $KH_2PO_4$, 25 mmol of $NaCHO_3$, 11.1 mmol of D-glucose, 0.03 mmol of EDTA along with 1 μg/ml each of atropin, phentolamine, mepiramine, cyproheptadine, propranolol and indometacin, and was adjusted to a pH of 7.4. Vasoconstriction was measured using an isometric transducer (Harward UF-1 Transducer and Sekonic SS-250F Graph recorder). An equilibration time of 3 hours was provided after the blood vessels were installed on the Magnus device, and fresh nutrient solution was replaced every 30 minutes during that time. 10 mg/ml of U-46619, having TXA2 action (to reach roughly 75% of maximum constriction), was applied for 30 minutes to constrict the vessels. The maximum stable constriction during this time was taken to be the control constriction (C1). Next, the blood vessels were washed several times with nutrient solution to remove the drug. After allowing a recovery period of 30 minutes, the test drugs were applied at various concentrations for 10 minutes followed by again constricting the vessels by applying 10 ng/ml of U-46619 for 30 minutes. The maximum stable constriction during this time was taken to be the constriction of the test drugs (C2). The inhibition rates of vasoconstriction induced by the drugs and U-46619 were determined according to the following formula, and the minimum concentration at which the inhibition rate was 50% or more was determined as the minimum inhibitory concentration (MIC).

$((C1-C2)/C1) \times 100$ = Inhibition rate (%)

The results of evaluation of the activity of the compounds of the present invention with this method are summarized in Table 2

TABLE 2

| | Vasoconstriction Inhibitory Action | | |
|---|---|---|---|
| Compound | Vasoconstriction Inhibitory Action MIC (g/ml) | Compound | Vasoconstriction Inhibitory Action MIC (g/ml) |
| (39) | $2.5 \times 10^{-7}$ | (68) | $1.0 \times 10^{-7}$ |
| (41) | $2.5 \times 10^{-7}$ | (70) | $3.0 \times 10^{-8}$ |
| (43) | $3.0 \times 10^{-7}$ | (72) | $3.0 \times 10^{-8}$ |
| (46) | $3.0 \times 10^{-8}$ | (76) | $3.0 \times 10^{-7}$ |
| (47) | $2.5 \times 10^{-8}$ | (76) | $3.0 \times 10^{-8}$ |
| (49) | $1.0 \times 10^{-8}$ | (88) | $3.0 \times 10^{-7}$ |
| (51) | $1.0 \times 10^{-7}$ | (90) | $3.0 \times 10^{-9}$ |
| (53) | $5.0 \times 10^{-8}$ | (92) | $1.0 \times 10^{-7}$ |
| (55) | $1.0 \times 10^{-7}$ | (94) | $1.0 \times 10^{-7}$ |
| (57) | $1.0 \times 10^{-8}$ | (102) | $3.0 \times 10^{-8}$ |
| (59) | $1.0 \times 10^{-7}$ | (121) | $3.0 \times 10^{-9}$ |
| (61) | $3.0 \times 10^{-8}$ | Control | $3.0 \times 10^{-7}$ |
| (63) | $1.0 \times 10^{-8}$ | | |

Control: 4-(2-benzenesulfonamido)ethyl)-phenoxyacetic acid (compound described in Japanese Unexamined Patent Publication No. 54-122250)

As is clear from Table 2, the compounds of the present invention have vasoconstriction inhibitory action equal to or greater than that of the control compound.

WORKING EXAMPLE 85

Receptor Binding Experiment

Whole blood from New Zealand White rabbits was collected into a container containing ACD solution (1.175 g of sodium citrate, 0.685 g of citric acid, and 1 g of dextrose dissolved in 50 ml of distilled water) followed by centrifuging at room temperature for 10 minutes at 180 ×g to obtain platelet-rich plasma. Moreover, this platelet-rich plasma was further centrifuged at room temperature and 2800 ×g to result in sedimentation of the platelets. The platelets were resuspended in 50 mM Tris hydrochloric acid buffer solution (pH 7.2, containing 10.154M NaCl) and again centrifuged at 4° C. for 15 minutes at 2800 ×g. This procedure was repeated twice to prepare the washed platelets, and adjusted to a final concentration of 10 mg/ml (wet weight). Tritium-labelled SQ29548 ([3H]SQ29548) was used for the TXA2 ligand. In an antagonism experiment, 20 μl of [3H]SQ29548 at a final concentration of 3 nM were added to 500 μl of a 10 mg/ml platelet suspension, together with adding 2.6 μl of the test drug dissolved in a suitable buffer. After incubating for 60 minutes at 25° C., the mixture was filtered over a glass filter using the Celherbster method, the filter was washed with 50 mM Tris hydrochloric acid buffer solution (3 ×4 ml), and radioactivity was measured with a scintillation counter to determine the amount of [3H]SQ29548 bound to the platelets. In addition, in a saturation test, 20 μl of [3H]SQ29548 were added to a final concentration of 0.1–50 nM followed by the addition of 2.6 μl of BM13505 at a final concentration of 1 μM in order to examine non-specific binding and carry out a binding experiment. The concentration of the test drug which inhibited binding of [3H]SQ29548 by 50% was determined as the $IC_{50}$ value.

The results of evaluating the activity of the compounds of the present invention with this method are summarized in Table 3.

TABLE 3

Thromboxane A2 Receptor Binding Test

| Compound | Binding Inhibitory Action IC$_{50}$ (g/ml) | Compound | Binding Inhibitory Action IC$_{50}$ (g/ml) |
|---|---|---|---|
| (41) | $8.1 \times 10^{-7}$ | (70) | $2.2 \times 10^{-8}$ |
| (43) | $1.3 \times 10^{-7}$ | (72) | $1.2 \times 10^{-8}$ |
| (45) | $2.0 \times 10^{-6}$ | (74) | $3.6 \times 10^{-7}$ |
| (46) | $9.7 \times 10^{-9}$ | (76) | $5.3 \times 10^{-8}$ |
| (47) | $3.0 \times 10^{-9}$ | (78) | $9.5 \times 10^{-10}$ |
| (49) | $3.7 \times 10^{-9}$ | (82) | $4.7 \times 10^{-7}$ |
| (51) | $1.2 \times 10^{-8}$ | (84) | $5.4 \times 10^{-7}$ |
| (53) | $8.9 \times 10^{-9}$ | (88) | $2.6 \times 10^{-7}$ |
| (55) | $1.4 \times 10^{-9}$ | (90) | $3.3 \times 10^{-9}$ |
| (57) | $1.0 \times 10^{-8}$ | (92) | $2.4 \times 10^{-8}$ |
| (59) | $1.0 \times 10^{-8}$ | (94) | $6.5 \times 10^{-9}$ |
| (61) | $1.0 \times 10^{-9}$ | (96) | $1.8 \times 10^{-7}$ |
| (63) | $1.2 \times 10^{-8}$ | (102) | $1.8 \times 10^{-7}$ |
| (65) | $4,6 \times 10^{-8}$ | (121) | $5.0 \times 10^{-10}$ |
| (68) | $4.1 \times 10^{-7}$ | Control | $1.4 \times 10^{-6}$ |

Control: 4-(2-(benzenesulfonamido)ethyl) phenoxyacetic acid (compound described in Japanese Unexamined Patent Publication No. 54-122250)

As is clear from Table 3, the compounds of the present invention have TXA2 receptor antagonistic action equal to or greater than that of the control compound.

INDUSTRIAL APPLICABILITY

Since the compounds of the present invention have excellent stability in the body and powerful thromboxane A2 receptor antagonistic action, they have pharmacological actions such as platelet aggregation inhibitory action, vasoconstriction inhibitory action and bronchial muscle contraction inhibitory action, thus making them useful as pharmaceuticals.

We claim:

1. Sulfonic acid represented by formula I:

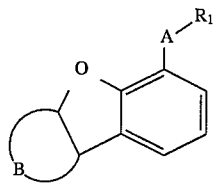 (I)

wherein, $R_1$ is (i) —COOR$_2$ (wherein, R$_2$ is (1) hydrogen, (2) a pharmacologically acceptable cation, or (3) an alkyl having 1 to 14 carbon atoms) or the group:

(ii)

wherein

R$_3$ represents an alkyl having 1 to 4 carbon atoms;

A is (i) —(CH$_2$)n— (wherein, n represents an integer of 0 to 3), (ii) —CH=CH—, or the group:

(iii)

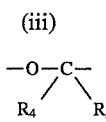

wherein

R$_4$ and R$_5$ represent (1) hydrogen or (2) an alkyl having 1 to 4 carbon atoms, and R$_4$ and R$_5$ may be identical or different); and, B is represented with either formula II or formula III:

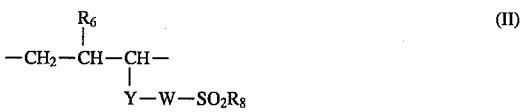 (II)

 (III)

wherein

R$_6$ represents (i) hydrogen, or (ii) —OR$_9$ (wherein, R$_9$ represents (1) hydrogen, (2) an alkyl having 1 to 4 carbon atoms, (3) an acyl group having 2 to 5 carbon atoms, or (4) an aroyl group having 7 to 11 carbon atoms), Y is —(CH$_2$)m— (where, m represents 0 or 1), W is

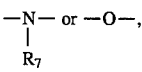

R$_7$ is (i) hydrogen, or (ii) an alkyl having 1 to 4 carbon atoms,

R$_8$ is (i) an alkyl having 1 to 14 carbon atoms, or (ii) —Z—R$_{11}$ (wherein, Z is a valence bond or a straight or branched alkylene represented by C$_t$H$_{2t}$ (where, t is an integer of 1 to 5) and R$_{11}$ represents an aryl group or aryl group having 6 to 16 carbon atoms substituted by 1 to 4 groups selected from the group consisting of alkyl, methoxy, chlorine, bromine, fluorine, iodine, trifluoromethyl, nitro, cyano, phenyl and phenoxy)).

2. The sulfonic acid as set forth in claim 1 wherein B is represented by the formula (II) or formula (III')

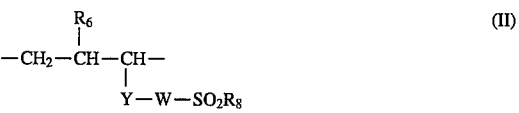 (II)

 (III')

(wherein,

R$_6$, R$_7$, R$_8$, Y and W are the same as previously defined).

3. The sulfonic acid as set forth in either of claims 1 or 2 which are sulfonamide derivatives represented by formula (I')

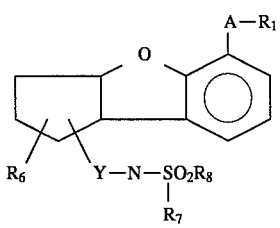

(wherein,

R$_1$, R$_6$, R$_7$, R$_8$, A and Y are the same as previously defined).

4. The sulfonamide as set forth in claim 3 wherein
R$_6$ is
(i) hydrogen, or
(ii) —OR$_2$ (wherein, R$_2$ is (1) hydrogen, (2) an alkyl having 1 to 4 carbon atoms, or (3) an acyl group), and R$_8$ is
(i) an alkyl having 1 to 14 carbon atoms,
(ii) —Z—R$_{11}$ (wherein, Z is a valence bond or a straight or branched alkylene represented by C$_t$H$_{2t}$ (wherein, t is an integer of 1 to 4), and R$_{11}$ represents a phenyl group or a phenyl group substituted by 1–4 groups selected from the group consisting of alkyl, methoxy, chlorine, bromine, fluorine, iodine, trifluoromethyl, nitro, cyano, phenyl and phenoxy), or
(iii) —Z—R$_{12}$ (wherein, Z is the same as previously defined, and R$_{12}$ represents a 1-naphthyl group, 2-naphthyl group or a 1-naphthyl or 2-naphthyl group substituted with 1 to 4 groups selected from the group consisting of alkyl, methoxy, chlorine, bromine, fluorine, iodine, trifluoromethyl, nitro, cyano, phenyl and phenoxy), and R$_1$, R$_7$, A and Y are same as previously defined.

5. A thromboxane A2 receptor antagonistic drug containing any one of the sulfonic acid derivatives as set forth in any of claims 1, 2 and 4 as an active ingredient.

6. Sulfonic acid represented by formula I:

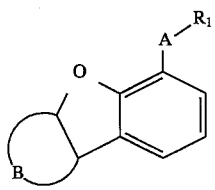

wherein,

R$_1$ is
(i) —COOR$_2$ (wherein, R$_2$ is (1) hydrogen, (2) a pharmacologically acceptable cation, or (3) an alkyl having 1 to 14 carbon atoms) or the group:
(ii)

(wherein

R$_3$ represents an alkyl having 1 to 4 carbon atoms);

A is
(i) —(CH$_2$)n— (wherein, n represents an integer of 0 to 3),
(ii) —CH=CH—, or the group:
(iii)

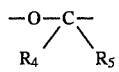

(wherein

R$_4$ and R$_5$ represent (1) hydrogen or (2) an alkyl having 1 to 4 carbon atoms, and R$_4$ and R$_5$ may be identical or different); and, B is represented with either formula III or formula III:

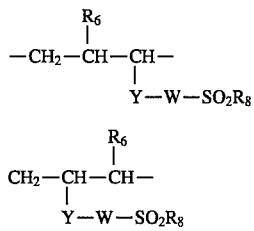

(wherein

R$_6$ represents
(i) hydrogen,
(ii) OH,
(iii) OAc, or
(iv) OMe

Y is —(CH$_2$)m— (where, m represents 0 or 1),
W is

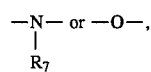

R$_7$ is
(i) hydrogen, or
(ii) an alkyl having 1 to 4 carbon atoms,

R$_8$ is
(i) an alkyl having 1 to 14 carbon atoms, or
(ii) —Z—R$_{11}$ (wherein, Z is a valance bond or a straight or branched alkylene represented by C$_t$H$_{2t}$ (where, t is an integer of 1 to 5) and R$_{11}$ represents an aryl group or aryl group having 6 to 16 carbon atoms substituted by 1 to 4 groups selected from the group consisting of alkyl, methoxy, chlorine, bromine, fluorine, iodine, trifluoromethyl, nitro, cyano, phenyl and phenoxy)).

7. A thromboxane A2 receptor antagonistic drug containing any one of the sulfonic acid derivatives as set forth in claim 3 as an active ingredient.

* * * * *

UNITED STATES PATENT AND TRADEMARK OFFICE
CERTIFICATE OF CORRECTION

PATENT NO. : 5,496,849
DATED : March 5, 1996
INVENTOR(S) : Kiyotaka Ohno et al

Page 1 of 5

It is certified that error appears in the above-indentified patent and that said Letters Patent is hereby corrected as shown below:

In Column 15, comprising lines 45-57, please change

"
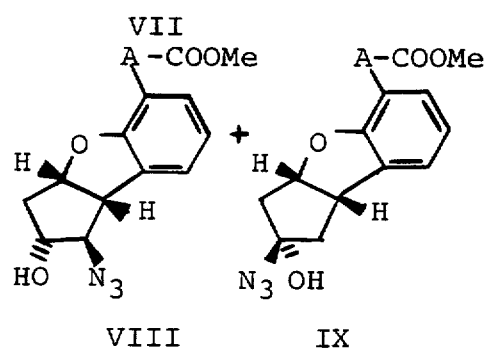
"

to

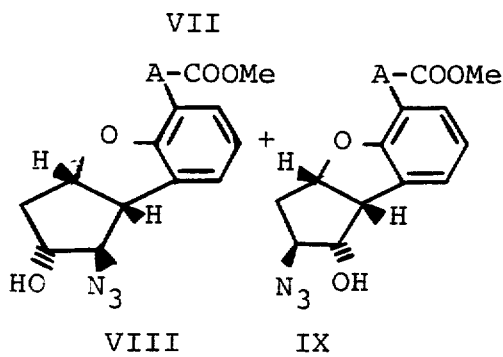

--.

UNITED STATES PATENT AND TRADEMARK OFFICE
CERTIFICATE OF CORRECTION

PATENT NO. : 5,496,849
DATED : March 5, 1996
INVENTOR(S) : Kiyotaka Ohno et al

It is certified that error appears in the above-indentified patent and that said Letters Patent is hereby corrected as shown below:

In Column 16, comprising lines 3-14, please change

"
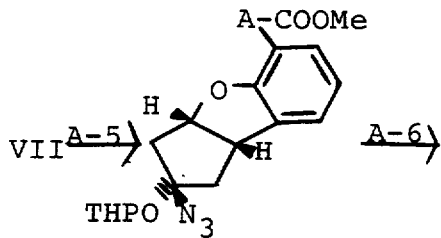
"

to

--
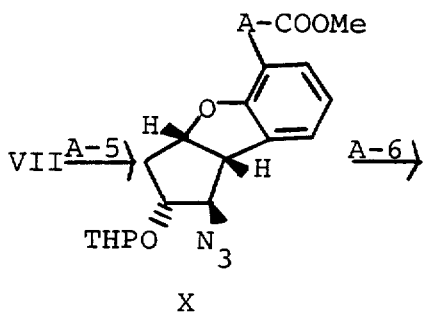
--.

UNITED STATES PATENT AND TRADEMARK OFFICE
CERTIFICATE OF CORRECTION

PATENT NO. : 5,496,849
DATED : March 5, 1996
INVENTOR(S) : Kiyotaka Ohno et al

It is certified that error appears in the above-indentified patent and that said Letters Patent is hereby corrected as shown below:

In Column 38, line 64, please change "232" to --2232--.

In Column 39, line 47, please change "56" to --756--.

In Column 56, line 5, after "for", please insert --6--.

In Column 65, line 20, please change "(30" to --(430--;

and line 24, please change "1085", second occurrence, to --1044--.

In Column 71, line 16, please change "3.54" to --2.54--.

In Column 74, line 59, please change "(361mg)" to --(631mg)--; and bridging lines 66-67, please change "3 78" to --3.78--.

In Column 75, line 27, please change "3196" to --3186--.

In Column 80, line 31, after "1740,", please insert --1607,--.

UNITED STATES PATENT AND TRADEMARK OFFICE
CERTIFICATE OF CORRECTION

PATENT NO. : 5,496,849
DATED : March 5, 1996
INVENTOR(S) : Kiyotaka Ohno et al

It is certified that error appears in the above-indentified patent and that said Letters Patent is hereby corrected as shown below:

In Column 83, line 3, please change "6.9-6.92" to --6.91-6.92--.

In Column 88, line 19, please change "(2.49" to --(249--;

and line 22, please change "3t66" to --3166--.

In Column 89, line 36, pleas change "$C_{22}$" to --$C_{21}$--.

In Column 101, line 27, please change "t79°" to --179--

In Column 104, line 23, after "400 ml", please insert --+--; and line 62, please change "452," to --1452,--.

In Column 106, line 8, after "7.75", please insert --(4H,-- line 59, please change "-1.45.52" to ---145.52--;

and line 61, please change "448," to --1448,--.

In Column 109, line 10, please change "$\gamma$" to --$\delta$--.

UNITED STATES PATENT AND TRADEMARK OFFICE
CERTIFICATE OF CORRECTION

PATENT NO. : 5,496,849
DATED : March 5, 1996
INVENTOR(S) : Kiyotaka Ohno et al

It is certified that error appears in the above-indentified patent and that said Letters Patent is hereby corrected as shown below:

In Column 118, under "Table 2", under the subheading "Compound", five rows down, please change "(76)" to --(78)--.

In Column 119, line 61, please change "wherein" to --(wherein--.

In Column 120, line 7, please change "wherein" to --(wherein--; and line 21, please change "wherein" to --(wherein--.

Signed and Sealed this

Eighteenth Day of June, 1996

BRUCE LEHMAN

Attest:

Attesting Officer

Commissioner of Patents and Trademarks